US009873704B2

(12) United States Patent
Bui et al.

(10) Patent No.: US 9,873,704 B2
(45) Date of Patent: *Jan. 23, 2018

(54) HETEROCYCLIC COMPOUNDS AND THEIR USES

(71) Applicant: Amgen Inc., Thousand Oaks, CA (US)

(72) Inventors: Minna Bui, Oakland, CA (US); Yi Chen, San Jose, CA (US); Timothy David Cushing, Pacifica, CA (US); Jason A. Duquette, Millbrae, CA (US); Benjamin Fisher, San Mateo, CA (US); Felix Gonzalez Lopez De Turiso, Cambridge, MA (US); Xiaolin Hao, Foster City, CA (US); Xiao He, Foster City, CA (US); Michael G. Johnson, San Francisco, CA (US); Brian Lucas, Arlington, MA (US)

(73) Assignee: AMGEN INC., Thousand Oaks, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/219,624

(22) Filed: Jul. 26, 2016

(65) Prior Publication Data

US 2016/0333017 A1 Nov. 17, 2016

Related U.S. Application Data

(63) Continuation of application No. 12/823,449, filed on Jun. 25, 2010, now abandoned.

(60) Provisional application No. 61/220,488, filed on Jun. 25, 2009.

(51) Int. Cl.
| | | |
|---|---|---|
| C07D 345/00 | (2006.01) | |
| C07D 517/00 | (2006.01) | |
| C07D 487/04 | (2006.01) | |
| C07D 401/12 | (2006.01) | |
| C07D 401/14 | (2006.01) | |
| C07D 471/04 | (2006.01) | |
| C07D 473/34 | (2006.01) | |

(52) U.S. Cl.
CPC ......... *C07D 487/04* (2013.01); *C07D 401/12* (2013.01); *C07D 401/14* (2013.01); *C07D 471/04* (2013.01); *C07D 473/34* (2013.01)

(58) Field of Classification Search
USPC .......................................................... 540/1
See application file for complete search history.

(56) References Cited

U.S. PATENT DOCUMENTS 6,355,636 B1  3/2002 Wissner et al.
6,384,251 B1  5/2002 Frost et al.

FOREIGN PATENT DOCUMENTS

| EP | 0 567 107 A1 | 10/1993 |
|---|---|---|
| EP | 0 608 870 A1 | 8/1994 |
| EP | 2 194 044 A1 | 6/2010 |
| WO | 95/24394 A1 | 9/1995 |
| WO | 2008/118455 A1 | 10/2008 |
| WO | 2008/118468 A1 | 10/2008 |
| WO | 2009/041521 A1 | 4/2009 |
| WO | 2010/036380 A1 | 4/2010 |
| WO | 2010/056865 A1 | 5/2010 |
| WO | 2010/061180 A1 | 6/2010 |
| WO | 201/092340 A1 | 8/2010 |
| WO | 2010/151740 A2 | 12/2010 |
| WO | 2011/058113 A1 | 5/2011 |
| WO | 2011/075628 A1 | 6/2011 |

OTHER PUBLICATIONS

J. G. Cannon, Chapter Nineteen in Burger's Medicinal Chemistry and Drug Discovery, Fifth Edition, vol. I: Principles and Practice, Wiley-Interscience 1995, pp. 783-802.*
Berndt, et al., "The p110δstructure: Mechanisms for selectivity and potency of new PI(3)K inhibitors" Nature Chemical Biology, Jan. 10, 2010 pp. 1-8.
Berndt, et al., "Supplementary Methods and Results the p110δ structure: Mechanisms for selectivity and potency of new PI(3)K inhibitors" Nature Chemical Biology, Jan. 2010 pp. 1-34.
Bhat, Chemical Abstract, "Syntheses of 3-chloro-5, 8-disubstituted-6,7- or 8-monosubstituted-2-(substituted, . . . )" 1982.
Liu, Chemical Abstract, "Synthesis of benzoxepinoquinolinones" 1987.
Wang, Chemical Abstract, "Synthesis and elucidation of indoprofen analogues" 2003.
Price, "A Synthesis of Substituted 4-Aminoquinolines" J of Am Chem Soc (1946) pp. 1246-1250, vol. 68.

(Continued)

*Primary Examiner* — Marcos Sznaidman
(74) *Attorney, Agent, or Firm* — Richard V. Person

(57) ABSTRACT

Substituted bicyclic heteroaryls and compositions containing them, for the treatment of general inflammation, arthritis, rheumatic diseases, osteoarthritis, inflammatory bowel disorders, inflammatory eye disorders, inflammatory or unstable bladder disorders, psoriasis, skin complaints with inflammatory components, chronic inflammatory conditions, including but not restricted to autoimmune diseases such as systemic lupus erythematosis (SLE), myestenia gravis, rheumatoid arthritis, acute disseminated encephalomyelitis, idiopathic thrombocytopenic purpura, multiples sclerosis, Sjoegren's syndrome and autoimmune hemolytic anemia, allergic conditions including all forms of hypersensitivity, The present invention also enables methods for treating cancers that are mediated, dependent on or associated with p110δ activity, including but not restricted to leukemias, such as Acute Myeloid leukaemia (AML) Myelo-dysplastic syndrome (MDS) myelo-proliferative diseases (MPD) Chronic Myeloid Leukemia (CML) T-cell Acute Lymphoblastic leukaemia (T-ALL) B-cell Acute Lymphoblastic leukaemia (B-ALL) Non Hodgkins Lymphoma (NHL) B-cell lymphoma and solid tumors, such as breast cancer.

3 Claims, No Drawings

(56) References Cited

OTHER PUBLICATIONS

Boschelli, "Facile preparation of new 4-phenylamino-3-quinolinecarboritrile Src kinase inhibitors via 7-fluoro intermediates: Identification of potent 7-amino analogs", Bioorganic & Medicinal Chem (2008) pp. 405-412, vol. 16 No. 1.
Crespo, "Redesigning kinase inhibitors to enhance specificity", J of Medicinal Chem (2008) pp. 4890-4898, vol. 51, No. 16.

* cited by examiner

HETEROCYCLIC COMPOUNDS AND THEIR USES

This application is a continuation of application Ser. No. 12/823,449, filed Jun. 25, 2010, which claims the benefit of U.S. Provisional Application No. 61/220,488, filed Jun. 25, 2009, which is hereby incorporated by reference.

The present invention relates generally to phosphatidylinositol 3-kinase (PI3K) enzymes, and more particularly to selective inhibitors of PI3K activity and to methods of using such materials.

BACKGROUND OF THE INVENTION

Cell signaling via 3'-phosphorylated phosphoinositides has been implicated in a variety of cellular processes, e.g., malignant transformation, growth factor signaling, inflammation, and immunity (see Rameh et al., J. Biol Chem, 274:8347-8350 (1999) for a review). The enzyme responsible for generating these phosphorylated signaling products, phosphatidylinositol 3-kinase (PI 3-kinase; PI3K), was originally identified as an activity associated with viral oncoproteins and growth factor receptor tyrosine kinases that phosphorylates phosphatidylinositol (PI) and its phosphorylated derivatives at the 3'-hydroxyl of the inositol ring (Panayotou et al., Trends Cell Biol 2:358-60 (1992)).

The levels of phosphatidylinositol-3,4,5-triphosphate (PIP3), the primary product of PI 3-kinase activation, increase upon treatment of cells with a variety of stimuli. This includes signaling through receptors for the majority of growth factors and many inflammatory stimuli, hormones, neurotransmitters and antigens, and thus the activation of PI3Ks represents one, if not the most prevalent, signal transduction events associated with mammalian cell surface receptor activation (Cantley, Science 296:1655-1657 (2002); Vanhaesebroeck et al. Annu. Rev. Biochem, 70: 535-602 (2001)). PI 3-kinase activation, therefore, is involved in a wide range of cellular responses including cell growth, migration, differentiation, and apoptosis (Parker et al., Current Biology, 5:577-99 (1995); Yao et al., Science, 267:2003-05 (1995)). Though the downstream targets of phosphorylated lipids generated following PI 3-kinase activation have not been fully characterized, it is known that pleckstrin-homology (PH) domain- and FYVE-finger domain-containing proteins are activated when binding to various phosphatidylinositol lipids (Sternmark et al., J Cell Sci, 112:4175-83 (1999); Lemmon et al., Trends Cell Biol, 7:237-42 (1997)). Two groups of PH-domain containing PI3K effectors have been studied in the context of immune cell signaling, members of the tyrosine kinase TEC family and the serine/threonine kinases of the AGC family. Members of the Tec family containing PH domains with apparent selectivity for PtdIns (3,4,5)P$_3$ include Tec, Btk, Itk and Etk. Binding of PH to PIP$_3$ is critical for tyrsosine kinase activity of the Tec family members (Schaeffer and Schwartzberg, Curr. Opin. Immunol. 12: 282-288 (2000)) AGC family members that are regulated by PI3K include the phosphoinositide-dependent kinase (PDK1), AKT (also termed PKB) and certain isoforms of protein kinase C (PKC) and S6 kinase. There are three isoforms of AKT and activation of AKT is strongly associated with PI3K-dependent proliferation and survival signals. Activation of AKT depends on phosphorylation by PDK1, which also has a 3-phosphoinositide-selective PH domain to recruit it to the membrane where it interacts with AKT. Other important PDK1 substrates are PKC and S6 kinase (Deane and Fruman, Annu. Rev. Immunol. 22_563-598 (2004)). In vitro, some isoforms of protein kinase C (PKC) are directly activated by PIP3. (Burgering et al., Nature, 376:599-602 (1995)).

Presently, the PI 3-kinase enzyme family has been divided into three classes based on their substrate specificities. Class I PI3Ks can phosphorylate phosphatidylinositol (PI), phosphatidylinositol-4-phosphate, and phosphatidylinositol-4,5-biphosphate (PIP2) to produce phosphatidylinositol-3-phosphate (PIP), phosphatidylinositol-3,4-biphosphate, and phosphatidylinositol-3,4,5-triphosphate, respectively. Class II PI3Ks phosphorylate PI and phosphatidylinositol-4-phosphate, whereas Class III PI3Ks can only phosphorylate PI.

The initial purification and molecular cloning of PI 3-kinase revealed that it was a heterodimer consisting of p85 and p110 subunits (Otsu et al., Cell, 65:91-104 (1991); Hiles et al., Cell, 70:419-29 (1992)). Since then, four distinct Class I PI3Ks have been identified, designated PI3K α, β, δ, and γ, each consisting of a distinct 110 kDa catalytic subunit and a regulatory subunit. More specifically, three of the catalytic subunits, i.e., p110α, p110β and p110δ, each interact with the same regulatory subunit, p85; whereas p110γ interacts with a distinct regulatory subunit, p101. As described below, the patterns of expression of each of these PI3Ks in human cells and tissues are also distinct. Though a wealth of information has been accumulated in recent past on the cellular functions of PI 3-kinases in general, the roles played by the individual isoforms are not fully understood.

Cloning of bovine p110α has been described. This protein was identified as related to the *Saccharomyces cerevisiae* protein: Vps34p, a protein involved in vacuolar protein processing. The recombinant p110α product was also shown to associate with p85α, to yield a PI3K activity in transfected COS-1 cells. See Hiles et al., Cell, 70, 419-29 (1992).

The cloning of a second human p110 isoform, designated p110β, is described in Hu et al., Mol Cell Biol, 13:7677-88 (1993). This isoform is said to associate with p85 in cells, and to be ubiquitously expressed, as p110β mRNA has been found in numerous human and mouse tissues as well as in human umbilical vein endothelial cells, Jurkat human leukemic T cells, 293 human embryonic kidney cells, mouse 3T3 fibroblasts, HeLa cells, and NBT2 rat bladder carcinoma cells. Such wide expression suggests that this isoform is broadly important in signaling pathways.

Identification of the p110δ isoform of PI 3-kinase is described in Chantry et al., J Biol Chem, 272:19236-41 (1997). It was observed that the human p110δ isoform is expressed in a tissue-restricted fashion. It is expressed at high levels in lymphocytes and lymphoid tissues and has been shown to play a key role in PI 3-kinase-mediated signaling in the immune system (Al-Alwan etl al. JI 178: 2328-2335 (2007); Okkenhaug et al JI, 177: 5122-5128 (2006); Lee et al. PNAS, 103: 1289-1294 (2006)). P110δ has also been shown to be expressed at lower levels in breast cells, melanocytes and endothelial cells (Vogt et al. Virology, 344: 131-138 (2006) and has since been implicated in conferring selective migratory properties to breast cancer cells (Sawyer et al. Cancer Res. 63:1667-1675 (2003)). Details concerning the P110δ isoform also can be found in U.S. Pat. Nos. 5,858,753; 5,822,910; and 5,985,589. See also, Vanhaesebroeck et al., Proc Nat. Acad Sci USA, 94:4330-5 (1997), and international publication WO 97/46688.

In each of the PI3Kα, β, and δ subtypes, the p85 subunit acts to localize PI 3-kinase to the plasma membrane by the interaction of its SH2 domain with phosphorylated tyrosine residues (present in an appropriate sequence context) in target proteins (Rameh et al., Cell, 83:821-30 (1995)). Five isoforms of p85 have been identified (p85α, p85β, p55γ, p55α and p50α) encoded by three genes. Alternative transcripts of Pik3r1 gene encode the p85α, p55α and p50α proteins (Deane and Fruman, Annu. Rev. Immunol. 22: 563-598 (2004)). p85α is ubiquitously expressed while p85β, is primarily found in the brain and lymphoid tissues (Volinia et al., Oncogene, 7:789-93 (1992)). Association of the p85 subunit to the PI 3-kinase p110α, β, or δ catalytic subunits appears to be required for the catalytic activity and stability of these enzymes. In addition, the binding of Ras proteins also upregulates PI 3-kinase activity.

The cloning of p110γ revealed still further complexity within the PI3K family of enzymes (Stoyanov et al., Science, 269:690-93 (1995)). The p110γ isoform is closely related to p110α and p110β (45-48% identity in the catalytic domain), but as noted does not make use of p85 as a targeting subunit. Instead, p110γ binds a p101 regulatory subunit that also binds to the βγ subunits of heterotrimeric G proteins. The p101 regulatory subunit for PI3K gamma was originally cloned in swine, and the human ortholog identified subsequently (Krugmann et al., J Biol Chem, 274:17152-8 (1999)). Interaction between the N-terminal region of p101 with the N-terminal region of p110γ is known to activate PI3Kγ through Gβγ. Recently, a p101-homologue has been identified, p84 or p87$^{PIKAP}$ (PI3Kγ adapter protein of 87 kDa) that binds p110γ (Voigt et al. JBC, 281: 9977-9986 (2006), Suire et al. Curr. Biol. 15: 566-570 (2005)). p87$^{PIKAP}$ is homologous to p101 in areas that bind p110γ and Gβγ and also mediates activation of p110γ downstream of G-protein-coupled receptors. Unlike p101, p87$^{PIKAP}$ is highly expressed in the heart and may be crucial to PI3Kγ cardiac function.

A constitutively active PI3K polypeptide is described in international publication WO 96/25488. This publication discloses preparation of a chimeric fusion protein in which a 102-residue fragment of p85 known as the inter-SH2 (iSH2) region is fused through a linker region to the N-terminus of murine p110. The p85 iSH2 domain apparently is able to activate PI3K activity in a manner comparable to intact p85 (Klippel et al., Mol Cell Biol, 14:2675-85 (1994)).

Thus, PI 3-kinases can be defined by their amino acid identity or by their activity. Additional members of this growing gene family include more distantly related lipid and protein kinases including Vps34 TOR1, and TOR2 of *Saccharomyces cerevisiae* (and their mammalian homologs such as FRAP and mTOR), the ataxia telangiectasia gene product (ATR) and the catalytic subunit of DNA-dependent protein kinase (DNA-PK). See generally, Hunter, Cell, 83:1-4 (1995).

PI 3-kinase is also involved in a number of aspects of leukocyte activation. A p85-associated PI 3-kinase activity has been shown to physically associate with the cytoplasmic domain of CD28, which is an important costimulatory molecule for the activation of T-cells in response to antigen (Pages et al., Nature, 369:327-29 (1994); Rudd, Immunity, 4:527-34 (1996)). Activation of T cells through CD28 lowers the threshold for activation by antigen and increases the magnitude and duration of the proliferative response. These effects are linked to increases in the transcription of a number of genes including interleukin-2 (IL2), an important T cell growth factor (Fraser et al., Science, 251:313-16 (1991)). Mutation of CD28 such that it can no longer interact with PI 3-kinase leads to a failure to initiate IL2 production, suggesting a critical role for PI 3-kinase in T cell activation.

Specific inhibitors against individual members of a family of enzymes provide invaluable tools for deciphering functions of each enzyme. Two compounds, LY294002 and wortmannin, have been widely used as PI 3-kinase inhibitors. These compounds, however, are nonspecific PI3K inhibitors, as they do not distinguish among the four members of Class I PI 3-kinases. For example, the IC$_{50}$ values of wortmannin against each of the various Class I PI 3-kinases are in the range of 1-10 nM. Similarly, the IC$_{50}$ values for LY294002 against each of these PI 3-kinases is about 1 μM (Fruman et al., Ann Rev Biochem, 67:481-507 (1998)). Hence, the utility of these compounds in studying the roles of individual Class I PI 3-kinases is limited.

Based on studies using wortmannin, there is evidence that PI 3-kinase function also is required for some aspects of leukocyte signaling through G-protein coupled receptors (Thelen et al., Proc Natl Acad Sci USA, 91:4960-64 (1994)). Moreover, it has been shown that wortmannin and LY294002 block neutrophil migration and superoxide release. However, inasmuch as these compounds do not distinguish among the various isoforms of PI3K, it remains unclear from these studies which particular PI3K isoform or isoforms are involved in these phenomena and what functions the different Class I PI3K enzymes perform in both normal and diseased tissues in general. The co-expression of several PI3K isoforms in most tissues has confounded efforts to segregate the activities of each enzyme until recently.

The separation of the activities of the various PI3K isozymes has been advanced recently with the development of genetically manipulated mice that allowed the study of isoform-specific knock-out and kinase dead knock-in mice and the development of more selective inhibitors for some of the different isoforms. P110α and p110β knockout mice have been generated and are both embryonic lethal and little information can be obtained from these mice regarding the expression and function of p110 alpha and beta (Bi et al. Mamm. Genome, 13:169-172 (2002); Bi et al. J. Biol. Chem. 274:10963-10968 (1999)). More recently, p110α kinase dead knock in mice were generated with a single point mutation in the DFG motif of the ATP binding pocket (p110αD$^{933A}$) that impairs kinase activity but preserves mutant p110α kinase expression. In contrast to knock out mice, the knockin approach preserves signaling complex stoichiometry, scaffold functions and mimics small molecule approaches more realistically than knock out mice. Similar to the p110α KO mice, p110αD$^{933A}$ homozygous mice are embryonic lethal. However, heterozygous mice are viable and fertile but display severely blunted signaling via insulin-receptor substrate (IRS) proteins, key mediators of insulin, insulin-like growth factor-1 and leptin action. Defective responsiveness to these hormones leads to hyperinsulinemia, glucose intolerance, hyperphagia, increase adiposity and reduced overall growth in heterozygotes (Foukas, et al. Nature, 441: 366-370 (2006)). These studies revealed a defined, non-redundant role for p110α as an intermediate in IGF-1, insulin and leptin signaling that is not substituted for by other isoforms. We will have to await the description of the p110β kinase-dead knock in mice to further understand the function of this isoform (mice have been made but not yet published; Vanhaesebroeck).

P110γ knock out and kinase-dead knock in mice have both been generated and overall show similar and mild phenotypes with primary defects in migration of cells of the innate immune system and a defect in thymic development of T cells (Li et al. Science, 287: 1046-1049 (2000), Sasaki et al. Science, 287: 1040-1046 (2000), Patrucco et al. Cell, 118: 375-387 (2004)).

Similar to p110γ, PI3K delta knock out and kinase-dead knock-in mice have been made and are viable with mild and like phenotypes. The p110δ$^{D910A}$ mutant knock in mice demonstrated an important role for delta in B cell development and function, with marginal zone B cells and CDS+ B1 cells nearly undetectable, and B- and T cell antigen receptor signaling (Clayton et al. J. Exp. Med. 196:753-763 (2002); Okkenhaug et al. Science, 297: 1031-1034 (2002)). The p110δ$^{D910A}$ mice have been studied extensively and have elucidated the diverse role that delta plays in the immune system. T cell dependent and T cell independent immune responses are severely attenuated in p110δ$^{D910A}$ and secretion of TH1 (INF-γ) and TH2 cytokine (IL-4, IL-5) are impaired (Okkenhaug et al. J. Immunol. 177: 5122-5128 (2006)). A human patient with a mutation in p110δ has also recently been described. A taiwanese boy with a primary B cell immunodeficiency and a gamma-hypoglobulinemia of previously unknown aetiology presented with a single base-pair substitution, m.3256G to A in codon 1021 in exon 24 of p110δ. This mutation resulted in a mis-sense amino acid substitution (E to K) at codon 1021, which is located in the highly conserved catalytic domain of p110δ protein. The patient has no other identified mutations and his phenotype is consistent with p110δ deficiency in mice as far as studied. (Jou et al. Int. J. Immunogenet. 33: 361-369 (2006)).

Isoform-selective small molecule compounds have been developed with varying success to all Class I PI3 kinase isoforms (Ito et al. J. Pharm. Exp. Therapeut., 321:1-8 (2007)). Inhibitors to alpha are desirable because mutations in p110α have been identified in several solid tumors; for example, an amplification mutation of alpha is associated with 50% of ovarian, cervical, lung and breast cancer and an activation mutation has been described in more than 50% of bowel and 25% of breast cancers (Hennessy et al. Nature Reviews, 4: 988-1004 (2005)). Yamanouchi has developed a compound YM-024 that inhibits alpha and delta equipotently and is 8- and 28-fold selective over beta and gamma respectively (Ito et al. J. Pharm. Exp. Therapeut., 321:1-8 (2007)).

P110β is involved in thrombus formation (Jackson et al. Nature Med. 11: 507-514 (2005)) and small molecule inhibitors specific for this isoform are thought after for indication involving clotting disorders (TGX-221: 0.007 uM on beta; 14-fold selective over delta, and more than 500-fold selective over gamma and alpha) (Ito et al. J. Pharm. Exp. Therapeut., 321:1-8 (2007)).

Selective compounds to p110γ are being developed by several groups as immunosuppressive agents for autoimmune disease (Rueckle et al. Nature Reviews, 5: 903-918 (2006)). Of note, AS 605240 has been shown to be efficacious in a mouse model of rheumatoid arthritis (Camps et al. Nature Medicine, 11: 936-943 (2005)) and to delay onset of disease in a model of systemic lupus erythematosis (Barber et al. Nature Medicine, 11: 933-935 (205)).

Delta-selective inhibitors have also been described recently. The most selective compounds include the quinazolinone purine inhibitors (PIK39 and IC87114). IC87114 inhibits p110δ in the high nanomolar range (triple digit) and has greater than 100-fold selectivity against p110α, is 52 fold selective against p110β but lacks selectivity against p110γ (approx. 8-fold). It shows no activity against any protein kinases tested (Knight et al. Cell, 125: 733-747 (2006)). Using delta-selective compounds or genetically manipulated mice (p110δ$^{D910A}$) it was shown that in addition to playing a key role in B and T cell activation, delta is also partially involved in neutrophil migration and primed neutrophil respiratory burst and leads to a partial block of antigen-IgE mediated mast cell degranulation (Condliffe et al. Blood, 106: 1432-1440 (2005); Ali et al. Nature, 431: 1007-1011 (2002)). Hence p110δ is emerging as an important mediator of many key inflammatory responses that are also known to participate in aberrant inflammatory conditions, including but not limited to autoimmune disease and allergy. To support this notion, there is a growing body of p110δ target validation data derived from studies using both genetic tools and pharmacologic agents. Thus, using the delta-selective compound IC 87114 and the p110δ$^{D910A}$ mice, Ali et al. (Nature, 431: 1007-1011 (2002)) have demonstrated that delta plays a critical role in a murine model of allergic disease. In the absence of functional delta, passive cutaneous anaphylaxis (PCA) is significantly reduced and can be attributed to a reduction in allergen-IgE induced mast cell activation and degranulation. In addition, inhibition of delta with IC 87114 has been shown to significantly ameliorate inflammation and disease in a murine model of asthma using ovalbumin-induced airway inflammation (Lee et al. FASEB, 20: 455-465 (2006). These data utilizing compound were corroborated in p110δ$^{D910A}$ mutant mice using the same model of allergic airway inflammation by a different group (Nashed et al. Eur. J. Immunol. 37:416-424 (2007)).

There exists a need for further characterization of PI3Kδ function in inflammatory and auto-immune settings. Furthermore, our understanding of PI3Kδ requires further elaboration of the structural interactions of p110δ, both with its regulatory subunit and with other proteins in the cell. There also remains a need for more potent and selective or specific inhibitors of PI3K delta, in order to avoid potential toxicology associated with activity on isozymes p110 alpha (insulin signaling) and beta (platelet activation). In particular, selective or specific inhibitors of PI3Kδ are desirable for exploring the role of this isozyme further and for development of superior pharmaceuticals to modulate the activity of the isozyme.

SUMMARY

The present invention comprises a new class of compounds having the general formula

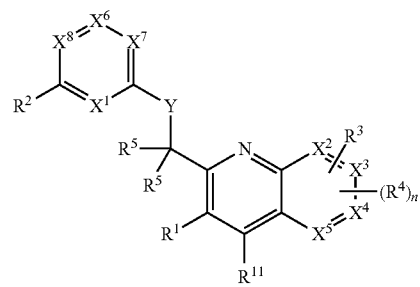

which are useful to inhibit the biological activity of human PI3Kδ. Another aspect of the invention is to provide compounds that inhibit PI3Kδ selectively while having relatively low inhibitory potency against the other PI3K isoforms. Another aspect of the invention is to provide methods of characterizing the function of human PI3Kδ. Another aspect of the invention is to provide methods of selectively modulating human PI3Kδ activity, and thereby promoting medical treatment of diseases mediated by PI3Kδ dysfunction. Other aspects and advantages of the invention will be readily apparent to the artisan having ordinary skill in the art.

DETAILED DESCRIPTION

One aspect of the invention relates to compounds having the structure:

or any pharmaceutically-acceptable salt thereof, wherein:
  $X^1$ is $C(R^{10})$ or N;
  $X^2$ is C or N;
  $X^3$ is C or N;
  $X^4$ is C or N;
  $X^5$ is C or N; wherein at least two of $X^2$, $X^3$, $X^4$ and $X^5$ are C;
  $X^6$ is $C(R^6)$ or N;
  $X^7$ is $C(R^7)$ or N;
  $X^8$ is $C(R^{10})$ or N; wherein no more than two of $X^1$, $X^6$, $X^7$ and $X^8$ are N;
  Y is $N(R^8)$, O or S;
  n is 0, 1, 2 or 3;
  $R^1$ is a direct-bonded, $C_{1-4}$alk-linked, $OC_{1-2}$alk-linked, $C_{1-2}$alkO-linked, $N(R^a)$-linked or O-linked saturated, partially-saturated or unsaturated 5-, 6- or 7-membered monocyclic or 8-, 9-, 10- or 11-membered bicyclic ring containing 0, 1, 2, 3 or 4 atoms selected from N, O and S, but containing no more than one O or S atom, substituted by 0, 1, 2 or 3 substituents independently selected from halo, $C_{1-6}$alk, $C_{1-4}$haloalk, cyano, nitro, —C(=O)$R^a$, —C(=O)O$R^a$, —C(=O)N$R^aR^a$, —C(=N$R^a$)N$R^aR^a$, —O$R^a$, —OC(=O)$R^a$, —OC(=O)N$R^aR^a$, —OC(=O)N($R^a$)S(=O)$_2R^a$, —OC$_{2-6}$alkN$R^aR^a$, —OC$_{2-6}$alkO$R^a$, —S$R^a$, —S(=O)$R^a$, —S(=O)$_2R^a$, —S(=O)$_2$N$R^aR^a$, —S(=O)$_2$N($R^a$)C(=O)$R^a$, —S(=O)$_2$N($R^a$)C(=O)O$R^a$, —S(=O)$_2$N($R^a$)C(=O) N$R^aR^a$, —N$R^aR^a$, —N($R^a$)C(=O)$R^a$, —N($R^a$)C(=O) O$R^a$, —N($R^a$)C(=O)N$R^aR^a$, —N($R^a$)C(=N$R^a$)N$R^aR^a$, —N($R^a$)S(=O)$_2R^a$, —N($R^a$)S(=O)$_2$N$R^aR^a$, —N$R^aC_{2-6}$alkN$R^aR^a$ and —N$R^aC_{2-6}$alkO$R^a$, wherein the available carbon atoms of the ring are additionally substituted by 0, 1 or 2 oxo or thioxo groups, and wherein the ring is additionally substituted by 0 or 1 directly bonded, SO$_2$ linked, C(=O) linked or CH$_2$ linked group selected from phenyl, pyridyl, pyrimidyl, morpholino, piperazinyl, piperidinyl, cyclopentyl and cyclohexyl all of which are further substituted by 0, 1, 2 or 3 independent $R^b$ groups;
  $R^2$ is selected from H, halo, $C_{1-6}$alk, $C_{1-4}$haloalk, cyano, nitro, O$R^a$, N$R^aR^a$, —C(=O)$R^a$, —C(=O)O$R^a$, —C(=O) N$R^aR^a$, —C(=N$R^a$)N$R^aR^a$, —S(=O)$R^a$, —S(=O)$_2R^a$, —S(=O)$_2$N$R^aR^a$, —S(=O)$_2$N($R^a$)C(=O)$R^a$, —S(=O)$_2$N($R^a$)C(=O)O$R^a$ and —S(=O)$_2$N($R^a$)C(=O)N$R^aR^a$;
  $R^3$ is selected from H, halo, nitro, cyano, $C_{1-4}$alk, OC$_{1-4}$alk, OC$_{1-4}$haloalk, NHC$_{1-4}$alk, N(C$_{1-4}$alk)C$_{1-4}$alk and $C_{1-4}$haloalk;
  $R^4$ is, independently, in each instance, halo, nitro, cyano, $C_{1-4}$alk, OC$_{1-4}$alk, OC$_{1-4}$haloalk, NHC$_{1-4}$alk, N(C$_{1-4}$alk)C$_{1-4}$alk, $C_{1-4}$haloalk or an unsaturated 5-, 6- or 7-membered monocyclic ring containing 0, 1, 2, 3 or 4 atoms selected from N, O and S, but containing no more than one O or S, the ring being substituted by 0, 1, 2 or 3 substituents selected from halo, $C_{1-4}$alk, $C_{1-3}$haloalk, —OC$_{1-4}$alk, —NH$_2$, —NHC$_{1-4}$alk and —N(C$_{1-4}$alk)C$_{1-4}$alk;
  $R^5$ is, independently, in each instance, H, halo, $C_{1-6}$alk, $C_{1-4}$haloalk, or $C_{1-6}$alk substituted by 1, 2 or 3 substituents selected from halo, cyano, OH, OC$_{1-4}$alk, $C_{1-3}$haloalk, OC$_{1-4}$alk, NH$_2$, NHC$_{1-4}$alk and N(C$_{1-4}$alk)C$_{1-4}$alk; or both $R^5$ groups together form a $C_{3-6}$spiroalk substituted by 0, 1, 2 or 3 substituents selected from halo, cyano, OH, OC$_{1-4}$alk, $C_{1-4}$alk, $C_{1-3}$haloalk, OC$_{1-4}$alk, NH$_2$, NHC$_{1-4}$alk and N(C$_{1-4}$alk)C$_{1-4}$alk;
  $R^6$ is selected from halo, cyano, OH, OC$_{1-4}$alk, $C_{1-4}$alk, $C_{1-3}$haloalk, OC$_{1-4}$alk, NH$R^9$, N(C$_{1-4}$alk)C$_{1-4}$alk, —C(=O) O$R^a$, —C(=O)N($R^a$)$R^a$, —N($R^a$)C(=O)$R^b$ and a 5- or 6-membered saturated or partially saturated heterocyclic ring containing 1, 2 or 3 heteroatoms selected from N, O and S, wherein the ring is substituted by 0, 1, 2 or 3 substituents selected from halo, cyano, OH, oxo, OC$_{1-4}$alk, $C_{1-4}$alk, $C_{1-3}$haloalk, OC$_{1-4}$alk, NH$_2$, NHC$_{1-4}$alk and N(C$_{1-4}$alk)C$_{1-4}$alk;
  $R^7$ is selected from H, halo, $C_{1-4}$haloalk, cyano, nitro, —C(=O)$R^a$, —C(=O)O$R^a$, —C(=O)N$R^aR^a$, —C(=N$R^a$)N$R^aR^a$, —O$R^a$, —OC(=O)$R^a$, —OC(=O) N$R^aR^a$, —OC(=O)N($R^a$)S(=O)$_2R^a$, —OC$_{2-6}$alkN$R^aR^a$, —OC$_{2-6}$alkO$R^a$, —S$R^a$, —S(=O)$R^a$, —S(=O)$_2R^a$, —S(=O)$_2$N$R^aR^a$, —S(=O)$_2$N($R^a$)C(=O)$R^a$, —S(=O)$_2$N($R^a$)C(=O)O$R^a$, —S(=O)$_2$N($R^a$)C(=O) N$R^aR^a$, —N$R^aR^a$, —N($R^a$)C(=O)$R^a$, —N($R^a$)C(=O) O$R^a$, —N($R^a$)C(=O)N$R^aR^a$, —N($R^a$)C(=N$R^a$)N$R^aR^a$, —N($R^a$)S(=O)$_2R^a$, —N($R^a$)S(=O)$_2$N$R^aR^a$, —N$R^aC_{2-6}$ alkN$R^aR^a$, —N$R^aC_{2-6}$alkO$R^a$ and $C_{1-6}$alk, wherein the $C_{1-6}$alk is substituted by 0, 1, 2 or 3 substituents selected from halo, $C_{1-4}$haloalk, cyano, nitro, —C(=O)$R^a$, —C(=O)O$R^a$, —C(=O)N$R^aR^a$, —C(=N$R^a$)N$R^aR^a$, —O$R^a$, —OC(=O)$R^a$, —OC(=O)N$R^aR^a$, —OC(=O)N ($R^a$)S(=O)$_2R^a$, —OC$_{2-6}$alkN$R^aR^a$, —OC$_{2-6}$alkO$R^a$, —S$R^a$, —S(=O)$R^a$, —S(=O)$_2R^a$, —S(=O)$_2$N$R^aR^a$, —S(=O)$_2$N($R^a$)C(=O)$R^a$, —S(=O)$_2$N($R^a$)C(=O)O$R^a$, —S(=O)$_2$N($R^a$)C(=O)N$R^aR^a$, —N$R^aR^a$, —N($R^a$)C(=O) $R^a$, —N($R^a$)C(=O)O$R^a$, —N($R^a$)C(=O)N$R^aR^a$, —N($R^a$) C(=N$R^a$)N$R^aR^a$, —N($R^a$)S(=O)$_2R^a$, —N($R^a$)S(=O)$_2$ N$R^aR^a$, —N$R^aC_{2-6}$alkN$R^aR^a$ and —N$R^aC_{2-6}$alkO$R^a$, and the $C_{1-6}$alk is additionally substituted by 0 or 1 saturated, partially-saturated or unsaturated 5-, 6- or 7-membered monocyclic rings containing 0, 1, 2, 3 or 4 atoms selected from N, O and S, but containing no more than one O or S, wherein the available carbon atoms of the ring are substituted by 0, 1 or 2 oxo or thioxo groups, wherein the ring is substituted by 0, 1, 2 or 3 substituents independently selected from halo, nitro, cyano, $C_{1-4}$alk, OC$_{1-4}$alk, OC$_{1-4}$haloalk, NHC$_{1-4}$alk, N(C$_{1-4}$alk)C$_{1-4}$alk and $C_{1-4}$haloalk; or $R^7$ and $R^8$ together form a —C=N— bridge wherein the carbon atom is substituted by H, halo, cyano, or a saturated, partially-saturated or unsaturated 5-, 6- or 7-membered monocyclic ring containing 0, 1, 2, 3 or 4 atoms selected from N, O and S, but containing no more than one O or S, wherein the available carbon atoms of the ring are substituted by 0, 1 or 2 oxo or thioxo groups, wherein the ring is substituted by 0, 1, 2, 3 or 4 substituents selected from halo, $C_{1-6}$alk, $C_{1-4}$haloalk, cyano, nitro, —C(=O)$R^a$, —C(=O)O$R^a$, —C(=O)N$R^aR^a$, —C(=N$R^a$)N$R^aR^a$, —O$R^a$, —OC(=O)$R^a$, —OC(=O)N$R^aR^a$, —OC(=O)N (R$^a$)S(=O)$_2R^a$, —OC$_{2-6}$ alkN$R^aR^a$, —OC$_{2-6}$ alkO$R^a$, —S$R^a$, —S(=O)$R^a$, —S(=O)$_2R^a$, —S(=O)$_2$N$R^aR^a$, —S(=O)$_2$N($R^a$)C(=O)$R^a$, —S(=O)$_2$N($R^a$)C(=O)O$R^a$, —S(=O)$_2$N(R$^a$)C(=O)NR$^a$R$^a$, —NR$^a$R$^a$, —N(R$^a$)C(=O)R$^a$, —N(R$^a$)C(=O)OR$^a$, —N(R$^a$)C(=O)NR$^a$R$^a$, —N(R$^a$)C(=NR$^a$)NR$^a$R$^a$, —N(R$^a$)S(=O)$_2$R$^a$, —N(R$^a$)S(=O)$_2$NR$^a$R$^a$, —NR$^a$C$_{2-6}$alkNR$^a$R$^a$ and —NR$^a$C$_{2-6}$alkOR$^a$; or R$^7$ and R$^9$ together form a —N=C— bridge wherein the carbon atom is substituted by H, halo, C$_{1-6}$alk, C$_{1-4}$haloalk, cyano, nitro, OR$^a$, NR$^a$R$^a$, —C(=O)R$^a$, —C(=O)OR$^a$, —C(=O)NR$^a$R$^a$, —C(=NR$^a$)NR$^a$R$^a$, —S(=O)R$^a$, —S(=O)$_2$R$^a$ or —S(=O)$_2$NR$^a$R$^a$;

R$^8$ is H, C$_{1-6}$alk, C(=O)N(R$^a$)R$^a$, C(=O)R$^b$ or C$_{1-4}$haloalk;

R$^9$ is H, C$_{1-6}$alk or C$_{1-4}$haloalk;

R$^{10}$ is in each instance H, halo, C$_{1-3}$alk, C$_{1-3}$haloalk or cyano;

R$^{11}$ is selected from H, halo, C$_{1-6}$alk, C$_{1-4}$haloalk, cyano, nitro, —C(=O)R$^a$, —C(=O)OR$^a$, —C(=O)NR$^a$R$^a$, —C(=NR$^a$)NR$^a$R$^a$, —OR$^a$, —OC(=O)R$^a$, —OC(=O)NR$^a$R$^a$, —OC(=O)N(R$^a$)S(=O)$_2$R$^a$, —OC$_{2-6}$alkNR$^a$R$^a$, —OC$_{2-6}$alkOR$^a$, —SR$^a$, —S(=O)R$^a$, —S(=O)$_2$R$^b$, —S(=O)$_2$NR$^a$R$^a$, —S(=O)$_2$N(R$^a$)C(=O)R$^a$, —S(=O)$_2$N(R$^a$)C(=O)OR$^a$, —S(=O)$_2$N(R$^a$)C(=O)NR$^a$R$^a$, —NR$^a$R$^a$, —N(R$^a$)C(=O)R$^a$, —N(R$^a$)C(=O)OR$^a$, —N(R$^a$)C(=O)NR$^a$R$^a$, —N(R$^a$)C(=NR$^a$)NR$^a$R$^a$, —N(R$^a$)S(=O)$_2$R$^a$, —N(R$^a$)S(=O)$_2$NR$^a$R$^a$, —NR$^a$C$_{2-6}$alkNR$^a$R$^a$, —NR$^a$C$_{2-6}$alkOR$^a$, —NR$^a$C$_{2-6}$alkCO$_2$R$^a$, —NR$^a$C$_{2-6}$alkSO$_2$R$^b$, —CH$_2$C(=O)R$^a$, —CH$_2$C(=O)OR$^a$, —CH$_2$C(=O)NR$^a$R$^a$, —CH$_2$C(=NR$^a$)NR$^a$R$^a$, —CH$_2$OR$^a$, —CH$_2$OC(=O)R$^a$, —CH$_2$OC(=O)NR$^a$R$^a$, —CH$_2$OC(=O)N(R$^a$)S(=O)$_2$R$^a$, —CH$_2$OC$_{2-6}$alkNR$^a$R$^a$, —CH$_2$OC$_{2-6}$alkOR$^a$, —CH$_2$SR$^a$, —CH$_2$S(=O)R$^a$, —CH$_2$S(=O)$_2$R$^b$, —CH$_2$S(=O)$_2$NR$^a$R$^a$, —CH$_2$S(=O)$_2$N(R$^a$)C(=O)R$^a$, —CH$_2$S(=O)$_2$N(R$^a$)C(=O)OR$^a$, —CH$_2$S(=O)$_2$N(R$^a$)C(=O)NR$^a$R$^a$, —CH$_2$NR$^a$R$^a$, —CH$_2$N(R$^a$)C(=O)R$^a$, —CH$_2$N(R$^a$)C(=O)OR$^a$, —CH$_2$N(R$^a$)C(=O)NR$^a$R$^a$, —CH$_2$N(R$^a$)C(=NR$^a$)NR$^a$R$^a$, —CH$_2$N(R$^a$)S(=O)$_2$R$^a$, —CH$_2$N(R$^a$)S(=O)$_2$NR$^a$R$^a$, —CH$_2$NR$^a$C$_{2-6}$alkNR$^a$R$^a$, —CH$_2$NR$^a$C$_{2-6}$alkOR$^a$, —CH$_2$NR$^a$C$_{2-6}$alkCO$_2$R$^a$, —CH$_2$NR$^a$C$_{2-6}$alkSO$_2$R$^b$, —CH$_2$R$^c$, —C(=O)R$^c$ and —C(=O)N(R$^a$)R$^c$;

R$^a$ is independently, at each instance, H or R$^b$;

R$^b$ is independently, at each instance, phenyl, benzyl or C$_{1-6}$alk, the phenyl, benzyl and C$_{1-6}$alk being substituted by 0, 1, 2 or 3 substituents selected from halo, C$_{1-4}$alk, C$_{1-3}$haloalk, —OH, —OC$_{1-4}$alk, —NH$_2$, —NHC$_{1-4}$alk and —N(C$_{1-4}$alk)C$_{1-4}$alk; and R$^c$ is a saturated or partially-saturated 4-, 5- or 6-membered ring containing 1, 2 or 3 heteroatoms selected from N, O and S, the ring being substituted by 0, 1, 2 or 3 substituents selected from halo, C$_{1-4}$alk, C$_{1-3}$haloalk, —OC$_{1-4}$alk, —NH$_2$, —NHC$_{1-4}$alk and —N(C$_{1-4}$alk)C$_{1-4}$alk.

Another aspect of the invention relates to compounds having the structure

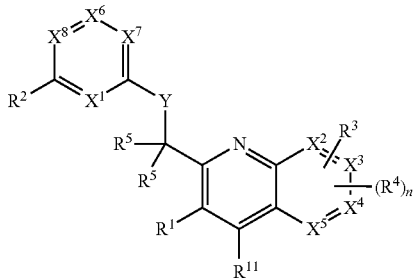

or any pharmaceutically-acceptable salt thereof, wherein:

X$^1$ is C(R$^{10}$) or N;

X$^2$ is C or N;

X$^3$ is C or N;

X$^4$ is C or N;

X$^5$ is C or N; wherein at least two of X$^2$, X$^3$, X$^4$ and X$^5$ are C;

X$^6$ is C(R$^6$) or N;

X$^7$ is C(R$^7$) or N;

X$^8$ is C(R$^{10}$) or N; wherein no more than two of X$^1$, X$^6$, X$^7$ and X$^8$ are N;

n is 0, 1, 2 or 3;

R$^1$ is a direct-bonded, C$_{1-4}$alk-linked, OC$_{1-2}$alk-linked, C$_{1-2}$alkO-linked, N(R$^a$)-linked or O-linked saturated, partially-saturated or unsaturated 5-, 6- or 7-membered monocyclic or 8-, 9-, 10- or 11-membered bicyclic ring containing 0, 1, 2, 3 or 4 atoms selected from N, O and S, but containing no more than one O or S atom, substituted by 0, 1, 2 or 3 substituents independently selected from halo, C$_{1-6}$alk, C$_{1-4}$haloalk, cyano, nitro, —C(=O)R$^a$, —C(=O)OR$^a$, —C(=O)NR$^a$R$^a$, —C(=NR$^a$)NR$^a$R$^a$, —OR$^a$, —OC(=O)R$^a$, —OC(=O)NR$^a$R$^a$, —OC(=O)N(R$^a$)S(=O)$_2$R$^a$, —OC$_{2-6}$alkNR$^a$R$^a$, —OC$_{2-6}$alkOR$^a$, —SR$^a$, —S(=O)R$^a$, —S(=O)$_2$R$^a$, —S(=O)$_2$NR$^a$R$^a$, —S(=O)$_2$N(R$^a$)C(=O)R$^a$, —S(=O)$_2$N(R$^a$)C(=O)OR$^a$, —S(=O)$_2$N(R$^a$)C(=O)NR$^a$R$^a$, —NR$^a$R$^a$, —N(R$^a$)C(=O)R$^a$, —N(R$^a$)C(=O)OR$^a$, —N(R$^a$)C(=O)NR$^a$R$^a$, —N(R$^a$)C(=NR$^a$)NR$^a$R$^a$, —N(R$^a$)S(=O)$_2$R$^a$, —N(R$^a$)S(=O)$_2$NR$^a$R$^a$, —NR$^a$C$_{2-6}$alkNR$^a$R$^a$ and —NR$^a$C$_{2-6}$alkOR$^a$, wherein the available carbon atoms of the ring are additionally substituted by 0, 1 or 2 oxo or thioxo groups, and wherein the ring is additionally substituted by 0 or 1 directly bonded, SO$_2$ linked, C(=O) linked or CH$_2$ linked group selected from phenyl, pyridyl, pyrimidyl, morpholino, piperazinyl, piperidinyl, cyclopentyl and cyclohexyl all of which are further substituted by 0, 1, 2 or 3 independent R$^b$ groups;

R$^2$ is selected from H, halo, C$_{1-6}$alk, C$_{1-4}$haloalk, cyano, nitro, OR$^a$, NR$^a$R$^a$, —C(=O)R$^a$, —C(=O)OR$^a$, —C(=O)NR$^a$R$^a$, —C(=NR$^a$)NR$^a$R$^a$, —S(=O)R$^a$, —S(=O)$_2$R$^a$, —S(=O)$_2$NR$^a$R$^a$, —S(=O)$_2$N(R$^a$)C(=O)R$^a$, —S(=O)$_2$N(R$^a$)C(=O)OR$^a$ and —S(=O)$_2$N(R$^a$)C(=O)NR$^a$R$^a$;

R$^3$ is selected from H, halo, nitro, cyano, C$_{1-4}$alk, OC$_{1-4}$alk, OC$_{1-4}$haloalk, NHC$_{1-4}$alk, N(C$_{1-4}$alk)C$_{1-4}$alk and C$_{1-4}$haloalk;

R$^4$ is, independently, in each instance, halo, nitro, cyano, C$_{1-4}$alk, OC$_{1-4}$alk, OC$_{1-4}$haloalk, NHC$_{1-4}$alk, N(C$_{1-4}$alk)C$_{1-4}$alk, C$_{1-4}$haloalk or an unsaturated 5-, 6- or 7-membered monocyclic ring containing 0, 1, 2, 3 or 4 atoms selected from N, O and S, but containing no more than one O or S, the ring being substituted by 0, 1, 2 or 3 substituents selected from halo, C$_{1-4}$alk, C$_{1-3}$haloalk, —OC$_{1-4}$alk, —NH$_2$, —NHC$_{1-4}$alk and —N(C$_{1-4}$alk)C$_{1-4}$alk;

R$^5$ is, independently, in each instance, H, halo, C$_{1-6}$alk, C$_{1-4}$haloalk, or C$_{1-6}$alk substituted by 1, 2 or 3 substituents selected from halo, cyano, OH, OC$_{1-4}$alk, C$_{1-4}$alk, C$_{1-3}$haloalk, OC$_{1-4}$alk, NH$_2$, NHC$_{1-4}$alk and N(C$_{1-4}$alk)C$_{1-4}$alk; or both R$^5$ groups together form a C$_{3-6}$spiroalk substituted by 0, 1, 2 or 3 substituents selected from halo, cyano, OH, OC$_{1-4}$alk, C$_{1-4}$alk, C$_{1-3}$haloalk, OC$_{1-4}$alk, NH$_2$, NHC$_{1-4}$alk and N(C$_{1-4}$alk)C$_{1-4}$alk;

R$^6$ is selected from halo, cyano, OH, OC$_{1-4}$alk, C$_{1-3}$haloalk, OC$_{1-4}$alk, NHR$^9$, N(C$_{1-4}$alk)C$_{1-4}$alk, —C(=O)OR$^a$, —C(=O)N(R$^a$)R$^a$, —N(R$^a$)C(=O)R$^b$ and a 5- or 6-membered saturated or partially saturated heterocyclic ring containing 1, 2 or 3 heteroatoms selected from N, O and S, wherein the ring is substituted by 0, 1, 2 or 3 substituents selected from halo, cyano, OH, oxo, $OC_{1-4}alk$, $C_{1-4}alk$, $C_{1-3}haloalk$, $OC_{1-4}alk$, $NH_2$, $NHC_{1-4}alk$ and $N(C_{1-4}alk)C_{1-4}alk$;

$R^7$ is selected from H, halo, $C_{1-4}haloalk$, cyano, nitro, —C(=O)$R^a$, —C(=O)O$R^a$, —C(=O)N$R^aR^a$, —C(=N$R^a$)N$R^aR^a$, —O$R^a$, —OC(=O)$R^a$, —OC(=O)N$R^aR^a$, —OC(=O)N($R^a$)S(=O)$_2R^a$, —OC$_{2-6}$alkN$R^aR^a$, —OC$_{2-6}$alkO$R^a$, —S$R^a$, —S(=O)$R^a$, —S(=O)$_2R^a$, —S(=O)$_2$N$R^aR^a$, —S(=O)$_2$N($R^a$)C(=O)$R^a$, —S(=O)$_2$N($R^a$)C(=O)O$R^a$, —S(=O)$_2$N($R^a$)C(=O)N$R^aR^a$, —N$R^aR^a$, —N($R^a$)C(=O)$R^a$, —N($R^a$)C(=O)O$R^a$, —N($R^a$)C(=O)N$R^aR^a$, —N($R^a$)C(=N$R^a$)N$R^aR^a$, —N($R^a$)S(=O)$_2R^a$, —N($R^a$)S(=O)$_2$N$R^aR^a$, —N$R^aC_{2-6}$alkN$R^aR^a$, —N$R^aC_{2-6}$alkO$R^a$ and $C_{1-6}$alk, wherein the $C_{1-6}$alk is substituted by 0, 1 2 or 3 substituents selected from halo, $C_{1-4}$haloalk, cyano, nitro, —C(=O)$R^a$, —C(=O)O$R^a$, —C(=O)N$R^aR^a$, —C(=N$R^a$)N$R^aR^a$, —O$R^a$, —OC(=O)$R^a$, —OC(=O)N$R^aR^a$, —OC(=O)N($R^a$)S(=O)$_2R^a$, —OC$_{2-6}$alkN$R^aR^a$, —OC$_{2-6}$alkO$R^a$, —S$R^a$, —S(=O)$R^a$, —S(=O)$_2R^a$, —S(=O)$_2$N$R^aR^a$, —S(=O)$_2$N($R^a$)C(=O)$R^a$, —S(=O)$_2$N($R^a$)C(=O)O$R^a$, —S(=O)$_2$N($R^a$)C(=O)N$R^aR^a$, —N$R^aR^a$, —N($R^a$)C(=O)$R^a$, —N($R^a$)C(=O)O$R^a$, —N($R^a$)C(=O)N$R^aR^a$, —N($R^a$)C(=N$R^a$)N$R^aR^a$, —N($R^a$)S(=O)$_2R^a$, —N($R^a$)S(=O)$_2$N$R^aR^a$, —N$R^aC_{2-6}$alkN$R^aR^a$ and —N$R^aC_{2-6}$alkO$R^a$, and the $C_{1-6}$alk is additionally substituted by 0 or 1 saturated, partially-saturated or unsaturated 5-, 6- or 7-membered monocyclic rings containing 0, 1, 2, 3 or 4 atoms selected from N, O and S, but containing no more than one O or S, wherein the available carbon atoms of the ring are substituted by 0, 1 or 2 oxo or thioxo groups, wherein the ring is substituted by 0, 1, 2 or 3 substituents independently selected from halo, nitro, cyano, $OC_{1-4}alk$, $OC_{1-4}haloalk$, $NHC_{1-4}alk$, $N(C_{1-4}alk)C_{1-4}alk$ and $C_{1-4}haloalk$; or $R^7$ and $R^8$ together form a —C=N— bridge wherein the carbon atom is substituted by H, halo, cyano, or a saturated, partially-saturated or unsaturated 5-, 6- or 7-membered monocyclic ring containing 0, 1, 2, 3 or 4 atoms selected from N, O and S, but containing no more than one O or S, wherein the available carbon atoms of the ring are substituted by 0, 1 or 2 oxo or thioxo groups, wherein the ring is substituted by 0, 1, 2, 3 or 4 substituents selected from halo, $C_{1-6}$alk, $C_{1-4}$haloalk, cyano, nitro, —C(=O)$R^a$, —C(=O)O$R^a$, —C(=O)N$R^aR^a$, —C(=N$R^a$)N$R^aR^a$, —O$R^a$, —OC(=O)$R^a$, —OC(=O)N$R^aR^a$, —OC(=O)N($R^a$)S(=O)$_2R^a$, —OC$_{2-6}$alkN$R^aR^a$, —OC$_{2-6}$alkO$R^a$, —S$R^a$, —S(=O)$R^a$, —S(=O)$_2R^a$, —S(=O)$_2$N$R^aR^a$, —S(=O)$_2$N($R^a$)C(=O)$R^a$, —S(=O)$_2$N($R^a$)C(=O)O$R^a$, —S(=O)$_2$N($R^a$)C(=O)N$R^aR^a$, —N$R^aR^a$, —N($R^a$)C(=O)$R^a$, —N($R^a$)C(=O)O$R^a$, —N($R^a$)C(=O)N$R^aR^a$, —N($R^a$)C(=N$R^a$)N$R^aR^a$, —N($R^a$)S(=O)$_2R^a$, —N($R^a$)S(=O)$_2$N$R^aR^a$, —N$R^aC_{2-6}$alkN$R^aR^a$ and —N$R^aC_{2-6}$alkO$R^a$; or $R^7$ and $R^9$ together form a —N=C— bridge wherein the carbon atom is substituted by H, halo, $C_{1-6}$alk, $C_{1-4}$haloalk, cyano, nitro, O$R^a$, N$R^aR^a$, —C(=O)$R^a$, —C(=O)O$R^a$, —C(=O)N$R^aR^a$, —C(=N$R^a$)N$R^aR^a$, —S(=O)$R^a$, —S(=O)$_2R^a$ or —S(=O)$_2$N$R^aR^a$;

$R^9$ is H, $C_{1-6}$alk or $C_{1-4}$haloalk;

$R^{10}$ is in each instance H, halo, $C_{1-3}$alk, $C_{1-3}$haloalk or cyano;

$R^{11}$ is selected from H, halo, $C_{1-6}$alk, $C_{1-4}$haloalk, cyano, nitro, —C(=O)$R^a$, —C(=O)O$R^a$, —C(=O)N$R^aR^a$, —C(=N$R^a$)N$R^aR^a$, —O$R^a$, —OC(=O)$R^a$, —OC(=O)N$R^aR^a$, —OC(=O)N($R^a$)S(=O)$_2R^a$, —OC$_{2-6}$alkN$R^aR^a$, —OC$_{2-6}$alkO$R^a$, —S$R^a$, —S(=O)$R^a$, —S(=O)$_2R^b$, —S(=O)$_2$N$R^aR^a$, —S(=O)$_2$N($R^a$)C(=O)$R^a$, —S(=O)$_2$N($R^a$)C(=O)O$R^a$, —S(=O)$_2$N($R^a$)C(=O)N$R^aR^a$, —N$R^aR^a$, —N$R^aR^a$, —N($R^a$)C(=O)$R^a$, —N($R^a$)C(=O)O$R^a$, —N($R^a$)C(=O)N$R^aR^a$, —N($R^a$)C(=N$R^a$)N$R^aR^a$, —N($R^a$)S(=O)$_2R^a$, —N($R^a$)S(=O)$_2$N$R^aR^a$, —N$R^aC_{2-6}$alkN$R^aR^a$, —N$R^aC_{2-6}$alkO$R^a$, —N$R^aC_{2-6}$alkCO$_2R^a$, —N$R^aC_{2-6}$alkSO$_2R^b$, —CH$_2$C(=O)$R^a$, —CH$_2$C(=O)O$R^a$, —CH$_2$C(=O)N$R^aR^a$, —CH$_2$C(=N$R^a$)N$R^aR^a$, —CH$_2$O$R^a$, —CH$_2$OC(=O)$R^a$, —CH$_2$OC(=O)N$R^aR^a$, —CH$_2$OC(=O)N($R^a$)S(=O)$_2R^a$, —CH$_2$OC$_{2-6}$alkN$R^aR^a$, —CH$_2$OC$_{2-6}$alkO$R^a$, —CH$_2$S$R^a$, —CH$_2$S(=O)$R^a$, —CH$_2$S(=O)$_2R^b$, —CH$_2$S(=O)$_2$N$R^aR^a$, —CH$_2$S(=O)$_2$N($R^a$)C(=O)$R^a$, —CH$_2$S(=O)$_2$N($R^a$)C(=O)O$R^a$, —CH$_2$S(=O)$_2$N($R^a$)C(=O)N$R^aR^a$, —CH$_2$N$R^aR^a$, —CH$_2$N($R^a$)C(=O)$R^a$, —CH$_2$N($R^a$)C(=O)O$R^a$, —CH$_2$N($R^a$)C(=O)N$R^aR^a$, —CH$_2$N($R^a$)C(=N$R^a$)N$R^aR^a$, —CH$_2$N($R^a$)S(=O)$_2R^a$, —CH$_2$N($R^a$)S(=O)$_2$N$R^aR^a$, —CH$_2$N$R^aC_{2-6}$alkN$R^aR^a$, —CH$_2$N$R^aC_{2-6}$alkO$R^a$, —CH$_2$N$R^aC_{2-6}$alkCO$_2R^a$, —CH$_2$N$R^aC_{2-6}$alkSO$_2R^b$, —CH$_2R^c$, —C(=O)$R^c$ and —C(=O)N($R^a$)$R^c$;

$R^a$ is independently, at each instance, H or $R^b$;

$R^b$ is independently, at each instance, phenyl, benzyl or $C_{1-6}$alk, the phenyl, benzyl and $C_{1-6}$alk being substituted by 0, 1, 2 or 3 substituents selected from halo, $C_{1-4}$alk, $C_{1-3}$haloalk, —OH, —O$C_{1-4}$alk, —NH$_2$, —NH$C_{1-4}$alk and —N($C_{1-4}$alk)$C_{1-4}$alk; and $R^c$ is a saturated or partially-saturated 4-, 5- or 6-membered ring containing 1, 2 or 3 heteroatoms selected from N, O and S, the ring being substituted by 0, 1, 2 or 3 substituents selected from halo, $C_{1-4}$alk, $C_{1-3}$haloalk, —O$C_{1-4}$alk, —NH$_2$, —NH$C_{1-4}$alk and —N($C_{1-4}$alk)$C_{1-4}$alk.

Another aspect of the invention relates to compounds having the structure

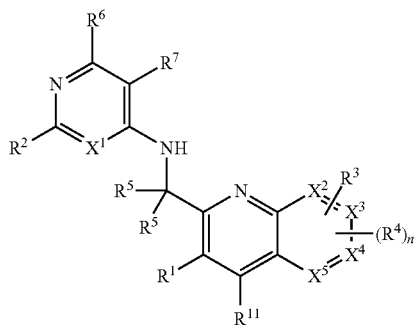

or any pharmaceutically-acceptable salt thereof, wherein:

$X^1$ is C($R^{10}$) or N;

$X^2$ is C or N;

$X^3$ is C or N;

$X^4$ is C or N;

$X^5$ is C or N; wherein at least two of $X^2$, $X^3$, $X^4$ and $X^5$ are C;

n is 0, 1, 2 or 3;

$R^1$ is a direct-bonded, $C_{1-4}$alk-linked, $OC_{1-2}$alk-linked, $C_{1-2}$alkO-linked, N($R^a$)-linked or O-linked saturated, partially-saturated or unsaturated 5-, 6- or 7-membered monocyclic or 8-, 9-, 10- or 11-membered bicyclic ring containing 0, 1, 2, 3 or 4 atoms selected from N, O and S, but containing no more than one O or S atom, substituted by 0, 1, 2 or 3 substituents independently selected from halo, $C_{1-6}$alk, $C_{1-4}$haloalk, cyano, nitro, —C(=O)$R^a$, —C(=O)O$R^a$, —C(=O)N$R^aR^a$, —C(=N$R^a$)N$R^aR^a$, —O$R^a$, —OC(=O)$R^a$, —OC(=O)N$R^aR^a$, —OC(=O)N($R^a$)S(=O)$_2R^a$, —OC$_{2-6}$alkN$R^aR^a$, —OC$_{2-6}$alkO$R^a$, —S$R^a$, —S(=O)$R^a$, —S(=O)$_2R^a$, —S(=O)$_2$N$R^aR^a$, —S(=O)$_2$N($R^a$)C(=O)$R^a$, —S(=O)$_2$N($R^a$)C(=O)O$R^a$, —S(=O)$_2$N($R^a$)C(=O)

NR$^a$R$^a$, —NR$^a$R$^a$, —N(R$^a$)C(=O)R$^a$, —N(R$^a$)C(=O)OR$^a$, —N(R$^a$)C(=O)NR$^a$R$^a$, —N(R$^a$)C(=NR$^a$)NR$^a$R$^a$, —N(R$^a$)S(=O)$_2$R$^a$, —N(R$^a$)S(=O)$_2$NR$^a$R$^a$, —NR$^a$C$_{2-6}$alkNR$^a$R$^a$ and —NR$^a$C$_{2-6}$alkOR$^a$, wherein the available carbon atoms of the ring are additionally substituted by 0, 1 or 2 oxo or thioxo groups, and wherein the ring is additionally substituted by 0 or 1 directly bonded, SO$_2$ linked, C(=O) linked or CH$_2$ linked group selected from phenyl, pyridyl, pyrimidyl, morpholino, piperazinyl, piperidinyl, cyclopentyl and cyclohexyl all of which are further substituted by 0, 1, 2 or 3 independent R$^b$ groups;

R$^2$ is selected from H, halo, C$_{1-6}$alk, C$_{1-4}$haloalk, cyano, nitro, OR$^a$, NR$^a$R$^a$, —C(=O)R$^a$, —C(=O)OR$^a$, —C(=O)NR$^a$R$^a$, —C(=NR$^a$)NR$^a$R$^a$, —S(=O)R$^a$, —S(=O)$_2$R$^a$, —S(=O)$_2$NR$^a$R$^a$, —S(=O)$_2$N(R$^a$)C(=O)R$^a$, —S(=O)$_2$N(R$^a$)C(=O)OR$^a$ and —S(=O)$_2$N(R$^a$)C(=O)NR$^a$R$^a$;

R$^3$ is selected from H, halo, nitro, cyano, C$_{1-4}$alk, OC$_{1-4}$alk, OC$_{1-4}$haloalk, NHC$_{1-4}$alk, N(C$_{1-4}$alk)C$_{1-4}$alk and C$_{1-4}$haloalk;

R$^4$ is, independently, in each instance, halo, nitro, cyano, C$_{1-4}$alk, OC$_{1-4}$alk, OC$_{1-4}$haloalk, NHC$_{1-4}$alk, N(C$_{1-4}$alk)C$_{1-4}$alk, C$_{1-4}$haloalk or an unsaturated 5-, 6- or 7-membered monocyclic ring containing 0, 1, 2, 3 or 4 atoms selected from N, O and S, but containing no more than one O or S, the ring being substituted by 0, 1 or 2 substituents selected from halo, C$_{1-4}$alk, C$_{1-3}$haloalk, —OC$_{1-4}$alk, —NH$_2$, —NHC$_{1-4}$alk and —N(C$_{1-4}$alk)C$_{1-4}$alk;

R$^5$ is, independently, in each instance, H, halo, C$_{1-6}$alk, C$_{1-4}$haloalk, or C$_{1-6}$alk substituted by 1, 2 or 3 substituents selected from halo, cyano, OH, OC$_{1-4}$alk, C$_{1-3}$haloalk, OC$_{1-4}$alk, NH$_2$, NHC$_{1-4}$alk and N(C$_{1-4}$alk)C$_{1-4}$alk; or both R$^5$ groups together form a C$_{3-6}$spiroalk substituted by 0, 1, 2 or 3 substituents selected from halo, cyano, OH, OC$_{1-4}$alk, C$_{1-4}$alk, C$_{1-3}$haloalk, OC$_{1-4}$alk, NH$_2$, NHC$_{1-4}$alk and N(C$_{1-4}$alk)C$_{1-4}$alk;

R$^6$ is H, halo, NHR$^9$ or OH, cyano, OC$_{1-4}$alk, C$_{1-4}$alk, C$_{1-3}$haloalk, OC$_{1-4}$alk, —C(=O)OR$^a$, —C(=O)N(R$^a$)R$^a$ or —N(R$^a$)C(=O)R$^b$;

R$^7$ is selected from H, halo, C$_{1-4}$haloalk, cyano, nitro, —C(=O)R$^a$, —C(=O)OR$^a$, —C(=O)NR$^a$R$^a$, —C(=NR$^a$)NR$^a$R$^a$, —OR$^a$, —OC(=O)R$^a$, —OC(=O)NR$^a$R$^a$, —OC(=O)N(R$^a$)S(=O)$_2$R$^a$, —OC$_{2-6}$alkNR$^a$R$^a$, —OC$_{2-6}$alkOR$^a$, —SR$^a$, —S(=O)R$^a$, —S(=O)$_2$R$^a$, —S(=O)$_2$NR$^a$R$^a$, —S(=O)$_2$N(R$^a$)C(=O)R$^a$, —S(=O)$_2$N(R$^a$)C(=O)OR$^a$, —S(=O)$_2$N(R$^a$)C(=O)NR$^a$R$^a$, —NR$^a$R$^a$, —N(R$^a$)C(=O)R$^a$, —N(R$^a$)C(=O)OR$^a$, —N(R$^a$)C(=O)NR$^a$R$^a$, —N(R$^a$)C(=NR$^a$)NR$^a$R$^a$, —N(R$^a$)S(=O)$_2$R$^a$, —N(R$^a$)S(=O)$_2$NR$^a$R$^a$, —NR$^a$C$_{2-6}$alkNR$^a$R$^a$, —NR$^a$C$_{2-6}$alkOR$^a$ and C$_{1-6}$alk, wherein the C$_{1-6}$alk is substituted by 0, 1 2 or 3 substituents selected from halo, C$_{1-4}$haloalk, cyano, nitro, —C(=O)R$^a$, —C(=O)OR$^a$, —C(=O)NR$^a$R$^a$, —C(=NR$^a$)NR$^a$R$^a$, —OR$^a$, —OC(=O)R$^a$, —OC(=O)NR$^a$R$^a$, —OC(=O)N(R$^a$)S(=O)$_2$R$^a$, —OC$_{2-6}$alkNR$^a$R$^a$, —OC$_{2-6}$alkOR$^a$, —SR$^a$, —S(=O)R$^a$, —S(=O)$_2$R$^a$, —S(=O)$_2$NR$^a$R$^a$, —S(=O)$_2$N(R$^a$)C(=O)R$^a$, —S(=O)$_2$N(R$^a$)C(=O)OR$^a$, —S(=O)$_2$N(R$^a$)C(=O)NR$^a$R$^a$, —NR$^a$R$^a$, —N(R$^a$)C(=O)R$^a$, —N(R$^a$)C(=O)OR$^a$, —N(R$^a$)C(=O)NR$^a$R$^a$, —N(R$^a$)C(=NR$^a$)NR$^a$R$^a$, —N(R$^a$)S(=O)$_2$R$^a$, —N(R$^a$)S(=O)$_2$NR$^a$R$^a$, —NR$^a$C$_{2-6}$alkNR$^a$R$^a$ and —NR$^a$C$_{2-6}$alkOR$^a$, and the C$_{1-6}$alk is additionally substituted by 0 or 1 saturated, partially-saturated or unsaturated 5-, 6- or 7-membered monocyclic rings containing 0, 1, 2, 3 or 4 atoms selected from N, O and S, but containing no more than one O or S, wherein the available carbon atoms of the ring are substituted by 0, 1 or 2 oxo or thioxo groups, wherein the ring is substituted by 0, 1, 2 or 3 substituents independently selected from halo, nitro, cyano, OC$_{1-4}$alk, OC$_{1-4}$haloalk, NHC$_{1-4}$alk, N(C$_{1-4}$alk)C$_{1-4}$alk and C$_{1-4}$haloalk; or R$^7$ and R$^8$ together form a —C=N— bridge wherein the carbon atom is substituted by H, halo, cyano, or a saturated, partially-saturated or unsaturated 5-, 6- or 7-membered monocyclic ring containing 0, 1, 2, 3 or 4 atoms selected from N, O and S, but containing no more than one O or S, wherein the available carbon atoms of the ring are substituted by 0, 1 or 2 oxo or thioxo groups, wherein the ring is substituted by 0, 1, 2, 3 or 4 substituents selected from halo, C$_{1-6}$alk, C$_{1-4}$haloalk, cyano, nitro, —C(=O)R$^a$, —C(=O)OR$^a$, —C(=O)NR$^a$R$^a$, —C(=NR$^a$)NR$^a$R$^a$, —OR$^a$, —OC(=O)R$^a$, —OC(=O)NR$^a$R$^a$, —OC(=O)N(R$^a$)S(=O)$_2$R$^a$, —OC$_{2-6}$alkNR$^a$R$^a$, —OC$_{2-6}$alkOR$^a$, —SR$^a$, —S(=O)R$^a$, —S(=O)$_2$R$^a$, —S(=O)$_2$NR$^a$R$^a$, —S(=O)$_2$N(R$^a$)C(=O)R$^a$, —S(=O)$_2$N(R$^a$)C(=O)OR$^a$, —S(=O)$_2$N(R$^a$)C(=O)NR$^a$R$^a$, —NR$^a$R$^a$, —N(R$^a$)C(=O)R$^a$, —N(R$^a$)C(=O)OR$^a$, —N(R$^a$)C(=O)NR$^a$R$^a$, —N(R$^a$)C(=NR$^a$)NR$^a$R$^a$, —N(R$^a$)S(=O)$_2$R$^a$, —N(R$^a$)S(=O)$_2$NR$^a$R$^a$, —NR$^a$C$_{2-6}$alkNR$^a$R$^a$ and —NR$^a$C$_{2-6}$alkOR$^a$; or R$^7$ and R$^9$ together form a —N=C— bridge wherein the carbon atom is substituted by H, C$_{1-6}$alk, C$_{1-4}$haloalk, cyano, nitro, OR$^a$, NR$^a$R$^a$, —C(=O)R$^a$, —C(=O)OR$^a$, —C(=O)NR$^a$R$^a$, —C(=NR$^a$)NR$^a$R$^a$, —S(=O)R$^a$, —S(=O)$_2$R$^a$ or —S(=O)$_2$NR$^a$R$^a$;

R$^9$ is H, C$_{1-6}$alk or C$_{1-4}$haloalk;

R$^{11}$ is selected from H, halo, C$_{1-6}$alk, C$_{1-4}$haloalk, cyano, nitro, —C(=O)R$^a$, —C(=O)OR$^a$, —C(=O)NR$^a$R$^a$, —C(=NR$^a$)NR$^a$R$^a$, —OR$^a$, —OC(=O)R$^a$, —OC(=O)NR$^a$R$^a$, —OC(=O)N(R$^a$)S(=O)$_2$R$^a$, —OC$_{2-6}$alkNR$^a$R$^a$, —OC$_{2-6}$alkOR$^a$, —SR$^a$, —S(=O)R$^a$, —S(=O)$_2$R$^b$, (=O)$_2$NR$^a$R$^a$, (=O)$_2$N(R$^a$)C(=O)R$^a$, —S(=O)$_2$N(R$^a$)C(=O)OR$^a$, —S(=O)$_2$N(R$^a$)C(=O)NR$^a$R$^a$, —NR$^a$R$^a$, —N(R$^a$)C(=O)R$^a$, —N(R$^a$)C(=O)OR$^a$, —N(R$^a$)C(=O)NR$^a$R$^a$, —N(R$^a$)C(=NR$^a$)NR$^a$R$^a$, —N(R$^a$)S(=O)$_2$R$^a$, —N(R$^a$)S(=O)$_2$NR$^a$R$^a$, —NR$^a$C$_{2-6}$alkNR$^a$R$^a$, —NR$^a$C$_{2-6}$alkOR$^a$, —NR$^a$C$_{2-6}$alkCO$_2$R$^a$, —NR$^a$C$_{2-6}$alkSO$_2$R$^b$, —CH$_2$C(=O)R$^a$, —CH$_2$C(=O)OR$^a$, —CH$_2$C(=O)NR$^a$R$^a$, —CH$_2$C(=NR$^a$)NR$^a$R$^a$, —CH$_2$OR$^a$, —CH$_2$OC(=O)R$^a$, —CH$_2$OC(=O)NR$^a$R$^a$, —CH$_2$OC(=O)N(R$^a$)S(=O)$_2$R$^a$, —CH$_2$OC$_{2-6}$alkNR$^a$R$^a$, —CH$_2$OC$_{2-6}$alkOR$^a$, —CH$_2$SR$^a$, —CH$_2$S(=O)R$^a$, —CH$_2$S(=O)$_2$R$^b$, —CH$_2$S(=O)$_2$NR$^a$R$^a$, —CH$_2$S(=O)$_2$N(R$^a$)C(=O)R$^a$, —CH$_2$S(=O)$_2$N(R$^a$)C(=O)OR$^a$, —CH$_2$S(=O)$_2$N(R$^a$)C(=O)NR$^a$R$^a$, —CH$_2$NR$^a$R$^a$, —CH$_2$N(R$^a$)C(=O)R$^a$, —CH$_2$N(R$^a$)C(=O)OR$^a$, —CH$_2$N(R$^a$)C(=O)NR$^a$R$^a$, —CH$_2$N(R$^a$)C(=NR$^a$)NR$^a$R$^a$, —CH$_2$N(R$^a$)S(=O)$_2$R$^a$, —CH$_2$N(R$^a$)S(=O)$_2$NR$^a$R$^a$, —CH$_2$NR$^a$C$_{2-6}$alkNR$^a$R$^a$, —CH$_2$NR$^a$C$_{2-6}$alkOR$^a$, —CH$_2$NR$^a$C$_{2-6}$alkCO$_2$R$^a$, —CH$_2$NR$^a$C$_{2-6}$alkSO$_2$R$^b$, —CH$_2$R$^c$, —C(=O)R$^c$ and —C(=O)N(R$^a$)R$^c$;

R$^a$ is independently, at each instance, H or R$^b$;

R$^b$ is independently, at each instance, phenyl, benzyl or C$_{1-6}$alk, the phenyl, benzyl and C$_{1-6}$alk being substituted by 0, 1, 2 or 3 substituents selected from halo, C$_{1-4}$alk, C$_{1-3}$haloalk, —OH, —OC$_{1-4}$alk, —NH$_2$, —NHC$_{1-4}$alk and —N(C$_{1-4}$alk)C$_{1-4}$alk; and R$^c$ is a saturated or partially-saturated 4-, 5- or 6-membered ring containing 1, 2 or 3 heteroatoms selected from N, O and S, the ring being substituted by 0, 1, 2 or 3 substituents selected from halo, C$_{1-4}$alk, C$_{1-3}$haloalk, —OC$_{1-4}$alk, —NH$_2$, —NHC$_{1-4}$alk and —N(C$_{1-4}$alk)C$_{1-4}$alk.

Another aspect of the invention relates to compounds having the structure

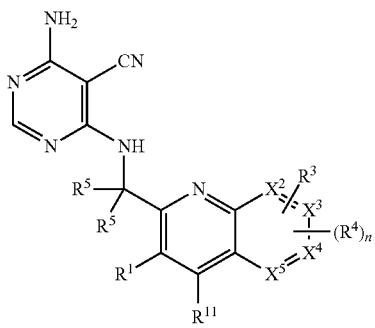

or any pharmaceutically-acceptable salt thereof, wherein:
X² is C or N;
X³ is C or N;
X⁴ is C or N;
X⁵ is C or N; wherein at least two of X², X³, X⁴ and X⁵ are C;
n is 0, 1, 2 or 3;
R¹ is a direct-bonded, $C_{1-4}$alk-linked, $OC_{1-2}$alk-linked, $C_{1-2}$alkO-linked, $N(R^a)$-linked or O-linked saturated, partially-saturated or unsaturated 5-, 6- or 7-membered monocyclic or 8-, 9-, 10- or 11-membered bicyclic ring containing 0, 1, 2, 3 or 4 atoms selected from N, O and S, but containing no more than one O or S atom, substituted by 0, 1, 2 or 3 substituents independently selected from halo, $C_{1-6}$alk, $C_{1-4}$haloalk, cyano, nitro, —C(=O)R$^a$, —C(=O)OR$^a$, —C(=O)NR$^a$R$^a$, —C(=NR$^a$)NR$^a$R$^a$, —OR$^a$, —OC(=O) R$^a$, —OC(=O)NR$^a$R$^a$, —OC(=O)N(R$^a$)S(=O)$_2$R$^a$, —OC$_{2-6}$alkNR$^a$R$^a$, —OC$_{2-6}$alkOR$^a$, —SR$^a$, —S(=O)R$^a$, —S(=O)$_2$R$^a$, —S(=O)$_2$NR$^a$R$^a$, —S(=O)$_2$N(R$^a$)C(=O) R$^a$, —S(=O)$_2$N(R$^a$)C(=O)OR$^a$, —S(=O)$_2$N(R$^a$)C(=O) NR$^a$R$^a$, —NR$^a$R$^a$, —N(R$^a$)C(=O)R$^a$, —N(R$^a$)C(=O) OR$^a$, —N(R$^a$)C(=O)NR$^a$R$^a$, —N(R$^a$)C(=NR$^a$)NR$^a$R$^a$, —N(R$^a$)S(=O)$_2$R$^a$, —N(R$^a$)S(=O)$_2$NR$^a$R$^a$, —NR$^a$C$_{2-6}$alkNR$^a$R$^a$ and —NR$^a$C$_{2-6}$alkOR$^a$, wherein the available carbon atoms of the ring are additionally substituted by 0, 1 or 2 oxo or thioxo groups, and wherein the ring is additionally substituted by 0 or 1 directly bonded, SO$_2$ linked, C(=O) linked or CH$_2$ linked group selected from phenyl, pyridyl, pyrimidyl, morpholino, piperazinyl, piperidinyl, cyclopentyl and cyclohexyl all of which are further substituted by 0, 1, 2 or 3 independent R$^b$ groups;

R² is selected from H, halo, $C_{1-6}$alk, $C_{1-4}$haloalk, cyano, nitro, OR$^a$, NR$^a$R$^a$, —C(=O)R$^a$, —C(=O)OR$^a$, —C(=O) NR$^a$R$^a$, —C(=NR$^a$)NR$^a$R$^a$, —S(=O)R$^a$, —S(=O)$_2$R$^a$, —S(=O)$_2$NR$^a$R$^a$, —S(=O)$_2$N(R$^a$)C(=O)R$^a$, —S(=O)$_2$N(R$^a$)C(=O)OR$^a$ and —S(=O)$_2$N(R$^a$)C(=O) NR$^a$R$^a$;

R³ is selected from H, halo, nitro, cyano, $C_{1-4}$alk, $OC_{1-4}$alk, $OC_{1-4}$haloalk, $NHC_{1-4}$alk, $N(C_{1-4}$alk)$C_{1-4}$alk and $C_{1-4}$haloalk;

R⁴ is, independently, in each instance, halo, nitro, cyano, $C_{1-4}$alk, $OC_{1-4}$alk, $OC_{1-4}$haloalk, $NHC_{1-4}$alk, $N(C_{1-4}$alk) $C_{1-4}$alk, $C_{1-4}$haloalk or an unsaturated 5-, 6- or 7-membered monocyclic ring containing 0, 1, 2, 3 or 4 atoms selected from N, O and S, but containing no more than one O or S, the ring being substituted by 0, 1, 2 or 3 substituents selected from halo, $C_{1-4}$alk, $C_{1-3}$haloalk, —OC$_{1-4}$alk, —NH$_2$, —NHC$_{1-4}$alk and —N(C$_{1-4}$alk)C$_{1-4}$alk;

R⁵ is, independently, in each instance, H, halo, $C_{1-6}$alk, $C_{1-4}$haloalk, or $C_{1-6}$alk substituted by 1, 2 or 3 substituents selected from halo, cyano, OH, OC$_{1-4}$alk, C$_{1-3}$haloalk, OC$_{1-4}$alk, NH$_2$, NHC$_{1-4}$alk and N(C$_{1-4}$alk)C$_{1-4}$alk; or both R⁵ groups together form a C$_{3-6}$spiroalk substituted by 0, 1, 2 or 3 substituents selected from halo, cyano, OH, OC$_{1-4}$alk, C$_{1-4}$alk, C$_{1-3}$haloalk, OC$_{1-4}$alk, NH$_2$, NHC$_{1-4}$alk and N(C$_{1-4}$alk)C$_{1-4}$alk;

R⁹ is H, C$_{1-6}$alk or C$_{1-4}$haloalk;

R¹¹ is selected from H, halo, C$_{1-6}$alk, C$_{1-4}$haloalk, cyano, nitro, —C(=O)R$^a$, —C(=O)OR$^a$, —C(=O)NR$^a$R$^a$, —C(=NR$^a$)NR$^a$R$^a$, —OR$^a$, —OC(=O)R$^a$, —OC(=O) NR$^a$R$^a$, —OC(=O)N(R$^a$)S(=O)$_2$R$^a$, —OC$_{2-6}$alkNR$^a$R$^a$, —OC$_{2-6}$alkOR$^a$, —SR$^a$, —S(=O)R$^a$, —S(=O)$_2$R$^b$, —S(=O)$_2$NR$^a$R$^a$, (=O)$_2$N(R$^a$)C(=O)R$^a$, —S(=O)$_2$N(R$^a$)C(=O)OR$^a$, —S(=O)$_2$N(R$^a$)C(=O)NR$^a$R$^a$, —NR$^a$R$^a$, —N(R$^a$)C(=O)R$^a$, —N(R$^a$)C(=O)OR$^a$, —N(R$^a$)C(=O)NR$^a$R$^a$, —N(R$^a$)C(=NR$^a$)NR$^a$R$^a$, —N(R$^a$)S(=O)$_2$R$^a$, —N(R$^a$)S(=O)$_2$NR$^a$R$^a$, —NR$^a$C$_{2-6}$alkNR$^a$R$^a$, —NR$^a$C$_{2-6}$alkOR$^a$, —NR$^a$C$_{2-6}$alkCO$_2$R$^a$, —NR$^a$C$_{2-6}$alkSO$_2$R$^b$, —CH$_2$C(=O)R$^a$, —CH$_2$C(=O)OR$^a$, —CH$_2$C(=O)NR$^a$R$^a$, —CH$_2$C(=NR$^a$)NR$^a$R$^a$, —CH$_2$OR$^a$, —CH$_2$OC(=O)R$^a$, —CH$_2$OC(=O)NR$^a$R$^a$, —CH$_2$OC(=O)N(R$^a$)S(=O)$_2$R$^a$, —CH$_2$OC$_{2-6}$alkNR$^a$R$^a$, —CH$_2$OC$_{2-6}$alkOR$^a$, —CH$_2$SR$^a$, —CH$_2$S(=O)R$^a$, —CH$_2$S(=O)$_2$R$^b$, —CH$_2$S(=O)$_2$NR$^a$R$^a$, —CH$_2$S(=O)$_2$N(R$^a$)C(=O)R$^a$, —CH$_2$S(=O)$_2$N(R$^a$)C(=O)OR$^a$, —CH$_2$S(=O)$_2$N(R$^a$)C(=O)NR$^a$R$^a$, —CH$_2$NR$^a$R$^a$, —CH$_2$N(R$^a$)C(=O)R$^a$, —CH$_2$N(R$^a$)C(=O)OR$^a$, —CH$_2$N(R$^a$)C(=O)NR$^a$R$^a$, —CH$_2$N(R$^a$)C(=NR$^a$)NR$^a$R$^a$, —CH$_2$N(R$^a$)S(=O)$_2$R$^a$, —CH$_2$N(R$^a$)S(=O)$_2$NR$^a$R$^a$, —CH$_2$NR$^a$C$_{2-6}$alkNR$^a$R$^a$, —CH$_2$NR$^a$C$_{2-6}$alkOR$^a$, —CH$_2$NR$^a$C$_{2-6}$alkCO$_2$R$^a$, —CH$_2$NR$^a$C$_{2-6}$alkSO$_2$R$^b$, —CH$_2$R$^c$, —C(=O)R$^c$ and —C(=O)N(R$^a$)R$^c$;

R$^a$ is independently, at each instance, H or R$^b$;

R$^b$ is independently, at each instance, phenyl, benzyl or C$_{1-6}$alk, the phenyl, benzyl and C$_{1-6}$alk being substituted by 0, 1, 2 or 3 substituents selected from halo, C$_{1-4}$alk, C$_{1-3}$haloalk, —OH, —OC$_{1-4}$alk, —NH$_2$, —NHC$_{1-4}$alk and —N(C$_{1-4}$alk)C$_{1-4}$alk; and R$^c$ is a saturated or partially-saturated 4-, 5- or 6-membered ring containing 1, 2 or 3 heteroatoms selected from N, O and S, the ring being substituted by 0, 1, 2 or 3 substituents selected from halo, C$_{1-4}$alk, C$_{1-3}$haloalk, —OC$_{1-4}$alk, —NH$_2$, —NHC$_{1-4}$alk and —N(C$_{1-4}$alk)C$_{1-4}$alk.

Another aspect of the invention relates to compounds having the structure

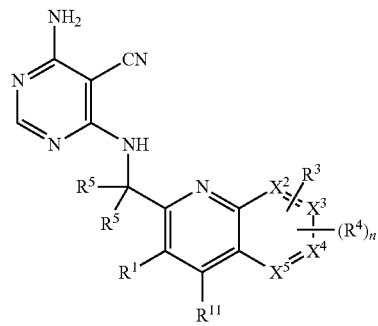

or any pharmaceutically-acceptable salt thereof, wherein:
X² is C or N;
X³ is C or N;
X⁴ is C or N;
X⁵ is C or N; wherein at least two of X², X³, X⁴ and X⁵ are C;
n is 0, 1, 2 or 3;
R¹ is a direct-bonded, $C_{1-4}$alk-linked, $OC_{1-2}$alk-linked, $C_{1-2}$alkO-linked, $N(R^a)$-linked or O-linked saturated, partially-saturated or unsaturated 5-, 6- or 7-membered monocyclic or 8-, 9-, 10- or 11-membered bicyclic ring containing 0, 1, 2, 3 or 4 atoms selected from N, O and S, but containing no more than one O or S atom, substituted by 0, 1, 2 or 3 substituents independently selected from halo, $C_{1-6}$alk, $C_{1-4}$haloalk, cyano, nitro, —C(=O)$R^a$, —C(=O)O$R^a$, —C(=O)N$R^aR^a$, —C(=N$R^a$)N$R^aR^a$, —O$R^a$, —OC(=O) $R^a$, —OC(=O)N$R^aR^a$, —OC(=O)N($R^a$)S(=O)$_2R^a$, —O$C_{2-6}$alkN$R^aR^a$, —O$C_{2-6}$alkO$R^a$, —S$R^a$, —S(=O)$R^a$, —S(=O)$_2R^a$, —S(=O)$_2$N$R^aR^a$, —S(=O)$_2$N($R^a$)C(=O) $R^a$, —S(=O)$_2$N($R^a$)C(=O)O$R^a$, —S(=O)$_2$N($R^a$)C(=O) N$R^aR^a$, —N$R^aR^a$, —N($R^a$)C(=O)$R^a$, —N($R^a$)C(=O) O$R^a$, —N($R^a$)C(=O)N$R^aR^a$, —N($R^a$)C(=N$R^a$)N$R^aR^a$, —N($R^a$)S(=O)$_2R^a$, —N($R^a$)S(=O)$_2$N$R^aR^a$, —N$R^aC_{2-6}$alkN$R^aR^a$ and —N$R^aC_{2-6}$alkO$R^a$, wherein the available carbon atoms of the ring are additionally substituted by 0, 1 or 2 oxo or thioxo groups, and wherein the ring is additionally substituted by 0 or 1 directly bonded, SO$_2$ linked, C(=O) linked or CH$_2$ linked group selected from phenyl, pyridyl, pyrimidyl, morpholino, piperazinyl, piperidinyl, cyclopentyl and cyclohexyl all of which are further substituted by 0, 1, 2 or 3 independent $R^b$ groups;

$R^3$ is selected from H, halo, nitro, cyano, $C_{1-4}$alk, O$C_{1-4}$alk, O$C_{1-4}$haloalk, NH$C_{1-4}$alk, N($C_{1-4}$alk)$C_{1-4}$alk or $C_{1-4}$haloalk;

$R^4$ is, independently, in each instance, halo, nitro, cyano, O$C_{1-4}$alk, O$C_{1-4}$haloalk, NH$C_{1-4}$alk, N($C_{1-4}$alk)$C_{1-4}$alk, $C_{1-4}$haloalk or an unsaturated 5-, 6- or 7-membered monocyclic ring containing 0, 1, 2, 3 or 4 atoms selected from N, O and S, but containing no more than one O or S, substituted by 0, 1, 2 or 3 substituents selected from halo, $C_{1-4}$alk, $C_{1-3}$haloalk, —O$C_{1-4}$alk, —NH$_2$, —NH$C_{1-4}$alk and —N($C_{1-4}$alk)$C_{1-4}$alk;

$R^5$ is, independently, in each instance, H, halo, $C_{1-6}$alk, $C_{1-4}$haloalk, or $C_{1-6}$alk substituted by 1, 2 or 3 substituents selected from halo, cyano, OH, O$C_{1-4}$alk, $C_{1-3}$haloalk, O$C_{1-4}$alk, NH$_2$, NH$C_{1-4}$alk and N($C_{1-4}$alk)$C_{1-4}$alk; or both $R^5$ groups together form a $C_{3-6}$spiroalk substituted by 0, 1, 2 or 3 substituents selected from halo, cyano, OH, O$C_{1-4}$alk, $C_{1-4}$alk, $C_{1-3}$haloalk, O$C_{1-4}$alk, NH$_2$, NH$C_{1-4}$alk and N($C_{1-4}$alk)$C_{1-4}$alk;

$R^9$ is H, $C_{1-6}$alk or $C_{1-4}$haloalk;

$R^{11}$ is selected from —C(=O)$R^a$, —C(=O)O$R^a$, —C(=O)N$R^aR^a$, —C(=N$R^a$)N$R^aR^a$, —O$R^a$, —OC(=O) $R^a$, —OC(=O)N$R^aR^a$, —OC(=O)N($R^a$)S(=O)$_2R^a$, —O$C_{2-6}$alkN$R^aR^a$, —O$C_{2-6}$alkO$R^a$, —S$R^a$, —S(=O)$R^a$, —S(=O)$_2R^b$, —S(=O)$_2$N$R^aR^a$, —S(=O)$_2$N($R^a$)C(=O) $R^a$, —S(=O)$_2$N($R^a$)C(=O)O$R^a$, —S(=O)$_2$N($R^a$)C(=O) N$R^aR^a$, —N$R^aR^a$, —N($R^a$)C(=O)$R^a$, —N($R^a$)C(=O) O$R^a$, —N($R^a$)C(=O)N$R^aR^a$, —N($R^a$)C(=N$R^a$)N$R^aR^a$, —N($R^a$)S(=O)$_2R^a$, —N($R^a$)S(=O)$_2$N$R^aR^a$, —N$R^aC_{2-6}$alkN$R^aR^a$, —N$R^aC_{2-6}$alkO$R^a$, —N$R^aC_{2-6}$alkCO$_2R^a$, —N$R^aC_{2-6}$alkSO$_2R^b$, —CH$_2$C(=O)$R^a$, —CH$_2$C(=O) O$R^a$, —CH$_2$C(=O)N$R^aR^a$, —CH$_2$C(=N$R^a$)N$R^aR^a$, —CH$_2$O$R^a$, —CH$_2$OC(=O)$R^a$, —CH$_2$OC(=O)N$R^aR^a$, —CH$_2$OC(=O)N($R^a$)S(=O)$_2R^a$, —CH$_2$O$C_{2-6}$alkN$R^aR^a$, —CH$_2$O$C_{2-6}$alkO$R^a$, —CH$_2$S$R^a$, —CH$_2$S(=O)$R^a$, —CH$_2$S(=O)$_2R^b$, —CH$_2$S(=O)$_2$N$R^aR^a$, —CH$_2$S(=O)$_2$N ($R^a$)C(=O)$R^a$, —CH$_2$S(=O)$_2$N($R^a$)C(=O)O$R^a$, —CH$_2$S (=O)$_2$N($R^a$)C(=O)N$R^aR^a$, —CH$_2$N$R^aR^a$, —CH$_2$N($R^a$)C (=O)$R^a$, —CH$_2$N($R^a$)C(=O)O$R^a$, —CH$_2$N($R^a$)C(=O) N$R^aR^a$, —CH$_2$N($R^a$)C(=N$R^a$)N$R^aR^a$, —CH$_2$N($R^a$)S (=O)$_2R^a$, —CH$_2$N($R^a$)S(=O)$_2$N$R^aR^a$, —CH$_2$N$R^aC_{2-6}$alkN$R^aR^a$, CH$_2$N$R^aC_{2-6}$alkO$R^a$, —CH$_2$N$R^aC_{2-6}$alkCO$_2R^a$, —CH$_2$N$R^aC_{2-6}$alkSO$_2R^b$, —CH$_2R^c$, —C(=O)$R^c$ and —C(=O)N($R^a$)$R^c$;

$R^a$ is independently, at each instance, H or $R^b$;

$R^b$ is independently, at each instance, phenyl, benzyl or $C_{1-6}$alk, the phenyl, benzyl and $C_{1-6}$alk being substituted by 0, 1, 2 or 3 substituents selected from halo, $C_{1-4}$alk, $C_{1-3}$haloalk, —OH, —O$C_{1-4}$alk, —NH$_2$, —NH$C_{1-4}$alk and —N($C_{1-4}$alk)$C_{1-4}$alk; and $R^c$ is a saturated or partially-saturated 4-, 5- or 6-membered ring containing 1, 2 or 3 heteroatoms selected from N, O and S, the ring being substituted by 0, 1, 2 or 3 substituents selected from halo, $C_{1-4}$alk, $C_{1-3}$haloalk, —O$C_{1-4}$alk, —NH$_2$, —NH$C_{1-4}$alk and —N($C_{1-4}$alk)$C_{1-4}$alk.

Another aspect of the invention relates to compounds having the structure

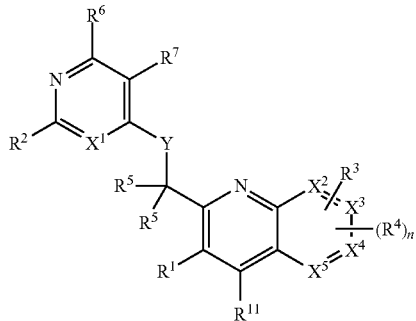

or any pharmaceutically-acceptable salt thereof, wherein:

$X^1$ is C($R^{10}$) or N;

$X^2$ is C or N;

$X^3$ is C or N;

$X^4$ is C or N;

$X^5$ is C or N; wherein at least two of $X^2$, $X^3$, $X^4$ and $X^5$ are C;

Y is N($R^8$), O or S;

n is 0, 1, 2 or 3;

$R^1$ is a direct-bonded, $C_{1-4}$alk-linked, $C_{1-2}$alkO-linked or O-linked saturated, partially-saturated or unsaturated 5-, 6- or 7-membered monocyclic or 8-, 9-, 10- or 11-membered bicyclic ring containing 0, 1, 2, 3 or 4 atoms selected from N, O and S, but containing no more than one O or S atom, substituted by 0, 1, 2 or 3 substituents independently selected from halo, $C_{1-6}$alk, $C_{1-4}$haloalk, cyano, nitro, —C(=O)$R^a$, —C(=O)O$R^a$, —C(=O)N$R^aR^a$, —C(=N$R^a$)N$R^aR^a$, —O$R^a$, —OC(=O)$R^a$, —OC(=O) N$R^aR^a$, —OC(=O)N($R^a$)S(=O)$_2R^a$, —O$C_{2-6}$alkN$R^aR^a$, —O$C_{2-6}$alkO$R^a$, —S$R^a$, —S(=O)$R^a$, —S(=O)$_2R^a$, —S(=O)$_2$N$R^aR^a$, —S(=O)$_2$N($R^a$)C(=O)$R^a$, —S(=O)$_2$N($R^a$)C(=O)O$R^a$, —S(=O)$_2$N($R^a$)C(=O) N$R^aR^a$, —N$R^aR^a$, —N($R^a$)C(=O)$R^a$, —N($R^a$)C(=O) O$R^a$, —N($R^a$)C(=O)N$R^aR^a$, —N($R^a$)C(=N$R^a$)N$R^aR^a$, —N($R^a$)S(=O)$_2R^a$, —N($R^a$)S(=O)$_2$N$R^aR^a$, —N$R^aC_{2-6}$alkN$R^aR^a$ and —N$R^aC_{2-6}$alkO$R^a$, wherein the available carbon atoms of the ring are additionally substituted by 0, 1 or 2 oxo or thioxo groups;

$R^2$ is, independently in each instance, selected from H, halo, $C_{1-6}$alk, cyano, nitro, O$R^a$, N$R^aR^a$, —C(=O)$R^a$, —C(=O)O$R^a$, —C(=O)N$R^aR^a$, —C(=N$R^a$)N$R^aR^a$, —S(=O)$R^a$, —S(=O)$_2R^a$, —S(=O)$_2$N$R^aR^a$, —S(=O)$_2$N ($R^a$)C(=O)$R^a$, —S(=O)$_2$N($R^a$)C(=O)O$R^a$, —S(=O)$_2$N ($R^a$)C(=O)N$R^aR^a$;

$R^3$ is selected from H, halo, nitro, cyano, $C_{1-4}$alk, O$C_{1-4}$alk, O$C_{1-4}$haloalk, NH$C_{1-4}$alk, N($C_{1-4}$alk)$C_{1-4}$alk or $C_{1-4}$haloalk;

R⁴ is, independently, in each instance, halo, nitro, cyano, $C_{1-4}$alk, $OC_{1-4}$alk, $OC_{1-4}$ haloalk, $NHC_{1-4}$alk, $N(C_{1-4}$alk$)C_{1-4}$alk, $C_{1-4}$haloalk or an unsaturated 5-, 6- or 7-membered monocyclic ring containing 0, 1, 2, 3 or 4 atoms selected from N, O and S, but containing no more than one O or S, substituted by 0, 1, 2 or 3 substituents selected from halo, $C_{1-4}$alk, $C_{1-3}$haloalk, —$OC_{1-4}$alk, —$NH_2$, —$NHC_{1-4}$alk, —$N(C_{1-4}$alk$)C_{1-4}$alk;

R⁵ is, independently, in each instance, H, halo, $C_{1-6}$alk, $C_{1-4}$haloalk, or $C_{1-6}$alk substituted by 1, 2 or 3 substituents selected from halo, cyano, OH, $OC_{1-4}$alk, $C_{1-3}$haloalk, $OC_{1-4}$alk, $NH_2$, $NHC_{1-4}$alk, $N(C_{1-4}$alk$)C_{1-4}$alk; or both R⁵ groups together form a $C_{3-6}$spiroalk substituted by 0, 1, 2 or 3 substituents selected from halo, cyano, OH, $OC_{1-4}$alk, $C_{1-3}$haloalk, $OC_{1-4}$alk, $NH_2$, $NHC_{1-4}$alk, $N(C_{1-4}$alk$)C_{1-4}$alk;

R⁶ is H, halo, NHR⁹ or OH;

R⁷ is selected from H, halo, $C_{1-4}$haloalk, cyano, nitro, —C(=O)Rᵃ, —C(=O)ORᵃ, —C(=O)NRᵃRᵃ, —C(=NRᵃ)NRᵃRᵃ, —ORᵃ, —OC(=O)Rᵃ, —OC(=O)NRᵃRᵃ, —OC(=O)N(Rᵃ)S(=O)₂Rᵃ, —OC₂₋₆alkNRᵃRᵃ, —OC₂₋₆alkORᵃ, —SRᵃ, —S(=O)Rᵃ, —S(=O)₂Rᵃ, —S(=O)₂NRᵃRᵃ, —S(=O)₂N(Rᵃ)C(=O)Rᵃ, —S(=O)₂N(Rᵃ)C(=O)ORᵃ, —S(=O)₂N(Rᵃ)C(=O)NRᵃRᵃ, —NRᵃRᵃ, —N(Rᵃ)C(=O)Rᵃ, —N(Rᵃ)C(=O)ORᵃ, —N(Rᵃ)C(=O)NRᵃRᵃ, —N(Rᵃ)C(=NRᵃ)NRᵃRᵃ, —N(Rᵃ)S(=O)₂Rᵃ, —N(Rᵃ)S(=O)₂NRᵃRᵃ, —NRᵃC₂₋₆alkNRᵃRᵃ, —NRᵃC₂₋₆alkORᵃ and $C_{1-6}$alk, wherein the $C_{1-6}$alk is substituted by 0, 1 2 or 3 substituents selected from halo, $C_{1-4}$haloalk, cyano, nitro, —C(=O)Rᵃ, —C(=O)ORᵃ, —C(=O)NRᵃRᵃ, —C(=NRᵃ)NRᵃRᵃ, —ORᵃ, —OC(=O)Rᵃ, —OC(=O)NRᵃRᵃ, —OC(=O)N(Rᵃ)S(=O)₂Rᵃ, —OC₂₋₆alkNRᵃRᵃ, —OC₂₋₆alkORᵃ, —SRᵃ, —S(=O)Rᵃ, —S(=O)₂Rᵃ, —S(=O)₂NRᵃRᵃ, —S(=O)₂N(Rᵃ)C(=O)Rᵃ, —S(=O)₂N(Rᵃ)C(=O)ORᵃ, —S(=O)₂N(Rᵃ)C(=O)NRᵃRᵃ, —NRᵃRᵃ, —N(Rᵃ)C(=O)Rᵃ, —N(Rᵃ)C(=O)ORᵃ, —N(Rᵃ)C(=O)NRᵃRᵃ, —N(Rᵃ)C(=NRᵃ)NRᵃRᵃ, —N(Rᵃ)S(=O)₂Rᵃ, —N(Rᵃ)S(=O)₂NRᵃRᵃ, —NRᵃC₂₋₆alkNRᵃRᵃ and —NRᵃC₂₋₆alkORᵃ, and the $C_{1-6}$alk is additionally substituted by 0 or 1 saturated, partially-saturated or unsaturated 5-, 6- or 7-membered monocyclic rings containing 0, 1, 2, 3 or 4 atoms selected from N, O and S, but containing no more than one O or S, wherein the available carbon atoms of the ring are substituted by 0, 1 or 2 oxo or thioxo groups, wherein the ring is substituted by 0, 1, 2 or 3 substituents independently selected from halo, nitro, cyano, $OC_{1-4}$alk, $OC_{1-4}$haloalk, $NHC_{1-4}$alk, $N(C_{1-4}$alk$)C_{1-4}$alk and $C_{1-4}$haloalk; or R⁷ and R⁸ together form a —C=N— bridge wherein the carbon atom is substituted by H, halo, cyano, or a saturated, partially-saturated or unsaturated 5-, 6- or 7-membered monocyclic ring containing 0, 1, 2, 3 or 4 atoms selected from N, O and S, but containing no more than one O or S, wherein the available carbon atoms of the ring are substituted by 0, 1 or 2 oxo or thioxo groups, wherein the ring is substituted by 0, 1, 2, 3 or 4 substituents selected from halo, $C_{1-6}$alk, cyano, nitro, —C(=O)Rᵃ, —C(=O)ORᵃ, —C(=O)NRᵃRᵃ, —C(=NRᵃ)NRᵃRᵃ, —ORᵃ, —OC(=O)Rᵃ, —OC(=O)NRᵃRᵃ, —OC(=O)N(Rᵃ)S(=O)₂Rᵃ, —OC₂₋₆ alkNRᵃRᵃ, —OC₂₋₆ alkORᵃ, —SRᵃ, —S(=O)Rᵃ, —S(=O)₂Rᵃ, —S(=O)₂NRᵃRᵃ, —S(=O)₂N(Rᵃ)C(=O)Rᵃ, —S(=O)₂N(Rᵃ)C(=O)ORᵃ, —S(=O)₂N(Rᵃ)C(=O)NRᵃRᵃ, —NRᵃRᵃ, —N(Rᵃ)C(=O)Rᵃ, —N(Rᵃ)C(=O)ORᵃ, —N(Rᵃ)C(=O)NRᵃRᵃ, —N(Rᵃ)C(=NRᵃ)NRᵃRᵃ, —N(Rᵃ)S(=O)₂Rᵃ, —N(Rᵃ)S(=O)₂NRᵃRᵃ, —NRᵃC₂₋₆alkNRᵃRᵃ and —NRᵃC₂₋₆alkORᵃ; or R⁷ and R⁹ together form a —N=C— bridge wherein the carbon atom is substituted by H, halo, $C_{1-6}$alk, cyano, nitro, ORᵃ, NRᵃRᵃ, —C(=O)Rᵃ, —C(=O)ORᵃ, —C(=O)NRᵃRᵃ, —C(=NRᵃ)NRᵃRᵃ, —S(=O)Rᵃ, —S(=O)₂Rᵃ, —S(=O)₂NRᵃRᵃ;

R⁸ is H or $C_{1-6}$alk;

R⁹ is H, $C_{1-6}$alk or $C_{1-4}$haloalk;

R¹⁰ is H halo, $C_{1-3}$alk, $C_{1-3}$haloalk or cyano;

R¹¹ is selected from halo, $C_{1-6}$alk, $C_{1-4}$haloalk, cyano, nitro, —C(=O)Rᵃ, —C(=O)ORᵃ, —C(=O)NRᵃRᵃ, —C(=NRᵃ)NRᵃRᵃ, —ORᵃ, —OC(=O)Rᵃ, —OC(=O)NRᵃRᵃ, —OC(=O)N(Rᵃ)S(=O)₂Rᵃ, —OC₂₋₆alkNRᵃRᵃ, —OC₂₋₆ alkORᵃ, —SRᵃ, —S(=O)Rᵃ, —S(=O)₂Rᵇ, —S(=O)₂NRᵃRᵃ, —S(=O)₂N(Rᵃ)C(=O)Rᵃ, —S(=O)₂N(Rᵃ)C(=O)ORᵃ, —S(=O)₂N(Rᵃ)C(=O)NRᵃRᵃ, —NRᵃRᵃ, —N(Rᵃ)C(=O)Rᵃ, —N(Rᵃ)C(=O)ORᵃ, —N(Rᵃ)C(=O)NRᵃRᵃ, —N(Rᵃ)C(=NRᵃ)NRᵃRᵃ, —N(Rᵃ)S(=O)₂Rᵃ, —N(Rᵃ)S(=O)₂NRᵃRᵃ, —NRᵃC₂₋₆alkNRᵃRᵃ and —NRᵃC₂₋₆alkORᵃ;

Rᵃ is independently, at each instance, H or Rᵇ; and

Rᵇ is independently, at each instance, phenyl, benzyl or $C_{1-6}$alk, the phenyl, benzyl and $C_{1-6}$alk being substituted by 0, 1, 2 or 3 substituents selected from halo, $C_{1-4}$alk, $C_{1-3}$haloalk, —$OC_{1-4}$alk, —$NH_2$, —$NHC_{1-4}$alk and —$N(C_{1-4}$alk$)C_{1-4}$alk.

In another embodiment, in conjunction with any of the above or below embodiments, the compound has the structure

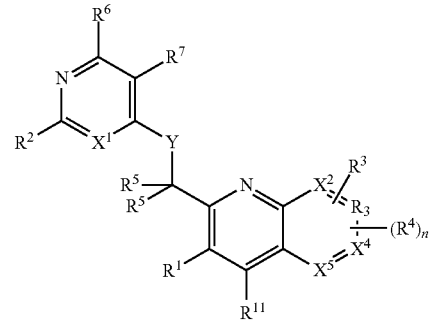

wherein R⁷ is selected from H, halo, $C_{1-4}$haloalk, cyano, nitro, —C(=O)Rᵃ, —C(=O)ORᵃ, —C(=O)NRᵃRᵃ, —C(=NRᵃ)NRᵃRᵃ, —ORᵃ, —OC(=O)Rᵃ, —OC(=O)NRᵃRᵃ, —OC(=O)N(Rᵃ)S(=O)₂Rᵃ, —OC₂₋₆alkNRᵃRᵃ, —OC₂₋₆alkORᵃ, —SRᵃ, —S(=O)Rᵃ, —S(=O)₂Rᵃ, —S(=O)₂NRᵃRᵃ, —S(=O)₂N(Rᵃ)C(=O)Rᵃ, —S(=O)₂N(Rᵃ)C(=O)ORᵃ, —S(=O)₂N(Rᵃ)C(=O)NRᵃRᵃ, —NRᵃRᵃ, —N(Rᵃ)C(=O)Rᵃ, —N(Rᵃ)C(=O)ORᵃ, —N(Rᵃ)C(=O)NRᵃRᵃ, —N(Rᵃ)C(=NRᵃ)NRᵃRᵃ, —N(Rᵃ)S(=O)₂Rᵃ, —N(Rᵃ)S(=O)₂NRᵃRᵃ, —NRᵃC₂₋₆alkNRᵃRᵃ, —NRᵃC₂₋₆alkORᵃ and $C_{1-6}$alk, wherein the $C_{1-6}$alk is substituted by 0, 1 2 or 3 substituents selected from halo, $C_{1-4}$haloalk, cyano, nitro, —C(=O)Rᵃ, —C(=O)ORᵃ, —C(=O)NRᵃRᵃ, —C(=NRᵃ)NRᵃRᵃ, —ORᵃ, —OC(=O)Rᵃ, —OC(=O)NRᵃRᵃ, —OC(=O)N(Rᵃ)S(=O)₂Rᵃ, —OC₂₋₆alkNRᵃRᵃ, —OC₂₋₆alkORᵃ, —SRᵃ, —S(=O)Rᵃ, —S(=O)₂Rᵃ, —S(=O)₂NRᵃRᵃ, —S(=O)₂N(Rᵃ)C(=O)Rᵃ, —S(=O)₂N(Rᵃ)C(=O)ORᵃ, —S(=O)₂N(Rᵃ)C(=O)NRᵃRᵃ, —NRᵃRᵃ, —N(Rᵃ)C(=O)Rᵃ, —N(Rᵃ)C(=O)ORᵃ, —N(Rᵃ)C(=O)NRᵃRᵃ, —N(Rᵃ)C(=NRᵃ)NRᵃRᵃ, —N(Rᵃ)S(=O)₂Rᵃ, —N(Rᵃ)S(=O)₂NRᵃRᵃ, —NRᵃC₂₋₆alkNRᵃRᵃ and —NRᵃC₂₋₆alkORᵃ, and the $C_{1-6}$alk is additionally substituted by 0 or 1 saturated, partially-saturated or unsaturated 5-, 6- or 7-membered monocyclic rings containing 0, 1, 2, 3 or 4 atoms selected from N, O and S, but containing no more than one O or S, wherein the available carbon atoms of the ring are substituted by 0, 1 or 2 oxo or thioxo groups, wherein the ring is substituted by 0, 1, 2 or 3 substituents independently selected from halo, nitro, cyano, $C_{1-4}$alk, $OC_{1-4}$alk, $OC_{1-4}$haloalk, $NHC_{1-4}$alk, $N(C_{1-4}alk)C_{1-4}$alk and $C_{1-4}$haloalk.

In another embodiment, in conjunction with any of the above or below embodiments, the compound has the structure

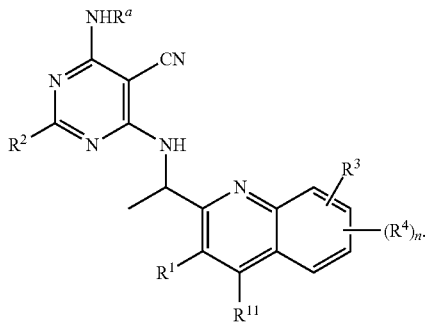

In another embodiment, in conjunction with any of the above or below embodiments, the compound has the structure

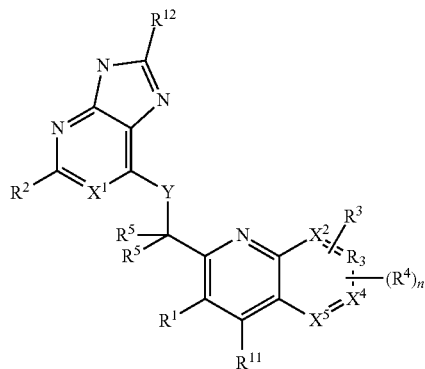

wherein $R^{12}$ is selected from H, halo, $C_{1-6}$alk, $C_{1-4}$haloalk, cyano, nitro, $OR^a$, $NR^aR^a$, —C(═O)$R^a$, —C(═O)O$R^a$, —C(═O)N$R^aR^a$, —C(═N$R^a$)N$R^aR^a$, —S(═O)$R^a$, —S(═O)$_2R^a$, —S(═O)$_2NR^aR^a$.

In another embodiment, in conjunction with any of the above or below embodiments, the compound has the structure

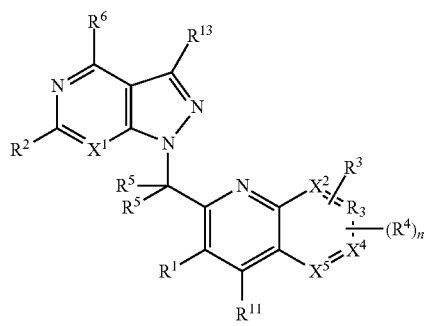

wherein $R^{13}$ is H, halo, cyano, or a saturated, partially-saturated or unsaturated 5-, 6- or 7-membered monocyclic ring containing 0, 1, 2, 3 or 4 atoms selected from N, O and S, but containing no more than one O or S, wherein the available carbon atoms of the ring are substituted by 0, 1 or 2 oxo or thioxo groups, wherein the ring is substituted by 0, 1, 2, 3 or 4 substituents selected from halo, $C_{1-6}$alk, $C_{1-4}$haloalk, cyano, nitro, —C(═O)$R^a$, —C(═O)O$R^a$, —C(═O)NR$^a$R$^a$, —C(═NR$^a$)NR$^a$R$^a$, —OR$^a$, —OC(═O)R$^a$, —OC(═O)NR$^a$R$^a$, —OC(═O)N(R$^a$)S(═O)$_2$R$^a$, —OC$_{2-6}$alkNR$^a$R$^a$, —OC$_{2-6}$alkOR$^a$, —SR$^a$, —S(═O)R$^a$, —S(═O)$_2$R$^a$, —S(═O)$_2$NR$^a$R$^a$, —S(═O)$_2$N(R$^a$)C(═O) R$^a$, —S(═O)$_2$N(R$^a$)C(═O)OR$^a$, —S(═O)$_2$N(R$^a$)C(═O) NR$^a$R$^a$, —NR$^a$R$^a$, —N(R$^a$)C(═O)R$^a$, —N(R$^a$)C(═O) OR$^a$, —N(R$^a$)C(═O)NR$^a$R$^a$, —N(R$^a$)C(═NR$^a$)NR$^a$R$^a$, —N(R$^a$)S(═O)$_2$R$^a$, —N(R$^a$)S(═O)$_2$NR$^a$R$^a$, —NR$^a$C$_{2-6}$alkNR$^a$R$^a$ and —NR$^a$C$_{2-6}$alkOR$^a$; or $R^7$ and $R^9$ together form a —N═C— bridge wherein the carbon atom is substituted by H, halo, $C_{1-6}$alk, $C_{1-4}$haloalk, cyano, nitro, OR$^a$, NR$^a$R$^a$, —C(═O)R$^a$, —C(═O)OR$^a$, —C(═O) NR$^a$R$^a$, —C(═NR$^a$)NR$^a$R$^a$, —S(═O)R$^a$, —S(═O)$_2$R$^a$, —S(═O)$_2$NR$^a$R$^a$.

In another embodiment, in conjunction with any of the above or below embodiments, $X^1$ is N.

In another embodiment, in conjunction with any of the above or below embodiments, $X^1$ is C($R^{10}$).

In another embodiment, in conjunction with any of the above or below embodiments, $X^2$, $X^3$, $X^4$ and $X^5$ are each C.

In another embodiment, in conjunction with any of the above or below embodiments, $X^2$ is N.

In another embodiment, in conjunction with any of the above or below embodiments, $X^3$ is N.

In another embodiment, in conjunction with any of the above or below embodiments, $X^4$ is N.

In another embodiment, in conjunction with any of the above or below embodiments, $X^5$ is N.

In another embodiment, in conjunction with any of the above or below embodiments, Y is N($R^8$).

In another embodiment, in conjunction with any of the above or below embodiments, $R^1$ is a direct-bonded, $C_{1-4}$alk-linked, $OC_{1-2}$alk-linked, $C_{1-2}$alkO-linked or O-linked saturated, partially-saturated or unsaturated 5-, 6- or 7-membered monocyclic or 8-, 9-, 10- or 11-membered bicyclic ring containing 0, 1, 2, 3 or 4 atoms selected from N, O and S, but containing no more than one O or S atom, substituted by 0, 1, 2 or 3 substituents independently selected from halo, $C_{1-6}$alk, $C_{1-4}$haloalk, cyano, nitro, —C(═O)R$^a$, —C(═O)OR$^a$, —C(═O)NR$^a$R$^a$, —C(═NR$^a$)NR$^a$R$^a$, —OR$^a$, —OC(═O)R$^a$, —OC(═O) NR$^a$R$^a$, —OC(═O)N(R$^a$)S(═O)$_2$R$^a$, —OC$_{2-6}$alkNR$^a$R$^a$, —OC$_{2-6}$alkOR$^a$, —SR$^a$, —S(═O)R$^a$, —S(═O)$_2$R$^a$, —S(═O)$_2$NR$^a$R$^a$, —S(═O)$_2$N(R$^a$)C(═O)R$^a$, —S(═O)$_2$N(R$^a$)C(═O)OR$^a$, —S(═O)$_2$N(R$^a$)C(═O) NR$^a$R$^a$, —NR$^a$R$^a$, —N(R$^a$)C(═O)R$^a$, —N(R$^a$)C(═O) OR$^a$, —N(R$^a$)C(═O)NR$^a$R$^a$, —N(R$^a$)C(═NR$^a$)NR$^a$R$^a$, —N(R$^a$)S(═O)$_2$R$^a$, —N(R$^a$)S(═O)$_2$NR$^a$R$^a$, —NR$^a$C$_{2-6}$alkNR$^a$R$^a$ and —NR$^a$C$_{2-6}$alkOR$^a$, wherein the available carbon atoms of the ring are additionally substituted by 0, 1 or 2 oxo or thioxo groups;

In another embodiment, in conjunction with any of the above or below embodiments, $R^1$ is a direct-bonded, carbon-linked or oxygen-linked saturated, partially-saturated or unsaturated 5-, 6- or 7-membered monocyclic or 8-, 9-, 10- or 11-membered bicyclic ring containing 0, 1, 2, 3 or 4 atoms selected from N, O and S, but containing no more than one O or S, wherein the available carbon atoms of the ring are substituted by 0, 1 or 2 oxo or thioxo groups, wherein the ring is additionally substituted by 0 or 1 $R^2$ substituents, and the ring is additionally substituted by 0, 1, 2 or 3 substituents independently selected from halo, nitro, cyano, $C_{1-4}$alk, $OC_{1-4}$alk, $OC_{1-4}$haloalk, $NHC_{1-4}$alk, $N(C_{1-4}$alk$)C_{1-4}$alk and $C_{1-4}$haloalk.

In another embodiment, in conjunction with any of the above or below embodiments, $R^1$ is a direct bonded unsaturated 6-membered monocyclic ring containing 0, 1 or 2 N atoms, substituted by 0, 1, 2 or 3 substituents independently selected from halo, nitro, cyano, $C_{1-4}$alk, $OC_{1-4}$alk, $OC_{1-4}$haloalk, $NHC_{1-4}$alk, $N(C_{1-4}$alk$)C_{1-4}$alk and $C_{1-4}$haloalk.

In another embodiment, in conjunction with any of the above or below embodiments, $R^1$ is phenyl or pyridyl, both of which are substituted by 0, 1, 2 or 3 substituents independently selected from halo, $C_{1-6}$alk, $C_{1-4}$haloalk cyano, nitro, —C(=O)$R^a$, —C(=O)O$R^a$, —C(=O)N$R^aR^a$, —C(=N$R^a$)N$R^aR^a$, —O$R^a$, —OC(=O)$R^a$, —OC(=O)N$R^aR^a$, —OC(=O)N($R^a$)S(=O)$_2R^a$, —OC$_{2-6}$alkN$R^aR^a$, —OC$_{2-6}$alkO$R^a$, —S$R^a$, —S(=O)$R^a$, —S(=O)$_2R^a$ and —S(=O)$_2$N$R^aR^a$.

In another embodiment, in conjunction with any of the above or below embodiments, $R^1$ is phenyl or substituted by 0, 1, 2 or 3 substituents independently selected from halo, $C_{1-6}$alk, $C_{1-4}$haloalk, cyano, nitro, —C(=O)$R^a$, —C(=O)O$R^a$, —C(=O)N$R^aR^a$, —C(=N$R^a$)N$R^aR^a$, —O$R^a$, —OC(=O)$R^a$, —OC(=O)N$R^aR^a$, —OC(=O)N($R^a$)S(=O)$_2R^a$, —OC$_{2-6}$alkN$R^aR^a$, —OC$_{2-6}$alkO$R^a$, —S$R^a$, —S(=O)$R^a$, —S(=O)$_2R^a$ and —S(=O)$_2$N$R^aR^a$.

In another embodiment, in conjunction with any of the above or below embodiments, $R^1$ is phenyl.

In another embodiment, in conjunction with any of the above or below embodiments, $R^2$ is H.

In another embodiment, in conjunction with any of the above or below embodiments, $R^6$ is NH$R^9$.

In another embodiment, in conjunction with any of the above or below embodiments, $R^6$ is NH$_2$.

In another embodiment, in conjunction with any of the above or below embodiments, $R^{11}$ is selected from —C(=O)$R^a$, —C(=O)O$R^a$, —C(=O)N$R^aR^a$, —C(=N$R^a$)N$R^aR^a$, —O$R^a$, —OC(=O)$R^a$, —OC(=O)N$R^aR^a$, —OC(=O)N($R^a$)S(=O)$_2R^a$, —OC$_{2-6}$alkN$R^aR^a$, —OC$_{2-6}$alkO$R^a$, —S$R^a$, —S(=O)$R^a$, —S(=O)$_2R^b$, —S(=O)$_2$N$R^aR^a$, —S(=O)$_2$N($R^a$)C(=O)$R^a$, —S(=O)$_2$N($R^a$)C(=O)O$R^a$, —S(=O)$_2$N($R^a$)C(=O)N$R^aR^a$, —N$R^aR^a$, —N($R^a$)C(=O)$R^a$, —N($R^a$)C(=O)O$R^a$, —N($R^a$)C(=O)N$R^aR^a$, —N($R^a$)C(=N$R^a$)N$R^aR^a$, —N($R^a$)S(=O)$_2R^a$, —N($R^a$)S(=O)$_2$N$R^aR^a$, —N$R^aC_{2-6}$alkN$R^aR^a$, —N$R^aC_{2-6}$alkO$R^a$, —N$R^aC_{2-6}$alkCO$_2R^a$, —N$R^aC_{2-6}$alkSO$_2R^b$, —CH$_2$C(=O)$R^a$, —CH$_2$C(=O)O$R^a$, —CH$_2$C(=O)N$R^aR^a$, —CH$_2$C(=N$R^a$)N$R^aR^a$, —CH$_2$O$R^a$, —CH$_2$OC(=O)$R^a$, —CH$_2$OC(=O)N$R^aR^a$, —CH$_2$OC(=O)N($R^a$)S(=O)$_2R^a$, —CH$_2$OC$_{2-6}$alkN$R^aR^a$, —CH$_2$OC$_{2-6}$alkO$R^a$, —CH$_2$S$R^a$, —CH$_2$S(=O)$R^a$, —CH$_2$S(=O)$_2R^b$, —CH$_2$S(=O)$_2$N$R^aR^a$, —CH$_2$S(=O)$_2$N($R^a$)C(=O)$R^a$, —CH$_2$S(=O)$_2$N($R^a$)C(=O)O$R^a$, —CH$_2$S(=O)$_2$N($R^a$)C(=O)N$R^aR^a$, —CH$_2$N$R^aR^a$, —CH$_2$N($R^a$)C(=O)$R^a$, —CH$_2$N($R^a$)C(=O)O$R^a$, —CH$_2$N($R^a$)C(=O)N$R^aR^a$, —CH$_2$N($R^a$)C(=N$R^a$)N$R^aR^a$, —CH$_2$N($R^a$)S(=O)$_2R^a$, —CH$_2$N($R^a$)S(=O)$_2$N$R^aR^a$, —CH$_2$N$R^aC_{2-6}$alkN$R^aR^a$, —CH$_2$N$R^a$C$_{2-6}$alkO$R^a$, —CH$_2$N$R^aC_{2-6}$alkCO$_2R^a$, —CH$_2$N$R^a$C$_{2-6}$alkSO$_2R^b$, —CH$_2R^c$, —C(=O)$R^c$ and —C(=O)N($R^a$)$R^c$;

In another embodiment, in conjunction with any of the above or below embodiments, $R^{11}$ is selected from —C(=O)$R^a$, —C(=O)O$R^a$, —C(=O)N$R^aR^a$, —C(=N$R^a$)N$R^aR^a$, —N($R^a$)C(=O)$R^a$, —N($R^a$)C(=O)O$R^a$, —N($R^a$)C(=O)N$R^aR^a$, —N($R^a$)C(=N$R^a$)N$R^aR^a$ and —N($R^a$)S(=O)$_2R^a$.

Another aspect of the invention relates to a method of treating PI3K-mediated conditions or disorders.

In certain embodiments, the PI3K-mediated condition or disorder is selected from rheumatoid arthritis, ankylosing spondylitis, osteoarthritis, psoriatic arthritis, psoriasis, inflammatory diseases, and autoimmune diseases. In other embodiments, the PI3K-mediated condition or disorder is selected from cardiovascular diseases, atherosclerosis, hypertension, deep venous thrombosis, stroke, myocardial infarction, unstable angina, thromboembolism, pulmonary embolism, thrombolytic diseases, acute arterial ischemia, peripheral thrombotic occlusions, and coronary artery disease. In still other embodiments, the PI3K-mediated condition or disorder is selected from cancer, colon cancer, glioblastoma, endometrial carcinoma, hepatocellular cancer, lung cancer, melanoma, renal cell carcinoma, thyroid carcinoma, cell lymphoma, lymphoproliferative disorders, small cell lung cancer, squamous cell lung carcinoma, glioma, breast cancer, prostate cancer, ovarian cancer, cervical cancer, and leukemia. In yet another embodiment, the PI3K-mediated condition or disorder is selected from type II diabetes. In still other embodiments, the PI3K-mediated condition or disorder is selected from respiratory diseases, bronchitis, asthma, and chronic obstructive pulmonary disease. In certain embodiments, the subject is a human.

Another aspect of the invention relates to the treatment of rheumatoid arthritis, ankylosing spondylitis, osteoarthritis, psoriatic arthritis, psoriasis, inflammatory diseases or autoimmune diseases comprising the step of administering a compound according to any of the above embodiments.

Another aspect of the invention relates to the treatment of rheumatoid arthritis, ankylosing spondylitis, osteoarthritis, psoriatic arthritis, psoriasis, inflammatory diseases and autoimmune diseases, inflammatory bowel disorders, inflammatory eye disorders, inflammatory or unstable bladder disorders, skin complaints with inflammatory components, chronic inflammatory conditions, autoimmune diseases, systemic lupus erythematosis (SLE), myestenia gravis, rheumatoid arthritis, acute disseminated encephalomyelitis, idiopathic thrombocytopenic purpura, multiples sclerosis, Sjoegren's syndrome and autoimmune hemolytic anemia, allergic conditions and hypersensitivity, comprising the step of administering a compound according to any of the above or below embodiments.

Another aspect of the invention relates to the treatment of cancers that are mediated, dependent on or associated with p110δ activity, comprising the step of administering a compound according to any of the above or below embodiments.

Another aspect of the invention relates to the treatment of cancers are selected from acute myeloid leukaemia, myelodysplastic syndrome, myelo-proliferative diseases, chronic myeloid leukaemia, T-cell acute lymphoblastic leukaemia, B-cell acute lymphoblastic leukaemia, non-hodgkins lymphoma, B-cell lymphoma, solid tumors and breast cancer, comprising the step of administering a compound according to any of the above or below embodiments.

Another aspect of the invention relates to a pharmaceutical composition comprising a compound according to any of the above embodiments and a pharmaceutically-acceptable diluent or carrier.

Another aspect of the invention relates to the use of a compound according to any of the above embodiments as a medicament.

Another aspect of the invention relates to the use of a compound according to any of the above embodiments in the manufacture of a medicament for the treatment of rheumatoid arthritis, ankylosing spondylitis, osteoarthritis, psoriatic arthritis, psoriasis, inflammatory diseases, and autoimmune diseases.

The compounds of this invention may have in general several asymmetric centers and are typically depicted in the form of racemic mixtures. This invention is intended to encompass racemic mixtures, partially racemic mixtures and separate enantiomers and diastereomers.

Unless otherwise specified, the following definitions apply to terms found in the specification and claims:

"$C_{\alpha-\beta}$alk" means an alk group comprising a minimum of $\alpha$ and a maximum of $\beta$ carbon atoms in a branched, cyclical or linear relationship or any combination of the three, wherein $\alpha$ and $\beta$ represent integers. The alk groups described in this section may also contain one or two double or triple bonds. Examples of $C_{1-6}$alk include, but are not limited to the following:

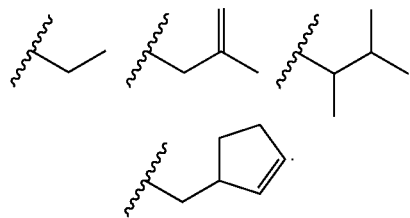

"Benzo group", alone or in combination, means the divalent radical $C_4H_4=$, one representation of which is —CH=CH—CH=CH—, that when vicinally attached to another ring forms a benzene-like ring—for example tetrahydronaphthylene, indole and the like.

The terms "oxo" and "thioxo" represent the groups =O (as in carbonyl) and =S (as in thiocarbonyl), respectively.

"Halo" or "halogen" means a halogen atoms selected from F, Cl, Br and I.

"$C_{V-W}$haloalk" means an alk group, as described above, wherein any number—at least one—of the hydrogen atoms attached to the alk chain are replaced by F, Cl, Br or I.

"Heterocycle" means a ring comprising at least one carbon atom and at least one other atom selected from N, O and S. Examples of heterocycles that may be found in the claims include, but are not limited to, the following:

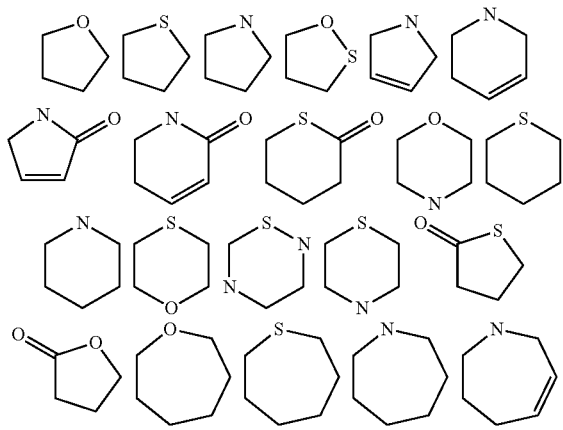

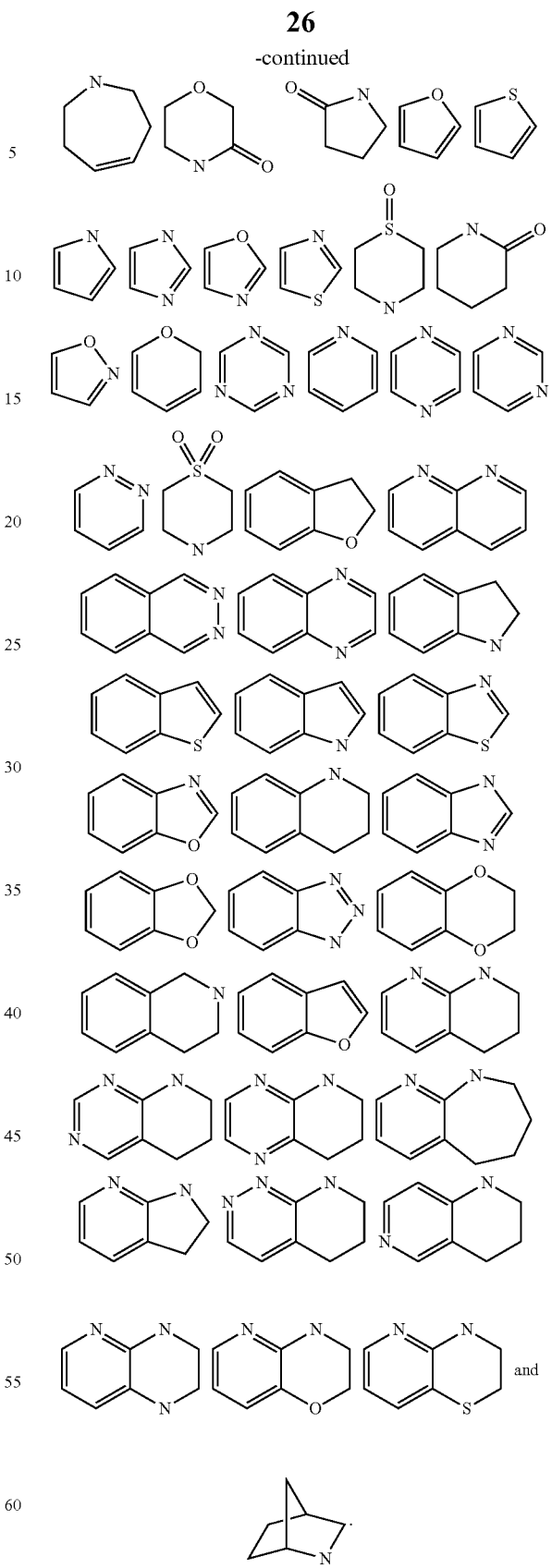

"$C_{\alpha-\beta}$spiroalk" means a geminally-attached alkyl ring comprising a minimum of $\alpha$ and a maximum of $\beta$ carbon atoms that is attached to a chain or another ring—such as:

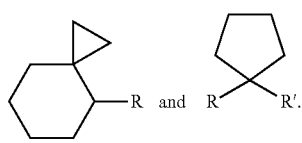

"Available nitrogen atoms" are those nitrogen atoms that are part of a heterocycle and are joined by two single bonds (e.g. piperidine), leaving an external bond available for substitution by, for example, H or CH₃.

"Pharmaceutically-acceptable salt" means a salt prepared by conventional means, and are well known by those skilled in the art. The "pharmacologically acceptable salts" include basic salts of inorganic and organic acids, including but not limited to hydrochloric acid, hydrobromic acid, sulfuric acid, phosphoric acid, methanesulfonic acid, ethanesulfonic acid, malic acid, acetic acid, oxalic acid, tartaric acid, citric acid, lactic acid, fumaric acid, succinic acid, maleic acid, salicylic acid, benzoic acid, phenylacetic acid, mandelic acid and the like. When compounds of the invention include an acidic function such as a carboxy group, then suitable pharmaceutically acceptable cation pairs for the carboxy group are well known to those skilled in the art and include alkaline, alkaline earth, ammonium, quaternary ammonium cations and the like. For additional examples of "pharmacologically acceptable salts," see infra and Berge et al., J. Pharm. Sci. 66:1 (1977).

"Saturated, partially saturated or unsaturated" includes substituents saturated with hydrogens, substituents completely unsaturated with hydrogens and substituents partially saturated with hydrogens.

"Leaving group" generally refers to groups readily displaceable by a nucleophile, such as an amine, a thiol or an alcohol nucleophile. Such leaving groups are well known in the art. Examples of such leaving groups include, but are not limited to, N-hydroxysuccinimide, N-hydroxybenzotriazole, halides, triflates, tosylates and the like. Preferred leaving groups are indicated herein where appropriate.

"Protecting group" generally refers to groups well known in the art which are used to prevent selected reactive groups, such as carboxy, amino, hydroxy, mercapto and the like, from undergoing undesired reactions, such as nucleophilic, electrophilic, oxidation, reduction and the like. Preferred protecting groups are indicated herein where appropriate. Examples of amino protecting groups include, but are not limited to, aralk, substituted aralk, cycloalkenylalk and substituted cycloalkenyl alk, allyl, substituted allyl, acyl, alkoxycarbonyl, aralkoxycarbonyl, silyl and the like. Examples of aralk include, but are not limited to, benzyl, ortho-methylbenzyl, trityl and benzhydryl, which can be optionally substituted with halogen, alk, alkoxy, hydroxy, nitro, acylamino, acyl and the like, and salts, such as phosphonium and ammonium salts. Examples of aryl groups include phenyl, naphthyl, indanyl, anthracenyl, 9-(9-phenylfluorenyl), phenanthrenyl, durenyl and the like. Examples of cycloalkenylalk or substituted cycloalkenylalk radicals, preferably have 6-10 carbon atoms, include, but are not limited to, cyclohexenyl methyl and the like. Suitable acyl, alkoxycarbonyl and aralkoxycarbonyl groups include benzyloxycarbonyl, t-butoxycarbonyl, iso-butoxycarbonyl, benzoyl, substituted benzoyl, butyryl, acetyl, trifluoroacetyl, trichloro acetyl, phthaloyl and the like. A mixture of protecting groups can be used to protect the same amino group, such as a primary amino group can be protected by both an aralk group and an aralkoxycarbonyl group. Amino protecting groups can also form a heterocyclic ring with the nitrogen to which they are attached, for example, 1,2-bis (methylene)benzene, phthalimidyl, succinimidyl, maleimidyl and the like and where these heterocyclic groups can further include adjoining aryl and cycloalk rings. In addition, the heterocyclic groups can be mono-, di- or tri-substituted, such as nitrophthalimidyl. Amino groups may also be protected against undesired reactions, such as oxidation, through the formation of an addition salt, such as hydrochloride, toluenesulfonic acid, trifluoroacetic acid and the like. Many of the amino protecting groups are also suitable for protecting carboxy, hydroxy and mercapto groups. For example, aralk groups. Alk groups are also suitable groups for protecting hydroxy and mercapto groups, such as tert-butyl.

Silyl protecting groups are silicon atoms optionally substituted by one or more alk, aryl and aralk groups. Suitable silyl protecting groups include, but are not limited to, trimethylsilyl, triethylsilyl, triisopropylsilyl, tert-butyldimethylsilyl, dimethylphenylsilyl, 1,2-bis(dimethylsilyl)benzene, 1,2-bis (dimethylsilyl)ethane and diphenylmethylsilyl. Silylation of an amino groups provide mono- or di-silylamino groups. Silylation of aminoalcohol compounds can lead to a N,N, O-trisilyl derivative. Removal of the silyl function from a silyl ether function is readily accomplished by treatment with, for example, a metal hydroxide or ammonium fluoride reagent, either as a discrete reaction step or in situ during a reaction with the alcohol group. Suitable silylating agents are, for example, trimethylsilyl chloride, tert-butyl-dimethylsilyl chloride, phenyldimethylsilyl chloride, diphenylmethyl silyl chloride or their combination products with imidazole or DMF. Methods for silylation of amines and removal of silyl protecting groups are well known to those skilled in the art. Methods of preparation of these amine derivatives from corresponding amino acids, amino acid amides or amino acid esters are also well known to those skilled in the art of organic chemistry including amino acid/amino acid ester or aminoalcohol chemistry.

Protecting groups are removed under conditions which will not affect the remaining portion of the molecule. These methods are well known in the art and include acid hydrolysis, hydrogenolysis and the like. A preferred method involves removal of a protecting group, such as removal of a benzyloxycarbonyl group by hydrogenolysis utilizing palladium on carbon in a suitable solvent system such as an alcohol, acetic acid, and the like or mixtures thereof. A t-butoxycarbonyl protecting group can be removed utilizing an inorganic or organic acid, such as HCl or trifluoroacetic acid, in a suitable solvent system, such as dioxane or methylene chloride. The resulting amino salt can readily be neutralized to yield the free amine. Carboxy protecting group, such as methyl, ethyl, benzyl, tert-butyl, 4-methoxyphenylmethyl and the like, can be removed under hydrolysis and hydrogenolysis conditions well known to those skilled in the art.

It should be noted that compounds of the invention may contain groups that may exist in tautomeric forms, such as cyclic and acyclic amidine and guanidine groups, heteroatom substituted heteroaryl groups (Y'=O, S, NR), and the like, which are illustrated in the following examples:

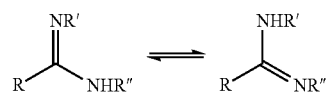

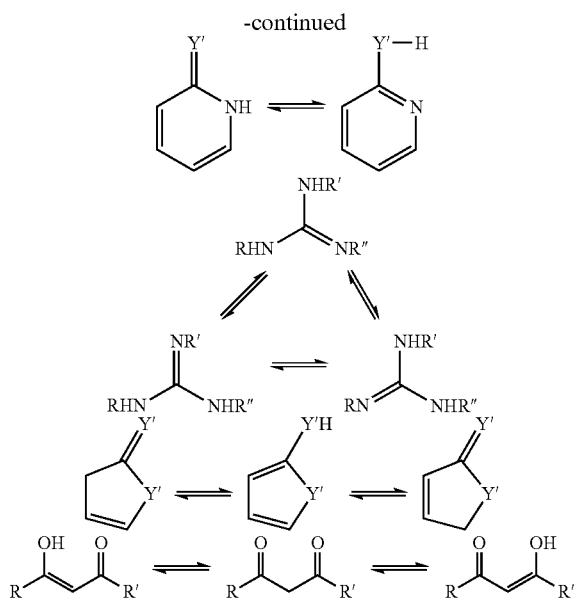

and though one form is named, described, displayed and/or claimed herein, all the tautomeric forms are intended to be inherently included in such name, description, display and/or claim.

Prodrugs of the compounds of this invention are also contemplated by this invention. A prodrug is an active or inactive compound that is modified chemically through in vivo physiological action, such as hydrolysis, metabolism and the like, into a compound of this invention following administration of the prodrug to a patient. The suitability and techniques involved in making and using prodrugs are well known by those skilled in the art. For a general discussion of prodrugs involving esters see Svensson and Tunek Drug Metabolism Reviews 165 (1988) and Bundgaard Design of Prodrugs, Elsevier (1985). Examples of a masked carboxylate anion include a variety of esters, such as alk (for example, methyl, ethyl), cycloalk (for example, cyclohexyl), aralk (for example, benzyl, p-methoxybenzyl), and alkcarbonyloxyalk (for example, pivaloyloxymethyl). Amines have been masked as arylcarbonyloxymethyl substituted derivatives which are cleaved by esterases in vivo releasing the free drug and formaldehyde (Bungaard J. Med. Chem. 2503 (1989)). Also, drugs containing an acidic NH group, such as imidazole, imide, indole and the like, have been masked with N-acyloxymethyl groups (Bundgaard Design of Prodrugs, Elsevier (1985)). Hydroxy groups have been masked as esters and ethers. EP 039,051 (Sloan and Little, Apr. 11, 1981) discloses Mannich-base hydroxamic acid prodrugs, their preparation and use.

The specification and claims contain listing of species using the language "selected from . . . and . . . " and "is . . . or . . . " (sometimes referred to as Markush groups). When this language is used in this application, unless otherwise stated it is meant to include the group as a whole, or any single members thereof, or any subgroups thereof. The use of this language is merely for shorthand purposes and is not meant in any way to limit the removal of individual elements or subgroups as needed.

The present invention also includes isotopically-labelled compounds, which are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, fluorine and chlorine, such as $^{2}H$, $^{3}H$, $^{13}C$, $^{14}C$, $^{15}N$, $^{16}O$, $^{17}O$, $^{31}P$, $^{32}P$, $^{35}S$, $^{18}F$, and $^{36}Cl$.

Compounds of the present invention that contain the aforementioned isotopes and/or other isotopes of other atoms are within the scope of this invention. Certain isotopically-labelled compounds of the present invention, for example those into which radioactive isotopes such as $^{3}H$ and $^{14}C$ are incorporated, are useful in drug and/or substrate tissue distribution assays. Tritiated, i.e., $^{3}H$, and carbon-14, i.e., $^{14}C$, isotopes are particularly preferred for their ease of preparation and detection. Further, substitution with heavier isotopes such as deuterium, i.e., $^{2}H$, can afford certain therapeutic advantages resulting from greater metabolic stability, for example increased in vivo half-life or reduced dosage requirements and, hence, may be preferred in some circumstances. Isotopically labelled compounds of this invention can generally be prepared by substituting a readily available isotopically labelled reagent for a non-isotopically labelled reagent.

EXPERIMENTAL

The following abbreviations are used:

aq.—aqueous

BINAP—2,2'-bis(diphenylphosphino)-1,1'-binaphthyl concd—concentrated

DCM—dichloromethane

DMF—N,N-dimethylformamide

Et$_2$O—diethyl ether

EtOAc—ethyl acetate

EtOH—ethyl alcohol h—hour(s)

min—minutes

MeOH—methyl alcohol

MsCl—methanesulfonyl chloride rt—room temperature satd—saturated

THF—tetrahydrofuran

General

Reagents and solvents used below can be obtained from commercial sources. $^{1}$H-NMR spectra were recorded on a Bruker 400 MHz and 500 MHz NMR spectrometer. Significant peaks are tabulated in the order: multiplicity (s, singlet; d, doublet; t, triplet; q, quartet; m, multiplet; br s, broad singlet), coupling constant(s) in hertz (Hz) and number of protons. Mass spectrometry results are reported as the ratio of mass over charge, followed by the relative abundance of each ion (in parentheses Electrospray ionization (ESI) mass spectrometry analysis was conducted on a Agilent 1100 series LC/MSD electrospray mass spectrometer. All compounds could be analyzed in the positive ESI mode using acetonitrile:water with 0.1% formic acid as the delivery solvent. Reverse phase analytical HPLC was carried out using a Agilent 1200 series on Agilent Eclipse XDB-C18 5 μm column (4.6×150 mm) as the stationary phase and eluting with acetonitrile:water with 0.1% TFA. Reverse phase Semi-Prep HPLC was carried out using a Agilent 1100 Series on a Phenomenex Gemini™ 10 μm C18 column Preparation of 4-amino-6-(3-aryl-quinolin-2-yl)methylamino)-pyrimidine-5-carbonitriles

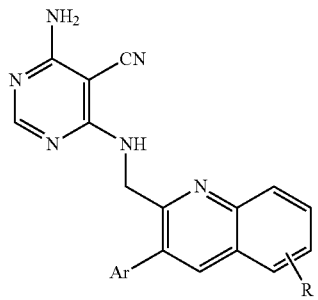

D2

General Method A:

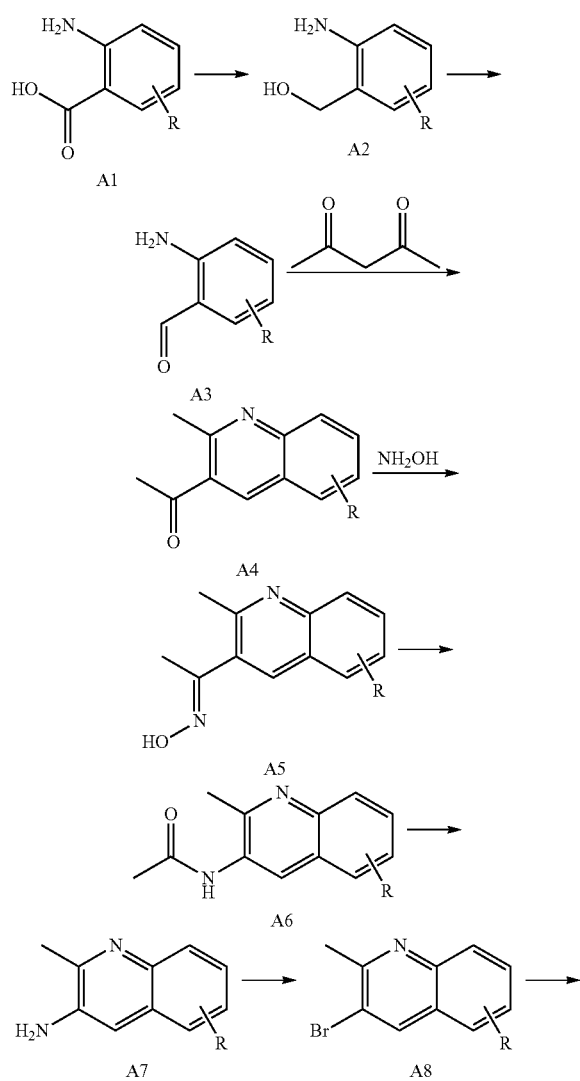

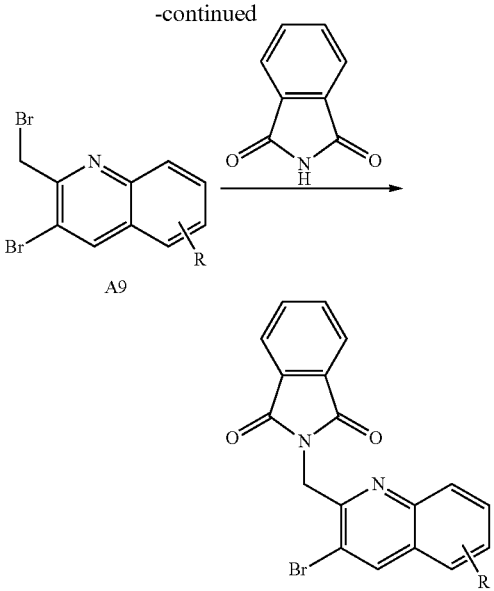

General Procedure: A solution of A1 (1 eq) in anhydrous THF was cooled to 0° C. and lithium aluminum hydride (LiAlH$_4$, 2 eq) was added as a solution in anhydrous Et$_2$O. The reaction was allowed to warm to rt and stirred for 3 h, after which time it was quenched by the subsequent addition of 1× water, 1×15% NaOH, and 3× water where X=grams of LiAlH$_4$ used. Filtration and concentration afforded compound A2. Compound A2 (1 eq) was dissolved in DCM, MnO$_2$ (8 eq) was added and the reaction was allowed to stir overnight. Filtration and concentration afforded A3. Compound A3 (1 eq) was added to acetylacetone (1.2 eq) and aq. 1M HCl (1 eq). The reaction was heated at 60° C. initially, then the temperature was raised to 90° C. When the reaction was determined to have reached completion, it was cooled to rt and the pH was adjusted to ~9 with 1N NaOH. The solid was filtered and washed with water to afford A4. Compound A4 (1 eq) was combined with hydroxylamine hydrochloride (1.1 eq) and pyridine (1.1 eq) in EtOH. The reaction was heated to reflux, and when the reaction was determined to have reached completion, the solvent was removed in vacuo. The residue was portioned between EtOAc and water and the layers were separated. The organic layer was washed with sat. CuSO$_4$, and brine, dried over MgSO$_4$, filtered, and concd. Purification by column chromatography afforded A5. Compound A5 was dissolved in acetone and cooled to 0° C. To this was added p-TsCl (1 eq) and aq. NaOH (1 eq). The reaction was heated to 70° C. After the reaction had reached completion, it was cooled to rt and the solvents were removed in vacuo. The resulting solids were dissolved in EtOAc and water. The layers were separated and the organic layer was washed with water, NaHCO$_3$, and brine. The organic layer was dried over MgSO$_4$, filtered, and concd in vacuo to afford A6. Compound A6 (1 eq) was dissolved in aq. 1N HCl (10 eq) and heated to 95° C. until the reaction was determined to have reached completion. The reaction was cooled back to 0° C. and the pH was adjusted to ~10 using 1N NaOH. The solid was filtered and washed with water to afford A7. Compound A7 was dissolved in 48% HBr at rt and then cooled to 0° C. To this solution was added sodium nitrite (1.5 eq) in water. After 10 min, the solution was transferred via pipette to a slurry of copper(I) bromide (1.1 eq) in HBr at 0° C. The mixture was allowed to warm to rt and monitored by LC/MS for reaction completion. After the reaction was complete, it was cooled back to 0° C. and adjusted to pH ~9 with 1N NaOH. The resultant solid was filtered and washed with water. After drying, the solid was slurried in DCM, filtered through a 0.45 µM filter, and concd. Purification by column chromatography (5% EA in hexanes) afforded A8. Compound A8 (1 eq) was dissolved in AcOH and N-bromo succinimide (1 eq) was added in a single portion. The reaction was heated to 80° C. for 1 h and subsequently cooled to rt and diluted with 10 mL of water and 50 mL of hexanes. The mixture was shaken vigorously until all solids had dissolved. The organic layer was washed with sat. NaHCO₃, dried over MgSO₄ and filtered. Purification by column chromatography afforded compound A9. Compound A9 was combined with phthalimide (1 eq) and potassium carbonate (1 eq) in DMF. The reaction was stirred at rt until it was determined to have reached completion by LC/MS. The reaction was diluted with EtOAc and washed with water, sat. NaHCO₃, and brine. The organic layer was dried over MgSO₄, filtered and concd to afford a crude product. The product was purified by slurring in boiling EtOAc and cooling back to 0° C. Filtration of the solid product and washing with 1:1 hexanes: EtOAc afforded A10.

General Method B

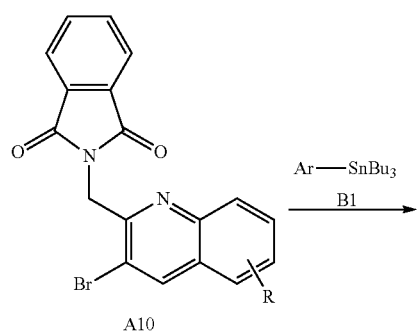

Compound A10 (1 eq), aryl-stannane B1 (1.5 eq) and tetrakistriphenylphosphine palladium(0) (0.1 eq) were combined and diluted with anhydrous 1,4-dioxane. The mixture was heated to 100° C. until judged complete by LC/MS. The reaction was cooled to rt, diluted with DCM, and filtered. Concentration and purification by column chromatography afforded B2.

General Method C:

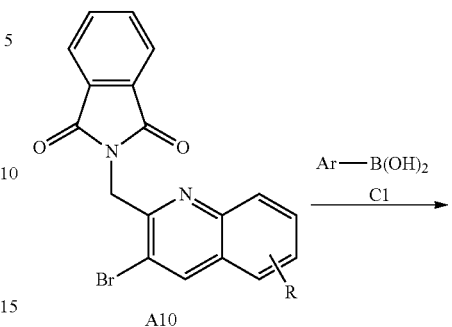

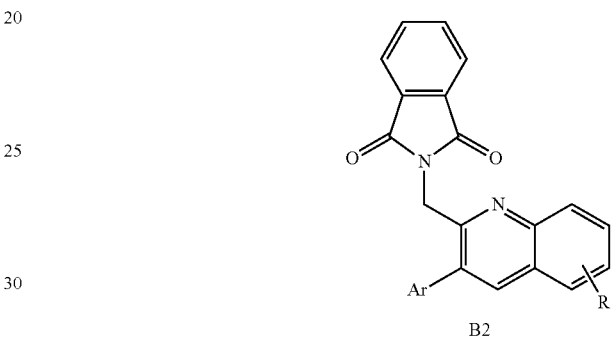

A mixture of 1,1'-bis(diphenylphosphino)ferrocene-palladium dichloride (0.1 eq), potassium carbonate (3 eq), boronic acid C1 (1.5 eq), A10 in of DMF was heated to 100° C. under a nitrogen atmosphere until the reaction was determined to be complete by LC/MS. After cooling to rt, the reaction was diluted with EtOAc and washed with NaHCO₃, water, brine. The organic layer was dried over MgSO₄, filtered and concd. Purification by column chromatography afforded compound B2.

General Method D:

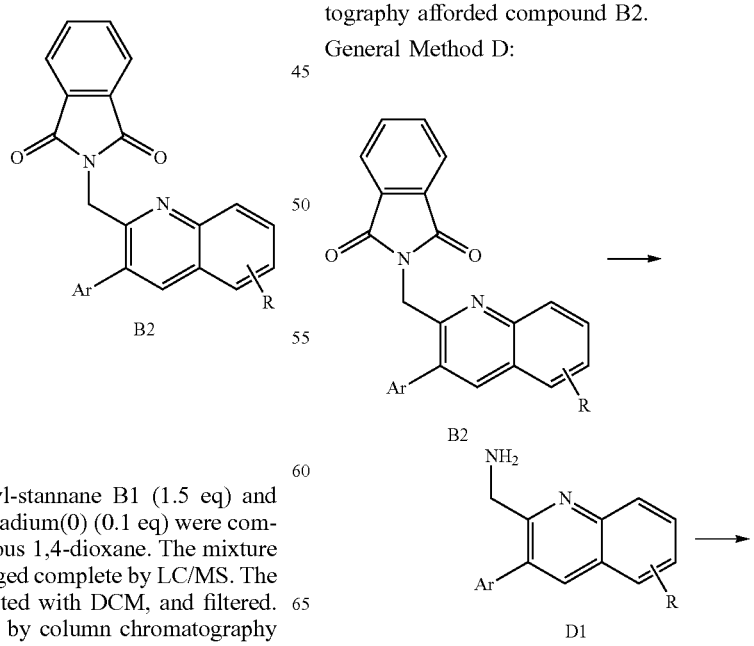

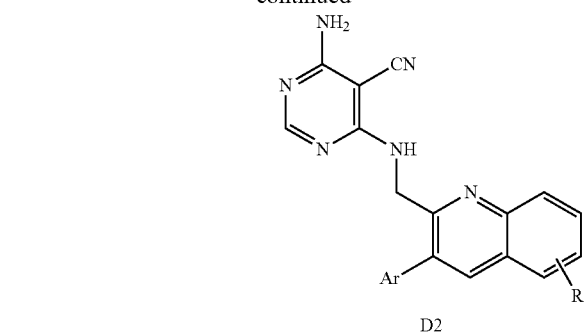

D2

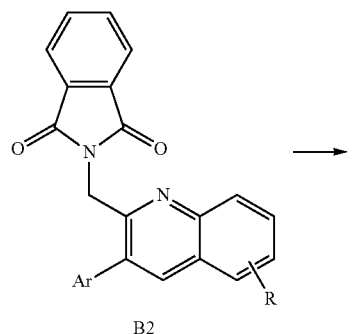

B2

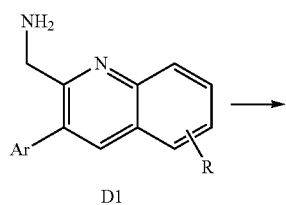

D1

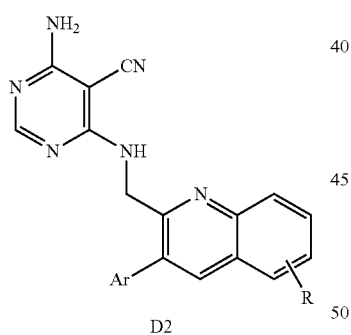

D2

Compound B2 was slurried in EtOH and treated with hydrazine hydrate (10 eq). The reaction was heated to 75° C. until determined to have reached completion by LC/MS. The reaction was then cooled to rt, diluted with EtOAc, and filtered. The filtrate was concd in vacuo, then dissolved in EtOAc/water. The layers were separated and the organic layer was washed with brine, dried over MgSO$_4$, filtered, and concd to afford D1. Compound D1 was combined with 4-amino-6-chloropyrimidine-5-carbonitrile (1.05 eq) and diisopropylethylamine (1.2 eq) in n-butanol. The mixture was heated to 115° C. for 1 h, then cooled to rt and filtered. The solid product was washed with cold EtOH/Et$_2$O and dried to afford final compounds D2. Additionally, purification by slurrying D2 in hot EtOAc may be performed.

General Method E:

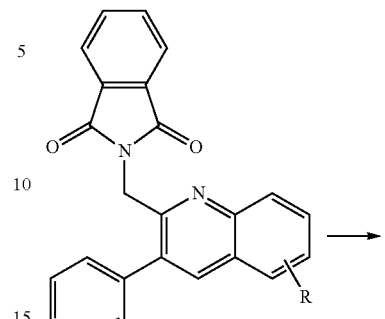

E1

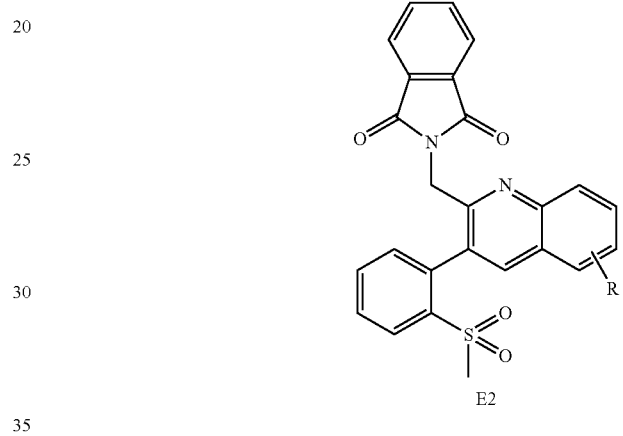

E2

Compound E1 was dissolved in DCM and treated with wet montmorillonite clay and oxone (2.5 eq). The mixture was stirred at rt until the reaction was determined complete by LC/MS and then filtered and concd to afford compound E2.

Specific Example: Method A

Synthesis of (2-amino-3-fluorophenyl)methanol

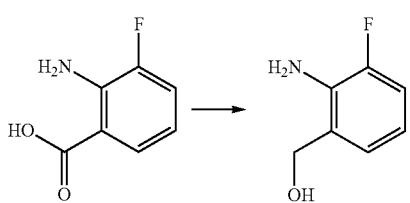 [SMILES: Nc1c(F)cccc1C(=O)O ; Nc1c(F)cccc1CO]

To a round bottomed flask containing 2-amino-3-fluorobenzoic acid (15.7 g, 101 mmol) was added 100 mL of anhydrous THF. The reaction was cooled to 0° C. and lithium aluminum hydride (7.68 g, 202 mmol) was added as a solution in 200 mL of anhydrous Et$_2$O. The reaction was allowed to warm to rt and stirred for 3 h, after which time it was quenched with 7.7 mL water, 7.7 mL of 15% NaOH, and 30 mL of water. The reaction was diluted with 300 mL of Et$_2$O and filtered. The filtrated was dried over MgSO$_4$ and filtered and concd to afford (2-amino-3-fluorophenyl)methanol. ¹H NMR (400 MHz, CDCl₃) δ 6.91 (ddd, J=10.8, 8.2, 1.2 Hz, 1H), 6.86 (br d, J=7.4 Hz, 1H), 6.64 (td, J=7.6, 5.1 Hz, 1H), 4.69 (s, 1H).

2-Amino-3-fluorobenzaldehyde

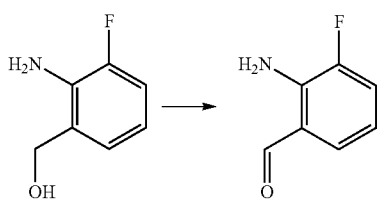 [SMILES: Nc1c(F)cccc1CO ; Nc1c(F)cccc1C=O]

(2-Amino-3-fluorophenyl)methanol (13.5 g, 96 mmol) was dissolved in 319 mL of DCM. Manganese dioxide (66.5 g, 765 mmol, 8 eq) was added and the resultant slurry was stirred at rt overnight. The reaction mixture was filtered through Celite™ and rinsed with DCM. The filtrate was concd in vacuo to afford 2-amino-3-fluorobenzaldehyde. ¹H NMR (400 MHz, CDCl₃) δ 9.91 (d, J=2.0 Hz, 1H), 7.32 (dt, J=7.8, 1.2 Hz, 1H), 7.16 (ddd, J=11.4, 8.0, 1.6 Hz, 1H), 6.69 (td, J=7.8, 4.7 Hz, 1H), 6.08 (br s, 2H).

1-(8-Fluoro-2-methylquinolin-3-yl)ethanone

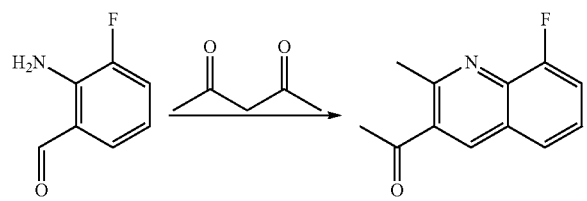

Acetylacetone (4.00 mL, 38.8 mmol) and 2-amino-3-fluorobenzaldehyde (4.5 g, 32.3 mmol) were combined at rt and stirred to dissolve. To this solution was added aq. 1N HCl (32.3 mL, 32.3 mmol) and the resultant mixture was heated to 60° C. for 20 min, then to 90° C. for 1 h. The reaction was cooled to rt and quenched with 34 mL of 1N NaOH to slightly basic (pH ~8). A voluminous solid precipitated and was filtered and washed with water. The solid was air-dried overnight to afford 1-(8-fluoro-2-methylquinolin-3-yl)ethanone. ¹H NMR (400 MHz, CDCl₃) δ 8.47 (d, J=1.6 Hz, 1H), 7.67 (m, 1H), 7.50 (m, 2H), 2.95 (s, 3H), 2.72 (s, 3H). Mass Spectrum (ESI) m/e=204.1 (M+1).

(E)-1-(8-Fluoro-2-methylquinolin-3-yl)ethanone oxime

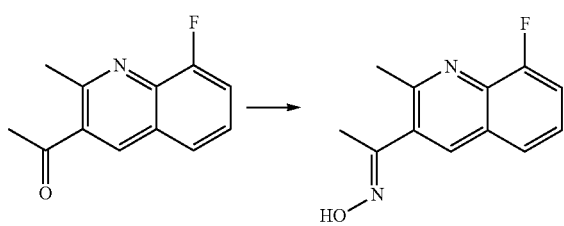 [SMILES: CC(=O)c1cc2cccc(F)c2nc1C ; C/C(=N\O)c1cc2cccc(F)c2nc1C]

To a round-bottomed flask containing 1-(8-fluoro-2-methylquinolin-3-yl)ethanone (1.5 g, 7.38 mmol) and hydroxylamine hydrochloride (0.338 mL, 8.12 mmol) was added EtOH (75 mL) and pyridine (0.662 mL, 8.12 mmol). The mixture was heated to reflux. After 3 h, the reaction was cooled to rt and the solvent was removed in vacuo. The residue was redissolved in EtOAc and washed with water, sat. CuSO₄, and brine. The organic layer was dried over MgSO₄, filtered, and concd. Purification by column chromatography afforded (E)-1-(8-fluoro-2-methylquinolin-3-yl)ethanone oxime. ¹H NMR (500 MHz, DMSO-d6) δ 8.32 (d, J=1.5 Hz, 1H), 7.80 (m, 1H), 7.55 (m, 2H), 2.70 (s, 3H), 2.22 (s, 3H). (Note: NMR only recorded up to 9.25 ppm).

N-(8-Fluoro-2-methylquinolin-3-yl)acetamide

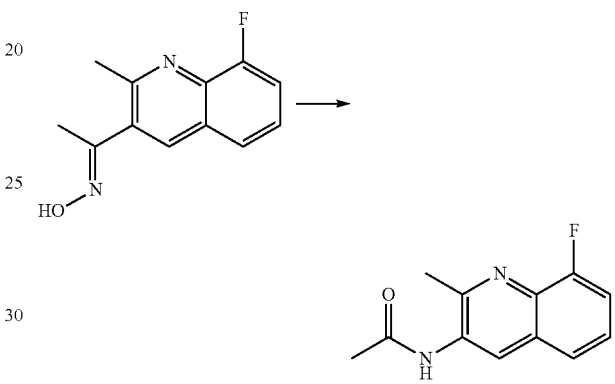

(E)-1-(8-fluoro-2-methylquinolin-3-yl)ethanone oxime (700 mg, 3.21 mmol) was dissolved in acetone (10 mL) and cooled to 0° C. To this solution was added p-TsCl (612 mg, 3.21 mmol) followed by NaOH (128 mg, 3.21 mmol) in 3.2 mL of water. The reaction was warmed to rt and then heated to 70° C. for 2 h. The solvent was removed in vacuo and the resulting solids were dissolved in EtOAc and water. The layers were separated and the organic layer was washed with water, NaHCO₃, and brine. Additional material was recovered by extraction of the aq. layer with 3×100 mL of EtOAc. The combined organic layers were dried over MgSO₄, filtered, and concd to afford N-(8-fluoro-2-methylquinolin-3-yl)-acetamide. ¹H NMR (500 MHz, DMSO-d6) δ 9.65 (br s, 1H), 8.54 (br s, 1H), 7.71 (dd, J=7.8, 1.5 Hz, 1H), 7.47 (m, 2H), 2.66 (s, 3H), 2.17 (s, 3H). Mass Spectrum (ESI) m/e=219.1 (M+1).

8-Fluoro-2-methylquinolin-3-amine

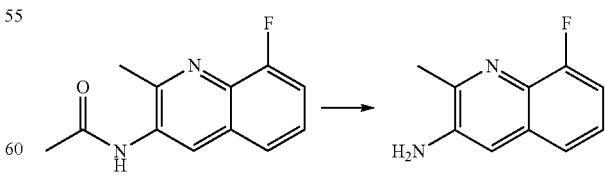

N-(8-Fluoro-2-methylquinolin-3-yl)acetamide (580 mg, 2.66 mmol) was dissolved in 1M aq. hydrogen chloride solution (26 mL, 26.6 mmol, 10 eq). The reaction was heated to 95° C. for 1.5 h and then cooled to 0° C. The acidic reaction was carefully quenched with ~30 mL of 1N NaOH to pH ~10. The precipitate was filtered, washed with water, and dried under vacuum to afford 8-fluoro-2-methylquinolin-3-amine. ¹H NMR (500 MHz, DMSO-d6) δ 7.37 dd (J=8.3, 1.2 Hz, 1H), 7.27 (td, J=7.8, 5.1 Hz, 1H), 7.17 (d, J=1.7 Hz, 1H), 7.05 (ddd, J=11.5, 7.6, 1.2 Hz, 1H), 5.60 (br s, 2H), 2.50 (s, 3H). Mass Spectrum (ESI) m/e=177.0 (M+1).

3-Bromo-8-fluoro-2-methylquinoline

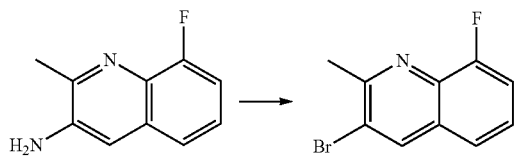

8-Fluoro-2-methylquinolin-3-amine (100 mg, 0.568 mmol) was dissolved in 1.0 mL of 48% HBr at rt and then cooled to 0° C. To this solution was added sodium nitrite (0.027 mL, 0.851 mmol) in 0.5 mL water. After 10 min, the solution was transferred via pipette to a slurry of copper(I) bromide (90 mg, 0.624 mmol) in 0.2 mL HBr at 0° C. The mixture was allowed to warm to rt and monitored by LC/MS for reaction completion. After the reaction was complete, it was cooled back to 0° C. and adjusted to pH ~9 with 1N NaOH (~10 mL). The resultant solid was filtered and washed with water. After drying, the solid was slurried in DCM, filtered through a 0.45 μm filter, and concd. Purification by column chromatography (5% EtOAc in hexanes) afforded 3-bromo-8-fluoro-2-methylquinoline. ¹H NMR (500 MHz, DMSO-d6) δ 8.80 (d, J=1.7 Hz, 1H), 7.77 (m, 1H), 7.60 (m, 2H), 7.88 (s, 3H). Mass Spectrum (ESI) m/e=239.9, 241.9 (M+1).

3-Bromo-2-(bromomethyl)-8-fluoroquinoline

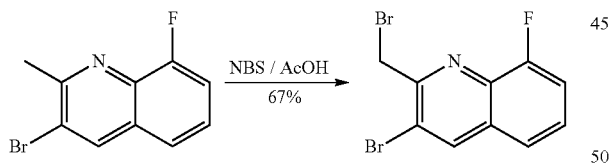

To a round-bottomed flask containing 3-bromo-8-fluoro-2-methylquinoline (90 mg, 0.375 mmol) was added AcOH (750 μL) followed by N-bromo succinimide (66.7 mg, 0.375 mmol). The reaction was heated to 80° C. for 1 h and subsequently cooled to rt and diluted with 10 mL water and 50 mL of hexanes. The mixture was shaken vigorously until all solids had dissolved. The organic layer was washed with 10 mL of sat. NaHCO₃, dried over MgSO₄ and filtered. Purification by column chromatography using 3% EA in hexanes afforded the desired product 3-bromo-2-(bromomethyl)-8-fluoroquinoline contaminated with 8% 3-bromo-8-fluoro-2-methylquinoline starting material. ¹H NMR (500 MHz, CDCl₃) δ 8.43 (d, J=1.6 Hz, 1H), 7.54 (m, 2H), 7.44 (m, 1H), 4.92 (s, 2H). Mass Spectrum (ESI) m/e=319.9 (M+1).

2-((3-Bromo-8-fluoroquinolin-2-yl)methyl)isoindoline-1,3-dione

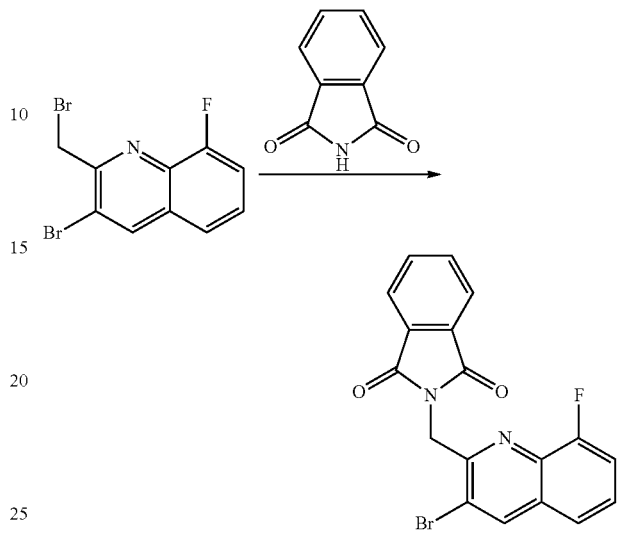

In an oven-dried flask was combined potassium carbonate (102 mg, 0.737 mmol), phthalimide (108 mg, 0.737 mmol) and 3-bromo-2-(bromomethyl)-8-fluoroquinoline (235 mg, 0.737 mmol). The flask was further dried under high vacuum for 30 min, then purged with N₂ before 3 mL of anhydrous DMF was added. The reaction was stirred at rt for 2 h, diluted with EtOAc and washed 2×10 mL water, 1×10 mL NaHCO₃, and 1×10 mL brine. The organic layer was dried over MgSO₄, filtered and concd to afford the crude product. The product was purified by slurring in 5 mL of boiling EtOAc and cooling back to 0° C. Filtration of the solid product and washing with 6 mL of 1:1 hexanes: EtOAc afforded 2-((3-bromo-8-fluoroquinolin-2-yl)methyl)isoindoline-1,3-dione. ¹H NMR (500 MHz, CDCl₃) δ 8.37 (d, J=1.5 Hz, 1H), 7.98 (m, 2H), 7.77 (m, 2H), 7.49 (br d, J=8.3 Hz, 1H), 7.42 (td, J=7.8, 4.6 Hz, 1H), 7.22 (ddd, J=10.0, 7.6, 1.2 Hz, 1H), 5.27 (s, 2H). Mass Spectrum (ESI) m/e=384.9, 387.0 (M+1).

Specific Example of Method B 2-((8-Fluoro-3-(pyridin-2-yl)quinolin-2-yl)methyl)isoindoline-1,3-dione

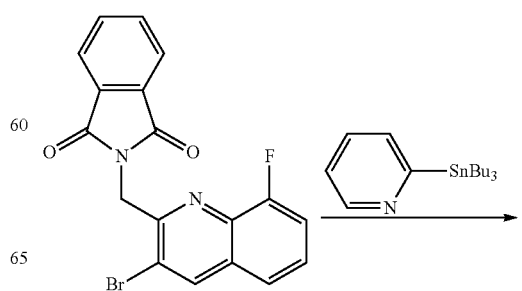

-continued

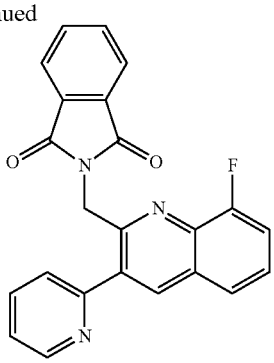

2-((3-bromo-8-fluoroquinolin-2-yl)methyl)isoindoline-1,3-dione (100 mg, 0.260 mmol), 2-(tributylstannyl)pyridine (104 μL, 0.312 mmol) and tetrakistriphenylphosphine palladium(0) (60.0 mg, 0.052 mmol) were combined and diluted with anhydrous 1,4-dioxane (3 mL). The mixture was heated to 100° C. for 24 h. The reaction was cooled to rt, diluted with DCM, and filtered. Concentration and purification by column chromatography (30-40% EtOAc in hexanes) afforded 2-((8-fluoro-3-(pyridin-2-yl)quinolin-2-yl)methyl)isoindoline-1,3-dione. $^1$H NMR (500 MHz, CDCl$_3$) δ 8.76 (m, 1H), 7.93 (m, 2H), 7.87 (td, J=7.2, 2.0 Hz, 1H), 7.75 (m, 2H), 7.65 (d, J=7.8 Hz, 1H), 7.60 (d, J=7.8 Hz, 1H), 7.41 (td, J=7.8, 4.6 Hz, 1H), 7.36 (dd, J=7.6, 4.9 Hz, 1H), 7.26 (dd, J=10.3, 7.6 Hz, 1H), 5.44 (s, 2H). Mass Spectrum (ESI) m/e=384.1 (M+1).

Specific Example of Method C 2-((8-Fluoro-3-phenylquinolin-2-yl)methyl)isoindoline-1,3-dione

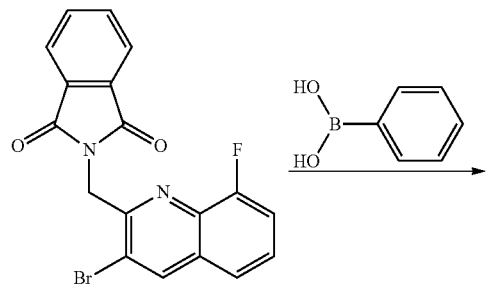

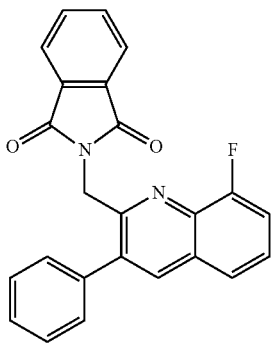

A mixture of 1,1'-bis(diphenylphosphino)ferrocene-palladium dichloride (21.20 mg, 0.026 mmol, 0.1 eq), potassium carbonate (108 mg, 0.779 mmol, 3 eq), phenylboronic acid (47.5 mg, 0.389 mmol, 1.5 eq), 2-((3-bromo-8-fluoroquinolin-2-yl)methyl)isoindoline-1,3-dione (100 mg, 0.260 mmol, 1 eq) in 3 mL of DMF was heated to 100° C. under a nitrogen atmosphere. After 3 h, the reaction was determined to be complete by LC/MS. After cooling to rt, the reaction was diluted with EtOAc and washed with NaHCO$_3$, water and brine. The organic layer was dried over MgSO$_4$, filtered and concd. Purification by column chromatography (25% EA in hexanes) afforded 2-((8-fluoro-3-phenylquinolin-2-yl)methyl)isoindoline-1,3-dione. $^1$H NMR (500 MHz, CDCl$_3$) δ 8.00 (d, J=1.5 Hz, 1H), 7.89 (m, 2H), 7.74 (m, 2H), 7.57 (d, J=8.3 Hz, 1H), 7.55-7.43 (series of m, 5H), 7.41 (td, J=8.1, 4.9 Hz, 1H), 7.23 (m, 1H), 5.12 (s, 2H). Mass Spectrum (ESI) m/e=383.0 (M+1).

Specific Example of Method D (8-Fluoro-3-(pyridin-2-yl)quinolin-2-yl)methanamine

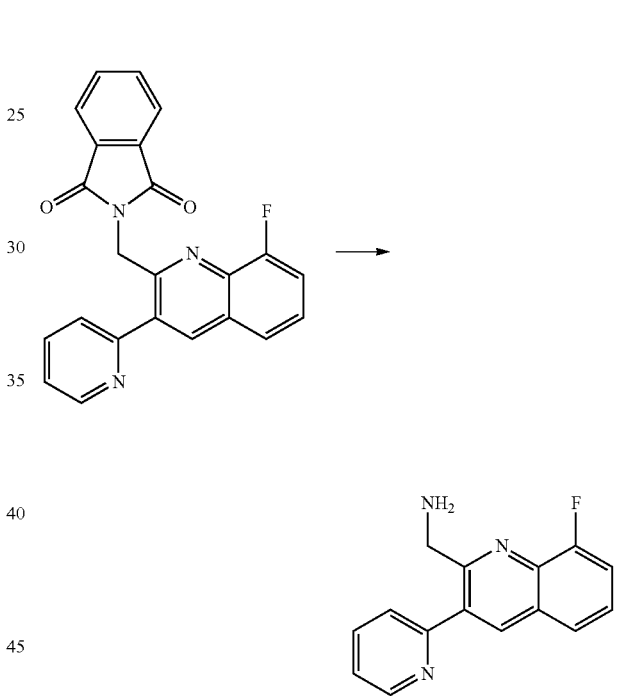

To an 83 mg portion of 2-((8-fluoro-3-(pyridin-2-yl)quinolin-2-yl)methyl)isoindoline-1,3-dione (0.216 mmol) was added 4 mL EtOH at 75° C. To this slurry was added hydrazine, monohydrate (105 μL, 2.165 mmol). After 2 h, the reaction was diluted with EtOAc, filtered, and concd in vacuo. The residue was dissolved in EtOAc/water with heating and sonication. The organic layer was separated and washed with water, brine, dried over MgSO$_4$, filtered, and concd in vacuo. The (8-fluoro-3-(pyridin-2-yl)quinolin-2-yl)methanamine was thus obtained was used without further purification. $^1$H NMR (500 MHz, CDCl$_3$) δ 8.78 (d, J=4.4 Hz, 1H), 8.21 (s, 1H), 7.86 (td, J=7.8, 1.2 Hz, 1H), 7.65 (d, J=8.1 Hz, 1H), 7.57 (d, J=8.1 Hz, 1h), 7.49 (td, J=7.8, 4.9 Hz, 1H), 7.37 (dd, J=7.6, 4.9 Hz, 1H), 4.20 (s, 2H), 2.00 (Hz, 2H), br s, 2H). Mass Spectrum (ESI) m/e=254.1 (M+1).

Example 1: Preparation of N-((5-chloro-3-(3-fluoro-phenyl)quinolin-2-yl)-methyl)-9H-purin-6-amine 2,5-Dichloroquinolin-3-ylboronic acid

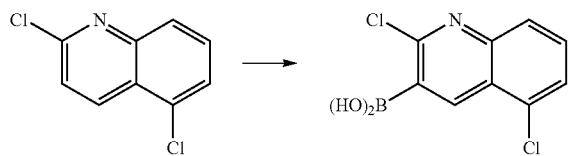 [SMILES: Clc1ccc2c(Cl)cccc2n1 ; OB(O)c1cc2c(Cl)cccc2nc1Cl]

To a cold solution of diisopropylamine (2.2 mL, 1.1 eq) in THF (33 mL) was added drop-wise a solution of n-BuLi (1.1 eq, 2.5M, 6.2 mL) in hexane at −20° C. The resulted LDA solution was kept in 0° C. for 30 min and cooled to −78° C. before addition of a solution of 2,5-dichloroquinoline (J. Am. Chem. Soc. 2005, 127, 12657) (2.8 g, 14 mmol) in THF (14 mL) drop-wise. The temperature was controlled below −72° C. by adjusting the addition rate (15 min). After another 5 min, trimethyl borate (2.4 mL, 1.5 eq) was added drop-wise. After 30 min, the reaction was quenched with water, acidified to pH 4 and partitioned between EtOAc (50 mL) and water (100 mL). The combined organics were washed with water, brine, dried over $Na_2SO_4$. Removal of solvent gave a pale yellow solid which was washed with EtOAc (10 mL×2) followed with hexane (10 mL). A pale yellow solid was obtained. $^1$H-NMR (500 MHz, $CDCl_3$) δ 9.24 (s, 1H), 7.98 (d, J=5.0 Hz, 1H), 7.74 (t, J=8.0 Hz, 1H), 7.69 (d, J=8.0 Hz, 1H) Mass Spectrum (ESI) m/e=242 (M+1).

2, 5-Dichloro-3-(3-fluorophenyl)quinoline

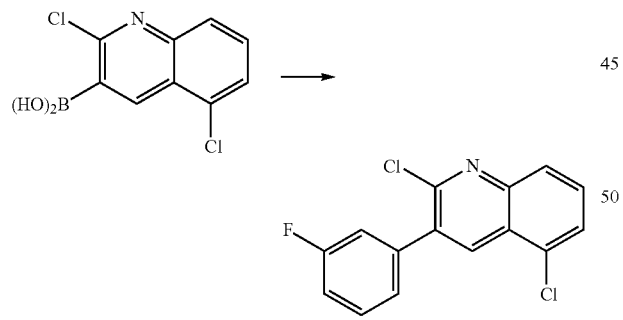

A mixture of 2,5-dichloroquinolin-3-ylboronic acid (1.6 g, 7.3 mmol), 1-fluoro-3-iodobenzene (0.89 mL, 1.1 eq), $Na_2CO_3$ (2.1 g, 3 eq), Pd(PPh$_3$)$_4$ (0.38 g, 3%), MeCN (60 mL) and water (20 mL) was heated to 85° C. under $N_2$ overnight. The mixture was cooled to rt and partitioned between EtOAc and water. The organic residue was purification by column chromatography on silica gel (DCM/hexane, 1/1) to give a pale yellow solid. $^1$H-NMR (400 Hz, $CDCl_3$) δ 8.43-8.47 (m, 2H), 7.88-7.90 (m, 1H), 7.57-7.59 (m, 3H), 7.44 (s, 1H), 7.41 (s, 1H). Mass Spectrum (ESI) m/e=292 (M+1).

5-Chloro-3-(3-fluorophenyl)quinoline-2-carbaldehyde

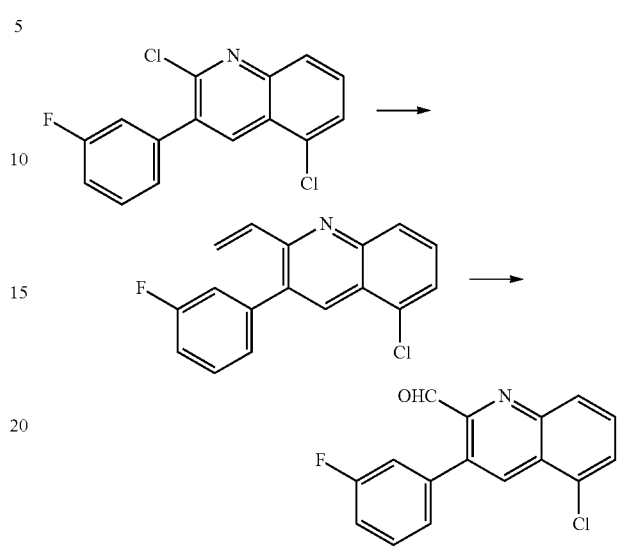

A mixture of 2, 5-dichloro-3-(3-fluorophenyl)quinoline (600 mg, 2.1 mmol), tributyl(vinyl)stannane (1.2 mL, 2.0 eq) and Pd(PPh$_3$)$_4$ (119 mg, 0.05 eq) in dioxane (10 mL) was heated to reflux under $N_2$ for 4 h before cooling to rt The reaction mixture was concd and purified by column chromatography on silica gel (EtOAc/hexane, 1/8) to give an off white solid. A mixture of this solid (230 mg, 0.81 mmol) and catalytic amount of $OsO_4$ in acetone (5 mL) and water (2 mL) was treated with N-methylmorpholineoxide (351 mg, 3.7 eq). The resulting mixture was stirred at rt for 2 h. The reaction was partitioned between EtOAc (20 mL) and water (10 mL). The organic layers were washed with $Na_2S_2O_3$, water, brine and dried over $Na_2SO_4$. A solution of the above residue in THF (10 mL) and water (5 mL) was treated with $NaIO_4$ (520 mg, 3 eq) followed with catalytic amount of $OsO_4$. After work up, the reaction mixture was purified by column chromatography to give a white solid. $^1$H-NMR (400 MHz, $CDCl_3$) δ 10.20 (s, 1H), 8.51 (s, 1H), 8.19 (d, J=8.0 Hz, 1H), 7.68-7.75 (m, 2H), 7.37-7.45 (m, 1H), 7.09-7.15 (m, 3H). Mass Spectrum (ESI) m/e=286 (M+1).

N-((5-Chloro-3-(3-fluorophenyl)quinolin-2-yl)methyl)-9H-purin-6-amine

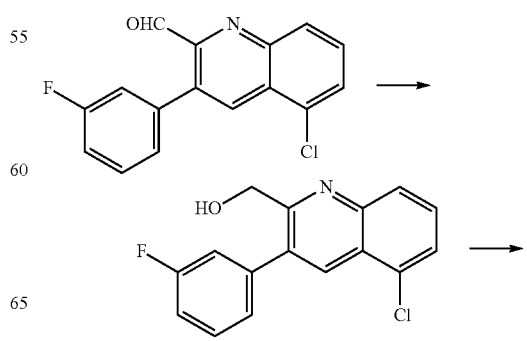

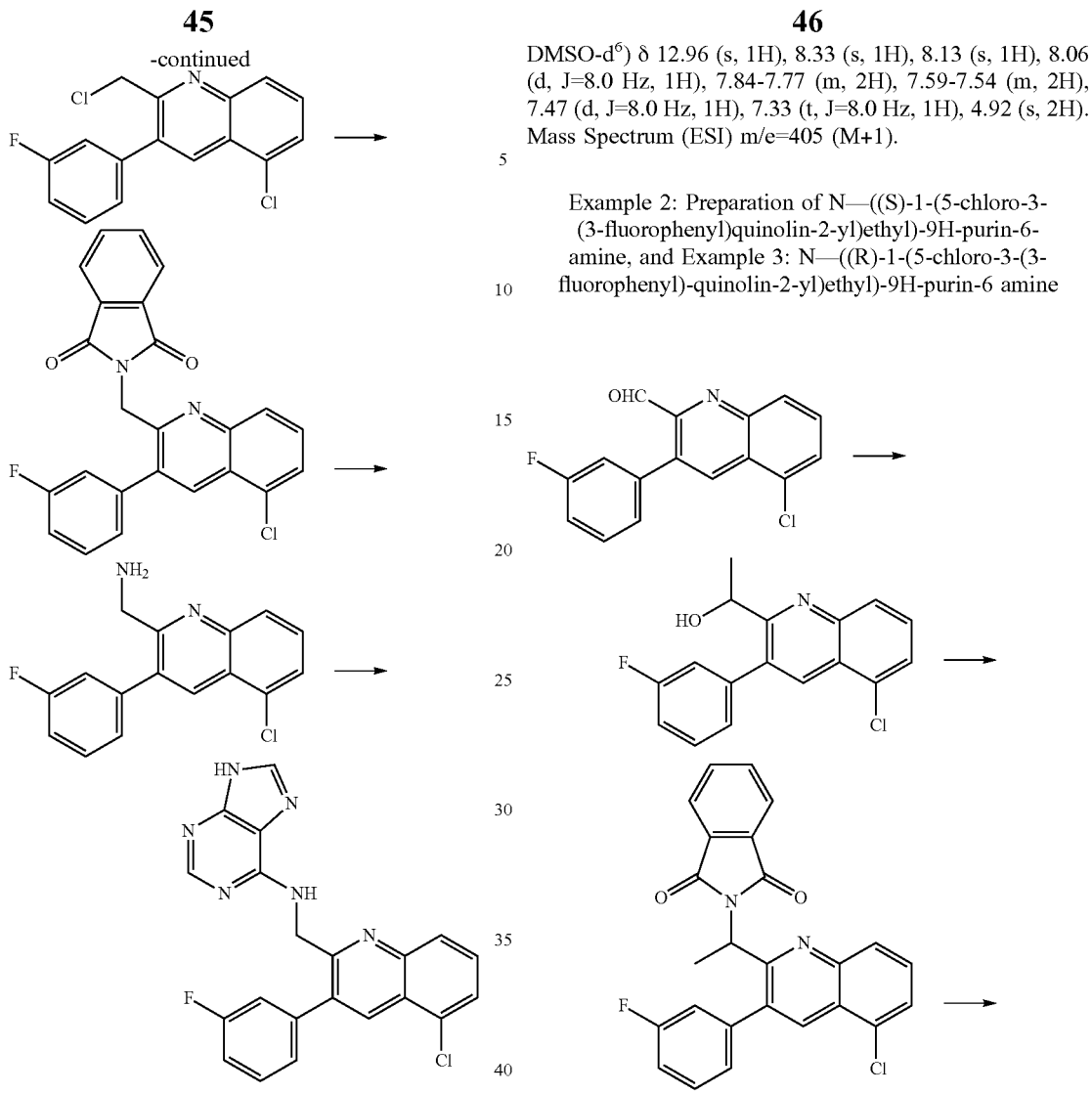

To a solution of 5-chloro-3-(3-fluorophenyl)quinoline-2-carbaldehyde (100 mg, 0.35 mmol) in THF (3 mL) at 0° C. was added NaBH₄ (20 mg, 1.5 eq) in one portion. The reaction mixture was then stirred at 0° C. for 2 h before quenching with water. The mixture was extracted with EtOAc (100 mL×2), and combined organics were washed with water, brine and dried over Na₂SO₄. Removal of solvents followed with column chromatography (EtOAc/hexane, 1/3) gave a white solid. A solution of the above material in DCM (3 mL) was treated with SOCl₂ (0.13 mL, 5 eq) at rt. Removal of solvents and treatment with aq. NaHCO₃ gave a pale yellow solid (80 mg). The above solid was treated with the potassium salt of phthalimide (65 mg, 0.35 mmol) in DMF (1 mL) at rt for 2 h. Water was added and the resulted solid was filtered and washed with water to give a white solid. A mixture of this white solid (105 mg, 0.25 mmol) and hydrazine (0.079 mL, 10 eq) in EtOH (2 mL) was heated to reflux for 2 h. After cooling to rt, the mixture was filtered, washed with EtOAc and worked up. Removal of solvent gave a yellow oil, which was treated with 6-chloropurine (47 mg, 1.2 eq), hunig's base (0.088 mL, 2 eq) in BuOH (1.5 mL) at reflux. After cool to rt, the solid was filtered, washed with EtOH and dried under vacuum, which gave N-((5-chloro-3-(3-fluorophenyl)quinolin-2-yl)methyl)-9H-purin-6-amine. ¹H-NMR (400 Hz, DMSO-d⁶) δ 12.96 (s, 1H), 8.33 (s, 1H), 8.13 (s, 1H), 8.06 (d, J=8.0 Hz, 1H), 7.84-7.77 (m, 2H), 7.59-7.54 (m, 2H), 7.47 (d, J=8.0 Hz, 1H), 7.33 (t, J=8.0 Hz, 1H), 4.92 (s, 2H). Mass Spectrum (ESI) m/e=405 (M+1).

Example 2: Preparation of N—((S)-1-(5-chloro-3-(3-fluorophenyl)quinolin-2-yl)ethyl)-9H-purin-6-amine, and Example 3: N—((R)-1-(5-chloro-3-(3-fluorophenyl)-quinolin-2-yl)ethyl)-9H-purin-6 amine

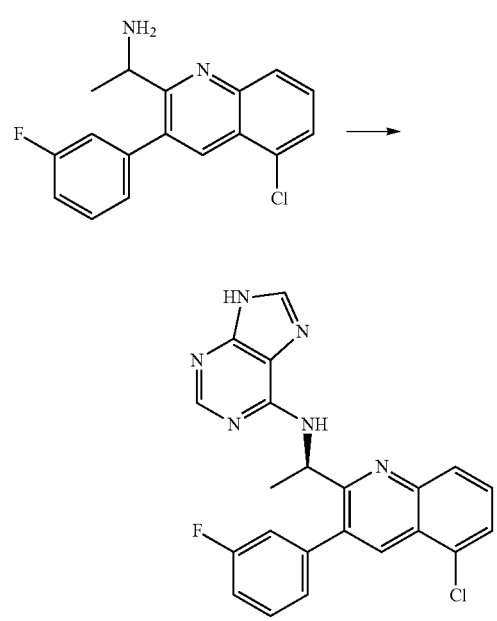

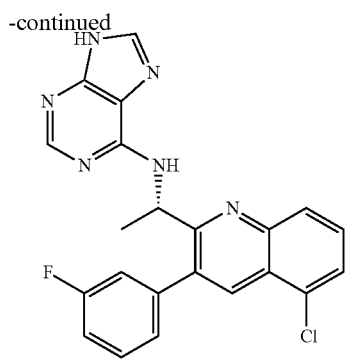

To a solution of 5-chloro-3-(3-fluorophenyl)quinoline-2-carbaldehyde (80 mg, 0.28 mmol) in THF (2 mL) at 0° C. was slowly added MeMgBr (1.2 eq, 0.11 mL). The reaction mixture was stirred at 0° C. for 3 hr. After removal of solvent, the residue was triturated with water and 70 mg crude product was obtained. To a solution of 1-(5-chloro-3-(3-fluorophenyl)quinolin-2-yl)ethanol (70 mg, 0.23 mmol) in THF (2 mL) were added PPh$_3$ (73 mg, 1.2 eq), phthalimide (41 mg, 1.2 eq), and DIAD (56 mg, 1.2 eq). The reaction mixture was stirred at rt for 2 h. LC-MS detected clear product peak. After removal of solvent, the residue was partitioned between EtOAc and water, and the combined organic layers were dried over Na$_2$SO$_4$. After removal of solvent, the crude residue was subjected to combi-flash chromatography and 81 mg desired product was obtained as 2-((5-chloro-3-(3-fluorophenyl)quinolin-2-yl)methyl)isoindoline-1,3-dione. A solution of this material (81 mg, 0.19 mmol) and hydrazine (60 mg, 10 eq) in 2 mL EtOH was heated to 90° C. for 3 h. LC-MS detected clear product peak. After the usual aq. quench, 50 mg of the desired product was obtained. A solution of (5-chloro-3-(3-fluorophenyl)-quinolin-2-yl)methanamine (50 mg, 0.17 mmol), 6-chloro-9H-purine (31 mg, 1.2 eq) and Hunig's base (0.038 mL, 1.3 eq) in EtOH (2 mL) was heated to 90° C. overnight. LC-MS detected a clear product peak. After the usual aq. quench, the crude residue was purified by combi-flash chromatography (MeOH/DCM, 0-15%) and 50 mg solid was obtained as racemates. Further separation by chiral HPLC (IA column, 10% IPA/90% Hexanes, 45 mins) gave N—((S)-1-(5-chloro-3-(3-fluorophenyl)quinolin-2-yl)ethyl)-9H-purin-6-amine, as a white solid, and N—((R)-1-(5-chloro-3-(3-fluorophenyl)-quinolin-2-yl)ethyl)-9H-purin-6 amine. For S enantiomer: $^1$H-NMR (500 Hz, CD$_3$OD) δ 8.28 (s, 1H), 8.07 (s, H), 8.01 (d, J=8.0 Hz, 2H), 7.63-7.57 (m, 2H), 7.44-7.40 (m, 2H), 7.29-7.26 (m, 2H), 7.11 (t, J=8.0 Hz, 1H), 5.77 (s, 1H). 1.41 (d, J=8.0 Hz, 3H), Mass Spectrum (ESI) m/e=419 (M+1); For R enantiomer: $^1$H-NMR (500 Hz, CD$_3$OD) δ 8.41 (s, 1H), 8.19 (s, 1H), 8.13 (d, J=8.0 Hz, 2H), 7.77-7.75 (m, 2H), 7.57-7.52 (m, 1H), 7.41-7.39 (m, 2H), 7.24 (t, J=8.0 Hz, 1H), 5.89 (s, 1H). 1.53 (d, J=8.0 Hz, 3H) Mass Spectrum (ESI) m/e=419 (M+1).

Example 4: Preparation of 1-(1-(6-fluoro-3-(5-fluoropyridin-3-yl)quinolin-2-yl)ethyl)-3-iodo-1H-pyrazolo[3,4-d]pyrimidin-4-amine 1-(6-Fluoro-3-hydroxyquinolin-2-yl)ethanone

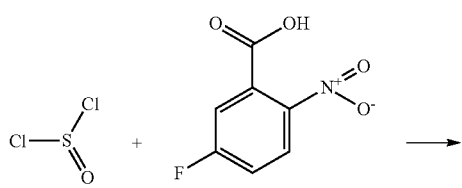

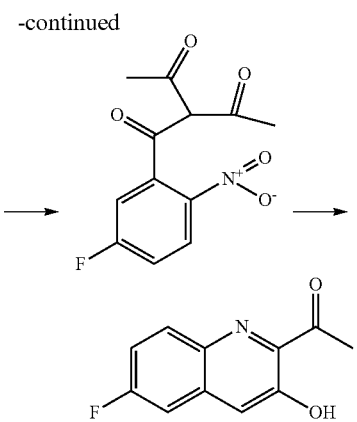

To 5-fluoro-2-nitrobenzoic acid (10.0 g, 54 mmol) was added SOCl$_2$ (20 mL, 54 mmol). The resultant mixture was heated at 80° C. for 2 h. After cooling to rt, the extra SOCl$_2$ was evaporated. The resulting acid chloride was dissolved in Et$_2$O (20 mL). To magnesium methoxide (47 mL, 10% Wt, 54 mmol), pentane-2,4-dione (6 mL, 59 mmol) in Et$_2$O (15 mL) was added drop-wise at rt. After stirring at 40° C. for 2 h, the mixture was concd and diluted with Et$_2$O, cooled at 0° C., and the acid chloride solution in Et$_2$O (20 mL) was added drop-wise into the mixture. The resultant reaction mixture was then heated to reflux for 30 min. After cooling to rt the mixture was poured into ice-water (10 mL) containing 2N HCl (2 mL), extracted with Et$_2$O, washed with water, brine, dried and concd, which gave crude intermediate 3-(5-fluoro-2-nitrobenzoyl) pentane-2,4-dione. Mass Spectrum (ESI) m/e=267.9 (M+1). A mixture of potassium hydroxide (100 mL, 20%, 54 mmol) and 3-(5-fluoro-2-nitrobenzoyl) pentane-2,4-dione (13.75 g, crude) was heated to reflux for 1 h. After cooling to rt, it was neutralized and acidified with conc. HCl to pH 5. extracted with EtOAc, washed with water, brine, dried, and concd, which gave crude 1-(6-fluoro-3-hydroxyquinolin-2-yl)ethanone. $^1$H-NMR (CDCl$_3$) δ 11.22 (s, 1H), 8.00 (dd, J=8.5, 5.0 Hz, 1H), 7.51 (s, 1H), 7.30-7.22 (m, 2H), 2.86 (s, 3H). Mass Spectrum (ESI) m/e=205.9 (M+1).

2-Acetyl-6-fluoroquinolin-3-yl trifluoromethanesulfonate

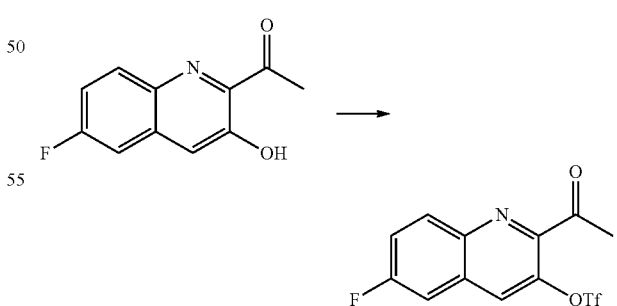

To a solution of 1-(6-fluoro-3-hydroxyquinolin-2-yl)ethanone (1.06 g, 5.2 mmol) in DCM (40 mL), pyridine (0.51 mL, 6.2 mmol) and trifluoromethanesulfonic anhydride (1.0 mL, 6.2 mmol) were added. The resultant mixture was stirred at rt for 4 h, diluted with DMC, washed with water, brine, dried and concd. Purification of the residue by flash chromatography over silica gel, gradient elution, 0-25% EtOAc in hexane, gave 2-acetyl-6-fluoroquinolin-3-yl trifluoromethanesulfonate. ¹H-NMR (DMSO-d⁶) δ 8.76 (s, 1H), 8.35 (dd, J=8.5, 5.0 Hz, 1H), 8.08 (dd, J=8.5, 5.0 Hz, 1H), 7.98-7.93 (m, 2H), 2.80 (s, 3H). Mass Spectrum (ESI) m/e=337.8 (M+1).

1-(6-Fluoro-3-(5-fluoropyridin-3-yl)quinolin-2-yl)ethanone

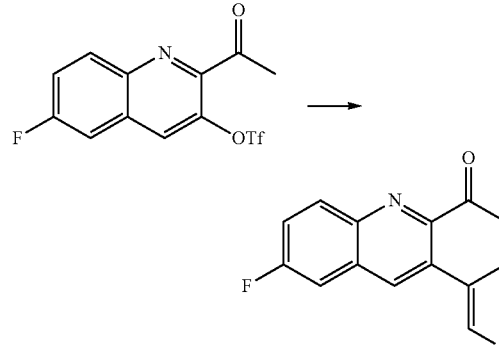

A mixture of 2-acetyl-6-fluoroquinolin-3-yl trifluoromethanesulfonate (561 mg, 1.66 mmol), 5-fluoropyridin-3-ylboronic acid (258 mg, 1.83 mmol), bis(tri-t-butylphosphine)palladium (0) (85 mg, 166 μmol), cesium fluoride (758 mg, 4.99 mmol) and copper(I) iodide (63 mg, 333 μmol) in DME (10 mL) was heated at 100° C. for 3 h, and then cooled to rt, and filtered. The filtrates were collected washed with EtOAc and concd. Purification of the residue by flash chromatography over silica gel, gradient elution, 0-60% EtOAc in hexane, gave 1-(6-fluoro-3-(5-fluoropyridin-3-yl)quinolin-2-yl)ethanone. Mass Spectrum (ESI) m/e=285.0 (M+1).

1-(6-Fluoro-3-(5-fluoropyridin-3-yl)quinolin-2-yl)ethanol

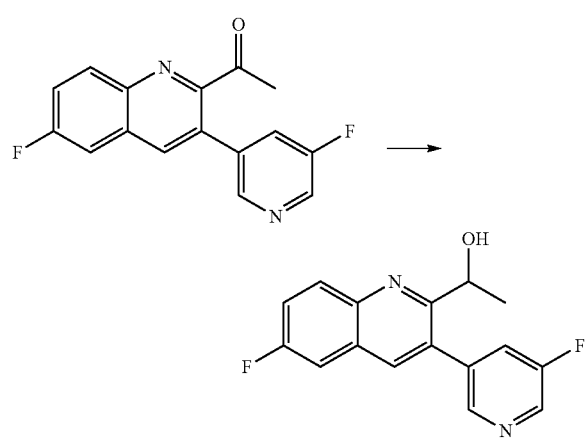

A mixture of 1-(6-fluoro-3-(5-fluoropyridin-3-yl)quinolin-2-yl)ethanone (300.0 mg, 1.055 mmol), THF (20 mL) and sodium borohydride (40 mg, 1.055 mmol) were stirred for 2 h. The reaction mixture was then filtered through a pad of Celite™ and rinsed with EtOAc, evaporation of the solvent, and purification of the residue by flash chromatography over silica gel, gradient elution, 0-100% EtOAc in hexane, gave 1-(6-fluoro-3-(5-fluoropyridin-3-yl)quinolin-2-yl)ethanol. ¹H-NMR (CDCl₃) δ 8.53 (d, J=5.0 Hz, 1H), 8.44 (br, 1H), 8.08 (dd, J=8.5, 5.0 Hz, 1H), 7.92 (s, 1H), 7.53-7.46 (m, 1H), 7.45-7.40 (m, 2H), 5.06 (q, J=5.0 Hz, 1H), 1.15 (d, J=5.0 Hz, 3H). Mass Spectrum (ESI) m/e=286.9 (M+1).

2-(1-Chloroethyl)-6-fluoro-3-(5-fluoropyridin-3-yl)quinoline

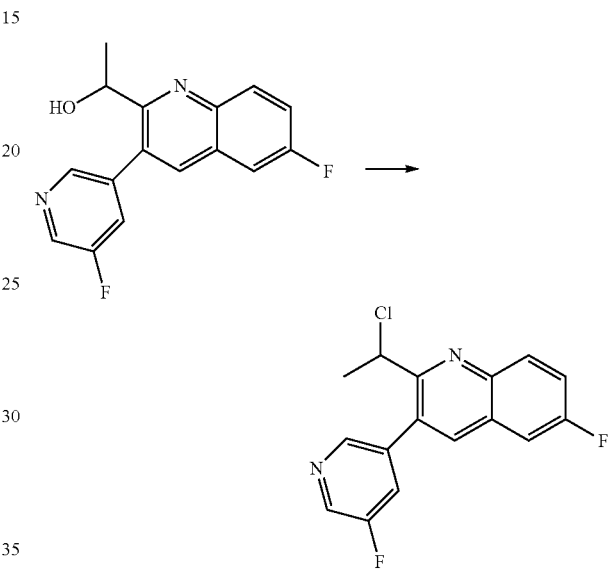

Thionyl chloride (0.4 mL, 5.68 mmol) was added to 1-(6-fluoro-3-(5-fluoropyridin-3-yl)quinolin-2-yl)ethanol (325.0 mg, 1.135 mmol) in DMF (1 mL) and DCM (20 mL). After the addition, the mixture was stirred at rt for 2 h. The solution was concd and diluted with Et₂O (20 mL). The Et₂O solution was washed with water, brine, dried and concd. Purification of the residue by flash chromatography over silica gel, using 10% EtOAc in Hex, gave 2-(1-chloroethyl)-6-fluoro-3-(5-fluoropyridin-3-yl)quinoline. ¹H-NMR (CDCl₃) δ 8.54 (d, J=2.0 Hz, 1H), 8.49 (s, 1H), 8.14 (dd, J=8.5, 5.0 Hz, 1H), 7.93 (s, 1H), 7.62-7.57 (m, 1H), 7.51-7.46 (m, 1H), 7.40-7.36 (m, 1H), 5.11 (q, J=5.0 Hz, 1H), 1.93 (d, J=5.0 Hz, 3H). Mass Spectrum (ESI) m/e=304.9 (M+1).

1-(1-(6-Fluoro-3-(5-fluoropyridin-3-yl)quinolin-2-yl)ethyl)-3-iodo-1H-pyrazolo[3,4-d]pyrimidin-4-amine

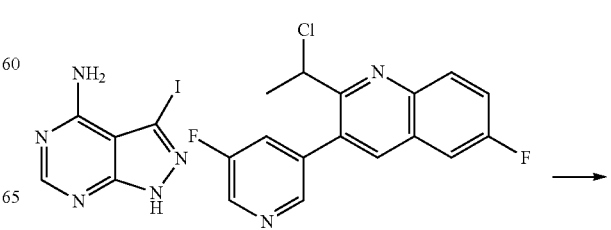

-continued

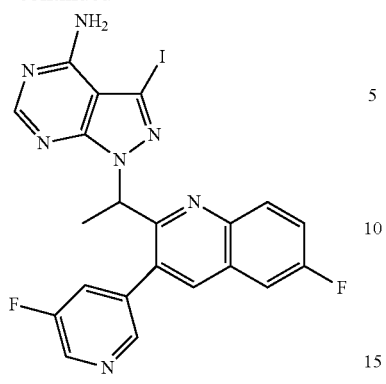

To a solution of 3-iodo-1H-pyrazolo[3,4-d]pyrimidin-4-amine (129 mg, 496 µl) in DMF (2 mL) was added sodium hydride (60% dispersion in mineral oil, 20 mg, 496 µmol) at 0° C., the resulting mixture was stirred at rt for 10 min. To the mixture was added a solution of 2-(1-chloroethyl)-6-fluoro-3-(5-fluoropyridin-3-yl)quinoline (151.0 mg, 496 µmol) in DMF (1 mL) and the mixture was stirred at rt for 24 h. The mixture was diluted with Et$_2$O. The residue was triturated with Et$_2$O, after filtration, which gavel-(1-(6-fluoro-3-(5-fluoropyridin-3-yl)quinolin-2-yl)ethyl)-3-iodo-1H-pyrazolo[3,4-d]pyrimidin-4-amine. $^1$H-NMR (DMSO-d$^6$) δ 8.25-8.22 (m, 2H), 8.17 (s, 1H), 7.99 (br, 1H), 7.97 (s, 1H), 7.84-7.76 (m, 2H), 7.64-7.58 (m, 1H), 6.49 (q, J=5.0 Hz, 1H), 1.86 (d, J=5.0 Hz, 3H). Mass Spectrum (ESI) m/e=530.0 (M+1).

Example 5: Preparation of 1-(1-(6-fluoro-3-(5-fluoropyridin-3-yl)quinolin-2-yl)ethyl)-3-(1H-pyrazol-4-yl)-1H-pyrazolo[3,4-d]pyrimidin-4-amine and Example 6: 1-(1-(6-fluoro-3-(5-fluoropyridin-3-yl)quinolin-2-yl)ethyl)-1H-pyrazolo[3,4-d]pyrimidin-4-amine

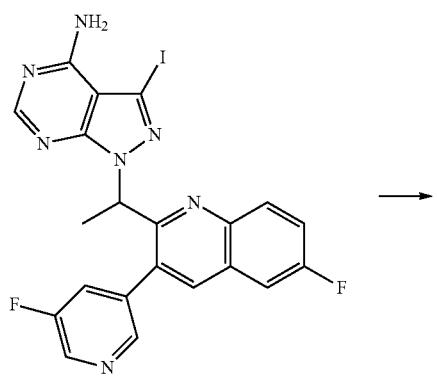

-continued

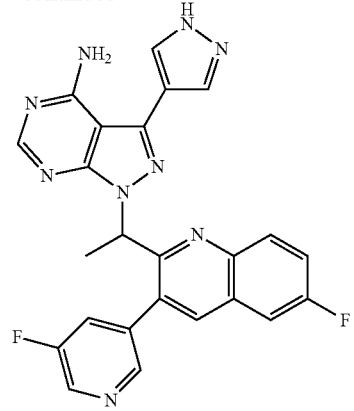

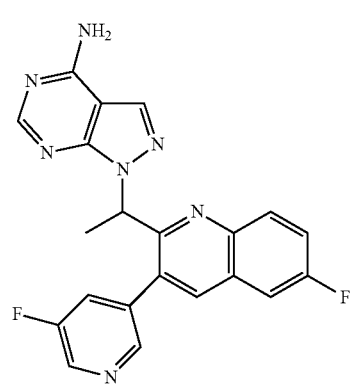

A solution of 1-(1-(6-fluoro-3-(5-fluoropyridin-3-yl)quinolin-2-yl)ethyl)-3-iodo-1H-pyrazolo[3,4-d]pyrimidin-4-amine (50.9 mg, 96 µmol) in DMF (2 mL) was treated with pyrazole-4-boronic acid pinacol ester (22 mg, 115 µmol), tetrakis(triphenylphosphine)palladium (11 mg, 10 µmol) and sodium carbonate (2.0M, 0.3 mL, 577 µmol). The resultant mixture was stirred at 100° C. for 16 h. An additional portion of pyrazole-4-boronic acid pinacol ester (22 mg, 115 µmol), bis(tri-t-butylphosphine)palladium (11 mg, 10 µmol) and sodium carbonate (2.0M, 0.3 mL, 577 µmol) was added. The reaction mixture was stirred at 100° C. for another 24 h. The resultant mixture was cooled and diluted with Et$_2$O, and the Et$_2$O solution was washed with water, brine, dried and concd. Purification of the residue by flash chromatography over silica gel, gradient elution, using 0-10% MeOH in CH$_2$Cl$_2$ with 0.1% aq. NR$_4$OH, gave 1-(1-(6-fluoro-3-(5-fluoropyridin-3-yl)quinolin-2-yl)ethyl)-3-(1H-pyrazol-4-yl)-1H-pyrazolo[3,4-d]pyrimidin-4-amine. $^1$H-NMR (CD$_3$OD) δ 8.14 (dd, J=8.5, 5.0 Hz, 1H), 7.98 (d, J=5.0 Hz, 1H), 7.94 (s, 1H), 7.93 (s, 1H), 7.88 (br, 1H), 7.77 (br, 2H), 7.57-7.49 (m, 2H), 7.35-7.26 (m, 1H), 6.40 (q, J=5.0 Hz, 1H), 1.94 (d, J=5.0 Hz, 3H). Mass Spectrum (ESI) m/e=469.9 (M+1); and 1-(1-(6-fluoro-3-(5-fluoropyridin-3-yl)quinolin-2-yl)ethyl)-1H-pyrazolo[3,4-d]pyrimidin-4-amine (6.6 mg, 17%), $^1$H-NMR (CD$_3$OD) δ 8.14 (dd, J=8.5, 5.0 Hz, 1H), 8.02 (d, J=5.0 Hz, 1H), 7.94 (s, 1H), 7.89 (s, 2H), 7.81 (s, 1H), 7.57-7.49 (m, 2H), 7.32-7.28 (m, 1H), 6.35 (q, J=5.0 Hz, 1H), 1.88 (d, J=5.0 Hz, 3H). Mass Spectrum (ESI) m/e=403.9 (M+1).

Example 7: Preparation of 3-ethynyl-1-(1-(6-fluoro-3-(5-fluoropyridin-3-yl)quinolin-2-yl)ethyl)-1H-pyrazolo[3,4-d]pyrimidin-4-amine

Example 8: Preparation of 1-(1-(6-fluoro-3-(5-fluoropyridin-3-yl)quinolin-2-yl)ethyl)-3-(1-methyl-1H-pyrazol-4-yl)-1H-pyrazolo[3,4-d]pyrimidin-4-amine

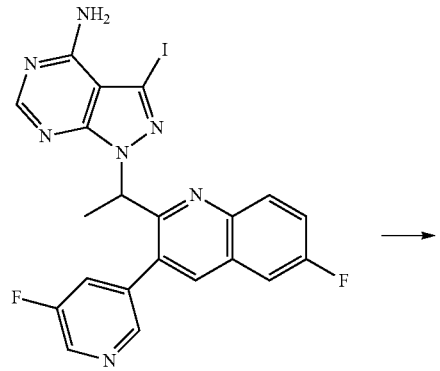

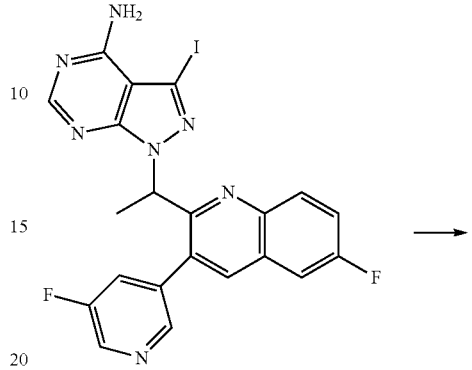

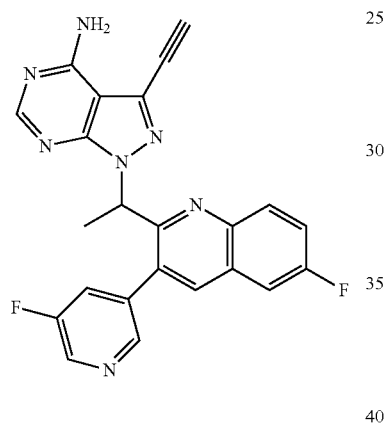

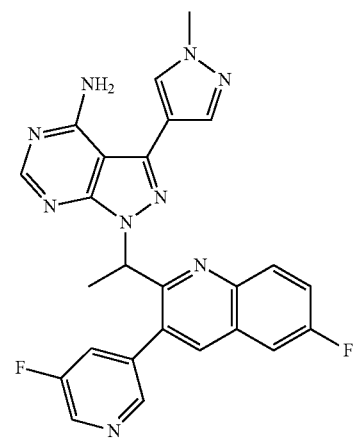

A mixture of 1-(1-(6-fluoro-3-(5-fluoropyridin-3-yl)quinolin-2-yl)ethyl)-3-iodo-1H-pyrazolo[3,4-d]pyrimidin-4-amine (57.6 mg, 109 μmol), copper(I) iodide (16 mg, 82 μmol), dichlorobis(triphenyl-phosphine)palladium (ii) (19 mg, 27 μmol) and ethynyltrimethylsilane (0.15 mL, 1088 μmol) in triethylamine (2.0 mL) and DMF (2.0 mL) was stirred under $N_2$ at rt for 1 h. Then potassium carbonate (15 mg, 109 μmol) in water (2 mL) was added and stirred for 30 min at rt. The mixture was diluted with $CH_2Cl_2$-MeOH (9:1) and washed with water, brine, dried and concd. Purification of the residue by flash chromatography over silica gel, gradient elution, 0-10% MeOH in $CH_2Cl_2$ with 0.1% aq. $NR_4OH$, gave 3-ethynyl-1-(1-(6-fluoro-3-(5-fluoropyridin-3-yl)quinolin-2-yl)ethyl)-1H-pyrazolo-[3,4-d]pyrimidin-4-amine. $^1$H-NMR (DMSO-$d^6$) δ 8.26 (d, J=2.0 Hz, 1H), 8.24-8.20 (m, 1H), 8.19 (s, 1H), 8.02 (br, 1H), 7.99 (s, 1H), 7.84-7.76 (m, 2H), 7.79-7.76 (m, 1H), 6.53 (q, J=5.0 Hz, 1H), 4.56 (s, 1H), 1.86 (d, J=5.0 Hz, 3H). Mass Spectrum (ESI) m/e=427.9 (M+1).

A solution of 1-(1-(6-fluoro-3-(5-fluoropyridin-3-yl)quinolin-2-yl)ethyl)-3-iodo-1H-pyrazolo[3,4-d]pyrimidin-4-amine (92.4 mg, 175 μmol) in DMF (3 mL) was treated with bis(tri-t-butylphosphine)palladium(0) (18 mg, 35 μmol), 1-methyl-pyrazole-4-boronic acid pinacol ester (54 mg, 262 μmol) and sodium carbonate (2.0M, 0.5 mL, 1.0 mmol). The resultant mixture was stirred at 100° C. for 16 h. The reaction mixture was cooled and diluted with $Et_2O$. The $Et_2O$ solution was washed with water, brine, dried and concd. Purification of the residue by flash chromatography over silica gel, gradient elution, using 0-10% MeOH in $CH_2Cl_2$ with 0.1% aq. $NH_4OH$, gave 1-(1-(6-fluoro-3-(5-fluoropyridin-3-yl)quinolin-2-yl)ethyl)-3-(1-methyl-1H-pyrazol-4-yl)-1H-pyrazolo[3,4-d]pyrimidin-4-amine.
$^1$H-NMR (CD$_3$OD) δ 8.14 (dd, J=8.5, 5.0 Hz, 1H), 7.97 (d, J=5.0 Hz, 1H), 7.93 (s, 1H), 7.91 (s, 1H), 7.87 (br, 1H), 7.77 (s, 1H), 7.58 (s, 1H), 7.57-7.46 (m, 2H), 7.34-7.27 (m, 1H), 6.39 (q, J=5.0 Hz, 1H), 3.82 (s, 1H), 1.92 (d, J=5.0 Hz, 3H). Mass Spectrum (ESI) m/e=483.9 (M+1).

Example 9: Preparation of 1-(1-(6-fluoro-3-(5-fluoropyridin-3-yl)quinolin-2-yl)ethyl)-3-(thiazol-4-yl)-1H-pyrazolo[3,4-d]pyrimidin-4-amine

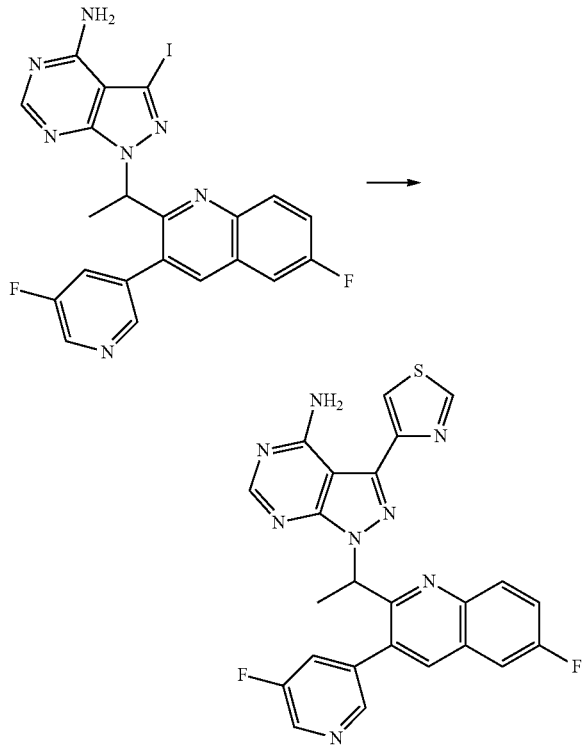

A solution of 1-(1-(6-fluoro-3-(5-fluoropyridin-3-yl)quinolin-2-yl)ethyl)-3-iodo-1H-pyrazolo[3,4-d]pyrimidin-4-amine (68.0 mg, 128 μmol) in DMF (3 mL) was treated with bis(tri-t-butylphosphine)palladium(o) (13 mg, 26 μmol), 4-(4,4,5,5-tetramethyl-1,3,2-dioxaborolan-2-yl)thiazole (41.0 mg, 193 μmol) and sodium carbonate (2.0M, 0.4 mL, 800 μmol). The resultant mixture was stirred at 100° C. for 16 h. The reaction mixture was cooled and diluted with Et$_2$O. The Et$_2$O solution was washed with water, brine, dried and concd. Purification of the residue by flash chromatography over silica gel, using MeOH—CH$_2$Cl$_2$-EtOAc (1:3:6), gave 1-(1-(6-fluoro-3-(5-fluoropyridin-3-yl)quinolin-2-yl)ethyl)-3-(thiazol-4-yl)-1H-pyrazolo[3,4-d]pyrimidin-4-amine. $^1$H-NMR (CD$_3$OD) δ 9.15 (d, J=2.0 Hz, 1H), 8.28 (dd, J=8.5, 5.0 Hz, 1H), 8.10 (d, J=5.0 Hz, 1H), 8.06 (s, 1H), 8.01 (s, 1H), 7.98 (br, 1H), 7.96 (s, 1H), 7.72-7.62 (m, 2H), 7.45-7.38 (m, 1H), 6.53 (q, J=5.0 Hz, 1H), 2.06 (d, J=5.0 Hz, 3H). Mass Spectrum (ESI) m/e=486.9 (M+1).

Example 10: Preparation of 1-(1-(6-fluoro-3-(5-fluoropyridin-3-yl)quinolin-2-yl)ethyl)-3-(thiazol-5-yl)-1H-pyrazolo[3,4-d]pyrimidin-4-amine

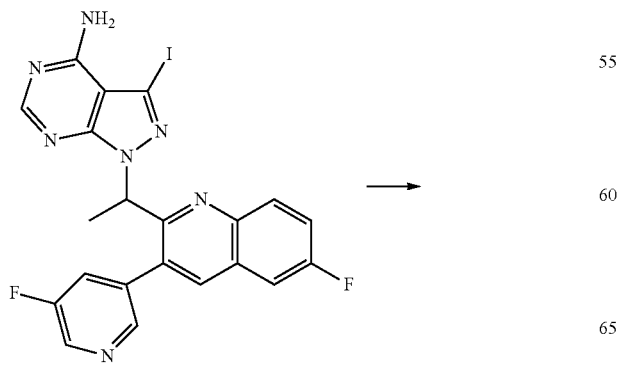

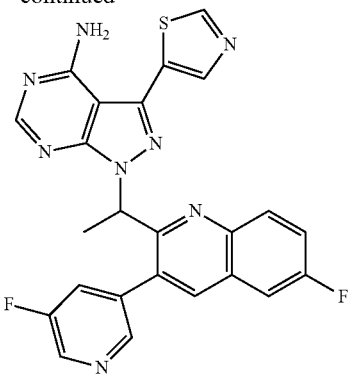

A mixture of 1-(1-(6-fluoro-3-(5-fluoropyridin-3-yl)quinolin-2-yl)ethyl)-3-iodo-1H-pyrazolo[3,4-d]pyrimidin-4-amine (50 mg, 94 μmol), bis(tri-t-butylphosphine)palladium (o) (4.8 mg, 9.4 μmol) and 5-(tributylstannyl)thiazole (42 mg, 113 μmol) in 1,4-dioxane (10 mL) was heated to 110° C. under N$_2$ for 16 h. The resultant mixture was cooled and diluted with CH$_2$Cl$_2$-MeOH (10:1), and the solution was washed with water and brine. The organic solvent layer was dried and concd. Purification of the residue by flash chromatography over silica gel, using MeOH—CH$_2$Cl$_2$-EtOAc (0.5:5:5), gave 1-(1-(6-fluoro-3-(5-fluoropyridin-3-yl)quinolin-2-yl)ethyl)-3-(thiazol-5-yl)-1H-pyrazolo[3,4-d]pyrimidin-4-amine. $^1$H-NMR (CD$_3$OD) δ 9.06 (s, 1H), 8.285 (dd, J=8.5, 5.0 Hz, 1H), 8.13 (s, 1H), 8.12 (d, J=5.0 Hz, 1H), 8.10 (s, 1H), 8.06 (s, 1H), 8.01 (br, 1H), 7.69-7.62 (m, 2H), 7.50-7.44 (m, 1H), 6.55 (q, J=5.0 Hz, 1H), 2.05 (d, J=5.0 Hz, 3H). Mass Spectrum (ESI) m/e=487.1 (M+1).

Example 11: Preparation of 4-amino-1-((S)-1-(6-fluoro-3-(5-fluoropyridin-3-yl)quinolin-2-yl)ethyl)-1H-pyrazolo[3,4-d]pyrimidine-3-carbonitrile and Example 12: 4-amino-1-((R)-1-(6-fluoro-3-(5-fluoropyridin-3-yl)quinolin-2-yl)ethyl)-1H-pyrazolo[3,4-d]pyrimidine-3-carbonitrile

4-Amino-1H-pyrazolo[3,4-d]pyrimidine-3-carbonitrile

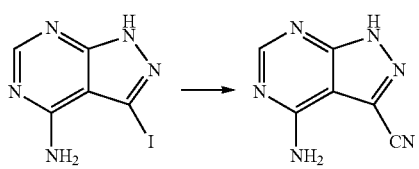 [SMILES: Nc1ncnc2[nH]nc(I)c12 ; N#Cc1n[nH]c2ncnc(N)c12]

A mixture of 3-iodo-1H-pyrazolo[3,4-d]pyrimidin-4-amine (1.04 g, 3.98 mmol), zinc cyanide (515 mg, 4.38 mmol), tris(dibenzylideneacetone)dipalladium (0) (182 mg, 0.199 mmol) and dichloro[1,1'-bis(diphenylphosphino)ferrocene]palladium (II) DCM adduct (292 mg, 398 μmol) in DMF (10 mL) was heated under N$_2$ at 120° C. for 3.5 h, cooled to rt, and concd. Purification of the residue by flash chromatography over silica gel, gradient elution, 0-10% MeOH in CH$_2$Cl$_2$, gave 4-amino-1H-pyrazolo[3,4-d]pyrimidine-3-carbonitrile. $^1$H-NMR (DMSO-d$^6$) δ 8.29 (s, 1H). Mass Spectrum (ESI) m/e=161.1 (M+1).

4-Amino-1-(1-(6-fluoro-3-(5-fluoropyridin-3-yl)
quinolin-2-yl)ethyl)-1H-pyrazolo[3,4-d]pyrimidine-
3-carbonitrile

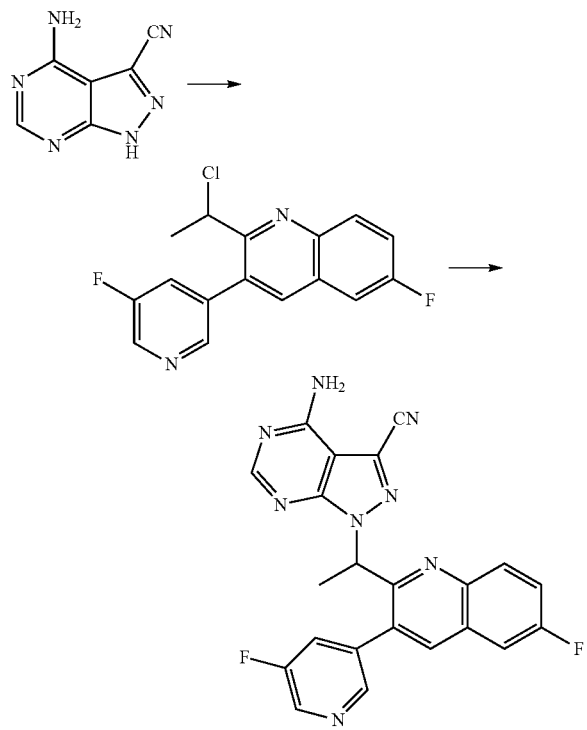

To a solution of 4-amino-1H-pyrazolo[3,4-d]pyrimidine-3-carbonitrile (60 mg, 374 μmol) in DMF (2.0 mL) was added sodium hydride (60% dispersion in mineral oil, (16 mg, 412 μmol) at 0° C. The resulting mixture was stirred at rt for 10 min. To the mixture was added a solution of 2-(1-chloroethyl)-6-fluoro-3-(5-fluoropyridin-3-yl)quinoline (114.1 mg, 374 μmol) in DMF (1.0 mL) and the mixture was stirred at rt for 24 h. The mixture was diluted with Et$_2$O and triturated with Et$_2$O, following a filtration 4-amino-1-(1-(6-fluoro-3-(5-fluoropyridin-3-yl)quinolin-2-yl)ethyl)-1H-pyrazolo[3,4-d]pyrimidine-3-carbonitrile was obtained.

4-Amino-1-((S)-1-(6-fluoro-3-(5-fluoropyridin-3-yl)
quinolin-2-yl)ethyl)-1H-pyrazolo[3,4-d]pyrimidine-
3-carbonitrile and 4-amino-1-((R)-1-(6-fluoro-3-(5-
fluoropyridin-3-yl)quinolin-2-yl)ethyl)-1H-pyrazolo
[3,4-d]pyrimidine-3-carbonitrile

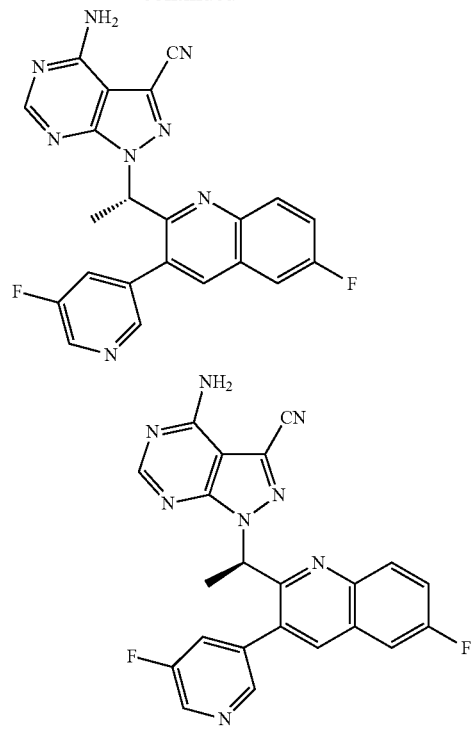

4-Amino-1-(1-(6-fluoro-3-(5-fluoropyridin-3-yl)quinolin-2-yl)ethyl)-1H-pyrazolo[3,4-d]pyrimidine-3-carbonitrile (66.6 mg) in THF-MeOH 10:1 (1.5 mL) was subjected to chiral HPLC resolution (Chiralpak IA column, 30×250 mm, 5 mm), using 15% isopropanol in hexane as eluent, which gave 4-amino-1-((S)-1-(6-fluoro-3-(5-fluoropyridin-3-yl)quinolin-2-yl)ethyl)-1H-pyrazolo[3,4-d]pyrimidine-3-carbonitrile, the first fraction collected with 99% ee at 254 nm, and 4-amino-1-((R)-1-(6-fluoro-3-(5-fluoropyridin-3-yl)quinolin-2-yl)ethyl)-1H-pyrazolo[3,4-d]pyrimidine-3-carbonitrile, the second fraction collected with 99% ee at 254 nm, $^1$H-NMR (DMSO-d$^6$) δ 8.34 (d, J=5.0 Hz, 1H), 8.24 (s, 1H), 8.24-8.18 (m, 1H), 8.14 (br, 1H), 8.10 (s, 1H), 7.86-7.76 (m, 3H), 6.62 (q, J=5.0 Hz, 1H), 1.89 (d, J=5.0 Hz, 3H). Mass Spectrum (ESI) m/e=429.1 (M+1).

Example 13: Preparation of (S)-4-amino-6-(1-(6-fluoro-3-(6-(methylsulfonyl)-pyridin-2-yl)quinolin-2-yl)ethylamino)pyrimidine-5-carbonitrile 2-(Methylthio)-6-(tributylstannyl)pyridine

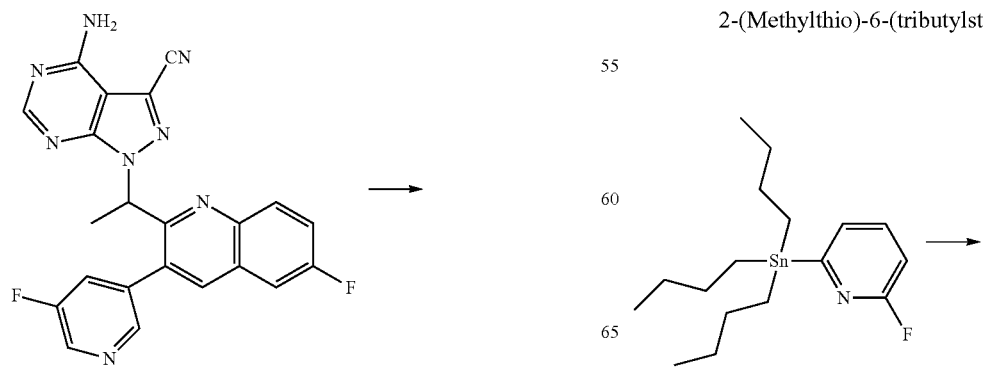

1-(6-Fluoro-3-(6-(methylsulfonyl)pyridin-2-yl)qui-nolin-2-yl)ethanone

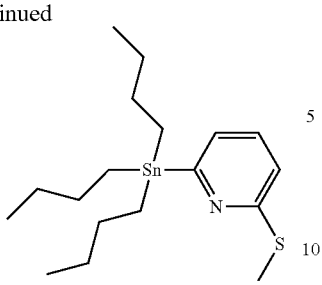

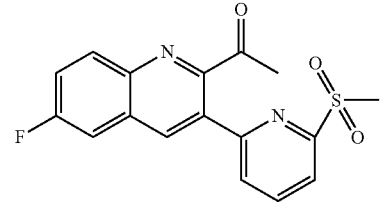

A mixture of 6-fluoro-2-(tributylstannyl)pyridine (5.00 mL, 13.0 mmol) and sodium thiomethoxide (1.0 g, 14.3 mmol) in 1-methylpyrrolidin-2-one (10 mL) was heated at 140° C. for 24 h. The mixture was, then diluted with Et$_2$O and washed with water, brine, dried and concd. The residue was purified by flash chromatography over silica gel, gradient elution, 0-50% EtOAc in hexane, which gave 2-(methylthio)-6-(tributylstannyl)pyridine. $^1$H-NMR (CD$_3$OD) δ 7.40 (t, J=5.0 Hz, 1H), 7.15 (d, J=5.0 Hz, 1H), 7.08 (d, J=5.0 Hz, 1H), 2.56 (s, 3H), 1.69-1.55 (m, 6H), 1.43-1.32 (m, 6H), 1.15 (t, J=10.0 Hz, 6H), 0.91 (t, J=10.0 Hz, 9H). Mass Spectrum (ESI) m/e=416.0 (M+1).

2-(Methylsulfonyl)-6-(tributylstannyl)pyridine

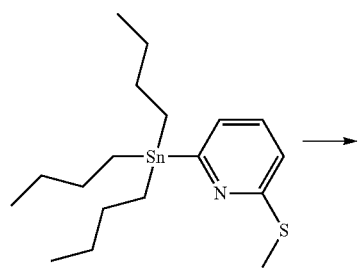

A solution of potassium permanganate (9.11 g, 57.6 mmol) in water (100 mL) was added to a solution of 2-(methylthio)-6-(tributylstannyl)pyridine (1.99 g, 4.80 mmol) and tetra-n-butylammonium iodide (0.018 g, 0.048 mmol) in a mixture of acetic acid (10 mL), and benzene (80 mL). The reaction mixture was stirred at rt for 6 h. A satd solution of Na$_2$S$_2$O$_5$ in water was added to the mixture until the purple color disappeared. The mixture was diluted with EtOAc and washed with water, brine, dried and concd. Purification of the residue by flash chromatography over silica gel, gradient elution, 0-50% EtOAc in hexane, gave 2-(methyl-sulfonyl)-6-(tributylstannyl)pyridine. $^1$H-NMR (CDCl$_3$) δ 7.82 (t, J=8.0 Hz, 1H), 7.67 (d, J=8.0 Hz, 1H), 7.55 (d, J=8.0 Hz, 1H), 3.19 (s, 3H), 1.54-1.46 (m, 6H), 1.31-1.22 (m, 6H), 1.08 (t, J=8.0 Hz, 6H), 0.82 (t, J=8.0 Hz, 9H). Mass Spectrum (ESI) m/e=448.1 (M+1).

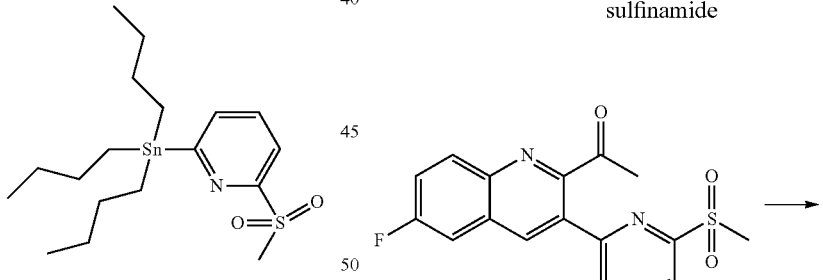

A mixture of 2-acetyl-6-fluoroquinolin-3-yl trifluoromethanesulfonate (778 mg, 2.31 mmol), tetrakis(triphenylphosphine)palladium(o) (222 mg, 0.192 mmol), bis(tri-t-butylphosphine)palladium (0) (98 mg, 0.192 mmol) and 2-(methyl-sulfonyl)-6-(tributylstannyl)pyridine (858 mg, 1.92 mmol) in 1,4-dioxane (10 mL) was heated to 110° C. under N$_2$ for 5 h. After cooling to rt, and removal of the solvent was followed by purification of the residue by flash chromatography over silica gel, gradient elution, 0-100% EtOAc in hexane, it gavel-(6-fluoro-3-(6-(methylsulfonyl)pyridin-2-yl)quinolin-2-yl)ethanone. $^1$H-NMR (DMSO-d$^6$) δ 8.92 (s, 1H), 8.33 (dd, J=8.0, 8.0 Hz, 1H), 8.28 (d, J=8.0 Hz, 1H), 8.24 (dd, J=8.0, 4.0 Hz, 1H), 8.07 (d, J=8.0 Hz, 1H), 7.95 (dd, J=8.0, 4.0 Hz, 1H), 7.86 (dd, J=8.0, 4.0 Hz, 1H), 3.26 (s, 3H), 2.76 (s, 3H). Mass Spectrum (ESI) m/e=345.0 (M+1).

(R)—N-(1-(6-Fluoro-3-(6-(methylsulfonyl)pyridin-2-yl)quinolin-2-yl)-ethylidene)-2-methylpropane-2-sulfinamide

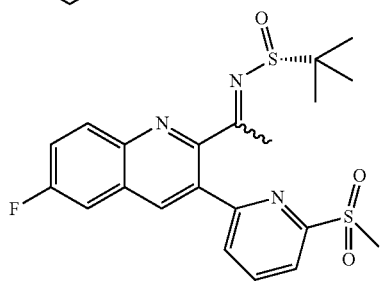

A solution of 1-(6-fluoro-3-(6-(methylsulfonyl)pyridin-2-yl)quinolin-2-yl)-ethanone (220 mg, 0.639 mmol), (r)-(+)-t-butylsulfinamide (0.077 g, 0.639 mmol) and titanium tetraethoxide (0.264 mL, 1.28 mmol) with molecular sieves 4A (1.0 g) in THF (30 mL) was stirred and heated to reflux for 4 days. The reaction was quenched with water and diluted with DCM (30 mL). The mixture was then filtered through a pad of Celite™ and rinsed with DCM. The combined organics were washed with water, brine, dried and concd. Purification of the residue by flash chromatography over silica gel, gradient elution, CH$_2$Cl$_2$-EtOAc (1:1) to CH$_2$Cl$_2$-EtOAc-MeOH (1:1:0.1) gave (R)—N-(1-(6-fluoro-3-(6-(methyl-sulfonyl)pyridin-2-yl)quinolin-2-yl)ethyl-idene)-2-methylpropane-2-sulfinamide. $^1$H-NMR (CD$_3$OD) δ 8.78 (s, 0.4H), 8.62 (s, 0.6H), 8.36-8.05 (m, 4H), 7.80-7.65 (m, 2H), 3.31 (s, 1.8H), 3.27 (s, 1.2H), 3.03 (s, 1.8H), 2.88 (s, 1.2H), 0.91 (s, 9H). Mass Spectrum (ESI) m/e=448.0 (M+1).

(R)—N—((S)-1-(6-Fluoro-3-(6-(methylsulfonyl) pyridin-2-yl)quinolin-2-yl)ethyl)-2-methylpropane-2-sulfinamide

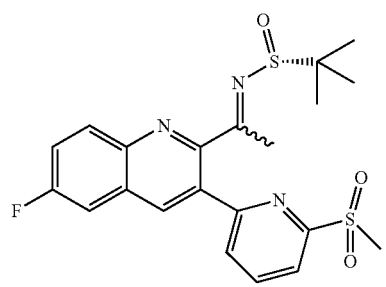

To a solution of (R)—N-(1-(6-fluoro-3-(6-(methylsulfo-nyl)pyridin-2-yl)quinolin-2-yl)ethylidene)-2-methylpro-pane-2-sulfinamide (225 mg, 0.503 mmol) in THF (10 mL) at −78° C. was added L-selectride (1.51 mL, 1.0M, 1.51 mmol) drop-wise. The resultant mixture was stirred at −78° C. for 4 h. The reaction was quenched with sat. NH$_4$Cl and diluted with EtOAc. The organics were washed with water, brine, dried and concd. Purification of the residue by flash chromatography over silica gel, gradient elution, CH$_2$Cl$_2$-EtOAc (1:1) to CH$_2$Cl$_2$-EtOAc-MeOH (5:5:0.5), gave (R)—N—((S)-1-(6-fluoro-3-(6-(methylsulfonyl)pyridin-2-yl)qui-nolin-2-yl)ethyl)-2-methylpropane-2-sulfinamide. $^1$H-NMR (CD$_3$OD) δ 8.49 (s, 1H), 8.34 (dd, J=8.0, 8.0 Hz, 1H), 8.22-8.19 (m, 2H), 8.10 (d, J=8.0 Hz, 1H), 7.73-7.64 (m, 2H), 5.30 (q, J=8.0 Hz, 1H), 1.72 (d, J=8.0 Hz, 3H), 1.13 (s, 9H). Mass Spectrum (ESI) m/e=450.1 (M+1).

(S)-1-(6-Fluoro-3-(6-(methylsulfonyl)pyridin-2-yl) quinolin-2-yl)ethanamine

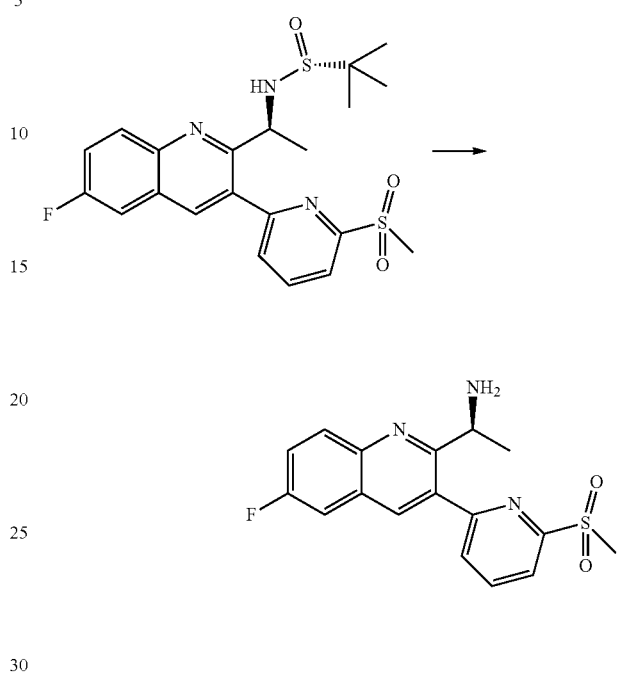

To a solution of (R)—N—((S)-1-(6-fluoro-3-(6-(methyl-sulfonyl)pyridin-2-yl)-quinolin-2-yl)ethyl)-2-methylpro-pane-2-sulfinamide (157 mg, 0.349 mmol) in MeOH (20 mL) was added HCl in dioxane (873 μL, 4.0M, 3.49 mmol). The mixture was stirred at rt for 1 h. The mixture was concd, and the residue was diluted with EtOAc. The organics were washed with water, brine, dried and concd. Purification of the residue by flash chromatography over silica gel, gradient elution, 0-10% MeOH—NH$_4$OH (10:0.05) in CH$_2$Cl$_2$, gave (S)-1-(6-fluoro-3-(6-(methylsulfonyl)pyridin-2-yl)quinolin-2-yl)ethanamine. $^1$H-NMR (CD$_3$OD) δ 8.47 (s, 1H), 8.34 (dd, J=8.0, 8.0 Hz, 1H), 8.22-8.18 (m, 2H), 8.09 (d, J=8.0 Hz, 1H), 7.73-7.64 (m, 2H), 4.71 (q, J=8.0 Hz, 1H), 3.30 (s, 3H), 1.48 (d, J=8.0 Hz, 3H). Mass Spectrum (ESI) m/e=346.0 (M+1).

(S)-4-Amino-6-(1-(6-fluoro-3-(6-(methylsulfonyl) pyridin-2-yl)quinolin-2-yl)ethylamino)pyrimidine-5-carbonitrile

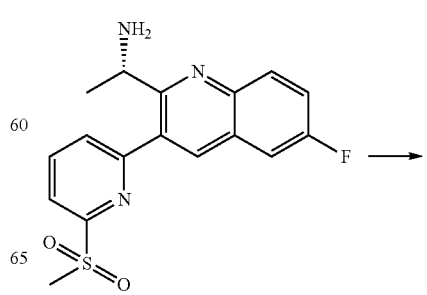

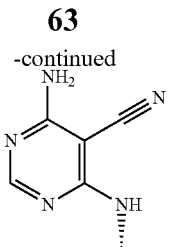

A mixture of (S)-1-(6-fluoro-3-(6-(methylsulfonyl)pyridin-2-yl)quinolin-2-yl)-ethanamine (85.1 mg, 0.246 mmol), 4-amino-6-chloropyrimidine-5-carbonitrile (38.1 mg, 0.246 mmol) and N-ethyl-N-isopropylpropan-2-amine (47.2 µL, 0.271 mmol) in BuOH (20 mL) was heated to 110° C. overnight. After cooling to rt, the mixture was concd. Purification of the residue by flash chromatography over silica gel, gradient elution, 0-10% MeOH in CH$_2$Cl$_2$, gave (S)-4-amino-6-(1-(6-fluoro-3-(6-(methylsulfonyl)pyridin-2-yl)quinolin-2-yl)ethylamino)pyrimidine-5-carbonitrile.
$^1$H-NMR (DMSO-d$^6$) δ 8.59 (s, 1H), 8.36 (dd, J=8.0, 8.0 Hz, 1H), 8.16-8.09 (m, 3H), 7.90-7.86 (m, 2H), 7.78 (dd, J=8.0, 4.0 Hz, 1H), 7.55 (d, J=8.0 Hz, 1H), 7.28 (br, 2H), 6.04 (m, 1H), 3.44 (s, 3H), 1.42 (d, J=8.0 Hz, 3H). Mass Spectrum (ESI) m/e=464.0 (M+1).

Example 14: Preparation of (S)—N-(1-(6-fluoro-3-(pyridin-2-yl)quinolin-2-yl)ethyl)-9H-purin-6-amine and Example 15: (R)—N-(1-(6-fluoro-3-(pyridin-2-yl)quinolin-2-yl)ethyl)-9H-purin-6-amine Tert-butyl 3-oxo-4-(pyridin-2-yl)butan-2-ylcarbamate

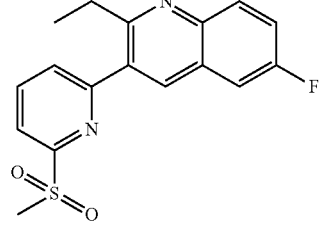

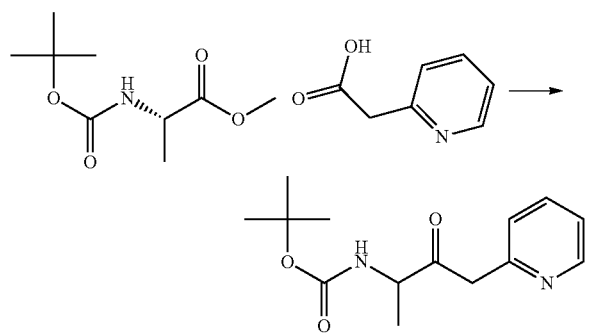

n-Butyllithium, 2.5M solution in hexane (12 mL, 29 mmol) and lithium bis(tri-methylsilyl)amide (102 mL, 102 mmol) was added drop-wise to a solution of 2-pyridylacetic acid hydrochloride (5.07 g, 29 mmol) in THF (100 mL) at −78° C. under N$_2$. The mixture was stirred at −78° C. for 30 min, then N-(tert-butoxycarbonyl)-1-alanine methyl ester (6 g, 29 mmol) in THF (20 mL) was added drop-wise. The resultant mixture was stirred overnight and the cold bath was warmed slowly to rt. The reaction mixture was washed with water and brine, dried, then concd. Purification of the residue by flash chromatography over silica gel, gradient elution, 0-100% EtOAc in hexane, gave tert-butyl 3-oxo-4-(pyridin-2-yl)butan-2-ylcarbamate. $^1$H NMR (500 MHz, DMSO-d$_6$) δ 8.46 (dd, J=5.0, 1.3 Hz, 1H), 7.72 (dd, J=5.0, 1.3 Hz, 1H), 7.25-7.23 (m, 2H), 4.11-4.06 (m, 1H), 3.96 (s, 2H), 1.37 (s, 9H), 1.17 (d, J=5.0 Hz, 3H). Mass Spectrum (ESI) m/e=265.1 (M+1).

(2-Amino-5-fluorophenyl)methanol

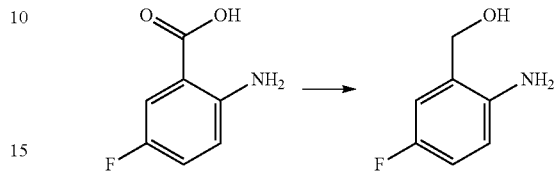

To 2-amino-5-fluorobenzoic acid (2.0 g, 13 mmol) in THF (20 mL) lithium aluminum hydride (0.73 g, 19 mmol) was added portion wise at 0° C. The resulting mixture was heated to reflux for 1.5 h. After the reaction mixture was cooled to rt, 1 mL of water, 1 mL of NaOH (1N) and 2 mL of water were added. The resulting mixture was filtered, rinsed with Et$_2$O, and concd. The residue, (2-amino-5-fluorophenyl)methanol was directly used for the next reaction: $^1$H NMR (400 MHz, DMSO-d$_6$) δ 6.91 (dd, J=8.0, 4.0 Hz, 1H), 6.77 (ddd, J=8.0, 8.0, 4.0 Hz, 1H), 6.59 (dd, J=8.0, 8.0 Hz, 1H), 5.12 (t, J=4.0 Hz, 1H), 4.75 (s, 2H), 4.35 (t, J=4.0 Hz, 2H). Mass Spectrum (ESI) m/e=142.0 (M+1).

2-Amino-5-fluorobenzaldehyde

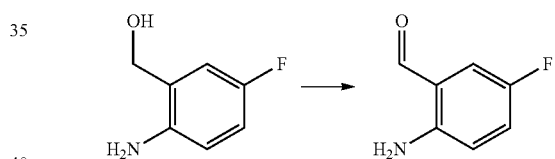

To (2-amino-5-fluorophenyl)methanol (1.8 g, 13 mmol) in DCM (50 mL), manganese dioxide (4.4 g, 51 mmol) (fresh activated by heating with flame and under oil pump vacuum for 5 min), was added together and stirred at rt overnight. LCMS showed completion of the reaction. Filtration on a pad of Celite™ and rinsing with DCM, followed by removal of the solvents, purification of the residue by flash chromatography over silica gel, gradient elution, 0-100% EtOAc in hexane gave 2-amino-5-fluorobenzaldehyde. $^1$H NMR (400 MHz, DMSO-d$_6$) δ 9.78 (s, 1H), 7.39 (dd, J=8.0, 4.0 Hz, 1H), 7.23 (ddd, J=8.0, 8.0, 4.0 Hz, 1H), 7.00 (br, 2H), 6.78 (dd, J=8.0, 4.0 Hz, 1H). Mass Spectrum (ESI) m/e=140.1 (M+1).

tert-Butyl-1-(6-fluoro-3-(pyridin-2-yl)quinolin-2-yl)ethylcarbamate

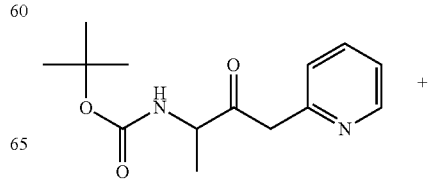

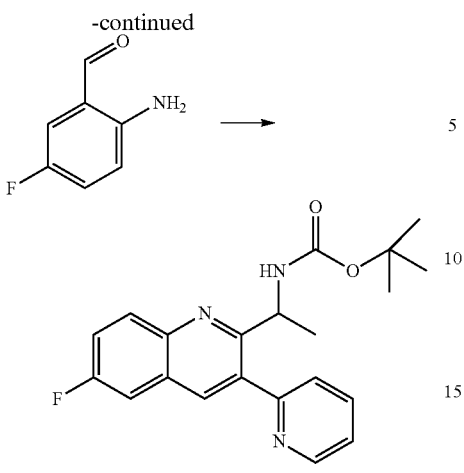

The mixture of tert-butyl 3-oxo-4-(pyridin-2-yl)butan-2-ylcarbamate (2.7 g, 10 mmol), 2-amino-5-fluorobenzaldehyde (1.43 g, 10 mmol) and potassium hydroxide (33 ml, 31 mmol) in EtOH (120 mL) was heated to reflux for 1 h. The resulting mixture was cooled to rt and concd. Purification of the residue by flash chromatography over silica gel, gradient elution, 0-100% EtOAc in hexane, gave tert-butyl-1-(6-fluoro-3-(pyridin-2-yl)quinolin-2-yl)ethylcarbamate. $^1$H NMR (500 MHz, DMSO-$d_6$) δ 8.75 (d, J=5.0 Hz, 1H), 8.38 (s, 1H), 8.13 (dd, 5.0 Hz, 1H), 8.01 (ddd, J=9.3, 5.0, 2.0 Hz, 1H), 7.85 (dd, 5.0 Hz, 1H), 7.75-7.70 (m, 2H), 7.50 (ddd, J=5.0, 5.0, 2.0 Hz, 1H), 7.00 (d, J=8.0 Hz, 1H), 5.34-5.27 (m, 1H), 1.32 (s, 9H), 1.28 (d, J=9.3 Hz, 3H). Mass Spectrum (ESI) m/e=368.1 (M+1).

1-(6-Fluoro-3-(pyridin-2-yl) quinolin-2-yl)ethanamine

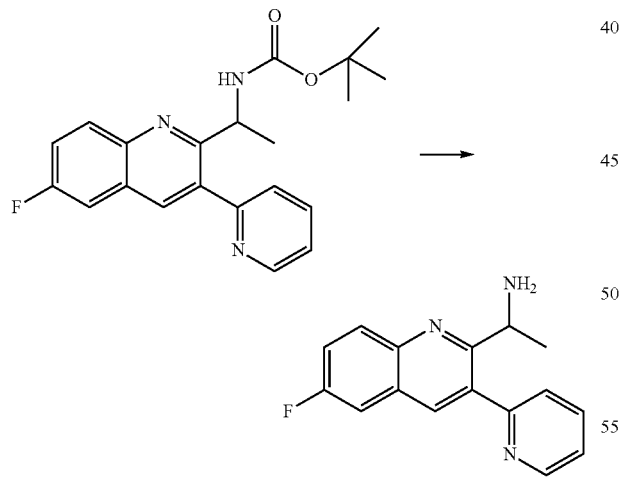

The mixture of tert-butyl 1-(6-fluoro-3-(pyridin-2-yl) quinolin-2-yl) ethylcarbamate (600 mg, 1.633 mmol), trifluoroacetic acid (3 mL, 38.9 mmol) in DCM (10 mL) was stirred at rt for 60 min. An additional amount of trifluoroacetic acid (3 mL, 38.9 mmol) was added at this time. Stirring was continued for another 10 min. The reaction mixture was concd and diluted with DCM (15 mL). The DCM solution was washed with sat. NaHCO$_3$, water, brine, dried and concd to provide 1-(6-fluoro-3-(pyridin-2-yl) quinolin-2-yl)ethanamine. $^1$H NMR (400 MHz, DMSO-$d_6$) δ 8.74 (dd, J=4.0 Hz, 1H), 8.34 (s, 1H), 8.10 (dd, J=8.0, 4.0 Hz, 1H), 8.00 (ddd, J=8.0, 8.0, 4.0 Hz, 1H), 7.82 (dd, J=8.0, 4.0 Hz, 1H), 7.72 (d, J=4.0 Hz, 1H), 7.68 (dd, J=8.0, 4.0 Hz, 1H), 7.49 (ddd, J=8.0, 8.0, 4.0 Hz, 1H), 4.41-4.36 (m, 1H), 2.22 (br, 2H), 1.26 (d, J=8.0 Hz, 3H). Mass Spectrum (ESI) m/e=268.1 (M+1).

N-(1-(6-Fluoro-3-(pyridin-2-yl)quinolin-2-yl)ethyl)-9H-purin-6-amine

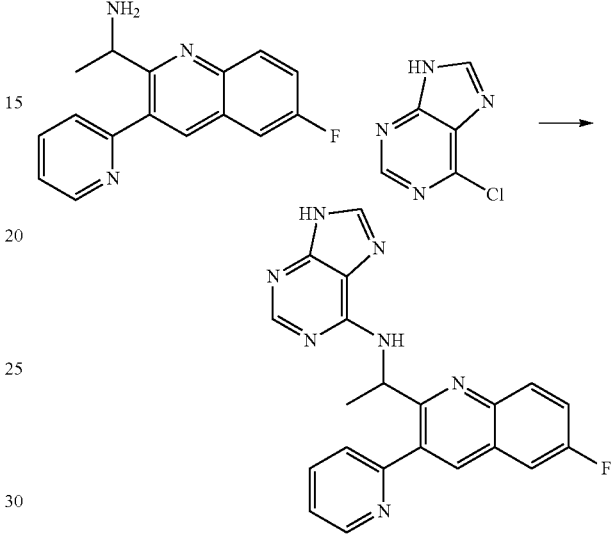

A mixture of 1-(6-fluoro-3-(pyridin-2-yl) quinolin-2-yl) ethanamine (441 mg, 1.650 mmol), 6-chloro-9H-purine (255 mg, 1.650 mmol) and N-ethyl-N-isopropylpropan-2-amine (345 μL, 1.980 mmol) in BuOH (20 mL) was heated at 110° C. overnight. After cooling to rt, the mixture was concd. Purification of the residue by flash chromatography over silica gel, gradient elution, 0-10% MeOH in CH$_2$Cl$_2$ gave N-(1-(6-fluoro-3-(pyridin-2-yl)quinolin-2-yl)ethyl)-9H-purin-6-amine. $^1$H NMR (500 MHz, MeOH-$d_4$) δ 8.74 (d, J=5.0 Hz, 1H), 8.32 (s, 1H), 8.27 (dd, J=9.3, 5.0 Hz, 1H), 8.16 (s, 1H), 8.14-8.08 (m, 1H), 8.00 (dd, J=9.3, 0.5 Hz, 1H), 7.78 (d, J=5.0 Hz, 1H), 7.71-7.62 (m, 2H), 7.52 (dd, J=9.3, 5.0 Hz, 1H), 6.09-5.96 (m, 1H), 1.56 (d, J=5.0 Hz, 3H). Mass Spectrum (ESI) m/e=386.0 (M+1).

(S)—N-(1-(6-Fluoro-3-(pyridin-2-yl)quinolin-2-yl) ethyl)-9H-purin-6-amine and (R)—N-(1-(6-fluoro-3-(pyridin-2-yl)quinolin-2-yl)ethyl)-9H-purin-6-amine

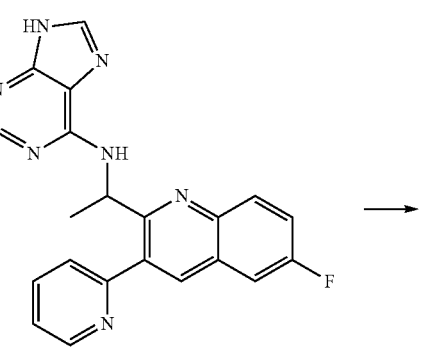

-continued

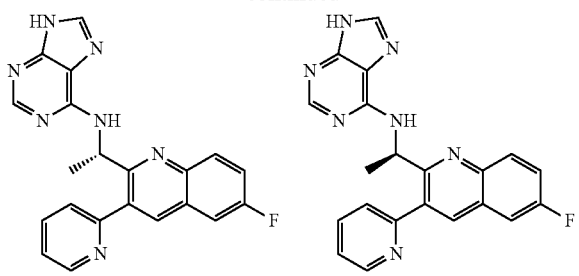

N-(1-(6-Fluoro-3-(pyridin-2-yl)quinolin-2-yl)ethyl)-9H-purin-6-amine was subjected to chiral separation (IC 250×30 mm column) to provide (S)—N-(1-(6-fluoro-3-(pyridin-2-yl)quinolin-2-yl)ethyl)-9H-purin-6-amine: $^1$H NMR (500 MHz, DMSO-d$_6$) δ 8.77 (br, 1H), 8.44 (s, 1H), 8.21-8.15 (m, 1H), 8.11 (br, 2H), 8.01 (br, 1H), 7.87 (dd, J=9.3, 5.0 Hz, 1H), 7.82 (d, J=5.0 Hz, 1H), 7.76-7.68 (m, 2H), 7.50 (br, 1H), 6.00 (br, 1H), 1.47 (br, 3H). Mass Spectrum (ESI) m/e=386.0 (M+1); and (R)—N-(1-(6-fluoro-3-(pyridin-2-yl)quinolin-2-yl)ethyl)-9H-purin-6-amine: $^1$H NMR (500 MHz, DMSO-d$_6$) δ 8.77 (br, 1H), 8.44 (s, 1H), 8.19 (dd, J=9.3, 5.0 Hz, 1H), 8.14 (br, 1H), 8.10 (s, 1H), 8.01 (br, 1H), 7.86 (dd, J=9.3, 5.0 Hz, 1H), 7.80 (d, J=9.3 Hz, 1H), 7.76-7.68 (m, 2H), 7.50 (br, 1H), 6.01 (br, 1H), 1.48 (d, J=5.0 Hz, 3H). Mass Spectrum (ESI) m/e=386.0 (M+1).

Using the same or analogous synthetic procedures and substituting with appropriate reagents, the following compounds were prepared:

Example 16: Preparation of N-(1-(6-fluoro-3-(pyridin-2-yl)quinolin-2-yl)-ethyl)pyrimidin-4-amine

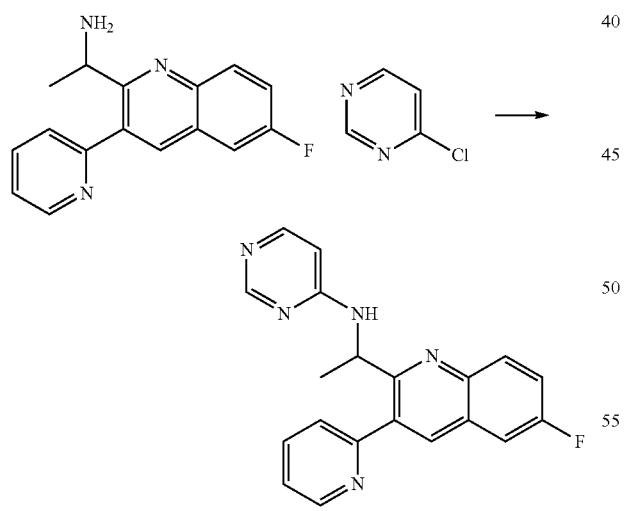

N-(1-(6-Fluoro-3-(pyridin-2-yl)quinolin-2-yl)ethyl)pyrimidin-4-amine. $^1$H NMR (500 MHz, DMSO-d$_6$) δ 8.72 (d, J=5.0 Hz, 1H), 8.38 (s, 1H), 8.18 (br, 1H), 8.12 (dd, J=9.3, 5.0 Hz, 1H), 7.98 (dd, J=9.3, 9.3 Hz, 1H), 7.93 (d, J=5.0 Hz, 1H), 7.84 (dd, J=9.3, 5.0 Hz, 1H), 7.80 (br, 1H), 7.77-7.68 (m, 2H), 7.46 (dd, J=9.3, 5.0 Hz, 1H), 6.52 (br, 1H), 1.47 (d, J=5.0 Hz, 3H). Mass Spectrum (ESI) m/e=346.0 (M+1).

Example 17: Preparation of N4-(1-(6-fluoro-3-(pyridin-2-yl)quinolin-2-yl)ethyl)pyrimidine-4,6-diamine

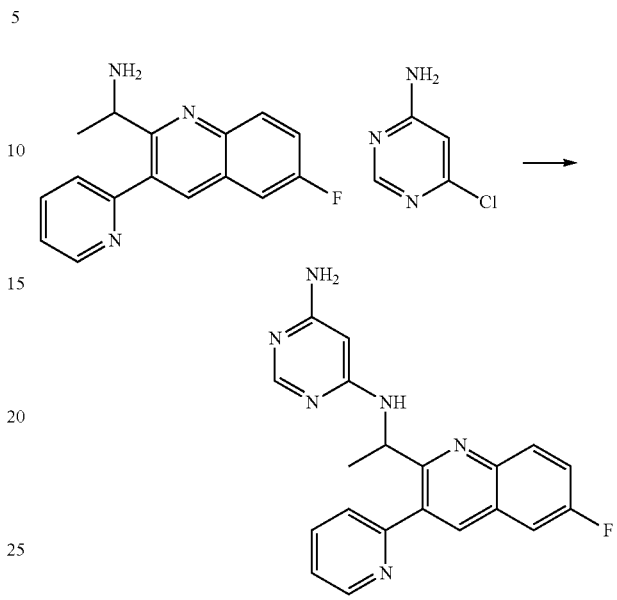

N4-(1-(6-Fluoro-3-(pyridin-2-yl)quinolin-2-yl)ethyl)pyrimidine-4,6-diamine. $^1$H NMR (400 MHz, DMSO-d$_6$) δ 8.73 (d, J=4.0 Hz, 1H), 8.34 (s, 1H), 8.11 (dd, J=9.2, 4.0 Hz, 1H), 7.98 (ddd, J=9.2, 9.2, 1.8 Hz, 1H), 7.82 (dd, J=9.2, 4.0 Hz, 1H), 7.77 (d, J=9.2 Hz, 1H), 7.72-7.65 (m, 2H), 7.47 (dd, J=9.2, 4.0 Hz, 1H), 5.94 (br, 2H), 5.52 (br, 1H), 1.38 (d, J=4.0 Hz, 3H). Mass Spectrum (ESI) m/e=361.1 (M+1).

Example 18: Preparation of N4-(1-(6-fluoro-3-(pyridin-2-yl)quinolin-2-yl)ethyl)pyrimidine-4,6-diamine

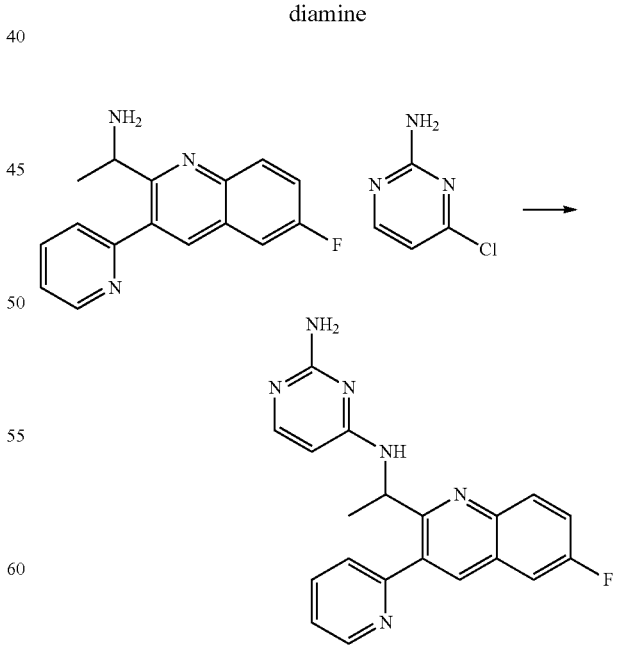

N4-(1-(6-Fluoro-3-(pyridin-2-yl)quinolin-2-yl)ethyl)pyrimidine-4,6-diamine. $^1$H NMR (400 MHz, DMSO-d$_6$) δ 8.55 (d, J=4.0 Hz, 1H), 8.14 (s, 1H), 7.89 (dd, J=9.2, 4.0 Hz, 1H), 7.78 (dd, J=9.2, 9.2 Hz, 1H), 7.63 (dd, J=9.2, 4.0 Hz, 1H), 7.57 (d, J=9.2 Hz, 1H), 7.49 (ddd, J=9.2, 9.2, 4.0 Hz, 1H), 7.33-7.24 (m, 2H), 5.55 (br, 1H), 5.31 (br, 2H), 1.23 (d, J=4.0 Hz, 3H). Mass Spectrum (ESI) m/e=361.1 (M+1).

Example 19: Preparation of 4-amino-6-(1-(6-fluoro-3-(pyridin-2-yl)quinolin-2-yl)ethylamino)pyrimidine-5-carbonitrile and 4-(1-(6-fluoro-3-(pyridin-2-yl)quinolin-2-yl)ethylamino)-6-hydroxypyrimidine-5-carbonitrile

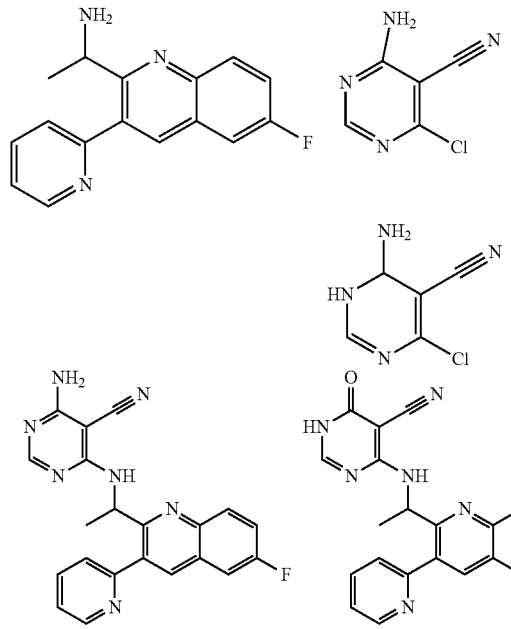

4-Amino-6-(1-(6-fluoro-3-(pyridin-2-yl)quinolin-2-yl)ethylamino)pyrimidine-5-carbonitrile. $^1$H NMR (400 MHz, DMSO-$d_6$) δ 8.73 (d, J=4.0 Hz, 1H), 8.44 (s, 1H), 8.07 (dd, J=9.2, 9.2 Hz, 1H), 7.99 (ddd, J=9.2, 9.2, 4.0 Hz, 1H), 7.95 (s, 1H), 7.85 (dd, J=9.2, 4.0 Hz, 1H), 7.78-7.72 (m, 2H), 7.48 (ddd, J=9.2, 9.2, 1.8 Hz, 1H), 7.26 (br, 1H), 5.92 (br, 1H), 1.30 (d, J=8.0 Hz, 3H). Mass Spectrum (ESI) m/e=386.0 (M+1). 4-(1-(6-Fluoro-3-(pyridin-2-yl)quinolin-2-yl)ethylamino)-6-hydroxypyrimidine-5-carbonitrile was obtained: $^1$H NMR (400 MHz, DMSO-$d_6$) δ 8.74 (d, J=4.0 Hz, 1H), 8.48 (s, 1H), 8.29 (d, J=9.2 Hz, 1H), 8.10 (dd, J=9.2, 4.0 Hz, 1H), 8.06 (s, 1H), 8.02 (ddd, J=9.2, 9.2, 1.8 Hz, 1H), 7.88 (dd, J=9.2, 4.0 Hz, 1H), 7.80-7.73 (m, 2H), 7.50 (ddd, J=9.2, 9.2, 2.3 Hz, 1H), 6.02 (br, 1H), 1.35 (d, J=8.0 Hz, 3H). Mass Spectrum (ESI) m/e=387.1 (M+1).

Example 20: 1-(6-Fluoro-3-(pyridin-2-yl)quinolin-2-yl)ethanone

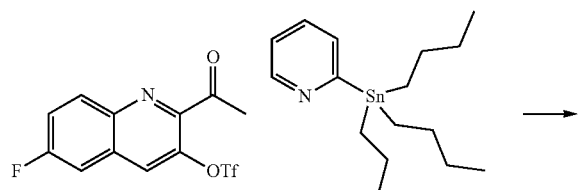

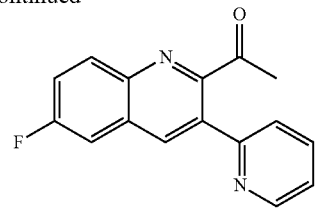

A mixture of 2-acetyl-6-fluoroquinolin-3-yl trifluoromethanesulfonate (2.0 g, 5.93 mmol), tetrakis(triphenylphosphine)palladium(0) (0.343 g, 0.297 mmol) and tributyl (2-pyridyl)tin (2.62 mL, 7.12 mmol) in 1,4-dioxane (30 mL) was heated to 110° C. under N$_2$ for 5 h. After cooling to rt, removal of the solvent, and purification of the residue by column chromatography on silica gel (EtOAc/hexane, 0:1 to 1:3) gave 1-(6-fluoro-3-(pyridin-2-yl)quinolin-2-yl)ethanone. $^1$H NMR (400 MHz, DMSO-$d_6$) δ 8.63 (s, 1H), 8.48 (d, J=4.0 Hz, 1H), 8.06 (dd, J=9.2, 4.0 Hz, 1H), 7.86-7.74 (m, 3H), 7.65 (ddd, J=9.2, 9.2, 4.0 Hz, 1H), 7.30-7.24 (m, 1H), 2.56 (s, 3H). Mass Spectrum (ESI) m/e=267.0 (M+1).

1-(6-Fluoro-3-(pyridin-2-yl)quinolin-2-yl)ethanol

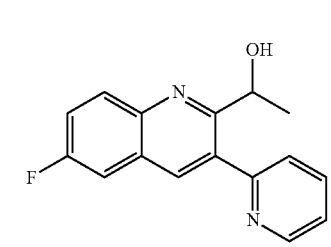

To 1-(6-fluoro-3-(pyridin-2-yl) quinolin-2-yl) ethanone (328.2 mg, 1.233 mmol) in THF (20 mL) sodium tetrahydroborate (46.6 mg, 1.233 mmol) was added at rt. The resulting mixture was stirred for 2 h. Filtration of the mixture on a pad of Celite™ and rinsing with EtOAc, evaporation of the solvent, and purification of the residue by flash chromatography over silica gel, gradient elution, 0-100% EtOAc in hexane gave 1-(6-fluoro-3-(pyridin-2-yl)quinolin-2-yl)ethanol. $^1$H NMR (400 MHz, DMSO-$d_6$) δ 8.57 (d, J=4.0 Hz, 1H), 8.28 (s, 1H), 7.98 (dd, J=9.2, 4.0 Hz, 1H), 7.86 (ddd, J=9.2, 9.2, 2.0 Hz, 1H), 7.69 (dd, J=9.2, 4.0 Hz, 1H), 7.63 (d, J=9.2 Hz, 1H), 7.56 (ddd, J=9.2, 9.2, 2.0 Hz, 1H), 7.35 (ddd, J=9.2, 9.2, 4.0 Hz, 1H), 5.31 (d, J=4.0 Hz, 1H), 5.02 (q, J=4.0 Hz, 1H), 1.19 (d, J=4.0 Hz, 3H). Mass Spectrum (ESI) m/e=269.0 (M+1).

2-(1-Chloroethyl)-6-fluoro-3-(pyridin-2-yl)quinoline

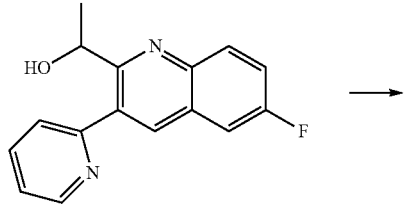

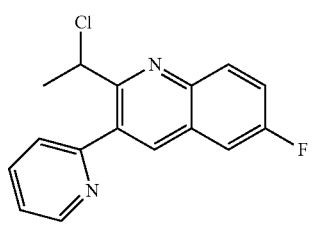

Sulfurous dichloride (0.058 mL, 0.792 mmol) was added to 1-(6-fluoro-3-(pyridin-2-yl) quinolin-2-yl) EtOH (213 mg, 0.792 mmol) in DCM (20 mL). After the addition, the mixture was stirred at rt for 2 min. The mixture was concd and the residue was diluted with DCM (10 mL), the organic phase was washed with 15 mL of diluted satd solution of NaHCO₃ (25%, v/v), followed by brine. The organic layers were dried and concd. Purification of the residue by flash chromatography over silica gel, using 20% hexane in EtOAc, gave 2-(1-chloroethyl)-6-fluoro-3-(pyridin-2-yl) quinoline. $^1$H NMR (400 MHz, DMSO-d$_6$) δ 8.80-8.75 (m, 1H), 8.49 (s, 1H), 8.18 (dd, J=9.2, 4.0 Hz, 1H), 8.04 (ddd, J=9.2, 9.2, 2.0 Hz, 1H), 7.88 (dd, J=9.2, 4.0 Hz, 1H), 7.82-7.73 (m, 2H), 7.53 (ddd, J=9.2, 9.2, 2.0 Hz, 1H), 6.11 (q, J=4.0 Hz, 1H), 1.98 (d, J=4.0 Hz, 3H). Mass Spectrum (ESI) m/e=287.0 (M+1).

(S)-4-Amino-1-(1-(6-fluoro-3-(pyridin-2-yl)quinolin-2-yl)ethyl)-1H-pyrazolo-[3,4-d]pyrimidine-3-carbonitrile and (R)-4-amino-1-(1-(6-fluoro-3-(pyridin-2-yl)quinolin-2-yl)ethyl)-1H-pyrazolo[3,4-d] pyrimidine-3-carbonitrile

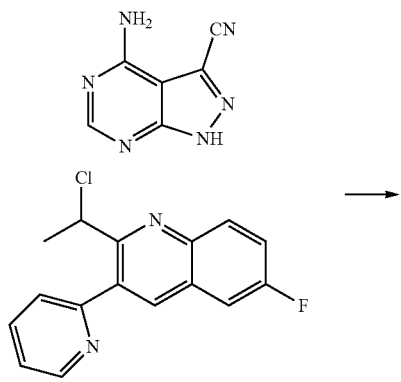

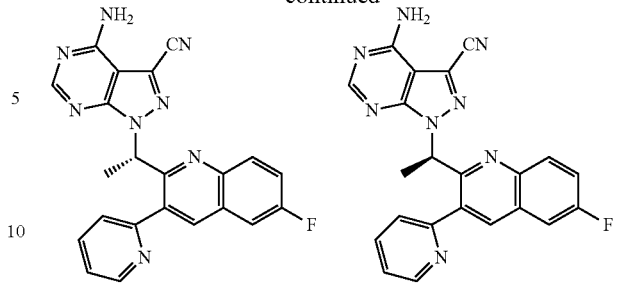

To a solution of 4-amino-1H-pyrazolo[3,4-d]pyrimidine-3-carbonitrile in DMF (2 mL) was added sodium hydride, 60% dispersion in mineral oil (27.8 mg, 0.694 mmol) with stirring at rt for 10 min. To the mixture was added a solution of 2-(1-chloroethyl)-6-fluoro-3-(pyridin-2-yl)quinoline (181 mg, 0.631 mmol) in DMF (1 mL) and the stirring continued at rt for 2 days. Then potassium carbonate (96 mg, 0.694 mmol) was added, and the stirring was continued at 70° C. for another 7 h. The mixture was diluted with Et₂O and the resulting solid triturated with Et₂O and filtered. The solid was rinsed with EtOAc. The filtrates were concd and purification of the residue by flash chromatography over silica gel, gradient elution, 50-100% EtOAc in hexane gave a racemic product. The racemic product was subjected to chiral separation (Chiralpak IA column, 30×250 mm, 5 mm), using 15% isopropanol in hexane as eluent, which gave (S)-4-amino-1-(1-(6-fluoro-3-(pyridin-2-yl)quinolin-2-yl) ethyl)-1H-pyrazolo[3,4-d]pyrimidine-3-carbonitrile. $^1$H NMR (500 MHz, DMSO-d$_6$) δ 8.51 (ddd, J=5.0, 2.0, 1.0 Hz, 1H), 8.37 (s, 1H), 8.11 (s, 1H), 8.08 (dd, J=9.3, 5.0 Hz, 1H), 7.85 (dd, J=9.3, 5.0 Hz, 1H), 7.80-7.70 (m, 2H), 7.42 (d, J=5.0 Hz, 1H), 7.25-7.21 (m, 1H), 7.03-6.95 (m, 1H), 1.90 (d, J=5.0 Hz, 3H). Mass Spectrum (ESI) m/e=411.1 (M+1); And (R)-4-amino-1-(1-(6-fluoro-3-(pyridin-2-yl)quinolin-2-yl)ethyl)-1H-pyrazolo[3,4-d]pyrimidine-3-carbonitrile. $^1$H NMR (500 MHz, DMSO-d$_6$) δ 8.51 (ddd, J=5.0, 2.0, 1.0 Hz, 1H), 8.37 (s, 1H), 8.11 (s, 1H), 8.08 (dd, J=9.3, 5.0 Hz, 1H), 7.85 (dd, J=9.3, 5.0 Hz, 1H), 7.80-7.70 (m, 2H), 7.42 (d, J=5.0 Hz, 1H), 7.25-7.21 (m, 1H), 7.03-6.95 (m, 1H), 1.90 (d, J=5.0 Hz, 3H). Mass Spectrum (ESI) m/e=411.1 (M+1).

Example 21: Preparation of 4-amino-6-(((1S)-1-(5-chloro-3-(2-pyridinyl)-2-quinolinyl)ethyl)amino)-5-pyrimidinecarbonitrile and Example 22: 4-amino-6-(((1R)-1-(5-chloro-3-(2-pyridinyl)-2-quinolinyl) ethyl)amino)-5-pyrimidinecarbonitrile 2-Amino-6-chlorobenzaldehyde

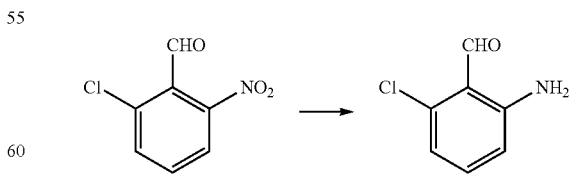

To a stirred solution of 2-chloro-6-nitrobenzaldehyde (2.0 g, 10.78 mmol) in 1M HCl (20 mL) was added iron powder (6.02 g, 108 mmol) and the reaction was heated at reflux for 2 h. After this time the reaction was cooled to rt and EtOAc was added. The separated organic layer was dried over MgSO₄, filtered and evaporated in vacuum to give 2-amino-6-chlorobenzaldehyde. Mass Spectrum (ESI) m/e=156.2 (M+1).

tert-Butyl 1-(5-chloro-3-(pyridin-2-yl)quinolin-2-yl)ethylcarbamate

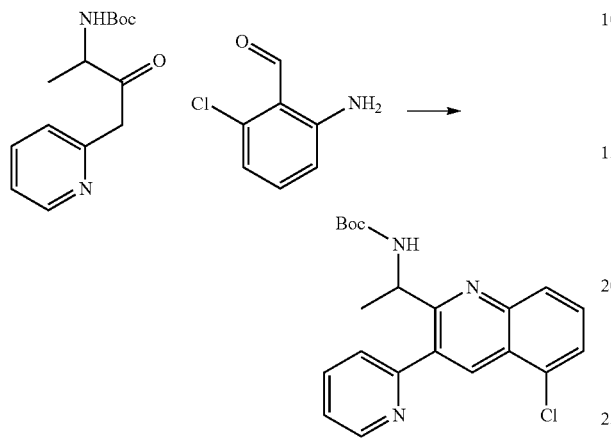

Tert-Butyl 3-oxo-4-(pyridin-2-yl)butan-2-ylcarbamate (0.600 g, 2.270 mmol) and 2-amino-6-chlorobenzaldehyde (0.530 g, 3.40 mmol) in EtOH (26.5 mL, 454 mmol) was treated with potassium hydroxide (0.382 g, 6.81 mmol). The reaction was heated at reflux for 1 h. After this time LC/MS shows desired product. The reaction was then cooled to rt and evaporated in vacuum. The product was purified by column chromatography (hexanes:EtOAc, 1:0 to 2:1) to give tert-butyl 1-(5-chloro-3-(pyridin-2-yl)quinolin-2-yl)ethylcarbamate.

1-(5-Chloro-3-(pyridin-2-yl)quinolin-2-yl)ethanamine

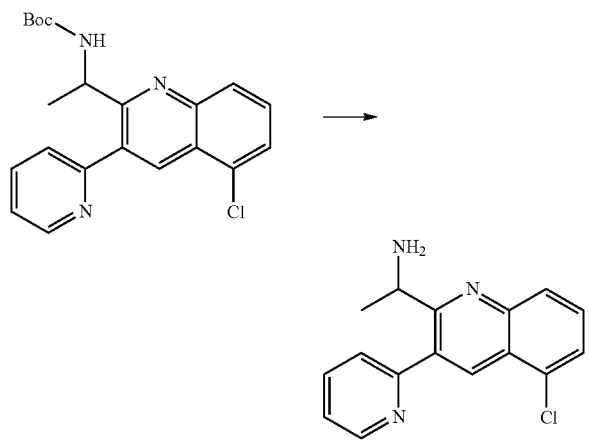

To a stirred solution of tert-butyl 1-(5-chloro-3-(pyridin-2-yl)quinolin-2-yl)ethylcarbamate (150 mg, 0.391 mmol) in DCM (2 mL) was added trifluoroacetic acid (602 μL, 7.82 mmol) and the reaction was stirred at rt for 2 h. After this time the reaction was evaporated in vacuum and the residue was dissolved in DCM (30 mL). HCl (1.0M) was then added and the separated aq. layer was washed with DCM (20 mL). The aq. layer was then basified to pH 14 and extracted with EtOAc (×2). The combined organic layers were dried over MgSO₄, filtered and evaporated in vacuum to give 1-(5-chloro-3-(pyridin-2-yl)quinolin-2-yl)ethanamine.

4-Amino-6-(((1S)-1-(5-chloro-3-(2-pyridinyl)-2-quinolinyl)ethyl)amino)-5-pyrimidinecarbonitrile and 4-amino-6-(((1R)-1-(5-chloro-3-(2-pyridinyl)-2-quinolinyl)ethyl)amino)-5-pyrimidinecarbonitrile

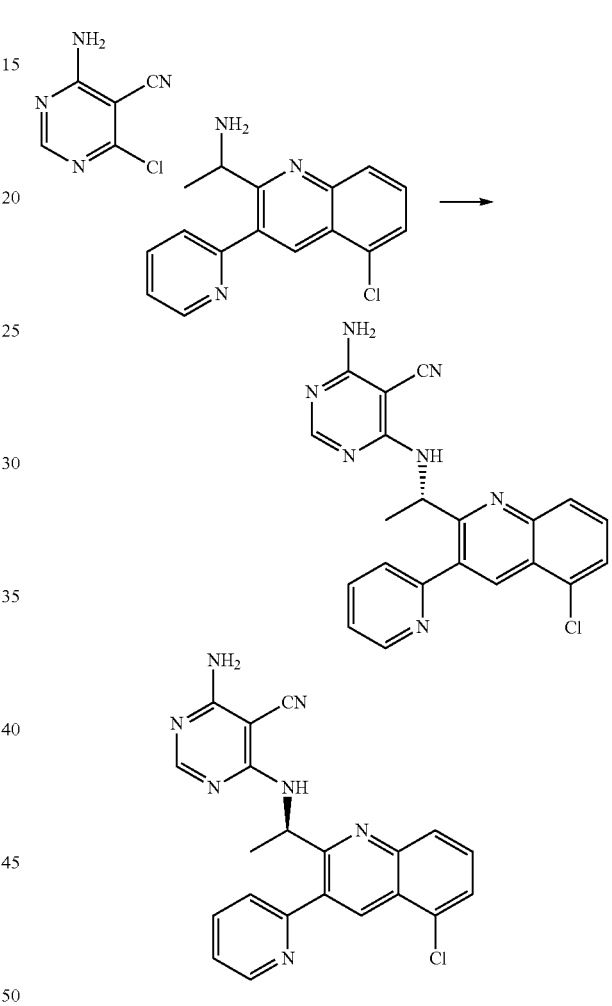

To a stirred solution of 1-(5-chloro-3-(pyridin-2-yl)quinolin-2-yl)ethanamine (95 mg, 0.335 mmol) in butanol (4.0 mL) was added Hunig's base (116 μL, 0.670 mmol) and 4-amino-6-chloropyrimidine-5-carbonitrile (56.9 mg, 0.368 mmol). The reaction was heated at 120° C. for 2 h. After this time the reaction was cooled to rt and the precipitate was collected and washed with hexanes to give a racemic mixture of 4-amino-6-(((1S, 1R)-1-(5-chloro-3-(2-pyridinyl)-2-quinolinyl)ethyl)-amino)-5-pyrimidinecarbonitrile. The racemic mixture was separated by chiral SFC to give 4-amino-6-(((1S)-1-(5-chloro-3-(2-pyridinyl)-2-quinolinyl)ethyl)-amino)-5-pyrimidinecarbonitrile 1H NMR (400 MHz, MeOH) δ ppm 8.76 (1H, ddd, J=4.9, 1.8, 1.0 Hz), 8.60 (1H, d, J=0.8 Hz), 8.11-8.14 (1H, m), 8.05 (1H, td, J=7.7, 1.8 Hz), 7.97 (1H, s), 7.75-7.83 (3H, m), 7.55 (1H, ddd, J=7.7, 4.9, 1.1 Hz), 5.98 (1H, q, J=6.8 Hz), 1.42 (3H, d, J=6.7 Hz)

Mass Spectrum (ESI) m/e=402.0 (M+1); and 4-amino-6-(((1R)-1-(5-chloro-3-(2-pyridinyl)-2-quinolinyl)ethyl)amino)-5-pyrimidinecarbonitrile (21 mg) 1H NMR (400 MHz, MeOH) δ ppm 8.76 (1H, ddd, J=4.9, 1.8, 1.0 Hz), 8.60 (1H, d, J=0.8 Hz), 8.11-8.14 (1H, m), 8.05 (1H, td, J=7.7, 1.8 Hz), 7.97 (1H, s), 7.75-7.83 (3H, m), 7.55 (1H, ddd, J=7.7, 4.9, 1.1 Hz), 5.98 (1H, q, J=6.8 Hz), 1.42 (3H, d, J=6.7 Hz). Mass Spectrum (ESI) m/e=402.0 (M+1). (Absolute configuration was assigned based on the PI3Kδ potency of each of the separated enantiomers).

Example 23: Preparation of 2-((1S)-1-((6-amino-5-cyano-4-pyrimidinyl)-amino)ethyl)-3-(2-pyridinyl)-5-quinolinecarbonitrile and Example 24: 2-((1R)-1-((6-amino-5-cyano-4-pyrimidinyl)amino)ethyl)-3-(2-pyridinyl)-5-quinolinecarbonitrile tert-Butyl 1-(5-cyano-3-(pyridin-2-yl)quinolin-2-yl)ethylcarbamate

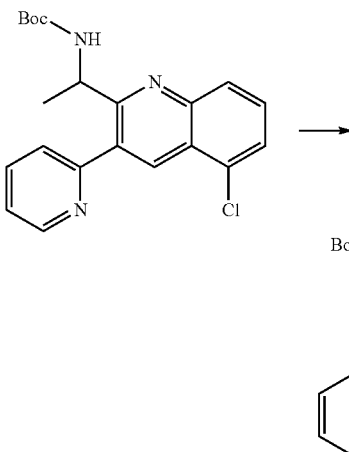

To a stirred solution of tert-butyl 1-(5-chloro-3-(pyridin-2-yl)quinolin-2-yl)ethylcarbamate (120 mg, 0.313 mmol) in NMP/Cy₂NMe (3.0 mL/1.0 mL) was added palladium bis(trifluoroacetate) (31.2 mg, 0.094 mmol), 2-(dicyclohexylphosphino)-2',4',6',-tri-i-propyl-1,1'-biphenyl (89 mg, 0.188 mmol) and cyanotributyltin (99 mg, 0.313 mmol) and the reaction was heated at 150° C. for 2 h. After this time the reaction was partitioned between EtOAc and water and the separated organic layer was dried, filtered and evaporated in vacuum. Column chromatography (hexanes:EtOAc, 1:0 to 1:1) gave tert-butyl 1-(5-cyano-3-(pyridin-2-yl)quinolin-2-yl)ethylcarbamate. Mass Spectrum (ESI) m/e=375.0

2-(1-Aminoethyl)-3-(pyridin-2-yl)quinoline-5-carbonitrile

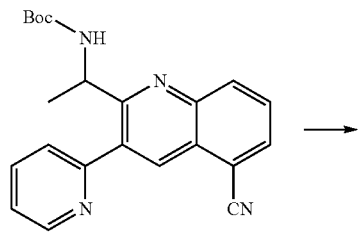

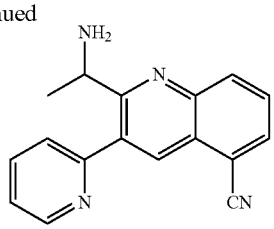

To a stirred solution of tert-butyl 1-(5-cyano-3-(pyridin-2-yl)quinolin-2-yl)ethylcarbamate (150 mg, 0.401 mmol) in DCM (1 mL) was added trifluoroacetic acid (309 μL, 4.01 mmol) and the reaction was stirred at rt for 90 min. After this time the reaction was evaporated in vacuum and the residue was dissolved in DCM (30 mL). HCl (1.0M) was then added and the separated aq. layer was washed with DCM (20 mL). The aq. layer was then basified to pH 14 and extracted with EtOAc. The separated organic layer was dried over MgSO₄, filtered and evaporated in vacuum to give 2-(1-aminoethyl)-3-(pyridin-2-yl)quinoline-5-carbonitrile. Mass Spectrum (ESI) m/e=275.2

2-((1S)-1-((6-Amino-5-cyano-4-pyrimidinyl)amino)ethyl)-3-(2-pyridinyl)-5-quinolinecarbonitrile and 2-((1R)-1-((6-amino-5-cyano-4-pyrimidinyl)-amino)ethyl)-3-(2-pyridinyl)-5-quinolinecarbonitrile

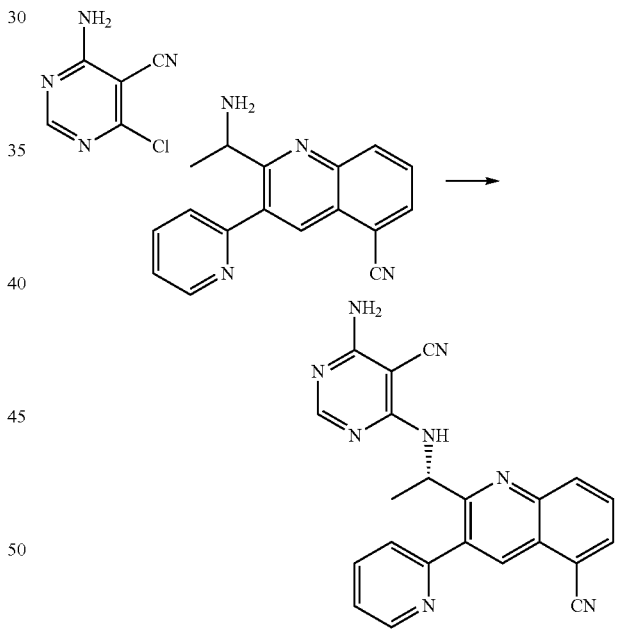

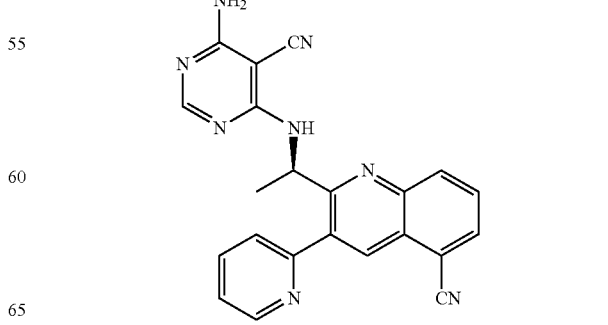

To a stirred solution of 2-(1-aminoethyl)-3-(pyridin-2-yl)quinoline-5-carbonitrile (43 mg, 0.157 mmol) in butanol (1.5 mL) was added Hunig's base (54.5 µL, 0.314 mmol) and 4-amino-6-chloropyrimidine-5-carbonitrile (26.6 mg, 0.172 mmol) and the reaction was heated at 110° C. for 2 h. After this time the reaction was allowed to cool to rt overnight. The resulting white solid was filtered and washed with hexanes to give a racemic mixture of 2-((1S, 1R)-1-((6-amino-5-cyano-4-pyrimidinyl)amino)ethyl)-3-(2-pyridinyl)-5-quinolinecarbonitrile. The racemic mixture was separated by chiral SFC to 2-((1S)-1-((6-amino-5-cyano-4-pyrimidinyl)amino)ethyl)-3-(2-pyridinyl)-5-quinolinecarbonitrile: 1H NMR (400 MHz, chloroform-d) δ ppm 8.85 (1H, ddd, J=4.9, 1.8, 1.0 Hz), 8.53 (1H, d, J=1.0 Hz), 8.45 (1H, dt, J=8.5, 1.1 Hz), 8.14 (1H, s), 8.02 (1H, dd, J=7.2, 1.4 Hz), 7.94 (1H, td, J=7.7, 1.8 Hz), 7.84 (1H, dd, J=8.6, 7.2 Hz), 7.65-7.73 (2H, m), 7.46 (1H, ddd, J=7.7, 4.8, 1.2 Hz), 6.17 (1H, dd, J=7.1, 6.7 Hz), 5.31 (2H, s), 1.41 (3H, d, J=6.7 Hz). Mass Spectrum (ESI) m/e=393.0; and 2-((1R)-1-((6-amino-5-cyano-4-pyrimidinyl)amino)ethyl)-3-(2-pyridinyl)-5-quinolinecarbonitrile: 1H NMR (400 MHz, chloroform-d) δ ppm 8.85 (1H, ddd, J=4.9, 1.8, 1.0 Hz), 8.53 (1H, d, J=1.0 Hz), 8.45 (1H, dt, J=8.5, 1.1 Hz), 8.14 (1H, s), 8.02 (1H, dd, J=7.2, 1.4 Hz), 7.94 (1H, td, J=7.7, 1.8 Hz), 7.84 (1H, dd, J=8.6, 7.2 Hz), 7.65-7.73 (2H, m), 7.46 (1H, ddd, J=7.7, 4.8, 1.2 Hz), 6.17 (1H, dd, J=7.1, 6.7 Hz), 5.31 (2H, s), 1.41 (3H, d, J=6.7 Hz). Mass Spectrum (ESI) m/e=393.0. (Absolute configuration was assigned based on the PI3Kδ potency of each of the separated enantiomers).

Example 25: Preparation of 4-amino-6-(((1S, 1R)-1-(3-(2-pyridinyl)-1,8-naphthyridin-2-yl)ethyl)amino)-5-pyrimidinecarbonitrile tert-Butyl 1-(3-(pyridin-2-yl)-1,8-naphthyridin-2-yl)ethylcarbamate

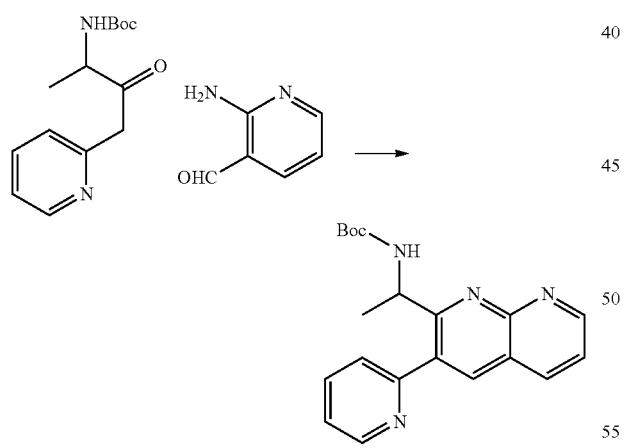

To a stirred solution of tert-butyl 3-oxo-4-(pyridin-2-yl)butan-2-ylcarbamate (0.6 g, 2.270 mmol) in EtOH (26.5 mL, 454 mmol) was added potassium hydroxide (0.382 g, 6.81 mmol) and 2-amino-3-formylpyridine (0.277 g, 2.270 mmol). The reaction was stirred at rt for 5 min and then it was heated at 90° C. for 2 h. After this time the reaction was cooled to rt, evaporated in vacuum and purified by column chromatography (hexanes:EtOAc, 1:0 to 0:1) to give tert-butyl 1-(3-(pyridin-2-yl)-1,8-naphthyridin-2-yl)ethylcarbamate.

1-(3-(Pyridin-2-yl)-1,8-naphthyridin-2-yl)ethanamine

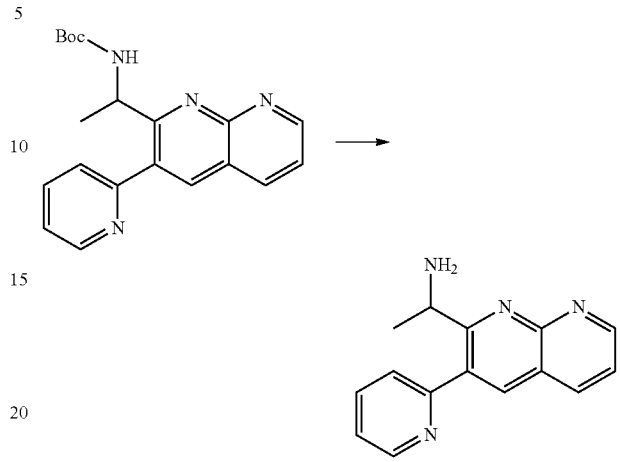

To a stirred solution of tert-butyl 1-(3-(pyridin-2-yl)-1,8-naphthyridin-2-yl)ethylcarbamate (45 mg, 0.128 mmol) in DCM (1.5 mL) was added trifluoroacetic acid (99 µL, 1.284 mmol). The reaction was stirred at rt for 4 h. After this time the reaction was partitioned between DCM (40 mL) and brine (10 mL). The separated organic layer was dried over MgSO₄, filtered and evaporated in vacuum to give 1-(3-(pyridin-2-yl)-1,8-naphthyridin-2-yl)ethanamine. Mass Spectrum (ESI) m/e=251.0.

4-Amino-6-(((1S, 1R)-1-(3-(2-pyridinyl)-1,8-naphthyridin-2-yl)ethyl)amino)-5-pyrimidinecarbonitrile

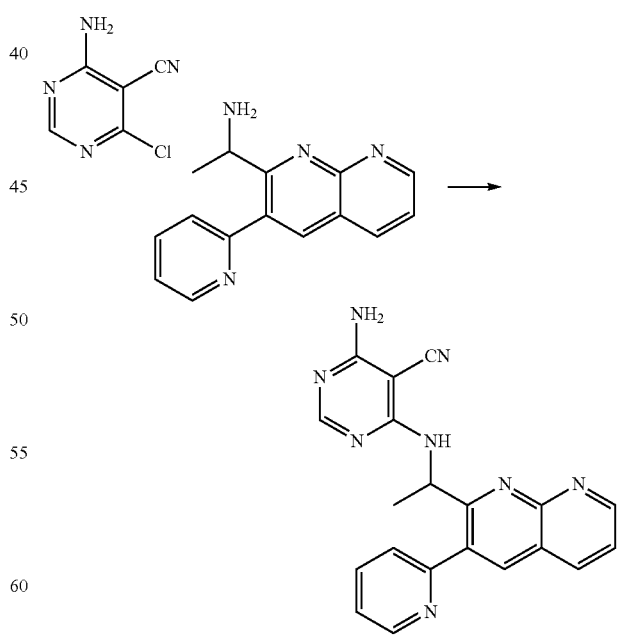

To a stirred solution of 1-(3-(pyridin-2-yl)-1,8-naphthyridin-2-yl)ethanamine (30 mg, 0.120 mmol), 4-amino-6-chloropyrimidine-5-carbonitrile (18.52 mg, 0.120 mmol) in n-butanol (1.5 mL) was added Hunig's base (41.7 µL, 0.240 mmol). The reaction was stirred at 120° C. for 4 h. After this time the reaction was cooled to rt and purified by reverse phase HPLC (gradient of acetonitrile:water, from 10% to 60%) to give a racemic mixture of 4-amino-6-(((1S,1R)-1-(3-(2-pyridinyl)-1,8-naphthyridin-2-yl)ethyl)amino)-5-pyrimidinecarbonitrile. 1H NMR (400 MHz, chloroform-d) δ ppm 9.18 (1H, dd, J=4.3, 2.0 Hz), 8.83 (1H, ddd, J=4.9, 2.0, 1.0 Hz), 8.23-8.28 (2H, m), 8.05 (1H, s), 7.90 (1H, td, J=7.7, 1.8 Hz), 7.66 (1H, dt, J=7.8, 1.2 Hz), 7.55 (1H, dd, J=8.1, 4.2 Hz), 7.42 (1H, ddd, J=7.6, 4.9, 1.2 Hz), 7.15-7.26 (1H, m), 6.06 (1H, t, J=7.1 Hz), 5.25-5.39 (2H, m), 1.56 (3H, d, J=6.7 Hz). Mass Spectrum (ESI) m/e=369.2.

Example 26: Preparation of 4-amino-6-(((1S, 1R)-1-(3-(2-pyridinyl)-1,6-naphthyridin-2-yl)ethyl) amino)-5-pyrimidinecarbonitrile tert-Butyl 1-(3-(pyridin-2-yl)-1,6-naphthyridin-2-yl)ethylcarbamate

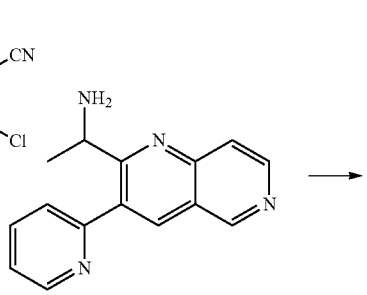

To a stirred solution of tert-butyl 3-oxo-4-(pyridin-2-yl)butan-2-ylcarbamate (0.20 g, 0.757 mmol) and 4-aminonicotinaldehyde (0.092 g, 0.757 mmol) in EtOH (8.84 mL, 151 mmol) was added potassium hydroxide (0.127 g, 2.270 mmol). The reaction was heated at reflux for 2 h. After this time the reaction was evaporated in vacuum and purified by column chromatography (hexanes:EtOAc, 1:0 to 0:1) to give tert-butyl 1-(3-(pyridin-2-yl)-1,6-naphthyridin-2-yl)ethylcarbamate.

1-(3-(Pyridin-2-yl)-1,6-naphthyridin-2-yl)ethanamine

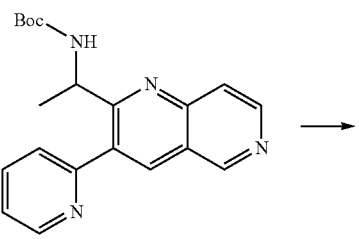

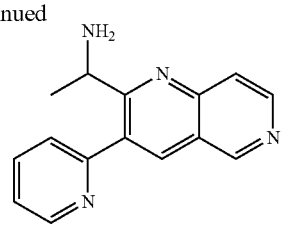

To a stirred solution of tert-butyl 1-(3-(pyridin-2-yl)-1,6-naphthyridin-2-yl)ethylcarbamate (30 mg, 0.086 mmol) in DCM (1.5 mL) was added trifluoroacetic acid (66.0 μL, 0.856 mmol). The reaction was stirred at rt for 4 h. After this time the reaction was partitioned between DCM (40 mL) and brine (10 mL). The separated organic layer was dried over MgSO₄, filtered and evaporated in vacuo to give 1-(3-(pyridin-2-yl)-1,6-naphthyridin-2-yl)ethanamine. Mass Spectrum (ESI) m/e=251.0.

4-Amino-6-(((1S, 1R)-1-(3-(2-pyridinyl)-1,6-naphthyridin-2-yl)ethyl)amino)-5-pyrimidinecarbonitrile

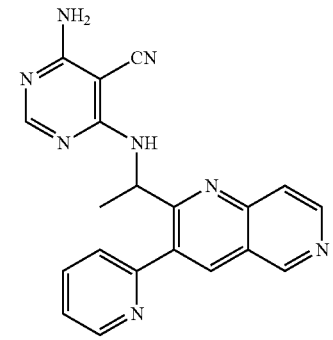

To a stirred solution of 1-(3-(pyridin-2-yl)-1,6-naphthyridin-2-yl)ethanamine (15 mg, 0.060 mmol) in butanol (1.5 mL) was added 4-amino-6-chloropyrimidine-5-carbonitrile (9.26 mg, 0.060 mmol) and N-ethyl-N-isopropylpropan-2-amine (20.93 μL, 0.120 mmol). The reaction was heated at 120° C. for 2 h. After this time the reaction was cooled to rt. The resulting precipitate was filtered and washed with hexanes to give racemic 4-amino-6-(((1S, 1R)-1-(3-(2-pyridinyl)-1,6-naphthyridin-2-yl)ethyl)amino)-5-pyrimidinecarbonitrile. 1H NMR (400 MHz, chloroform-d) δ ppm 9.33 (1H, s), 8.83 (2H, d, J=5.9 Hz), 8.33 (1H, s), 8.14 (1H, s), 8.02 (1H, d, J=5.9 Hz), 7.93 (1H, td, J=7.7, 1.8 Hz), 7.64 (2H, d, J=7.8 Hz), 7.44 (1H, ddd, J=7.6, 4.9, 1.0 Hz), 6.15 (1H, m), 5.28 (2H, bs), 1.38-1.43 (3H, m). Mass Spectrum (ESI) m/e=251.0. Mass Spectrum (ESI) m/e=369.2.

Example 27: Preparation of 4-amino-6-(1-(6-fluoro-4-(methylsulfonyl)-3-phenylquinolin-2-yl)ethyl-amino)-pyrimidine-5-carbonitrile 2,4-Dichloro-6-fluoro-3-phenylquinoline

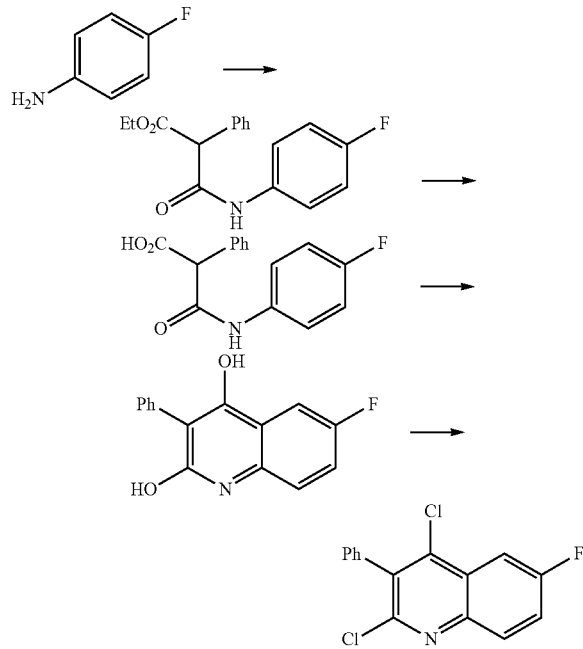

A stirred solution of diethyl 2-phenylmalonate (31.9 g, 135 mmol) in pyridine (14.56 mL, 180 mmol) was added 4-fluoroaniline (10.00 g, 90 mmol). The reaction mixture was heated to 130° C. Stirring continued for 16 h after which the LCMS show very little starting material. A further diethyl 2-phenylmalonate (31.9 g, 135 mmol) was added and stirring continued for 24 h. The reaction mixture was concd in vacuum. The residue was taken up in DCM (100 mL) and washed with NaHCO$_3$ (×2). The separated organic layer was dried, filtered and evaporated in vacuum. The residue was purified by column chromatography (hexanes:EtOAc, 3:1) to give crude ethyl 3-(4-fluorophenylamino)-3-oxo-2-phenylpropanoate as a red oil. A mixture of ethyl 3-(4-fluorophenylamino)-3-oxo-2-phenylpropanoate (12 g, crude) in THF-water (40 mL-10 mL) was treated with lithium hydroxide (1.0 eq) and stirred at rt for 1 h. After this time the reaction was acidified to pH 2 with concd HCl and then it was extracted with EtOAc. The separated organic layer was dried over MgSO$_4$, filtered and evaporated under reduced pressure to give 3-(4-fluorophenylamino)-3-oxo-2-phenylpropanoic acid, used as such for the next step. A mixture of 3-(4-fluorophenylamino)-3-oxo-2-phenylpropanoic acid in polyphosphoric acid (0.6M) was stirred at 130° C. for 2 h. After this time the reaction was cooled to rt and treated with 2M aq. sodium hydroxide until a precipitate formed. The precipitate was filtered and washed with 1M aq. sodium hydroxide and dried under vacuum to give 6-fluoro-3-phenylquinoline-2,4-diol. A mixture of 6-fluoro-3-phenylquinoline-2,4-diol (1 eq) and phosphorus oxychloride (10 eq) was heated at 100° C. for 2 h. After this time the reaction was cooled to rt and evaporated under reduced pressure. The resulting brown residue was taken up in DCM and washed with water. The separated organic layer was dried over MgSO$_4$, filtered and evaporated under reduced pressure. The product was then purified by column chromatography (using a 9:1 mixture of hexanes and EtOAc as eluant) to give 2,4-dichloro-6-fluoro-3-phenylquinoline. Mass Spectrum (ESI) m/e=292 (M+1).

4-Chloro-2-ethyl-6-fluoro-3-phenylquinoline

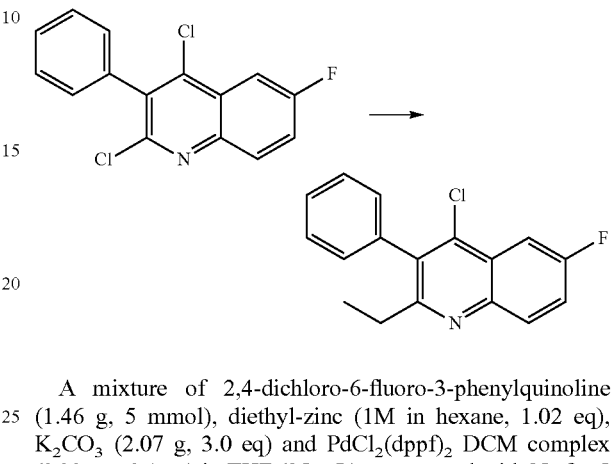

A mixture of 2,4-dichloro-6-fluoro-3-phenylquinoline (1.46 g, 5 mmol), diethyl-zinc (1M in hexane, 1.02 eq), K$_2$CO$_3$ (2.07 g, 3.0 eq) and PdCl$_2$(dppf)$_2$ DCM complex (366 mg, 0.1 eq) in THF (25 mL) was purged with N$_2$ for 5 min before heating to reflux. After 6 h, the reaction was quenched with NH$_4$Cl and extracted with EtOAc. The residue was purified by combi-flash on silica gel (EtOAc/hexane, 1/3) to give a white solid as 4-chloro-2-ethyl-6-fluoro-3-phenylquinoline. $^1$H-NMR (500 Hz, CDCl$_3$) δ 8.03 (dd, J=8.0, 4.0 Hz, 1H), 7.78 (dd, J=8.0, 4.0 Hz, 1H), 7.41-7.46 (m, 4H), 7.19-7.21 (m, 2H), 2.70 (q, J=8.0 Hz, 1H), 1.12 (t, J=8.0 Hz, 3H). Mass Spectrum (ESI) m/e=286 (M+1).

2-(1-Bromoethyl)-6-fluoro-4-(methylthio)-3-phenylquinoline

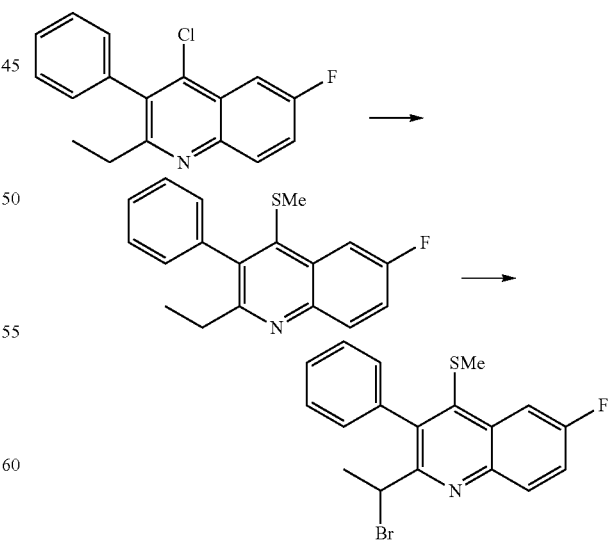

A mixture of 4-chloro-2-ethyl-6-fluoro-3-phenylquinoline (1.0 g, 3.5 mmol) and NaSMe (0.491 g, 2.0 eq) in DMF (8 mL) was heated to 60° C. under N$_2$ for 30 min. The reaction mixture was cooled to rt and partitioned between Et₂O and water. The organic layer was separated, washed with brine, dried and concd. The residue was purified on combi-flash on silica gel (EtOAc/hexane, 1/8) gave a white solid as 2-ethyl-6-fluoro-4-(methylthio)-3-phenylquinoline. 2-Ethyl-6-fluoro-4-(methylthio)-3-phenylquinoline (500 mg, 1.7 mmol) and 1,3-dibromo-5,5-dimethylhydantoin (336.5 mg, 0.7 eq) were suspended in carbon tetrachloride (20 mL). To the mixture was added benzoyl peroxide (41 mg, 0.1 eq) and the mixture was heated at reflux for 3 h. After cooling to rt, to the mixture was added satd aq. sodium bicarbonate solution (15 mL). The layers were separated and the aq. layer was extracted with CH₂CH₂ (10 mL×2). The combined organic layers were washed with brine (30 mL), dried over Na₂SO₄, filtered, and concd under reduced pressure to give an orange syrup. This material was used as such without further purification. Mass Spectrum (ESI) m/e=376, 378 (M+1).

2-(1-(6-Fluoro-4-(methylthio)-3-phenylquinolin-2-yl)ethyl)isoindoline-1,3-dione

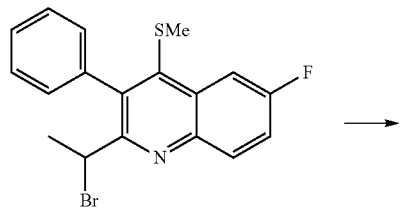

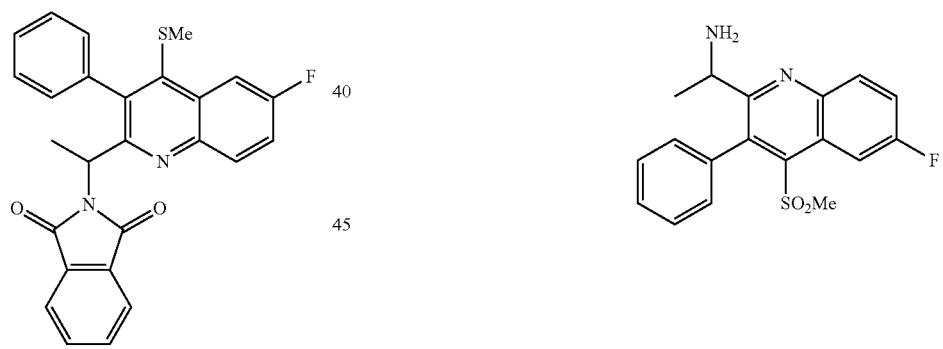

A mixture of 2-(1-bromoethyl)-6-fluoro-4-(methylthio)-3-phenylquinoline (120 mg, 0.32 mmol) in DMF (1.5 mL) was treated with phthalimide potassium salt (89 mg, 1.5 eq) overnight. At this time 50% SM remained. The reaction mixture was heated to 60° C. for 2 h. when LCMS showed completion. The reaction was repeated on a 500 mg scale. The two reaction mixtures were combined and partitioned between Et₂O and water. The organic layer was separated, washed with brine, dried, concd and purified by combi-flash (EtOAc/hexane, 0/1 to 1/3) to give a white solid as 2-(1-(6-fluoro-4-(methylthio)-3-phenylquinolin-2-yl)-ethyl)isoindoline-1,3-dione. ¹H-NMR (500 Hz, CDCl₃) δ 8.18 (dd, J=10, 5.0 Hz, 1H), 8.13 (dd, J=10, 4.0 Hz, 1H), 7.70-7.74 (m, 4H), 7.50-7.53 (m, 2H), 7.33-7.37 (m, 2H), 7.13-7.14 (m, 2H), 5.65 (q, J=10 Hz, 1H), 2.09 (s, 3H), 1.81 (d, J=5.0 Hz, 3H). Mass Spectrum (ESI) m/e=443 (M+1).

1-(6-Fluoro-4-(methylsulfonyl)-3-phenylquinolin-2-yl)ethanamine

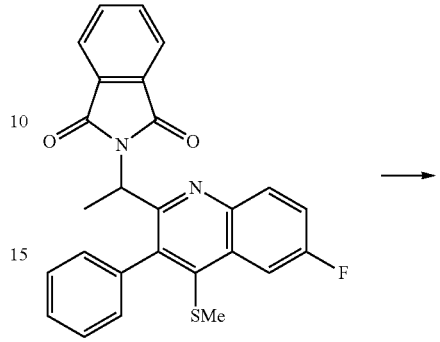

To solution of 2-(1-(6-fluoro-4-(methylthio)-3-phenylquinolin-2-yl)ethyl)isoindoline-1,3-dione (200 mg, 0.45 mmol) in THF (6 mL) and H₂O (2 mL) was added oxone (556 mg, 0.90 mmol, 2.0 eq) at rt. The resulting suspension was stirred at rt overnight. The reaction was incomplete. Oxone (556 mg, 2.0 eq) was added and the reaction mixture was stirred at rt overnight again. LCMS showed completion. The reaction mixture was partitioned between EtOAc and water. The organic layer was separated, washed with brine, dried, and concd. The residue was dissolved in EtOH (5 mL) and treated with NH₂NH₂ (0.5 mL) at 60° C. for 30 min. After cooling to rt, the reaction mixture was partitioned between EtOAc and water. The organic layer was separated, washed with water, brine, dried, and concd to give a pale yellow oil as 1-(6-fluoro-4-(methylsulfonyl)-3-phenylquinolin-2-yl) ethanamine. The material was used as such for the next step. Mass Spectrum (ESI) m/e=345 (M+1).

4-Amino-6-(1-(6-fluoro-4-(methylsulfonyl)-3-phenylquinolin-2-yl)ethyl-amino)-pyrimidine-5-carbonitrile

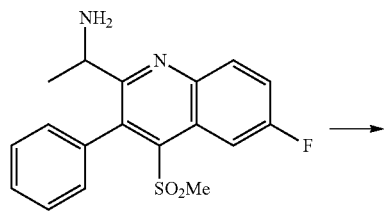

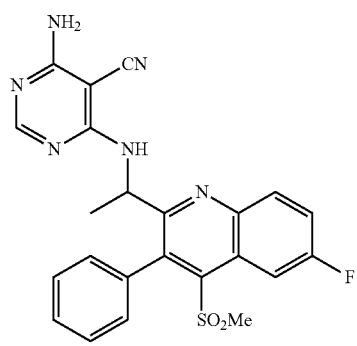

A mixture of 1-(6-fluoro-4-(methylsulfonyl)-3-phenylquinolin-2-yl)ethanamine (152 mg, 0.44 mmol), 4-amino-6-chloropyrimidine-5-carbonitrile (68.2 mg, 1.0 eq) and Hunig's base (0.094 mL, 1.2 eq) in n-BuOH (2 mL) was heated to 130° C. overnight. The mixture was cooled to rt, concd, then dissolved in DMF (2 mL) and purified by reverse HPLC. The fractions were combined, concd and filtered to give a white crystal as 4-amino-6-(1-(6-fluoro-4-(methylsulfonyl)-3-phenylquinolin-2-yl)ethylamino)pyrimidine-5-carbonitrile. $^1$H-NMR (400 Hz, DMSO-d$^6$) δ 8.61 (dd, J=8.0, 4.0 Hz, 1H), 8.25 (dd, J=8.0, 4.0 Hz, 1H), 7.87-7.92 (m, 2H), 7.37-7.50 (m, 5H), 7.25 (s, br, 2H), 5.09-5.13 (m, 1H), 3.22 (s, 3H), 1.29 (d, J=8.0 Hz, 3H). Mass Spectrum (ESI) m/e=463 (M+1).

Example 28: Preparation of 4-amino-6-(1-(6-fluoro-4-(methylsulfonyl)-3-phenylquinolin-2-yl)ethyl-amino)-pyrimidine-5-carbonitrile

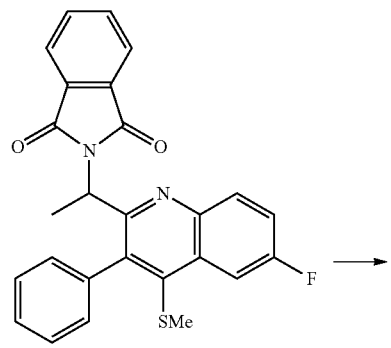

-continued

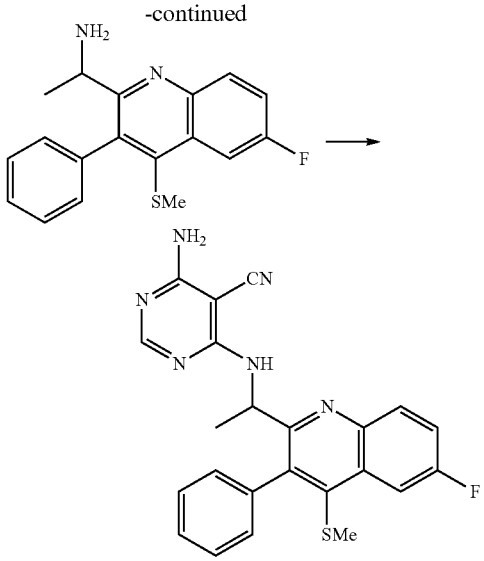

2-(1-(6-Fluoro-4-(methylthio)-3-phenylquinolin-2-yl)ethyl)isoindoline-1,3-dione (80 mg, 0.18 mmol) was dissolved in EtOH (2 mL) and treated with NH$_2$NH$_2$ (0.2 mL) at 60° C. for 30 min. After cooling to rt, the reaction mixture was partitioned between EtOAc and water. The organic layer was separated, washed with water, brine, dried, and concd to give a pale yellow oil. The material was used as such for the next step. A mixture of this material, 4-amino-6-chloropyrimidine-5-carbonitrile (28 mg, 1.0 eq) and Hunig's base (37.9 µL, 1.2 eq) in n-BuOH (2 mL) was heated to 130° C. overnight. The mixture was cooled to rt, concd, dissolved in DCM (2 mL) and purified by combi-flash (DCM/MeOH, 20/1) to give a pale yellow solid. $^1$H-NMR (400 Hz, DMSO-d$^6$) δ 8.06-8.12 (m, 2H), 7.86 (s, 1H), 7.72-7.75 (m, 1H), 7.34-7.47 (m, 5H), 7.22 (s, br, 2H), 5.14-5.17 (m, 1H), 2.07 (s, 3H), 1.21 (d, J=8.0 Hz, 3H). Mass Spectrum (ESI) m/e=431 (M+1).

Example 29: Preparation of 4-amino-6-((8-fluoro-3-(2-(methylsulfonyl)-phenyl)quinolin-2-yl)methyl-amino)pyrimidine-5-carbonitrile 2-(2-(Methylsulfinyl)phenyl)acetonitrile

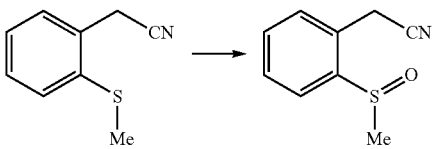 [SMILES: CSc1ccccc1CC#N ; CS(=O)c1ccccc1CC#N]

A mixture of oxone, monopersulfate compound (14.12 mL, 25.3 mmol), 2-(2-(methylthio)phenyl)acetonitrile (1.65 g, 10.11 mmol) and 5 g wet montmorillonite clay (ca. 20% water by weight) in DCM (60 mL) was stirred vigorously at rt for 4 h, after which time no starting material remained and predominantly sulfoxide was detected by LC-MS. The reaction was filtered to remove solids, rinsed with DCM, and the filtrate concd under reduced pressure to afford a colorless solid, which was used without further purification. Mass Spectrum (ESI) m/e=180.1 (M+1) (sulfoxide).

8-Fluoro-3-(2-(methylsulfinyl)phenyl)quinolin-2-amine

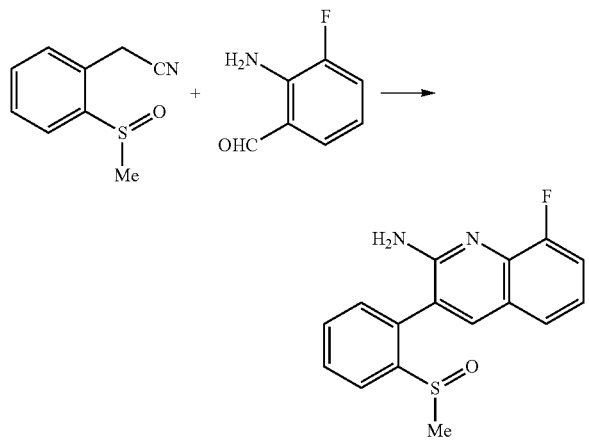

A mixture of sodium ethoxide (6.87 mL, 18.41 mmol), 2-(2-(methylsulfinyl)-phenyl)acetonitrile (1.65 g, 9.21 mmol) and 2-amino-3-fluorobenzaldehyde (1.281 g, 9.21 mmol) in EtOH (5 mL) was heated to 75° C. for 1 h then equilibrated to rt and left to sit at rt overnight. The reaction was partitioned between 100 mL water and 50 mL EtOAc and left to separate overnight. The organic layer was stirred over anhydrous magnesium sulfate, filtered and the filtrate concd under reduced pressure to afford dark yellow oil. The material was used without further purification. Mass Spectrum (ESI) m/e=301.1 (M+1).

8-Fluoro-3-(2-(methylsulfonyl)phenyl)quinolin-2-amine

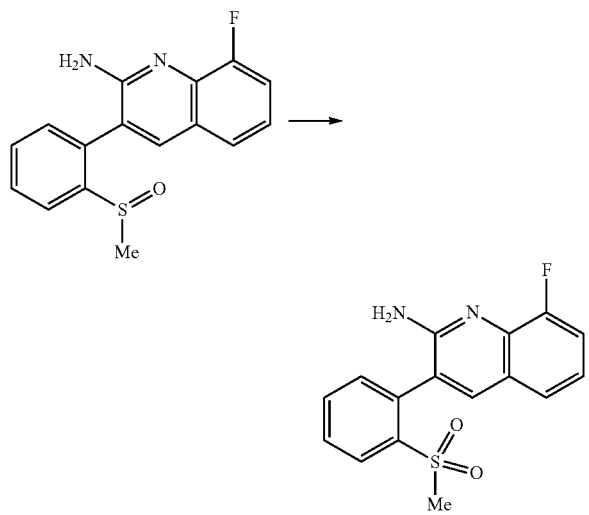

A mixture of 8-fluoro-3-(2-(methylsulfinyl)phenyl)quinolin-2-amine (2.26 g, 7.52 mmol), osmium tetroxide (0.118 mL, 0.376 mmol) and 4-methylmorpholine N-oxide (0.881 g, 7.52 mmol) in THF (20 mL) and water (5.00 mL) was stirred overnight at rt, after which time LC-MS indicated no starting material remained. The reaction was concd under reduced pressure and the concentrate partitioned between DCM and 10% sodium thiosulfate aq. solution. The organic layer was stirred over magnesium sulfate, filtered and the filtrate concd under reduced pressure to afford a yellow solid. The crude product was used without further purification. Mass Spectrum (ESI) m/e=317.0 (M+1).

8-Fluoro-3-(2-(methylsulfonyl)phenyl)quinolin-2(1H)-one

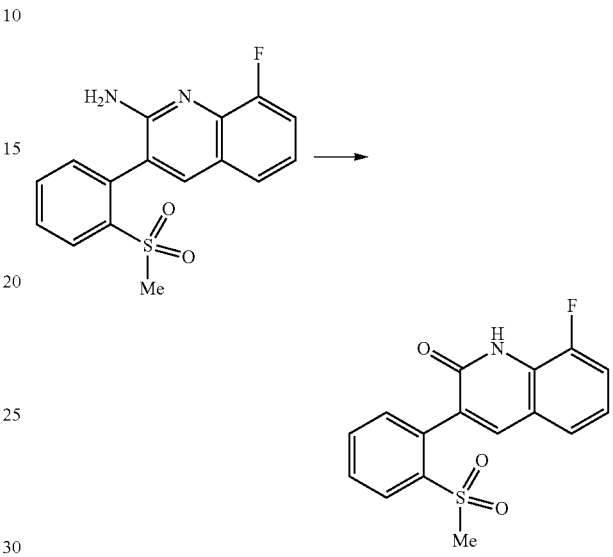

To a solution of 8-fluoro-3-(2-(methylsulfonyl)phenyl)quinolin-2-amine (205 mg, 0.648 mmol) dissolved in hydrochloric acid (2.00 mL, 65.8 mmol) at rt was added dropwise by pipet a solution of sodium nitrite (447 mg, 6.48 mmol) in water (2 mL) over a period of 2 min. Within several hours a precipitate developed. The precipitate was collected by filtration, rinsed with water and dried under vacuum over P₂O₅ to afford product as a colorless solid. Mass Spectrum (ESI) m/e=318.1 (M+1).

2-Chloro-8-fluoro-3-(2-(methylsulfonyl)phenyl)quinoline

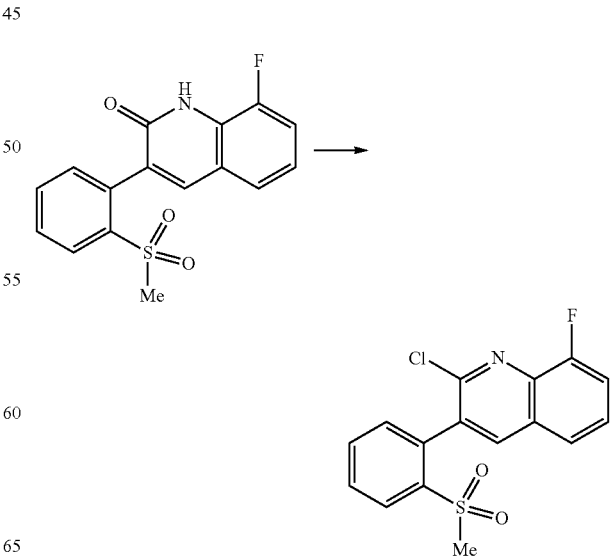

A mixture of 8-fluoro-3-(2-(methylsulfonyl)phenyl)quinolin-2(1H)-one (200 mg, 0.630 mmol) in phosphorus oxychloride (3 mL, 32.2 mmol) was heated to 120° C. After 24 h the reaction was concd under reduced pressure and the residue partitioned between 25 mL ea. DCM and satd aq. sodium bicarbonate solution. The organic separation was stirred over anhydrous magnesium sulfate, filtered and the filtrate concd under reduced pressure to afford product as a colorless solid. Mass Spectrum (ESI) m/e=336.0 (M+1).

8-Fluoro-3-(2-(methylsulfonyl)phenyl)-2-vinylquinoline

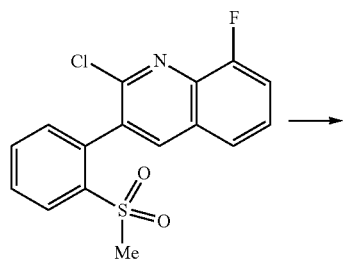

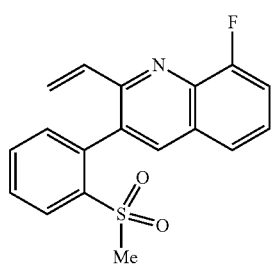

A mixture of cesium carbonate (256 mg, 0.786 mmol), 1,1'-bis (diphenyl-phosphino)ferrocene-palladium(ii)dichloride DCM complex (32.1 mg, 0.039 mmol), 2-chloro-8-fluoro-3-(2-(methylsulfonyl)phenyl)quinoline (132 mg, 0.393 mmol) and potassium vinyltrifluoroborate (263 mg, 1.966 mmol) in THF (3 mL) and water (0.500 mL) was purged with nitrogen then heated in a microwave at 120° C. for 1 h, after which time LC-MS indicated only desired product present. The reaction was partitioned between 25 mL EtOAc and 25 mL water. The organic layer was washed with 25 mL brine then stirred over anhydrous magnesium sulfate, filtered and the filtrate concd under reduced pressure to afford an intense orange-red film. The product was isolated as a colorless film by chromatography on silica gel eluting with 5% EtOAc in DCM. Mass Spectrum (ESI) m/e=328.1 (M+1).

8-Fluoro-3-(2-(methylsulfonyl)phenyl)quinoline-2-carbaldehyde

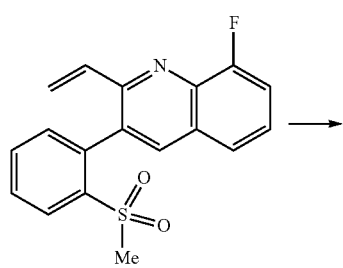

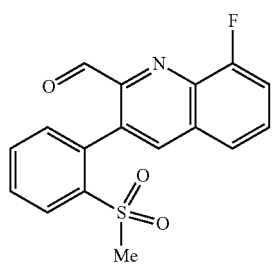

A mixture of 8-fluoro-3-(2-(methylsulfonyl)phenyl)-2-vinylquinoline (88 mg, 0.269 mmol), sodium periodate (172 mg, 0.806 mmol) and osmium tetroxide (4.22 µL, 0.013 mmol) in THF (3 mL) and water (1 mL) was stirred at rt for 2.5 h after which time a white precipitate had developed. The precipitate was removed by filtration and the filtrate partitioned between 25 mL ea EtOAc and water. The organic layer was washed with 25 mL brine then stirred over anhydrous magnesium sulfate, filtered and the filtrate concd under reduced pressure to afford a tan solid. The product was isolated as a colorless solid by chromatography on silica gel, eluting with 5% EtOAc in DCM. Mass Spectrum (ESI) m/e=330.1 (M+1).

(8-Fluoro-3-(2-(methylsulfonyl)phenyl)quinolin-2-yl)methanol

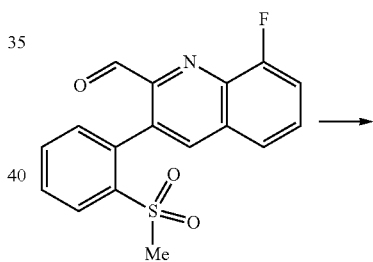

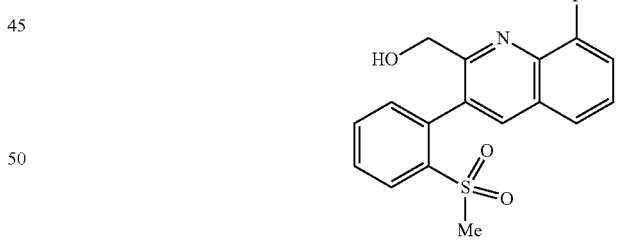

To a suspension of 8-fluoro-3-(2-(methylsulfonyl)phenyl)quinoline-2-carbaldehyde (57 mg, 0.173 mmol) in MeOH (4 mL) at rt was added sodium borohydride (9.82 mg, 0.260 mmol). The reaction was stirred at rt for 30 min, after which time the LC-MS indicated only the desired product was present. Water was added to the reaction and the MeOH was removed under reduced pressure. The residue was partitioned between EtOAc and water. The organic layer was stirred over anhydrous magnesium sulfate, filtered and the filtrate concd under reduced pressure to afford a colorless solid which was used without further purification. Mass Spectrum (ESI) m/e=332.0 (M+1).

(8-Fluoro-3-(2-(methylsulfonyl)phenyl)quinolin-2-yl)methyl methanesulfonate

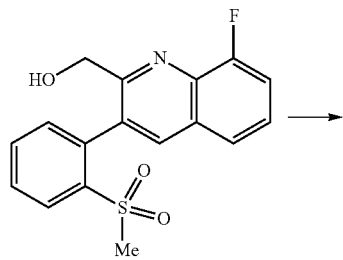

To a solution of MsCl (0.017 mL, 0.217 mmol) dissolved in DCM (3 mL) cooled by an ice bath was added a solution of (8-fluoro-3-(2-(methylsulfonyl)phenyl)-quinolin-2-yl) methanol (60 mg, 0.181 mmol) and triethylamine (0.038 mL, 0.272 mmol) in 2 mL DCM. After 20 min TLC and LC-MS indicated some starting material remained and an additional 0.2 equivalents each of MsCl and triethylamine were added. After 1 h the reaction was diluted with 20 mL DCM and 20 mL water was added. The organic layer was stirred over anhydrous magnesium sulfate, filtered and the filtrate concd under reduced pressure to afford a colorless film. The product was used without further purification. Mass Spectrum (ESI) m/e=410.0 (M+1).

2-(Azidomethyl)-8-fluoro-3-(2-(methylsulfonyl)phenyl)quinoline

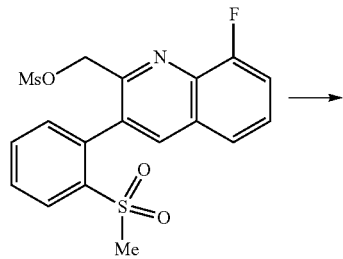

A mixture of sodium azide (22.23 mg, 0.342 mmol) and 18-crown-6 (2.259 mg, 8.55 μmol) in acetonitrile (2 mL) was stirred for 20 min at rt before (8-fluoro-3-(2-(methylsulfonyl)phenyl)quinolin-2-yl)methyl methanesulfonate (70 mg, 0.171 mmol) in 1 mL acetonitrile was added. The reaction mixture was stirred overnight at rt. After 16 h, TLC and LC-MS indicated no starting material remained and desired product predominated. The mixture was filtered and the filtrate concd under reduced pressure. The concentrate was partitioned between 25 mL each DCM and water. The organic separation was stirred over anhydrous magnesium sulfate, filtered and the filtrate concd under reduced pressure to afford a colorless film. The product was used without further purification. Mass Spectrum (ESI) m/e=357.1 (M+1).

(8-Fluoro-3-(2-(methylsulfonyl)phenyl)quinolin-2-yl)methanamine

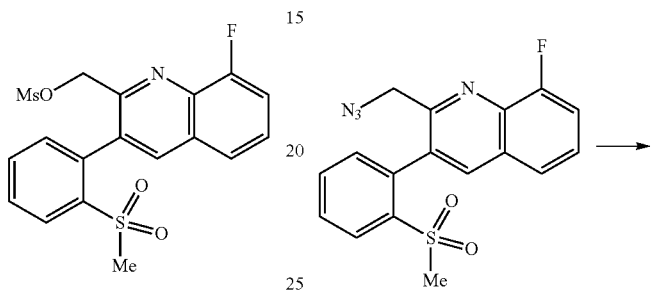

A mixture of triphenylphosphine (56.7 mg, 0.216 mmol) and 2-(azidomethyl)-8-fluoro-3-(2-(methylsulfonyl)phenyl) quinoline (70 mg, 0.196 mmol) in THF (3 mL) was stirred at rt overnight. After 22 h, LC-MS indicated no starting azide remained and 200 uL water was added to the reaction. The reaction was stirred at rt for 24 h then concd under reduced pressure. The concentrate was partitioned between 25 mL each Et₂O and 1N aq. hydrochloric acid solution. The aq. acidic layer was made alkaline with sodium hydroxide and extracted with 2×25 mL DCM. The combined organic layers were stirred over anhydrous magnesium sulfate, filtered and the filtrate concd under reduced pressure to afford a colorless film. The product was used without further purification. Mass Spectrum (ESI) m/e=331.1 (M+1).

4-Amino-6-((8-fluoro-3-(2-(methylsulfonyl)phenyl)quinolin-2-yl)methylamino)-pyrimidine-5-carbonitrile

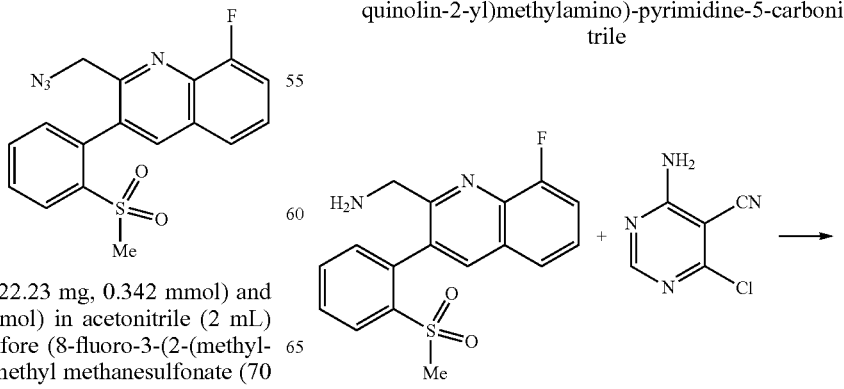

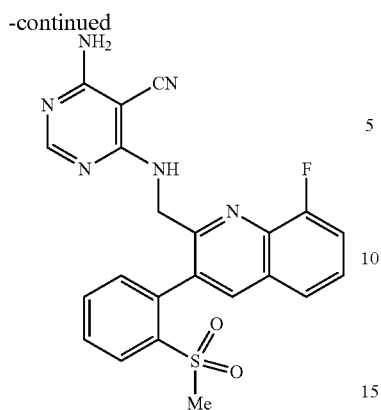

A mixture of (8-fluoro-3-(2-(methylsulfonyl)phenyl)quinolin-2-yl)methanamine (28 mg, 0.085 mmol), 4-amino-6-chloropyrimidine-5-carbonitrile (13.75 mg, 0.089 mmol) and diisopropylethylamine (0.016 mL, 0.093 mmol) in butan-1-ol (2 mL) was heated in a 80° C. oil bath. A precipitate developed within 60 min. After 2 h LC-MS indicated no starting amine remained and the reaction mixture was removed from the hot oil bath and equilibrated to rt for 90 min, after which time the precipitate was collected by filtration, rinsing with 5 mL 1:1 Et$_2$O:EtOH at rt. The isolated solid was dried under vacuum. $^1$H NMR (400 MHz, DMSO-d$_6$) δ ppm 8.42 (d, J=1.6 Hz, 1H), 8.10-8.21 (m, 1H), 7.91 (s, 1H), 7.75-7.89 (m, 3H), 7.55-7.73 (m, 4H), 7.30 (br. s., 2H), 4.48-4.64 (m, 1H), 4.34-4.48 (m, 1H), 3.03 (s, 3H). Mass Spectrum (ESI) m/e=449.0 (M+1).

Example 30: 4-Amino-6-((8-fluoro-3-(pyridin-2-yl)quinolin-2-yl)methyl-amino)pyrimidine-5-carbonitrile

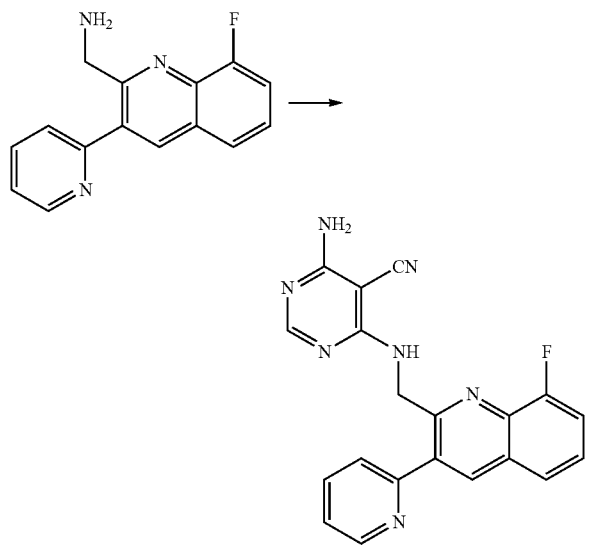

To a reaction vessel was added 4-amino-6-chloropyrimidine-5-carbonitrile (24.35 mg, 0.158 mmol), diisopropylethylamine (31.4 μL, 0.180 mmol), (8-fluoro-3-(pyridin-2-yl)quinolin-2-yl)methanamine (38 mg, 0.150 mmol), and 1.5 mL of n-butanol. The reaction was heated to 115° C. for 1 h, then cooled back to rt and filtered. The solid product was washed with cold 2:1 Et$_2$O/EtOH and dried under high vacuum to afford 4-amino-6-((8-fluoro-3-(pyridin-2-yl)quinolin-2-yl)-methylamino)pyrimidine-5-carbonitrile. $^1$H NMR (500 MHz, DMSO-d6) δ 8.76 (d, J=4.2 Hz, 1H), 8.59 (s, 1H), 8.03 (td, J=7.6, 1.5 Hz, 1H), 7.96 (m, 1H), 7.91 (m, 1H), 7.83 (m, 2H), 7.64 (m, 2H), 7.51 (dd, J=6.9, 4.9 Hz, 1H), 7.27 (br s, 2H), 4.99 (d, J=4.9 Hz, 1H). Mass Spectrum (ESI) m/e=372.1 (M+1).

Specific Example of Method E 2-((5-Fluoro-3-(2-(methylsulfonyl)phenyl)quinolin-2-yl)methyl)isoindoline-1,3-dione

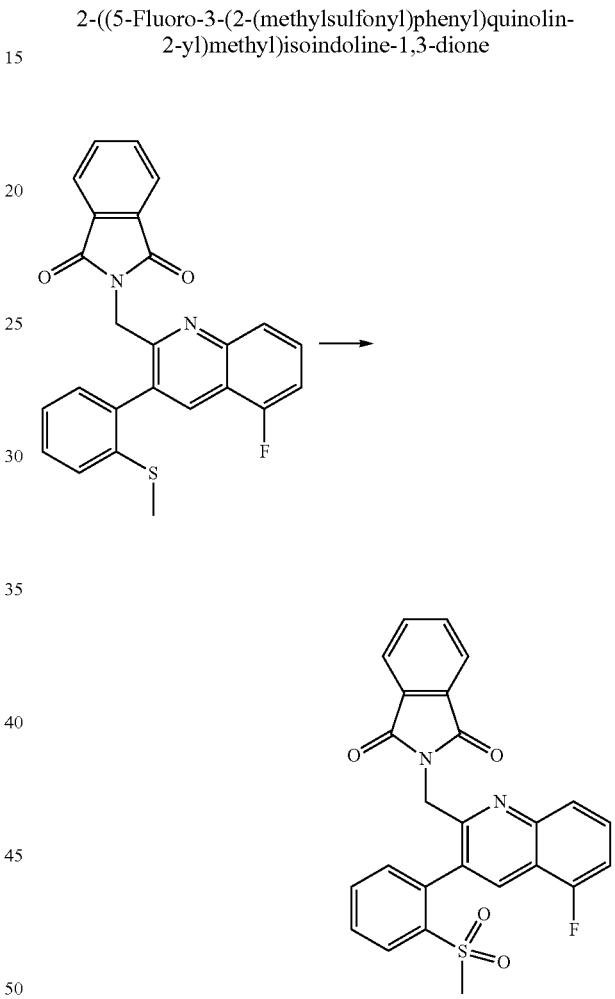

Substrate 2-((5-fluoro-3-(2-(methylthio)phenyl)quinolin-2-yl)methyl)isoindoline-1,3-dione (102 mg, 0.238 mmol) was dissolved in 2.4 mL of DCM. To this solution was added 288 mg of wet montmorillonite clay (0.2 g water per 1 g clay, 1.2 g wet clay per mmole of substrate) and oxone (366 mg, 0.595 mmol, 2.5 eq). The reaction was stirred overnight, filtered, and concd to afford 2-((5-fluoro-3-(2-(methylsulfonyl)phenyl)quinolin-2-yl)methyl)isoindoline-1,3-dione. $^1$H NMR (500 MHz, DMSO-d6) δ 8.43 (d, J=0.73 Hz, 1H), 8.20 (dd, J=8.1, 1.5 Hz, 1H), 7.89 (m, 5H), 7.81 (td, J=7.6, 1.5 Hz, 1H), 7.71 (m, 1H), 7.62 (m, 2H), 7.45 (ddd, J=9.8, 7.8, 0.7 Hz, 1H), 4.75 (ABq J$_{AB}$=16.9 Hz, Δv=122 Hz), 3.03 (s, 3H). Mass Spectrum (ESI) m/e=461.0 (M+1).

The compounds below were made via the same general methods described above:

Example 31: 4-Amino-6-((8-fluoro-3-phenylquinolin-2-yl)methylamino)-pyrimidine-5-carbonitrile

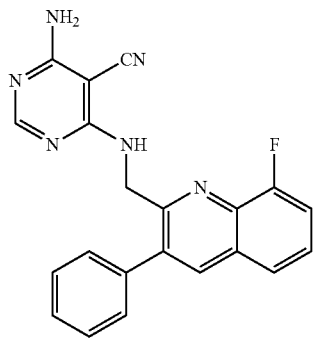 [SMILES: N#Cc1c(N)ncnc1NCc1nc2c(F)cccc2cc1-c1ccccc1]

4-Amino-6-((8-fluoro-3-phenylquinolin-2-yl)methylamino)pyrimidine-5-carbonitrile was synthesized from 2-((8-fluoro-3-phenylquinolin-2-yl)methyl)isoindoline-1,3-dione by Method D. $^1$H NMR (500 MHz, DMSO-d6) δ 8.33 (d, J=1.5 Hz, 1H), 7.95 (s, 1H), 7.86 (m, 1H), 7.70 (t, J=4.6 Hz, 1H), 7.62 (m, 2H), 7.57-7.47 (series of m, 5H), 7.31 (br s, 2H), 4.75 (d, J=4.6 Hz, 1H). Mass Spectrum (ESI) m/e=371.0 (M+1).

2-((3-Bromo-5-fluoroquinolin-2-yl)methyl)isoindoline-1,3-dione

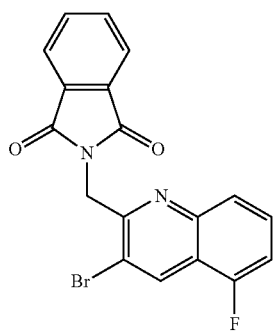 [SMILES: O=C1c2ccccc2C(=O)N1Cc1nc2cccc(F)c2cc1Br]

2-((3-Bromo-5-fluoroquinolin-2-yl)methyl)isoindoline-1,3-dione was synthesized from 2-amino-6-fluorobenzoic acid via Method A. $^1$H NMR (500 MHz, DMSO-d6) δ 8.81 (s, 1H), 7.99 (m, 2H), 7.94 (m, 2H), 7.69 (dt J=8.3, 6.1 Hz, 1H), 7.51 (d, J=8.6 Hz, 1H), 7.47 (ddd J=10.0, 7.8, 0.7 Hz, 1H), 5.16 (s, 2H). Mass Spectrum (ESI) m/e=385.0, 387.0 (M+1).

Example 32: 4-amino-6-((5-fluoro-3-phenylquinolin-2-yl)methylamino)-pyrimidine-5-carbonitrile

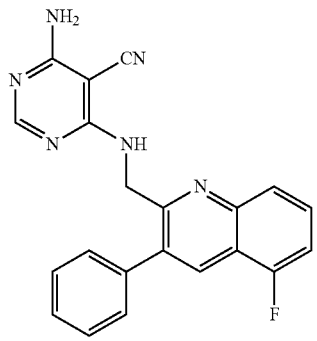 [SMILES: N#Cc1c(N)ncnc1NCc1nc2cccc(F)c2cc1-c1ccccc1]

4-Amino-6-((5-fluoro-3-phenylquinolin-2-yl)methylamino)pyrimidine-5-carbonitrile was synthesized from 2-((3-bromo-5-fluoroquinolin-2-yl)methyl)isoindoline-1,3-dione and phenylboronic acid via Methods C and D. $^1$H NMR (500 MHz, DMSO-d6) δ 8.25 (s, 1H), 7.94 (s, 1H), 7.86 (d, J=8.6 Hz, 1H), 7.81 (td, J=7.8, 6.1 Hz, 1H), 7.70 (t, J=4.6 Hz, 1H), 7.57 (m, 4H), 7.49 (m, 2H), 7.31 (br s, 2H), 4.75 (d, J=4.6 Hz, 1H). Mass Spectrum (ESI) m/e=371.0 (M+1).

Example 33: 4-Amino-6-((5-fluoro-3-(3-fluorophenyl)quinolin-2-yl)methyl-amino)pyrimidine-5-carbonitrile

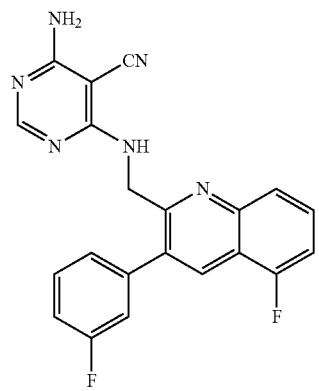 [SMILES: N#Cc1c(N)ncnc1NCc1nc2cccc(F)c2cc1-c1cccc(F)c1]

4-Amino-6-((5-fluoro-3-(3-fluorophenyl)quinolin-2-yl)methylamino)pyrimidine-5-carbonitrile was synthesized from 2-((3-bromo-5-fluoroquinolin-2-yl)methyl)-isoindoline-1,3-dione and 3-fluorophenylboronic acid via Methods C and D. $^1$H NMR (500 MHz, DMSO-d6) δ 8.29 (s, 1H), 7.94 (s, 1H), 7.86 (d, J=8.3 Hz, 1H), 7.81 (td, J=7.8, 6.1 Hz, 1H), 7.70 (t, J=4.6 Hz, 1H), 7.57 (d, J=8.1, 6.1 Hz, 1H), 7.31 (m, 3H), 4.76 (d, J=4.9 Hz, 2H). Mass Spectrum (ESI) m/e=389.0 (M+1).

Example 34: 4-Amino-6-((3-(3,5-difluorophenyl)-5-fluoroquinolin-2-yl)methylamino)pyrimidine-5-carbonitrile

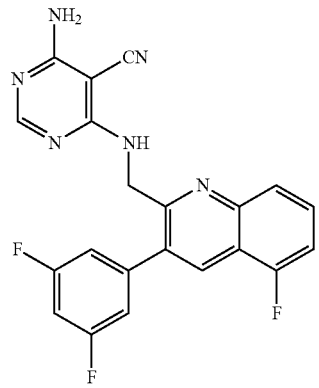 [SMILES: N#Cc1c(N)ncnc1NCc1nc2cccc(F)c2cc1-c1cc(F)cc(F)c1]

4-Amino-6-((3-(3,5-difluorophenyl)-5-fluoroquinolin-2-yl)methylamino)pyrimidine-5-carbonitrile was synthesized from 2-((3-bromo-5-fluoroquinolin-2-yl)-methyl)isoindoline-1,3-dione and 3, 5-difluorophenylboronic acid via Methods C and D. ¹H NMR (500 MHz, DMSO-d6) δ 8.32 (s, 1H), 7.94 (s, 1H), 7.87 (d, J=8.6 Hz, 1H), 7.82 (td, J=7.6, 5.9 Hz, 1H), 7.69 (t, J=4.6 Hz, 1H), 7.50 (dd, J=9.0, 7.6 Hz, 1H), 7.40-7.25 (series of m, 5), 4.79 (d, J=4.9 Hz, 1H). Mass Spectrum (ESI) m/e=407.0 (M+1).

Example 35: 4-Amino-6-((5-fluoro-3-(2-(methylsulfonyl)phenyl)quinolin-2-yl)methylamino)pyrimidine-5-carbonitrile

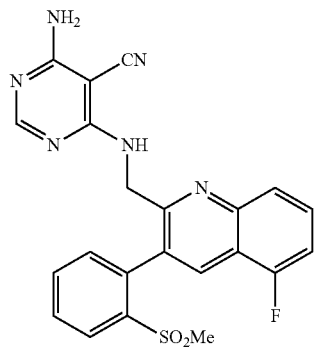 [SMILES: CS(=O)(=O)c1ccccc1-c1cc2c(F)cccc2nc1CNc1ncnc(N)c1C#N]

4-Amino-6-((5-fluoro-3-(2-(methylsulfonyl)phenyl)quinolin-2-yl)methylamino)-pyrimidine-5-carbonitrile was synthesized from 2-((3-bromo-5-fluoroquinolin-2-yl)methyl)isoindoline-1,3-dione and 2-(methylthio)phenylboronic acid via Methods C, E, D. ¹H NMR (500 MHz, DMSO-d6) δ 8.42 (d, J=0.7 Hz, 1H), 8.15 (dd, J=8.1, 1.2 Hz, 1H), 7.91 (s, 1H), 7.90-7.78 (series of m, 4H), 7.66 (t, J=4.6 Hz, 1H), 7.61 (dd, J=7.6, 1.2 Hz, 1H), 7.50 (ddd, J=9.8, 7.8, 1.2 Hz, 1H), 7.30 (s, 2H), 4.53 (A$\underline{B}$X, $J_{AB}$=17.4 Hz, $J_{AX}$=4.9 Hz, 1H), 4.42 (A$\underline{B}$X, $J_{AB}$=17.1 Hz, $J_{BS}$=4.6 Hz, 1H), 3.03 (s, 3H). Mass Spectrum (ESI) m/e=449.0 (M+1).

Example 36: 4-Amino-6-((5-fluoro-3-(pyridin-2-yl)quinolin-2-yl)methyl-amino)pyrimidine-5-carbonitrile

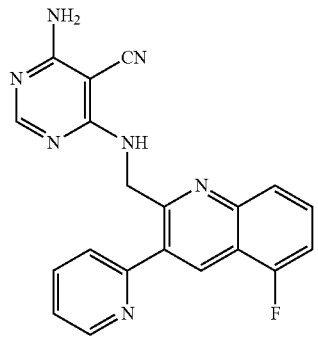 [SMILES: N#Cc1c(N)ncnc1NCc1nc2cccc(F)c2cc1-c1ccccn1]

4-Amino-6-((5-fluoro-3-(pyridin-2-yl)quinolin-2-yl)methylamino)pyrimidine-5-carbonitrile was synthesized from 2-((3-bromo-5-fluoroquinolin-2-yl)methyl)isoindoline-1,3-dione and 2-(tributylstannyl)pyridine via Methods B and D. ¹H NMR (500 MHz, DMSO-d6) δ 8.76 (ddd, J=4.9, 1.7, 0.7 Hz, 1H), 8.52 (d, J=0.7 Hz, 1H), 8.02 (td, J=7.8, 1.7 Hz, 1H), 7.95 (s, 1H), 7.90-7.79 (series of m, 4H), 7.50 (m, 2H), 4.97 (d, J=5.1 Hz, 2H). Mass Spectrum (ESI) m/e=372.1 (M+1).

Example 37: 2-(1-bromoethyl)-6-fluoro-4-methoxy-3-phenylquinoline

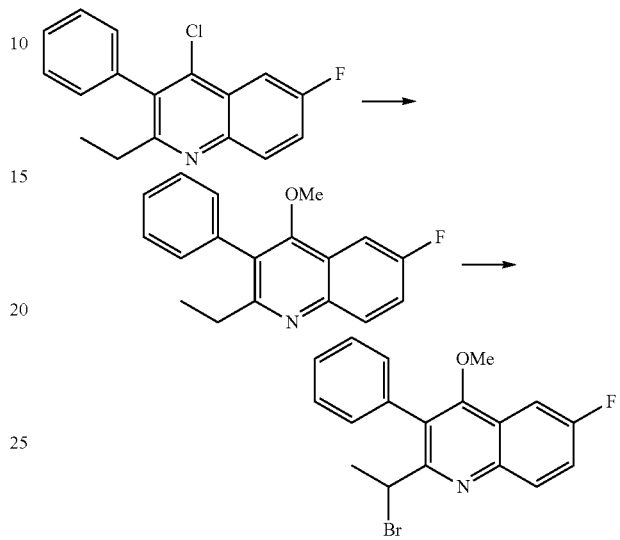

A mixture of 4-chloro-2-ethyl-6-fluoro-3-phenylquinoline (600 mg, 2.1 mmol) and NaOMe (125 mg, 500 mg 25% in MeOH, 1.1 eq) in MeOH (5 mL) was stirred at rt under N₂ for 30 min. No product was observed by LCMS. The reaction mixture was heated to 50° C. overnight. Trace amount of product was detected by LCMS. The reaction mixture was concd and dissolved in DMF (2 mL) and treated with 0.5 mL 25% NaOMe in MeOH at 80° C. for 5 h. After cooling to rt, the reaction mixture was neutralized with acid, diluted with EtOAc washed with water, brine and the organic layer concd and then purified by combiflash on 80 g column (EtOAc/hexane, up to 20%) to give a white solid. Mass Spectrum (ESI) m/e=282 (M+1). 2-Ethyl-6-fluoro-4-methoxy-3-phenylquinoline (284 mg, 1.0 mmol) and 1,3-dibromo-5,5-dimethylhydantoin (202 mg, 0.7 eq) were suspended in carbon tetrachloride (15 mL). To the mixture was added benzoyl peroxide (24.5 mg, 0.1 eq) and the mixture was heated at reflux for 3 h. To the mixture was added satd aq. sodium bicarbonate solution (3 mL). The layers were separated and the aq. layer was extracted with DCM (30 mL×2). The combined organic layers were washed with brine (30 mL), dried over sodium sulfate, filtered, and concd under reduced pressure to give an orange syrup. Mass Spectrum (ESI) m/e=360, 362 (M+1).

2-(1-(6-Fluoro-4-methoxy-3-phenylquinolin-2-yl)ethyl)isoindoline-1,3-dione

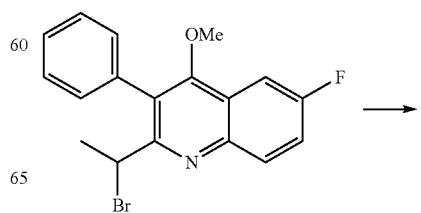

-continued

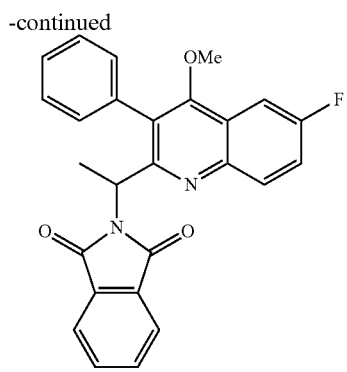

A mixture of 2-(1-bromoethyl)-6-fluoro-4-methoxy-3-phenylquinoline (360 mg, 1.0 mmol) in DMF (5 mL) was treated with phthalimide potassium salt (278 mg, 1.5 eq) overnight. The reaction mixture was heated to 60° C. for 2 h. LCMS showed completion. The reaction mixture was diluted with water (10 mL) and EtOAc (20 mL). The layers were separated and the aq. layer was extracted with EtOAc (10 mL×2). The combined organic layers were washed with water (10 mL×2), brine (10 mL), dried over sodium sulfate, filtered, and concd under reduced pressure to give a white solid. This material was purified by combiflash (EtOAc/hexane, 1/4) to give a white solid. M.S. (ESI) m/e=427 (M+1).

2-(1-(6-Fluoro-4-hydroxy-3-phenylquinolin-2-yl)ethyl)isoindoline-1,3-dione

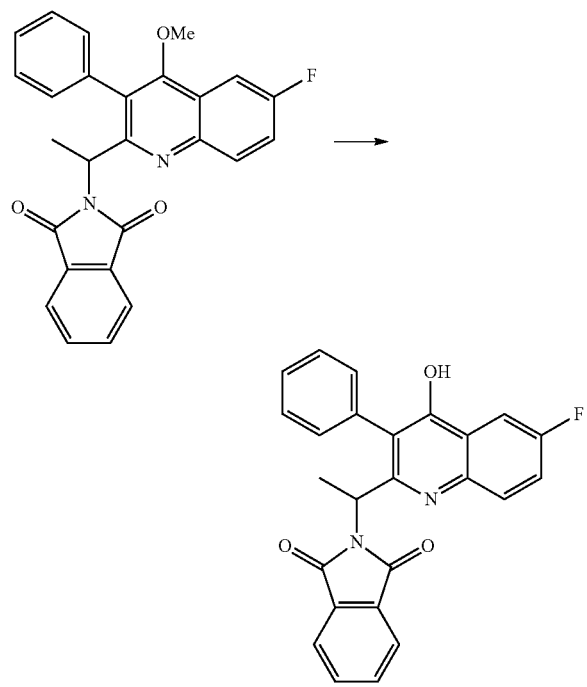

To a solution of 2-(1-(6-fluoro-4-hydroxy-3-phenylquinolin-2-yl)ethyl)isoindoline-1,3-dione (58 mg, 0.14 mmol) in DCM (3 mL) was added BBr₃ (1M, 0.7 mL, 5 eq) at 0° C. The reaction mixture was allowed to warm to rt overnight. The reaction mixture was partitioned between DCM (5 mL) and NaHCO₃ satd solution (5 mL). The organic layer was washed with water, brine, dried and concd to give a white solid, which was used as such for the next step. Mass Spectrum (ESI) m/e=413 (M+1).

4-Amino-6-(1-(6-fluoro-4-methoxy-3-phenylquinolin-2-yl)ethylamino)-pyrimidine-5-carbonitrile

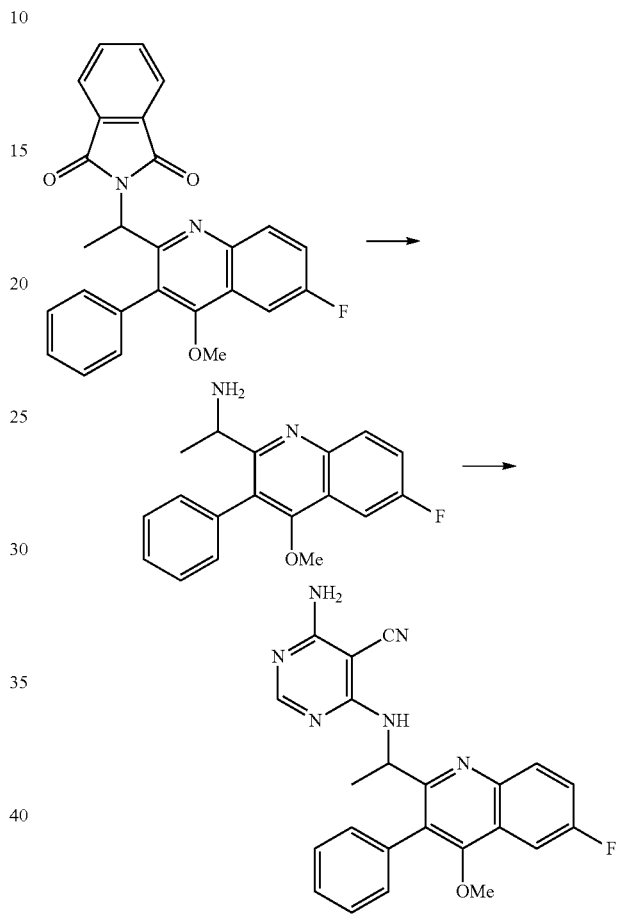

2-(1-(6-Fluoro-4-methoxy-3-phenylquinolin-2-yl)ethyl)isoindoline-1,3-dione (110 mg, 0.26 mmol) was suspended in EtOH (2 mL) and treated with NH₂NH₂ (0.2 mL) at 60° C. for 30 min. After cooling to rt, the reaction mixture was partitioned between EtOAc (10 mL) and water (5 mL). The organic layer was washed with water, brine, dried and concd to give a yellow foam, which was treated with 4-amino-6-chloropyrimidine-5-carbonitrile (40 mg, 1.0 eq) and Hunig's base (0.062 mL, 1.2 eq) in n-BuOH (3 mL) at 120° C. overnight. The reaction mixture was cooled to rt and purified by reverse phase HLPC (MeCN/H₂O, 10%-50% containing 0.1% TFA) to give a white powder as TFA salt. $^1$H-NMR (500 Hz, DMSO-d$^6$) δ 8.10 (dd, J=10.0, 5.0 Hz, 1H), 8.00 (s, 1H), 7.84 (dd, J=10.0, 5.0 Hz, 1H), 7.70-7.84 (m, 2H), 7.48-7.56 (m, 4H), 5.28-5.31 (m, 1H), 3.56 (s, 3H), 1.28 (d, J=10.0 Hz, 3H). Mass Spectrum (ESI) m/e=415 (M+1).

Chiral compounds are purified using isopropanol/hexane gradient, AD column.

The assignment of chirality is based on the biochemical data.

Rotamers of amides are arbitrarily assigned.

Example 38: (S)-4-amino-6-(1-(6-fluoro-4-methoxy-3-phenylquinolin-2-yl)-ethylamino)pyrimidine-5-carbonitrile and (R)-4-amino-6-(1-(6-fluoro-4-methoxy-3-phenylquinolin-2-yl)ethylamino)pyrimidine-5-carbonitrile

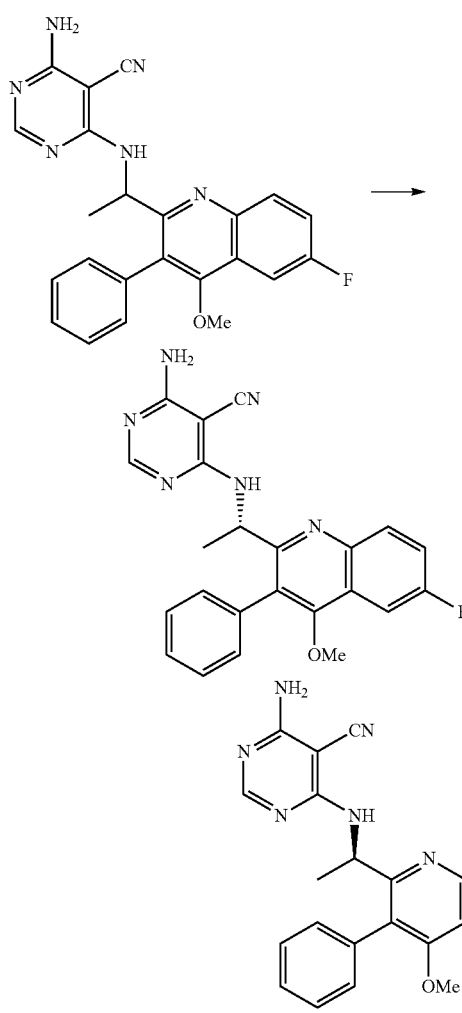

Example 39: 4-Amino-6-(1-(6-fluoro-4-hydroxy-3-phenylquinolin-2-yl)-ethylamino)pyrimidine-5-carbonitrile

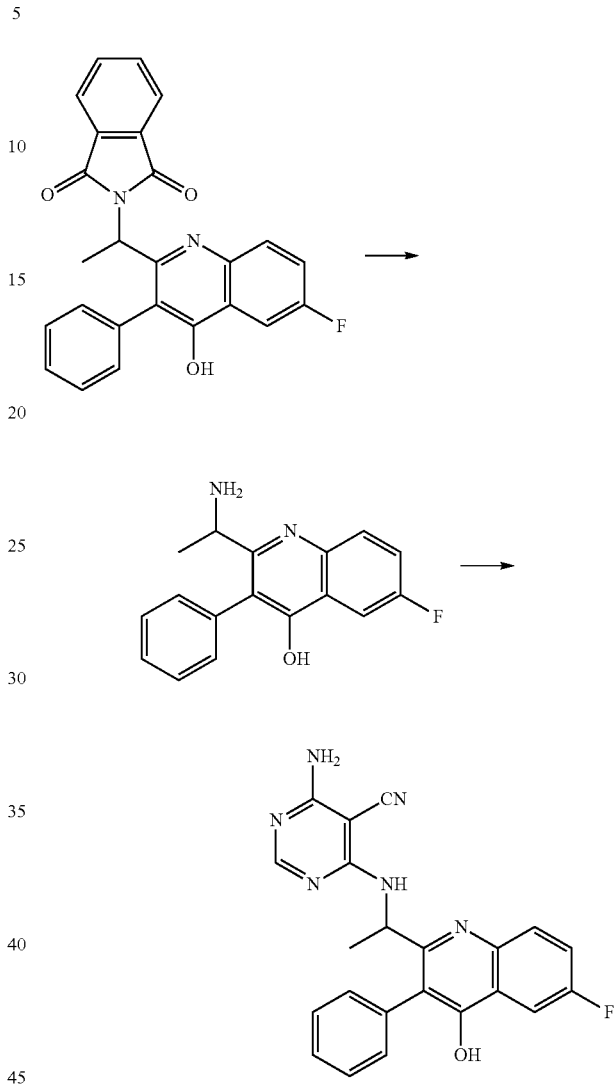

Racemic 4-amino-6-(1-(6-fluoro-4-methoxy-3-phenylquinolin-2-yl)ethylamino)-pyrimidine-5-carbonitrile (60 mg) was purified by AD column (isopropanol/hexane, up to 15% containing 0.1% Et$_2$NH). First fractions were combined and concd under reduced pressure and the resulted solid was washed with water to give a white solid as (S)-4-amino-6-(1-(6-fluoro-4-methoxy-3-phenylquinolin-2-yl)ethylamino)pyrimidine-5-carbonitrile (stereo center was assigned based on biological activity compared with earlier compounds), $^1$H-NMR (400 Hz, CDCl$_3$) δ 8.06 (dd, J=8.0, 4.0 Hz, 1H), 8.03 (s, 1H), 7.65 (dd, J=8.0, 4.0 Hz, 1H), 7.40-7.47 (m, 4H), 7.30-7.40 (m, 2H), 5.40-5.48 (m, 1H), 5.28 (s, 2H), 3.46 (s, 3H), 1.21 (d, J=8.0 Hz, 3H). Mass Spectrum (ESI) m/e=415 (M+1). (R)-4-Amino-6-(1-(6-fluoro-4-methoxy-3-phenylquinolin-2-yl)ethylamino)-pyrimidine-5-carbonitrile (16.8 mg). $^1$H-NMR (400 Hz, CDCl$_3$) δ 8.06 (dd, J=8.0, 4.0 Hz, 1H), 8.03 (s, 1H), 7.65 (dd, J=8.0, 4.0 Hz, 1H), 7.40-7.47 (m, 4H), 7.30-7.40 (m, 2H), 5.40-5.48 (m, 1H), 5.28 (s, 2H), 3.46 (s, 3H), 1.21 (d, J=8.0 Hz, 3H). Mass Spectrum (ESI) m/e=415 (M+1).

2-(1-(6-Fluoro-4-hydroxy-3-phenylquinolin-2-yl)ethyl)isoindoline-1,3-dione (crude, 60 mg, 0.145 mmol) was suspended in EtOH (2 mL) and treated with hydrazine (0.2 mL) at 60° C. for 30 min. After cool to rt, the reaction mixture was partitioned between EtOAc (10 mL) and water (5 mL). The organic layer was washed with water, brine, dried and concd to give a white solid, Mass Spectrum (ESI) m/e=283 (M+1). This solid was treated with 4-amino-6-chloropyrimidine-5-carbonitrile (22.5 mg, 1.0 eq) and Hunig's base (0.031 mL, 1.2 eq) in n-BuOH (1 mL) at 120° C. overnight. The reaction mixture was cooled to rt. and purified by reverse phase HLPC (MeCN/H$_2$O, 10%-50% containing 0.1% TFA) to give a white powder as TFA salt. $^1$H-NMR (400 Hz, CD$_3$OD) δ ppm 1.54 (3H, d) 5.24 (1H, q, J=7.17 Hz) 7.30 (1H, br. s.) 7.42 (1H, m) 7.50 (2H, t, J=7.53 Hz) 7.56 (2H, ddd, J=9.19, 8.02, 2.93 Hz) 7.82 (1H, dd, J=9.19, 4.50 Hz) 7.89 (1H, dd, J=9.19, 2.74 Hz) 8.09 (1H, s). Mass Spectrum (ESI) m/e=401 (M+1).

Example 40: 2-(1-Bromoethyl)-4-chloro-6-fluoro-3-phenylquinoline

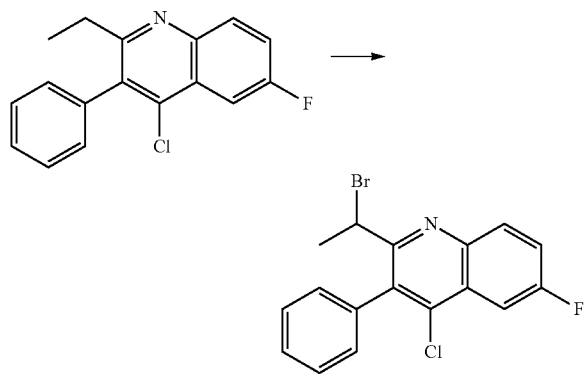

To a solution of 4-chloro-2-ethyl-6-fluoro-3-phenylquinoline (7 g, 24.50 mmol) and 1,3-dibromo-5,5-dimethylimidazolidine-2,4-dione (4.90 g, 17.15 mmol) in $CCl_4$ (200 mL) was added benzoic peroxyanhydride (0.593 g, 2.450 mmol) and the resulting mixture was heated to refluxed for 2 h. The reaction was monitored using LCMS. The reaction mixture was warmed to rt. To the mixture was added sat'd $NaHCO_3$ (200 mL). The layers were separated and the aq. layer was extracted with DCM (3×) and the combined organic layers was washed with brine and dried over sodium sulfate, filtered and concd under reduced pressure to afford 2-(1-bromoethyl)-4-chloro-6-fluoro-3-phenylquinoline.

2-(1-(4-Chloro-6-fluoro-3-phenylquinolin-2-yl)ethyl)isoindoline-1,3-dione

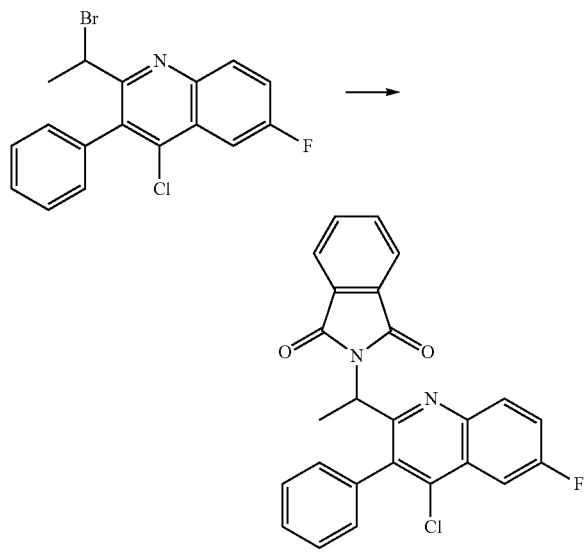

A mixture of 2-(1-bromoethyl)-4-chloro-6-fluoro-3-phenylquinoline (9.5 g, 26.1 mmol) and potassium 1,3-dioxoisoindolin-2-ide (7.24 g, 39.1 mmol) in DMF was heated to 60° C. for 2 h. EtOAc (200 mL) was added and washed with water (200 mL), brine and dried over sodium sulfate. The solvent was removed under reduced pressure. The crude residue was subject to combiflash using EtOAc/hexane (0% to 20%, Rf=0.4) to give 2-(1-(4-chloro-6-fluoro-3-phenylquinolin-2-yl)ethyl)isoindoline-1,3-dione as a yellowish solid.

2-(1-(1,3-Dioxoisoindolin-2-yl)ethyl)-6-fluoro-3-phenylquinoline-4-carbonitrile

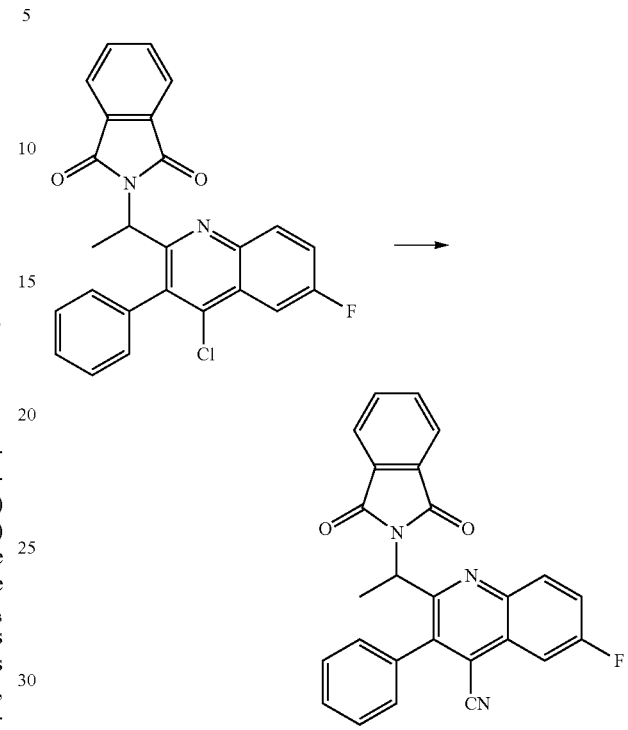

A mixture of 2-(1-(4-chloro-6-fluoro-3-phenylquinolin-2-yl)ethyl)isoindoline-1,3-dione (50 mg, 0.116 mmol), tributylstannanecarbonitrile (36.7 mg, 0.116 mmol), dicyclohexyl(2',4',6'-triisopropylbiphenyl-2-yl)phosphine (33.2 mg, 0.070 mmol) and palladium(II) trifluoroacetate (11.57 mg, 0.035 mmol) in NMP (2 mL) and $Cy_2NMe$ (0.66 mL) was purged with $N_2$ and the resulting mixture was heated to 150° C. using a microwave for 2 h. The reaction only showed starting materials. More $Pd(TFA)_2$ (up to 1 Eq) and dicyclohexyl(2',4',6'-triisopropylbiphenyl-2-yl)-phosphine was added and heated to 150° C. in the microwave for 1 h. At this time EtOAc was added. The organic extract was washed with water and dried over sodium sulfate. The solution was filtered and concd in vacuo. The crude residue was purified via combiflash using EtOAc/hexane (1:4) to obtain 2-(1-(1,3-dioxoisoindolin-2-yl)ethyl)-6-fluoro-3-phenylquinoline-4-carbonitrile as a light yellowish solid.

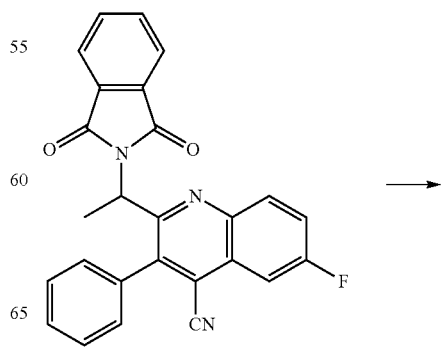

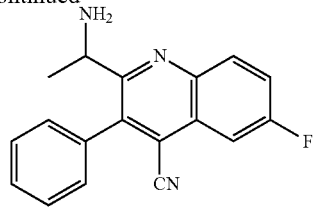

To a solution of 2-(1-(1,3-dioxoisoindolin-2-yl)ethyl)-6-fluoro-3-phenylquinoline-4-carbonitrile (73.9 mg, 0.175 mmol) in EtOH (2 mL) was added hydrazine (0.055 mL, 1.754 mmol) and the resulting mixture was heated to 60° C. for 20 min. The reaction mixture was allowed to warm to rt and solid was filtered. The filtrate was concd under reduced pressure and used crude for the next step.

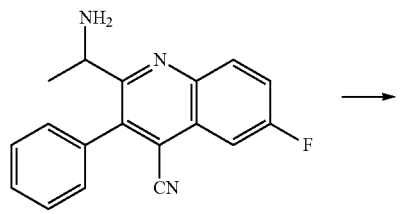

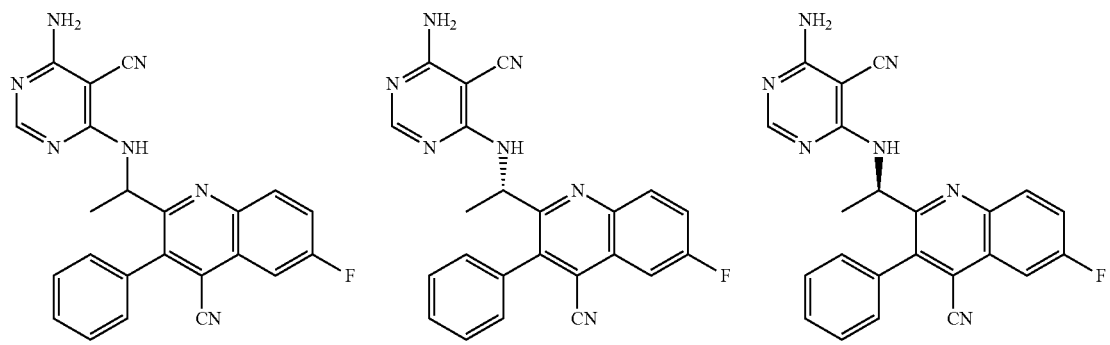

To the crude 2-(1-aminoethyl)-6-fluoro-3-phenylquinoline-4-carbonitrile (51.1 mg, 0.175 mmol) in BuOH (1 mL) was added DIEA (0.037 mL, 0.210 mmol) and the resulting mixture was heated at 120° C. overnight. The reaction mixture was allowed to warm to rt and solid was filtered and submitted for chiral separation. The filtrate was subjected to HPLC purification.

2-(1-((6-Amino-5-cyano-4-pyrimidinyl)amino)ethyl)-6-fluoro-3-phenyl-4-quinolinecarbonitrile $^1$H-NMR (500 Hz, CD$_3$OD) δ ppm 1.48 (3H, d) 5.67 (1H, q, J=6.77 Hz) 7.56 (1H, m) 7.61 (4H, m) 7.80 (1H, td, J=8.80, 2.45 Hz) 7.86 (1H, dd, J=8.80, 2.69 Hz) 8.06 (1H, s) 8.32 (1H, dd, J=9.17, 5.26 Hz). Mass Spectrum (ESI) m/e=410 (M+1).

2-((1S)-1-((6-Amino-5-cyano-4-pyrimidinyl)amino)ethyl)-6-fluoro-3-phenyl-4-quinolinecarbonitrile $^1$H-NMR (400 Hz, CD$_3$OD) δ ppm 1.41 (3H, d) 5.59 (1H, q, J=6.72 Hz) 7.53 (1H, m) 7.61 (4H, m) 7.80 (2H, m) 7.93 (1H, s) 8.30 (1H, dd, J=9.19, 5.28 Hz). Mass Spectrum (ESI) m/e=410 (M+1).

2-((1R)-1-((6-Amino-5-cyano-4-pyrimidinyl)amino)ethyl)-6-fluoro-3-phenyl-4-quinolinecarbonitrile $^1$H-NMR (400 Hz, CD$_3$OD) δ ppm 1.41 (3H, d) 5.59 (1H, q, J=6.78 Hz) 7.53 (1H, m) 7.61 (4H, m) 7.80 (2H, m) 7.93 (1H, s) 8.30 (1H, dd, J=9.29, 5.18 Hz). Mass Spectrum (ESI) m/e=410 (M+1).

Example 41

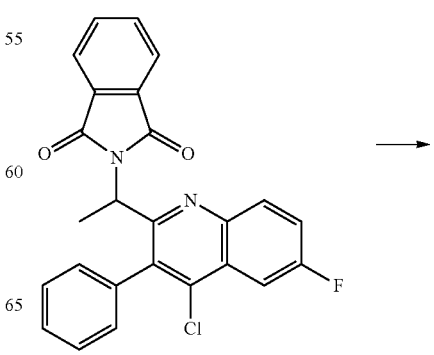

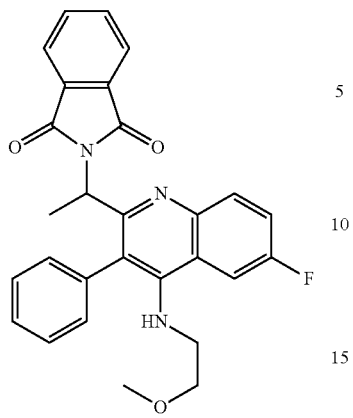

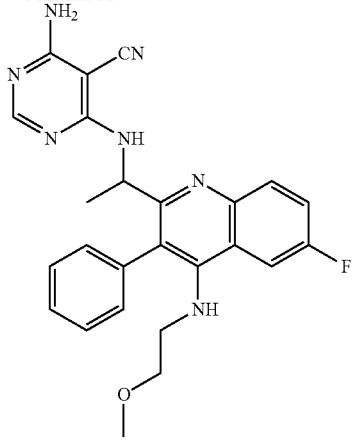

A solution of 2-(1-(4-chloro-6-fluoro-3-phenylquinolin-2-yl)ethyl)isoindoline-1,3-dione (50 mg, 0.116 mmol), 2-methoxyethanamine (8.72 mg, 0.116 mmol), dicyclohexyl (2',4',6'-triisopropylbiphenyl-2-yl)phosphine (11.06 mg, 0.023 mmol), sodium tert-butoxide (33.5 mg, 0.348 mmol) and $Pd_2(dba)_3$ (10.63 mg, 0.012 mmol) in toluene (1 mL) was stirred at 100° C. for 30 min. The reaction mixture was allowed to warm to rt and partitioned between EtOAc and water. The organic layer was washed with brine and dried over sodium sulfate solvent was removed under reduced pressure. The crude residue was purified via combiflash using EtOAc/hexane (30%) to obtain 2-(1-(6-fluoro-4-(2-methoxyethylamino)-3-phenylquinolin-2-yl)ethyl)isoindoline-1,3-dione as a yellow oil.

4-Amino-6-(1-(6-fluoro-4-((2-methoxyethyl)amino)-3-phenyl-2-quinolinyl)-ethyl)amino)-5-pyrimidinecarbonitrile

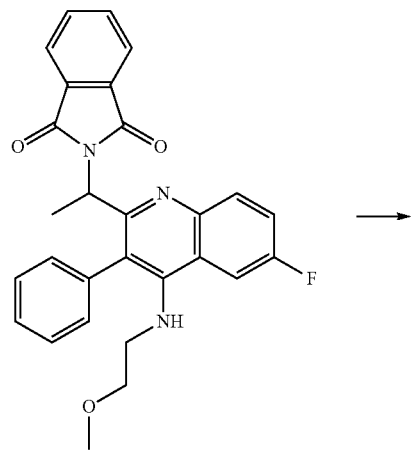

To a solution of 2-(1-(6-fluoro-4-(2-methoxyethylamino)-3-phenylquinolin-2-yl)-ethyl)isoindoline-1,3-dione (73.9 mg, 0.157 mmol) in EtOH (2 mL) was added hydrazine (0.049 mL, 1.574 mmol) and the resulting mixture was heated to 60° C. for 20 min. The reaction mixture was allowed to warm to rt and solid was filtered. The filtrate was concd under reduced pressure and used crude for the next step. To the crude solution of 2-(1-aminoethyl)-6-fluoro-N-(2-methoxyethyl)-3-phenylquinolin-4-amine (25 mg, 0.074 mmol) in BuOH (2 mL) was added DIEA (0.033 mL, 0.189 mmol) and 4-amino-6-chloropyrimidine-5-carbo-nitrile (24.33 mg, 0.157 mmol) and the resulting mixture was stirred at 110° C. overnight. The reaction mixture was cooled to rt and purified via HPLC.

4-Amino-6-(1-(6-fluoro-4-((2-methoxyethyl)amino)-3-phenyl-2-quinolinyl)-ethyl)amino)-5-pyrimidinecarbonitrile $^1$H-NMR (400 Hz, $CD_3OD$) δ ppm 1.53 (3H, d, J=7.24 Hz) 3.23 (2H, s) 3.33 (2H, m) 3.41 (2H, m) 4.99 (1H, m) 7.48 (1H, m) 7.64 (3H, m) 7.80 (2H, m) 8.03 (1H, s) 8.08 (1H, dd, J=9.39, 4.89 Hz) 8.22 (1H, dd, J=10.47, 2.64 Hz). Mass Spectrum (ESI) m/e=458 (M+1).

4-Amino-6-(((1S)-1-(6-fluoro-4-((2-methoxyethyl)amino)-3-phenyl-2-quinolinyl)ethyl)amino)-5-pyrimidinecarbonitrile $^1$H-NMR (400 Hz, $CD_3OD$) δ ppm 1.30 (d, J=6.46 Hz, 3H) 3.18 (s, 3H) 3.19-3.22 (m, 2H) 3.28-3.31 (m, 2H) 5.25 (q, J=6.65 Hz, 1H) 7.37-7.41 (m, 1H) 7.43-7.47 (m, 1H) 7.48-7.55 (m, 2H) 7.55-7.61 (m, 2H) 7.82 (dd, J=10.76, 2.74 Hz, 1H) 7.94 (s, 1H) 8.01 (dd, J=9.29, 5.58 Hz, 1H). Mass Spectrum (ESI) m/e=458 (M+1).

4-Amino-6-(((1R)-1-(6-fluoro-4-((2-methoxyethyl)amino)-3-phenyl-2-quinolinyl)ethyl)amino)-5-pyrimidinecarbonitrile $^1$H-NMR (400 Hz, $CD_3OD$) δ ppm 1.30 (d, J=6.65 Hz, 3H) 3.18 (s, 3H) 3.19 (d, J=1.56 Hz, 0H) 3.21 (d, J=5.28 Hz, 1H) 3.29-3.31 (m, 2H) 5.26 (q, J=6.52 Hz, 1H) 7.37-7.41 (m, 1H) 7.43-7.47 (m, 1H) 7.48-7.54 (m, 2H) 7.55-7.61 (m, 2H) 7.91-7.99 (m, 1H) 8.01 (dd, J=9.19, 5.67 Hz, 1H). Mass Spectrum (ESI) m/e=458 (M+1).

Example 42: 4-Amino-6-((1-(6-fluoro-4-((2-(methylsulfonyl)ethyl)amino)-3-phenyl-2-quinolinyl)ethyl)amino)-5-pyrimidinecarbonitrile

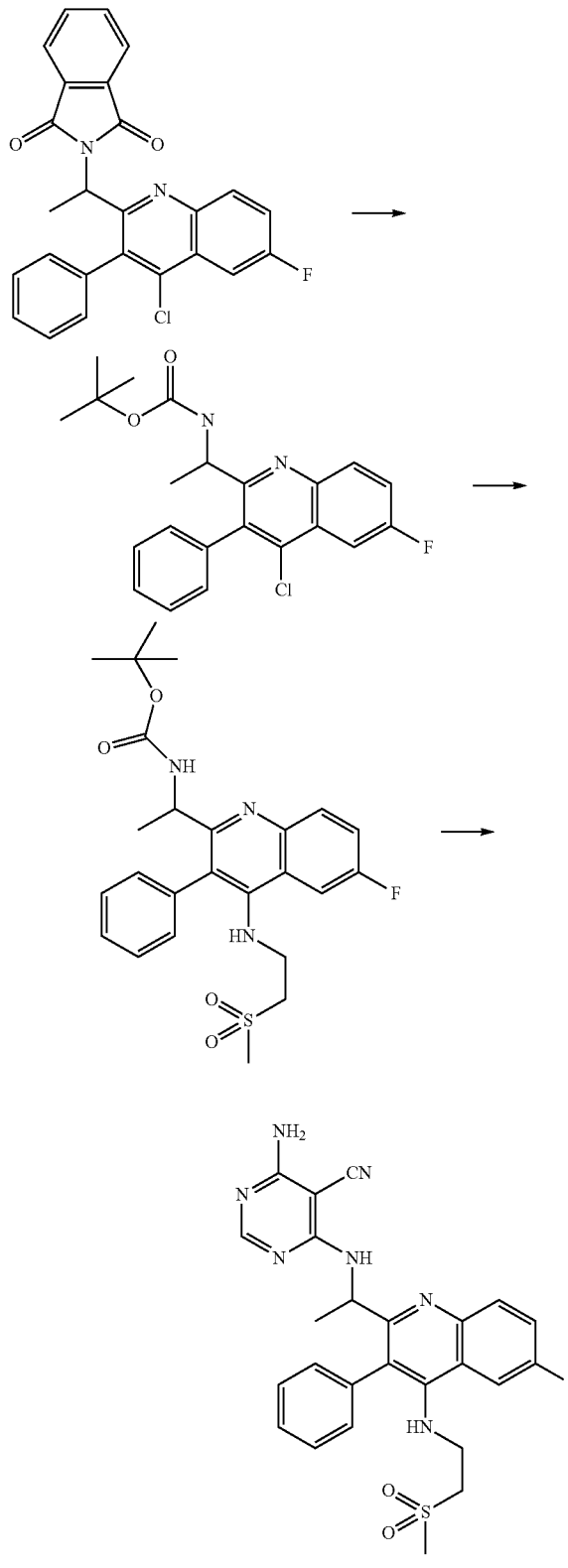

To a solution of 2-(1-(4-chloro-6-fluoro-3-phenylquinolin-2-yl)ethyl)isoindoline-1,3-dione (300 mg, 0.696 mmol) in EtOH (4 mL) was added hydrazine (0.219 mL, 6.96 mmol) and the resulting mixture was heated to 60° C. for 20 min. The reaction mixture was allowed to warm to rt and the solid was filtered. The filtrate was concd under reduced pressure and used crude for the next step. To a solution of 1-(4-chloro-6-fluoro-3-phenylquinolin-2-yl)ethanamine in DCM (4.00 mL) was added N-ethyl-N-isopropylpropan-2-amine (0.146 mL, 0.836 mmol) followed by the addition of di-tert-butyl dicarbonate (167 mg, 0.766 mmol) and the resulting mixture was stirred at rt for 2 h. The crude solution was washed with water, brine and dried over MgSO$_4$ and solvent was removed under reduced pressure to obtain tert-butyl 1-(4-chloro-6-fluoro-3-phenylquinolin-2-yl)ethylcarbamate. A solution of tert-butyl 1-(4-chloro-6-fluoro-3-phenylquinolin-2-yl)ethylcarbamate (50 mg, 0.125 mmol), 2-(methylsulfonyl)ethanamine (15.36 mg, 0.125 mmol), dicyclohexyl(2',6'-dimethoxybiphenyl-2-yl)phosphine (10.24 mg, 0.025 mmol), pd$_2$(dba)$_3$ (11.42 mg, 0.012 mmol) and sodium 2-methylpropan-2-olate (17.98 mg, 0.187 mmol) in toluene (1 mL) was heated to 110° C. overnight. The solvent was removed under reduced pressure and purified via combiflash using EtOAc/hexane (1:1). To the crude residue tert-butyl 1-(6-fluoro-4-(2-(methylsulfonyl)-ethylamino)-3-phenylquinolin-2-yl)ethylcarbamate (18 mg, 0.037 mmol) was added HCl (0.1 mL, 0.400 mmol) and the resulting mixture was stirred at rt. for 1 h. The reaction was monitored by LCMS. The solvent was removed and used as crude for the next step. To the crude solution of 2-(1-aminoethyl)-6-fluoro-N-(2-(methylsulfonyl)ethyl)-3-phenylquinolin-4-amine in BuOH (1 mL) was added N-ethyl-N-isopropylpropan-2-amine (0.019 mL, 0.111 mmol) and 4-amino-6-chloropyrimidine-5-carbonitrile (6.85 mg, 0.044 mmol) and the resulting mixture was heated to 110° C. for 3 h. The solvent was removed and purified via HPLC.

4-Amino-6-((1-(6-fluoro-4-((2-(methylsulfonyl)ethyl)amino)-3-phenyl-2-quinolinyl)ethyl)amino)-5-pyrimidinecarbonitrile $^1$H-NMR (400 Hz, CD$_3$OD) δ ppm 1.53 (3H, d, J=7.04 Hz) 2.91 (3H, s) 3.30 (3H, s) 3.49 (2H, m) 4.97 (1H, m) 7.55 (1H, dd, J=4.40, 2.25 Hz) 7.63 (2H, m) 7.81 (2H, ddd, J=9.29, 7.63, 2.64 Hz) 7.88 (1H, m) 8.02 (1H, s) 8.09 (1H, dd, J=9.39, 4.89 Hz) 8.16 (1H, dd, J=10.17, 2.54 Hz). Mass Spectrum (ESI) m/e=506 (M+1).

4-Amino-6-(((1S)-1-(6-fluoro-4-((2-(methylsulfonyl)ethyl)amino)-3-phenyl-2-quinolinyl)ethyl)amino)-5-pyrimidinecarbonitrile $^1$H-NMR (400 Hz, CD$_3$OD) δ ppm 1.55 (d, 3H) 2.92 (s, 3H) 3.28-3.32 (m, 2H) 3.44-3.55 (m, 2H) 5.00 (q, J=7.04 Hz, 1H) 7.57 (dt, J=4.50, 2.25 Hz, 1H) 7.62-7.70 (m, 3H) 7.82 (ddd, J=9.39, 7.63, 2.74 Hz, 1H) 7.90 (dd, J=6.94, 1.66 Hz, 1H) 8.04 (s, 1H) 8.11 (dd, J=9.39, 4.89 Hz, 1H) 8.17 (dd, J=10.17, 2.54 Hz, 1H). Mass Spectrum (ESI) m/e=506 (M+1).

Example 43: 4-Amino-6-((1-(6-fluoro-4-((2-hydroxyethyl)amino)-3-phenyl-2-quinolinyl)ethyl)amino)-5-pyrimidinecarbonitrile

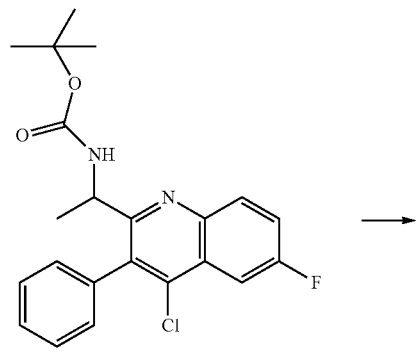

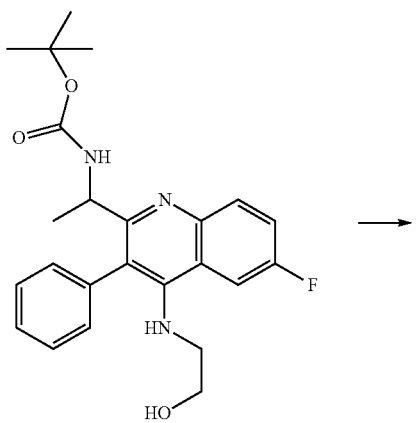

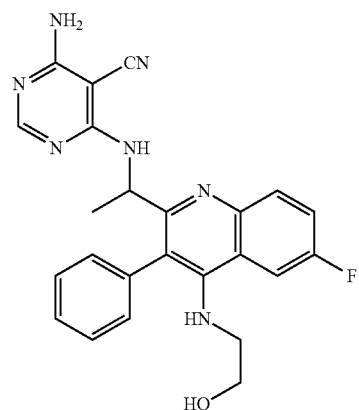

A solution of tert-butyl 1-(4-chloro-6-fluoro-3-phenylquinolin-2-yl)ethylcarbamate (100 mg, 0.249 mmol), 2-aminoethanol (15.24 mg, 0.249 mmol), dicyclohexyl(2',6'-dimethoxybiphenyl-2-yl)phosphine (20.48 mg, 0.050 mmol), sodium 2-methylpropan-2-olate (36.0 mg, 0.374 mmol) and pd$_2$(dba)$_3$ (22.84 mg, 0.025 mmol) in toluene (2 mL) was heated to 110° C. for 1 h. The solvent was removed under reduced pressure. EtOAc was added and washed with water, brine and dried over sodium sulfate and the solvent was removed under reduced pressure. The crude residue was purified using EtOAc/hexane (1:1). To the crude residue of tert-butyl 1-(6-fluoro-4-(2-hydroxyethylamino)-3-phenylquinolin-2-yl)ethylcarbamate (17 mg, 0.040 mmol) was added HCl (0.1 mL, 0.400 mmol) and the resulting mixture was stirred at rt for 1 h. The reaction was monitored by LCMS. The solvent was removed and used crude for the next step. To the crude solution of 2-(2-(1-aminoethyl)-6-fluoro-3-phenylquinolin-4-ylamino)ethanol in BuOH (1 mL) was added N-ethyl-N-isopropylpropan-2-amine (0.021 mL, 0.120 mmol) and 4-amino-6-chloropyrimidine-5-carbonitrile (7.41 mg, 0.048 mmol) and the resulting mixture was heated to 110° C. for 3 h. The solvent was removed and purified via combiflask using EtOAc/hexane (1:1) with satd ammonia.

4-Amino-6-((1-(6-fluoro-4-((2-hydroxyethyl)amino)-3-phenyl-2-quinolinyl)-ethyl)amino)-5-pyrimidinecarbonitrile $^1$H-NMR (400 Hz, CD$_3$OD) δ ppm 1.31 (3H, d, J=6.65 Hz) 3.08 (2H, m) 3.49 (2H, td, J=5.48, 2.15 Hz) 5.26 (1H, q, J=6.59 Hz) 7.41 (1H, m) 7.53 (5H, m) 7.88 (1H, dd, J=10.76, 2.74 Hz) 7.95 (1H, m) 8.01 (1H, dd, J=9.29, 5.58 Hz). Mass Spectrum (ESI) m/e=444 (M+1).

4-Amino-6-((1-(4-((2-(dimethylamino)ethyl)amino)-6-fluoro-3-phenyl-2-quinolinyl)ethyl)amino)-5-pyrimidinecarbonitrile This synthesis is performed as described above.

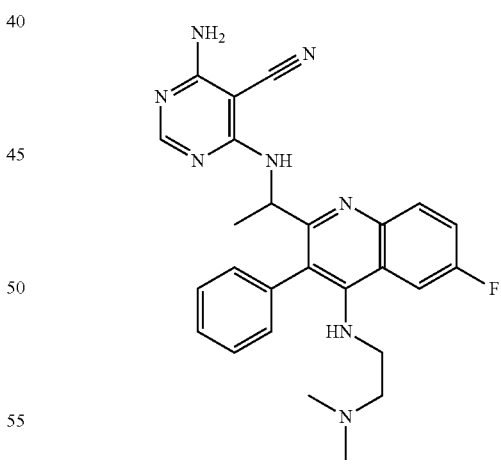

$^1$H-NMR (400 Hz, CD$_3$OD) δ ppm 5.24 (3H, d) 6.02 (6H, s) 6.27 (2H, m) 7.01 (2H, td, J=6.46, 1.17 Hz) 9.20 (1H, q, J=6.52 Hz) 11.35 (1H, m) 11.46 (5H, m) 11.78 (1H, dd, J=10.76, 2.54 Hz) 11.88 (1H, s) 11.94 (1H, dd, J=9.29, 5.58 Hz). Mass Spectrum (ESI) m/e=471 (M+1).

Example 44: N-(1-(6-Fluoro-4-(methylsulfonyl)-3-phenylquinolin-2-yl)ethyl)-9H-purin-6-amine, (S)—N-(1-(6-fluoro-4-(methylsulfonyl)-3-phenylquinolin-2-yl)ethyl)-9H-purin-6-amine, (R)—N-(1-(6-fluoro-4-(methylsulfonyl)-3-phenylquinolin-2-yl)ethyl)-9H-purin-6-amine

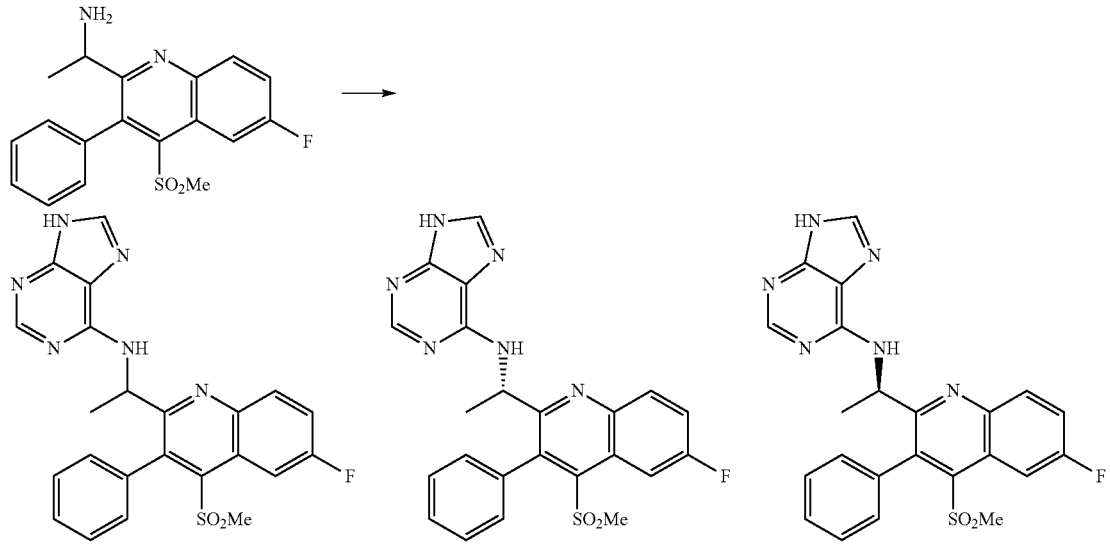

A mixture of 1-(6-fluoro-4-(methylsulfonyl)-3-phenylquinolin-2-yl)ethanamine (90 mg, 0.26 mmol), 6-chloropurine (40.4 mg, 1.0 eq) and Hunig's base (55 µL, 1.2 eq) in n-BuOH (2 mL) was heated to 130° C. overnight. The mixture was cooled to rt, and purified by reverse phase HLPC (MeCN/H$_2$O, 10%-50% containing 0.1% TFA) to give a white powder as TFA salt of N-(1-(6-fluoro-4-(methylsulfonyl)-3-phenylquinolin-2-yl)ethyl)-9H-purin-6-amine. $^1$H-NMR (400 Hz, CD$_3$OD) δ 8.73 (dd, J=8.0, 4.0 Hz, 1H), 8.23 (dd, J=8.0, 4.0 Hz, 1H), 8.14 (s, 1H), 8.08-8.14 (m, 1H), 7.73 (td, J=8.0, 4.0 Hz, 1H), 7.42-7.52 (m, 5H), 5.46 (m, 1H), 3.11 (s, 3H), 1.49 (d, J=8.0 Hz, 3H). Mass Spectrum (ESI) m/e=463 (M+1).

N-(1-(6-fluoro-4-(methylsulfonyl)-3-phenylquinolin-2-yl)ethyl)-9H-purin-6-amine was purified by chiral OD column (isopropanol/hexane, up to 15%). First fractions were combined and concd under reduced pressure to give a white solid as (S)—N-(1-(6-fluoro-4-(methylsulfonyl)-3-phenylquinolin-2-yl)ethyl)-9H-purin-6-amine (20 mg, stereo center was assigned based on biological activity compared with earlier compounds), $^1$H-NMR (400 Hz, CD$_3$OD) δ 8.73 (dd, J=8.0, 4.0 Hz, 1H), 8.23 (dd, J=8.0, 4.0 Hz, 1H), 8.14 (s, 1H), 8.08-8.14 (m, 1H), 7.73 (td, J=8.0, 4.0 Hz, 1H), 7.42-7.52 (m, 5H), 5.46 (m, 1H), 3.11 (s, 3H), 1.49 (d, J=8.0 Hz, 3H). Mass Spectrum (ESI) m/e=463 (M+1). (R)—N-(1-(6-fluoro-4-(methylsulfonyl)-3-phenylquinolin-2-yl)ethyl)-9H-purin-6-amine. $^1$H-NMR (400 Hz, CD$_3$OD) δ 8.73 (dd, J=8.0, 4.0 Hz, 1H), 8.23 (dd, J=8.0, 4.0 Hz, 1H), 8.14 (s, 1H), 8.08-8.14 (m, 1H), 7.73 (td, J=8.0, 4.0 Hz, 1H), 7.42-7.52 (m, 5H), 5.46 (m, 1H), 3.11 (s, 3H), 1.49 (d, J=8.0 Hz, 3H). Mass Spectrum (ESI) m/e=463 (M+1).

Example 45: 2,4-Dichloro-5-fluoro-3-phenylquinoline

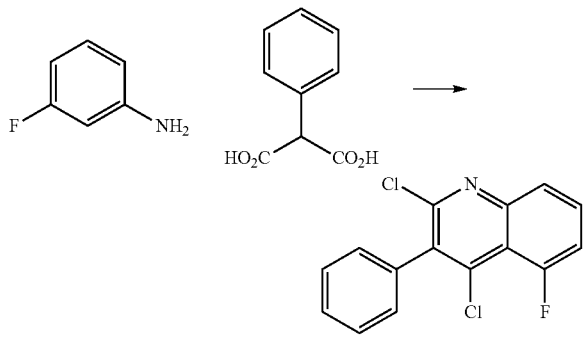

A mixture of 3-fluoroaniline (3.33 g, 30 mmol) and 2-phenylmalonic acid (7.89 g, 1.46 eq) was treated with POCl$_3$ with caution. The resulted suspension was heated to 95° C. and stirred overnight before increasing the temperature to 145° C. for 1 h. After cooling to rt, the reaction mixture was poured into ice and stirred for 10 min. The mixture was extracted with EtOAc (100 mL×2), washed, dried, concd and purified by combiflash (DCM/hexane, 0/1 to 2/3) to give 1st component undesired region-isomer as a yellow solid and 2nd fraction 2,4-dichloro-5-fluoro-3-phenylquinoline as a white solid. $^1$H-NMR (400 Hz, CDCl$_3$) δ 7.92 (d, J=8.0 Hz, 1H), 7.71-7.76 (m, 1H), 7.51-7.57 (m, 3H), 7.32-7.37 (m, 3H).

N-(1-(5-Fluoro-4-(methylsulfonyl)-3-phenylquinolin-2-yl)ethyl)-9H-purin-6-amine

Example 46: (S)-4-Amino-6-(1-(5-fluoro-4-(methylsulfonyl)-3-phenylquinolin-2-yl)ethylamino)pyrimidine-5-carbonitrile

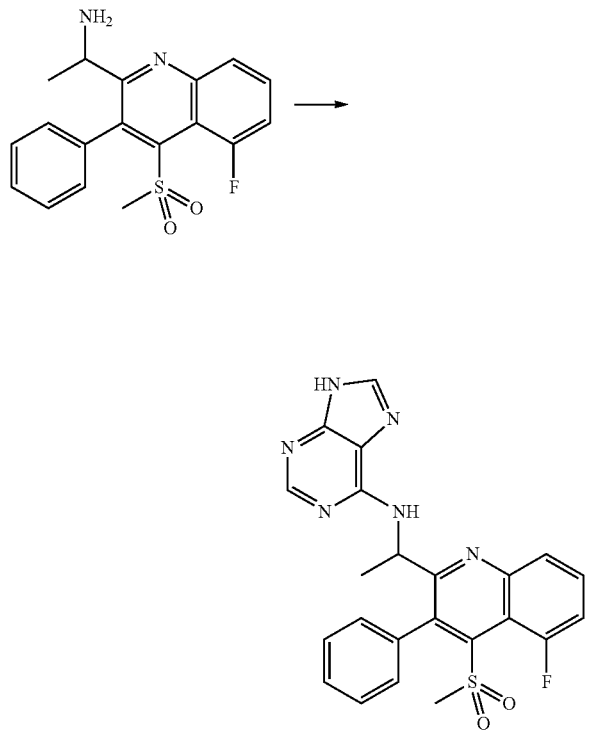

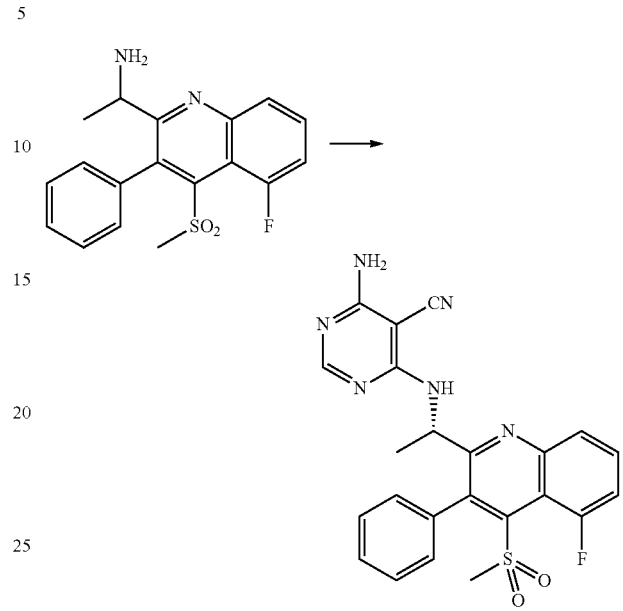

1-(5-Fluoro-4-(methylsulfonyl)-3-phenylquinolin-2-yl)ethanamine was synthesized from 2,4-dichloro-5-fluoro-3-phenylquinoline according to the procedure for 1-(6-fluoro-4-(methylsulfonyl)-3-phenylquinolin-2-yl)ethanamine. A mixture of 1-(5-fluoro-4-(methylsulfonyl)-3-phenylquinolin-2-yl)ethanamine (60 mg, 0.17 mmol), 6-chloropurine (27 mg, 1.0 eq) and Hunig's base (55 µL, 1.2 eq) in n-BuOH (2 mL) was heated to 130° C. overnight. The mixture was cooled to rt, concd, dissolved in DCM (2 mL) and purified by combiflash (DCM/MeOH, 20/1) to give a pale yellow solid. $^1$H-NMR (400 Hz, CD$_3$OD) δ 8.40-8.45 (m, 2H), 8.10 (d, J=8.0 Hz, 1H), 7.85-7.95 (m, 1H), 7.65 (d, J=8.0 Hz, 1H), 7.42-7.55 (m, 5H), 5.75-85 (m, 1H), 3.32 (s, 3H), 1.50 (d, J=8.0 Hz, 3H). Mass Spectrum (ESI) m/e=463 (M+1).

A mixture of 1-(5-fluoro-4-(methylsulfonyl)-3-phenylquinolin-2-yl)ethanamine (70 mg, 0.20 mmol), 4-amino-6-chloropyrimidine-5-carbonitrile (31.4 mg, 1.0 eq) and Hunig's base (42.6 µL, 1.2 eq) in n-BuOH (2 mL) was heated to 130° C. overnight. The mixture was cooled to rt, filtered and washed with cold EtOH to give a white solid as 4-amino-6-(1-(5-fluoro-4-(methylsulfonyl)-3-phenylquinolin-2-yl)ethylamino)pyrimidine-5-carbonitrile. This material was purified by chiral OD column (isopropanol/hexane, up to 15%). First fractions were combined and concd under reduced pressure to give a white solid as (S)-4-amino-6-(1-(5-fluoro-4-(methylsulfonyl)-3-phenylquinolin-2-yl)ethylamino)pyrimidine-5-carbonitrile (stereo center was assigned based on biological activity compared with earlier compounds), $^1$H-NMR (400 Hz, DMSO-d$^6$) δ 7.92-8.03 (m, 2H), 7.40-7.60 (m, 5H), 7.20-7.30 (m, 1H), 5.30-5.40 (m, 1H), 3.29 (s, 3H), 1.24 (d, J=8.0 Hz, 3H). Mass Spectrum (ESI) m/e=463 (M+1).

Example 47: 2-(1-(6-Fluoro-4-(2-hydroxyethylsulfinyl)-3-phenylquinolin-2-yl)ethyl)-isoindoline-1,3-dione

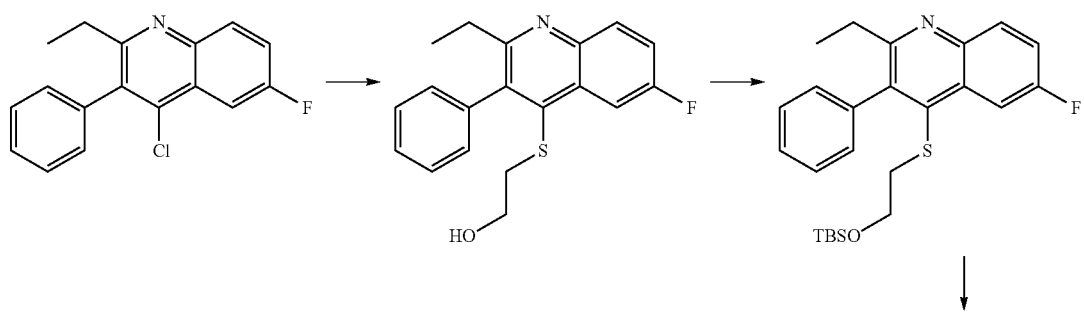

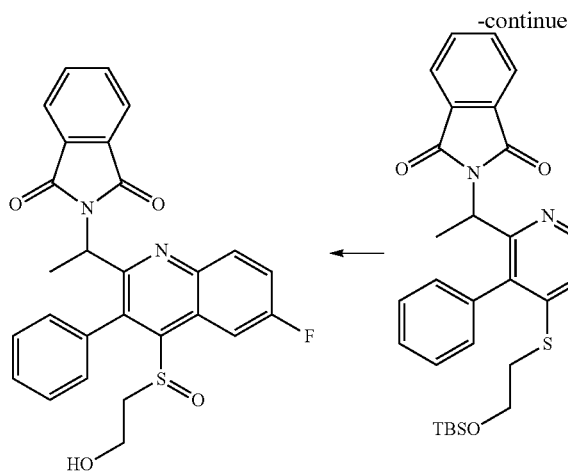 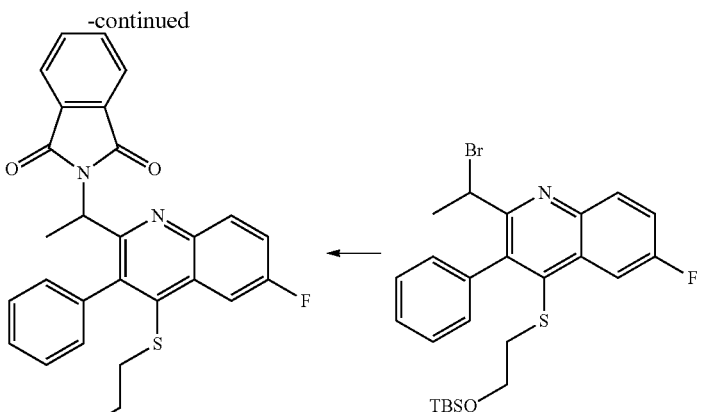

A mixture of 4-chloro-2-ethyl-6-fluoro-3-phenylquinoline (400 mg, 1.4 mmol), Hunig's base (293 μL, 1.2 eq) and HSCH$_2$CH$_2$OH (108 μL, 1.1 eq) in DMF (4 mL) was heated to 65° C. under N$_2$ for 2 h. LCMS showed no formation of product. The reaction mixture was then heated to 100° C. overnight. LCMS showed 60% product and 40% starting material. To the reaction mixture was added 50 μL thiol and heated to 100° C. The reaction mixture was diluted with water (10 mL) and EtOAc (20 mL). The layers were separated and the aq. layer was extracted with EtOAc (10 mL×2). The combined organic layers were washed with water (10 mL×2), brine (10 mL), dried over sodium sulfate, filtered, and concd under reduced pressure. The residue was purified by combiflashon silica gel (EtOAc/hexane, 1/8) to give a white solid as 2-(2-ethyl-6-fluoro-3-phenylquinolin-4-ylthio)ethanol. Mass Spectrum (ESI) m/e=328 (M+1). 2-(2-ethyl-6-fluoro-3-phenylquinolin-4-ylthio)ethanol (200 mg, 0.61 mmol), imidazole (45.7 mg, 1.1 eq) and TBS-Cl (110 mg, 1.2 eq) in DMF (3 mL) was stirred at rt overnight, 50% starting material remained. The reaction mixture was then treated with imidazole (45.7 mg, 1.1 eq) and TBS-Cl (110 mg, 1.2 eq). After 2 h, the reaction was complete. The reaction mixture was diluted with water (10 mL) and EtOAc (20 mL). The layers were separated and the aq. layer was extracted with EtOAc (10 mL×2). The combined organic layers were washed with water (10 mL×2), brine (10 mL), dried over sodium sulfate, filtered, and concd under reduced pressure. Purification on combiflash gave a colorless oil as 4-(2-(tert-butyldimethylsilyloxy)ethylthio)-2-ethyl-6-fluoro-3-phenylquinoline. Mass Spectrum (ESI) m/e=442 (M+1). 4-(2-(tert-Butyldimethylsilyloxy)-ethylthio)-2-ethyl-6-fluoro-3-phenylquinoline (262 mg, 0.59 mmol) and 1,3-dibromo-5,5-dimethylhydantoin (119 mg, 0.7 eq) were suspended in carbon tetrachloride (10 mL). To the mixture was added benzoyl peroxide (14.4 mg, 0.1 eq) and heated at reflux for 3 h. After cooling to rt, to the mixture was added satd aq. sodium bicarbonate solution (3 mL). The layers were separated and the aq. layer was extracted with DCM (3 mL×2). The combined organic layers were washed with water (3 mL), brine (3 mL), dried over sodium sulfate, filtered, and concd under reduced pressure to give an orange syrup as 2-(1-bromoethyl)-4-(2-(tert-butyldimethylsilyloxy)ethylthio)-6-fluoro-3-phenylquinoline. Mass Spectrum (ESI) m/e=520, 522 (M+1). A mixture of 2-(1-bromoethyl)-4-(2-(tert-butyldimethylsilyloxy)ethylthio)-6-fluoro-3-phenylquinoline (300 mg, 0.58 mmol) in DMF (3 mL) was treated with phthalimide potassium salt (213 mg, 2.0 eq) at 60° C. for 2 h. LCMS showed completion. The reaction mixture was partitioned between water and EtOAc, the layers were separated and the aq. layer was extracted with EtOAc (10 mL×2). The combined organic layers were washed with water (10 mL×2), brine (10 mL), dried over sodium sulfate, filtered, and concd under reduced pressure. The residue was purified by combiflash on silica gel (DCM/hexane, 0/1 to 1/1) to give a white foam as 2-(1-(4-(2-(tert-butyldimethylsilyloxy)ethylthio)-6-fluoro-3-phenylquinolin-2-yl)ethyl)-isoindoline-1,3-dione. To a solution of 2-(1-(4-(2-(tert-butyldimethylsilyloxy)-ethylthio)-6-fluoro-3-phenylquinolin-2-yl)ethyl)isoindoline-1,3-dione (80 mg, 0.14 mmol) in THF (6 mL) and H$_2$O (2 mL) was added oxone (335 mg, 0.55 mmol, 4.0 eq) at rt. The resulted suspension was stirred overnight. More oxone (335 mg, 0.55 mmol, 4.0 eq) was added and the reaction mixture was stirred at rt overnight again. The reaction mixture was extracted with EtOAc (10 mL×2). The combined organic layers were washed with brine (10 mL×2), dried over sodium sulfate, filtered, and concd under reduced pressure to give a yellow foam as 2-(1-(6-fluoro-4-(2-hydroxyethylsulfinyl)-3-phenylquinolin-2-yl)ethyl)-isoindoline-1,3-dione. Mass Spectrum (ESI) m/e=489 (M+1).

4-Amino-6-(1-(6-fluoro-4-((R)-2-hydroxyethylsulfinyl)-3-phenylquinolin-2-yl)ethylamino)pyrimidine-5-carbonitrile and 4-amino-6-(1-(6-fluoro-4-((S)-2-hydroxyethylsulfinyl)-3-phenylquinolin-2-yl)ethylamino)pyrimidine-5-carbonitrile

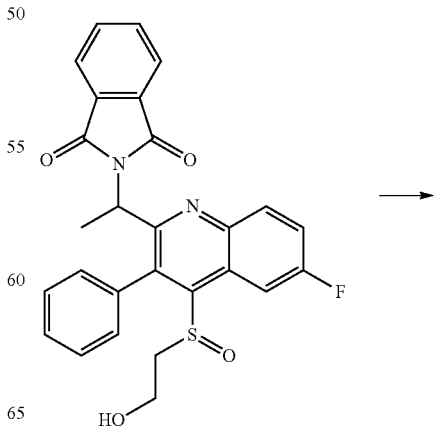

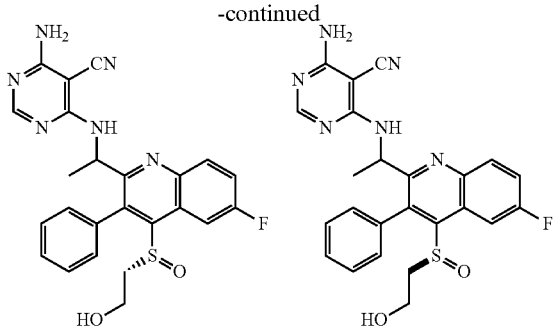

2-(1-(6-fluoro-4-(2-hydroxyethylsulfinyl)-3-phenylquinolin-2-yl)ethyl)isoindoline-1,3-dione was dissolved in EtOH (5 mL) and treated with hydrazine (0.5 mL) at 60° C. for 30 min. After cooling to rt, the reaction mixture was extracted with EtOAc (10 mL×2). The combined organic layers were washed with water, brine (10 mL×2), dried over sodium sulfate, filtered, and concd under reduced pressure to give a pale yellow oil as 2-(2-(1-aminoethyl)-6-fluoro-3-phenylquinolin-4-yl-sulfinyl)ethanol. Mass Spectrum (ESI) m/e=359 (M+1). To this oil was added 4-amino-6-chloropyrimidine-5-carbonitrile (15.8 mg, 1.0 eq), Hunig's base (1.2 eq) n-BuOH (1 mL) and the mixture was heated to 125° C. for 4 h. After cooling to rt, the mixture was purified by reverse HPLC (MeCN/H$_2$O, 10-50% containing 1% TFA) to give a white powders as 4-amino-6-(1-(6-fluoro-4-((R)-2-hydroxyethylsulfinyl)-3-phenylquinolin-2-yl)ethylamino)pyrimidine-5-carbonitrile. $^1$H-NMR (500 Hz, DMSO-d$^6$) δ 8.93 (dd, J=10.0, 5.0 Hz, 1H), 8.23 (dd, J=10.0, 5.0 Hz, 1H), 7.92 (s, 1H), 7.84 (td, J=10.0, 5.0 Hz, 1H), 7.46-7.53 (m, 5H), 7.37-7.39 (m, 1H), 7.27 (s, br, 1H), 5.10-5.18 (m, 1H), 4.96 (t, J=5.0 Hz, 1H), 3.75-3.84 (m, 2H), 3.17-3.21 (m, 1H), 1.32 (d, J=10.0 Hz, 3H). Mass Spectrum (ESI) m/e=477 (M+1). 4-Amino-6-(1-(6-fluoro-4-((S)-2-hydroxyethylsulfinyl)-3-phenylquinolin-2-yl)ethylamino)pyrimidine-5-carbonitrile. $^1$H-NMR (500 Hz, DMSO-d$^6$) δ 8.97 (dd, J=10.0, 5.0 Hz, 1H), 8.31 (dd, J=10.0, 5.0 Hz, 1H), 8.05 (s, 1H), 7.75 (td, J=10.0, 5.0 Hz, 1H), 7.59-7.63 (m, 1H), 7.51-7.54 (m, 3H), 7.37-7.39 (m, 1H), 5.46 (q, J=10.0 Hz, 1H), 4.96 (t, J=5.0 Hz, 1H), 3.97-4.01 (m, 1H), 3.86-3.89 (m, 1H), 3.65-3.70 (m, 1H), 3.17-3.19 (m, 1H), 1.46 (d, J=10.0 Hz, 3H). Mass Spectrum (ESI) m/e=477 (M+1).

Example 48: 2-(1-(3-Bromo-6-fluoro-4-(methylthio)quinolin-2-yl)ethyl)isoindoline-1,3-dione A solution of 4-fluoroaniline (11.11 g, 100 mmol), methyl propionylacetate (13.01 g, 100 mmol) and p-toluenesulfonic acid (0.25 g, 0.013 eq) in cyclohexane (35 mL) was heated at 95° C. in connection with a Dean-Stark water separator overnight. Filtration followed with removal of solvent gave a red oil. To a flask fitted with distillation head and dropping funnel was added Dowtherm™ A (35 mL) and heated to 240° C., internal temperature 220° C. The red oil was added dropwise in 10 min while keeping the temperature above 210° C. internally. After addition, the mixture was stirred at 240° C. for 15 min before cooling to rt. The resulted solid was filtered off and washed with a mixture of hexane and EtOAc (9/1). The solid formed in the filtrate was filtered again and washed with mixed solvents. A yellow solid was obtained as 2-ethyl-6-fluoroquinolin-4(1H)-one. $^1$H-NMR (500 Hz, CDCl$_3$) δ 9.7 (s, br, 1H), 7.91 (dd, J=10.0, 5.0 Hz, 1H), 7.39 (dd, J=10.0, 5.0 Hz, 1H), 7.26 (td, J=10.0, 5.0 Hz, 1H), 6.11 (s, 1H), 2.62 (q, J=10.0 Hz, 2H), 1.27 (t, J=10.0 Hz, 3H). A stirred solution of 2-ethyl-6-fluoroquinolin-4(1H)-one (2.6 g, 13.6 mmol) in AcOH (68 mL) was treated with pyridium tribromide (8.7 g, 2.0 eq) at rt. After stirring overnight, the reaction mixture was quenched with Na$_2$S$_2$O$_3$ solution. The resulted solid was washed with water, cold EtOH and dried in the air to give a white solid as 3-bromo-2-ethyl-6-fluoroquinolin-4(1H)-one. $^1$H-NMR (500 Hz, DMSO-d$^6$) δ 12.23 (s, 1H), 7.75 (dd, J=10.0, 5.0 Hz, 1H), 7.68 (dd, J=10.0, 5.0 Hz, 1H), 7.61 (td, J=10.0, 5.0 Hz, 1H), 2.90 (q, J=10.0 Hz, 2H), 1.29 (t, J=10.0 Hz, 3H). A suspension of 3-bromo-2-ethyl-6-fluoroquinolin-4(1H)-one (1.54 g, 5.7 mmol) in POCl$_3$ (5 mL) was heated to 100° C. for 2 h. After cooling to rt, the reaction mixture was poured into ice, the resulted semi-solid was neutralized with NaHCO$_3$ satd solution and extracted with EtOAc (20 mL). The organic layer was separated, washed with NaHCO$_3$, water, brine, dried, concd and purified by combiflash (EtOAc/hexane, 1/9) to give a white solid as 3-bromo-4-chloro-2-ethyl-6-fluoroquinoline. 2-(1-(3-Bromo-6-fluoro-4-(methylthio)quinolin-2-yl)ethyl)isoindoline-1,3-dione was made by 3 steps in the similar manner as previous described for preparation of 2-(1-(6-fluoro-4-(methylthio)-3-phenylquinolin-2-yl)ethyl)isoindoline-1,3-dione. Mass Spectrum (ESI) m/e=446 (M+1).

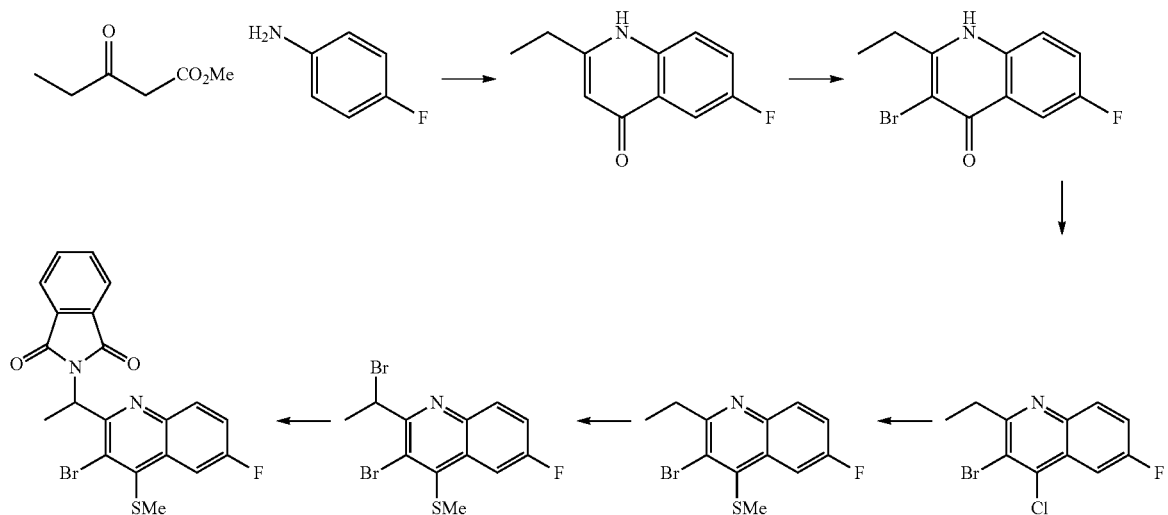

2-(1-(3-(3,5-Difluorophenyl)-6-fluoro-4-(methylsulfonyl)quinolin-2-yl)ethyl)-isoindoline-1,3-dione

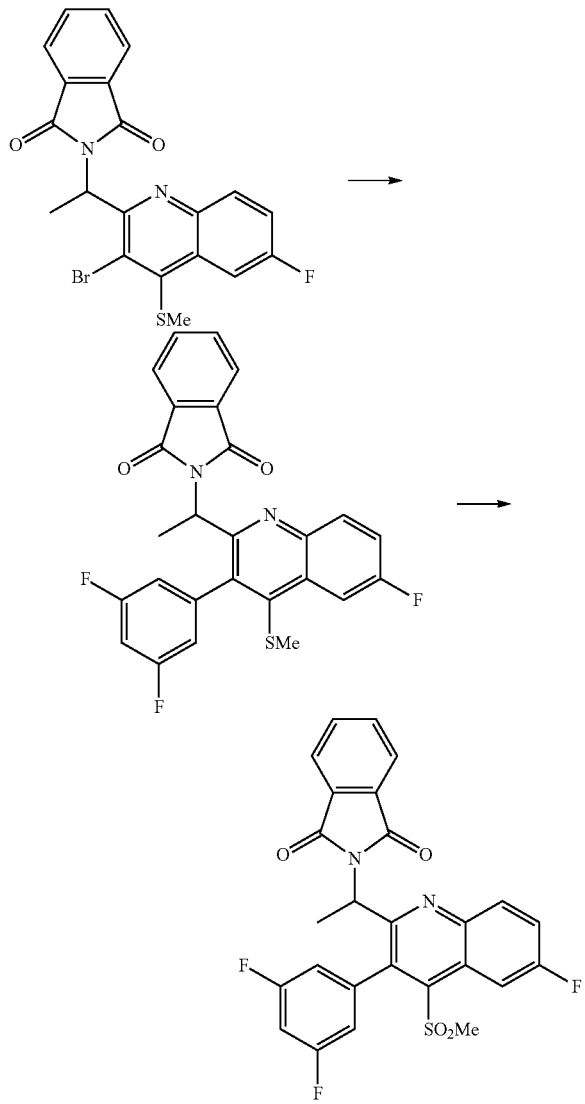

A mixture of 2-(1-(3-bromo-6-fluoro-4-(methylthio)quinolin-2-yl)ethyl)isoindoline-1,3-dione (100 mg, 0.23 mmol), 3,5-difluorophenylboronic acid (71 mg, 2.0 eq), $K_2CO_3$ (93 mg, 3.0 eq) and tetrakis(triphenylphosphine)palladium(0) (26 mg, 0.05 eq) in DME (5 mL) was purged with $N_2$ and heated to reflux. After stirring overnight, the reaction mixture was cooled to rt, partitioned between water and EtOAc, and the layers were separated. The aq. layer was extracted with EtOAc (10 mL×2). The combined organic layers were washed with water (10 mL×2), brine (10 mL), dried over sodium sulfate, filtered, and concd under reduced pressure. The residue was purified by combiflash on silica gel (EtOAc/hexane, 1/4) to give 2-(1-(3-(3,5-difluorophenyl)-6-fluoro-4-(methylthio)quinolin-2-yl)ethyl)isoindoline-1,3-dione as a white solid. Mass Spectrum (ESI) m/e=479 (M+1). To a solution of 2-(1-(3-(3,5-difluorophenyl)-6-fluoro-4-(methylthio)quinolin-2-yl)ethyl)isoindoline-1,3-dione (42 mg, 0.088 mmol) in THF (3 mL) and $H_2O$ (1 mL) was added oxone (108 mg, 0.18 mmol, 2.0 eq) at rt.

The resulted suspension was stirred at rt overnight. The reaction was incomplete. Oxone (108 mg, 2.0 eq) was added and the reaction mixture was stirred at rt overnight again. This procedure was repeated for twice and LCMS showed completion. The reaction mixture was extracted with EtOAc (10 mL×2). The combined organic layers were washed with water, $NaHCO_3$, brine (10 mL×2), dried over sodium sulfate, filtered, and concd under reduced pressure to give a white solid. Mass Spectrum (ESI) m/e=511 (M+1).

4-Amino-6-(1-(3-(3,5-difluorophenyl)-6-fluoro-4-(methylsulfonyl)quinolin-2-yl)ethylamino)pyrimidine-5-carbonitrile

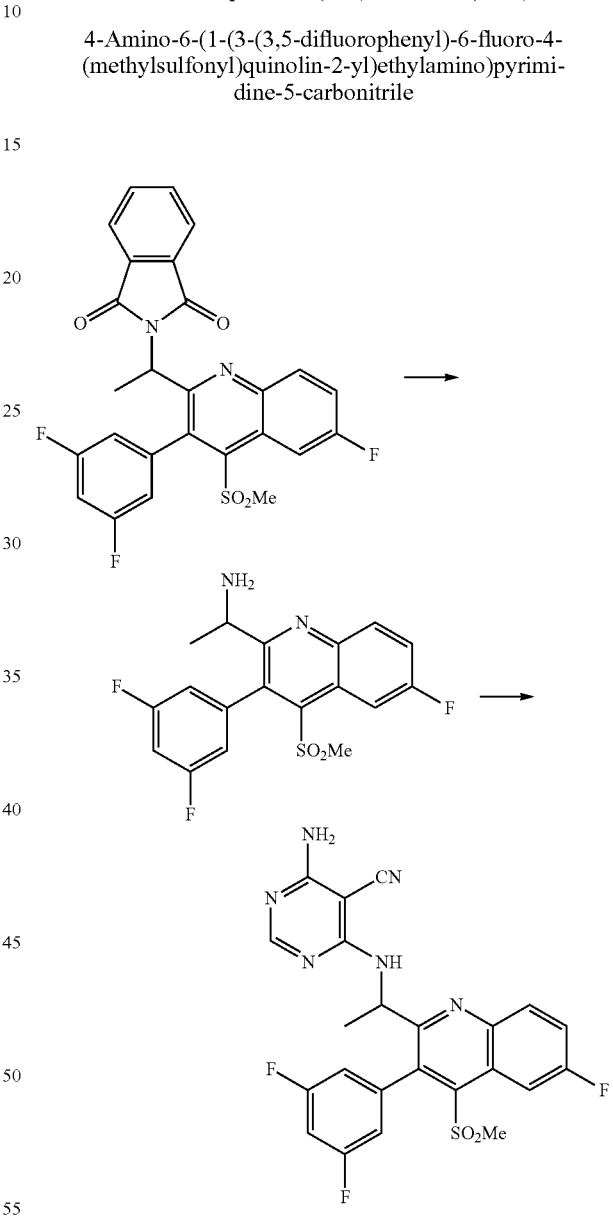

2-(1-(3-(3,5-Difluorophenyl)-6-fluoro-4-(methylsulfonyl)quinolin-2-yl)ethyl)-isoindoline-1,3-dione was suspended in EtOH (1 mL) and treated with 0.1 mL hydrazine at 70° C. for 30 min. After cooling to rt, the reaction mixture was extracted with EtOAc (5 mL×2). The combined organic layers were washed with water, brine (3 mL×2), dried over sodium sulfate, filtered, and concd under reduced pressure to give a white solid. 1-(3-(3,5-difluorophenyl)-6-fluoro-4-(methylsulfonyl)quinolin-2-yl)ethanamine (30 mg, 0.079 mmol), 4-amino-6-chloropyrimidine-5-carbonitrile (12.2 mg, 1.0 eq) and Hunig's base (16.5 μL, 1.2 eq) in n-BuOH (1 mL) was heated to 130° C. overnight. The mixture was cooled to rt and purified by reverse HPLC gave a white powder as TFA salt (25 mg, 63%). $^1$H-NMR (500 Hz, CD$_3$OD) δ 8.66 (dd, J=10.0, 5.0 Hz, 1H), 8.34 (dd, J=10.0, 5.0 Hz, 1H), 8.08 (s, 1H), 7.81 (td, J=10.0, 5.0 Hz, 1H), 7.12-7.18 (m, 2H), 7.05-7.10 (m, 1H), 5.40 (q, J=10.0 Hz, 1H), 3.27 (s, 3H), 1.52 (d, J=10.0 Hz, 3H). Mass Spectrum (ESI) m/e=499 (M+1).

Example 49: (S)-2-(1-(3-(3,5-Difluorophenyl)-6-fluoro-4-methoxyquinolin-2-yl)ethyl)-isoindoline-1,3-dione

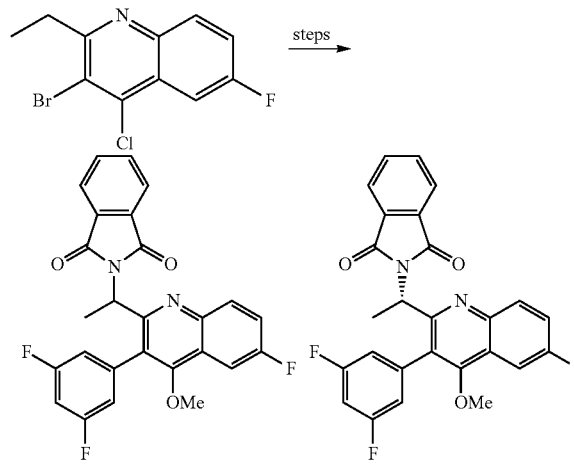

2-(1-(3-(3,5-Difluorophenyl)-6-fluoro-4-methoxyquinolin-2-yl)ethyl)isoindoline-1,3-dione was synthesized from 3-bromo-4-chloro-2-ethyl-6-fluoroquinoline in a similar manner as described in the preparation of the corresponding sulfur analog 2-(1-(3-(3,5-difluorophenyl)-6-fluoro-4-(methylthio)quinolin-2-yl)ethyl)isoindoline-1,3-dione. Mass Spectrum (ESI) m/e=463 (M+1). (S)-2-(1-(3-(3,5-difluorophenyl)-6-fluoro-4-methoxyquinolin-2-yl)ethyl) isoindoline-1,3-dione was obtained by chiral separation on OD column (i-PrOH/hexane, up to 15%).

(S)-4-Amino-6-(1-(3-(3,5-difluorophenyl)-6-fluoro-4-methoxyquinolin-2-yl)-ethylamino)pyrimidine-5-carbonitrile

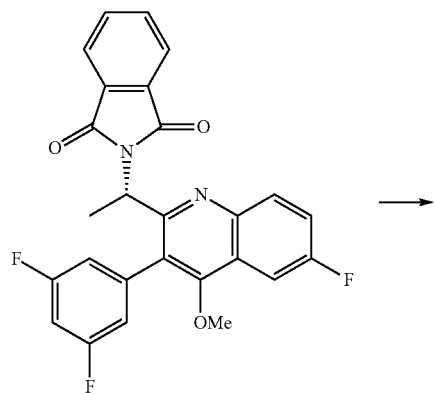

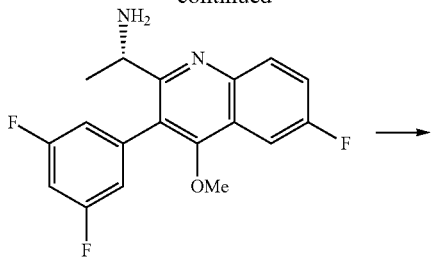

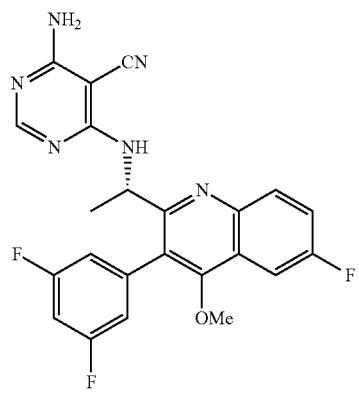

A solution of (S)-2-(1-(3-(3,5-difluorophenyl)-6-fluoro-4-methoxyquinolin-2-yl)-ethyl)isoindoline-1,3-dione (45 mg, 0.1 mmol) in EtOH (2 mL) was treated with hydrazine (0.1 mL) at 70° C. for 30 min. After cooling to rt, the reaction mixture was partitioned between water (5 mL) and EtOAc (5 mL). The organic layer was separated, washed with water, brine, dried and concd to give a white solid, which was dissolve in n-BuOH (1 mL) and treated with Hunig's base (0.021 mL, 1.2 eq) and 4-amino-6-chloropyrimidine-5-carbonitrile (17 mg, 1.1 eq). The reaction mixture was heated to 120° C. overnight. After cooling to rt, the reaction mixture was purified by reverse HPLC (MeCN/H$_2$O/0.1% TFA, 10-60%) to give a white powder. $^1$H-NMR (400 Hz, DMSO-d$^6$) δ 8.11 (dd, J=8.0, 4.0 Hz, 1H), 7.98 (s, 1H), 7.84 (dd, J=8.0, 4.0 Hz, 1H), 7.65-7.79 (m, 2H), 7.46 (s, br, 1H), 7.22-7.34 (m, 3H), 5.29-5.33 (m, 1H), 3.64 (s, 3H), 1.36 (t, J=8.0 Hz, 3H). Mass Spectrum (ESI) m/e=451 (M+1).

Example 50

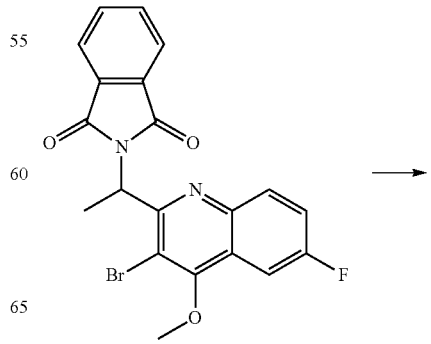

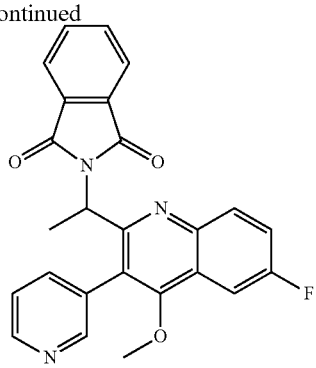

A solution of 2-(1-(3-bromo-6-fluoro-4-methoxyquinolin-2-yl)ethyl)isoindoline-1,3-dione (10 mg, 0.023 mmol), obtained in a similar why as described for 2-(1-(3-bromo-6-fluoro-4-(methylthio)quinolin-2-yl)ethyl)isoindoline-1,3-dione, and pyridin-3-ylboronic acid (5.73 mg, 0.047 mmol), K$_2$CO$_3$ (9.66 mg, 0.070 mmol) in DME (2 mL) was purged with N$_2$ followed by the addition of Pd(Ph$_3$P)$_4$ (2.69 mg, 2.330 μmol). The resulting mixture was heated to 100° C. overnight. The reaction mixture was allowed to cool to rt. The product isolated as previously described for similar analogs. 2-(1-(6-fluoro-4-methoxy-3-(pyridin-3-yl)quinolin-2-yl)ethyl)isoindoline-1,3-dione.

4-Amino-6-(((1R)-1-(6-fluoro-4-methoxy-3-(3-pyridinyl)-2-quinolinyl)ethyl)-amino)-5-pyrimidinecarbonitrile

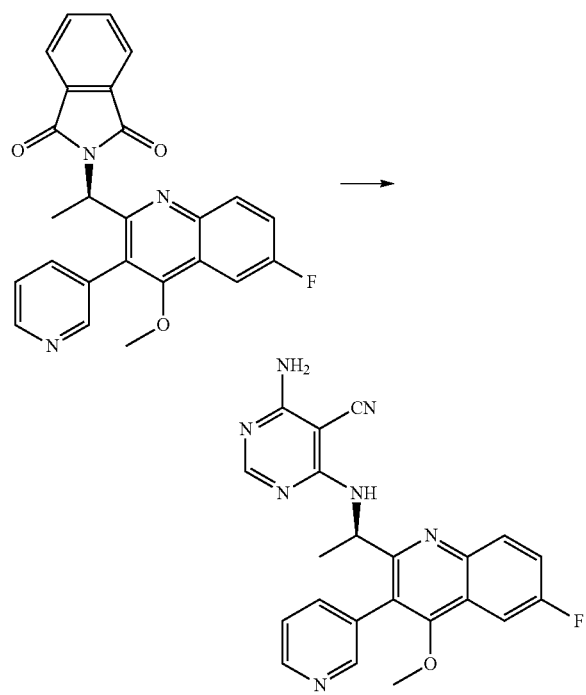

A solution of (R)-2-(1-(6-fluoro-4-methoxy-3-(pyridin-3-yl)quinolin-2-yl)ethyl)-isoindoline-1,3-dione (19.7 mg, 0.046 mmol) and hydrazine (1.447 μL, 0.046 mmol) in EtOH (1 mL) was heated to 60° C. for 30 min. The solvent was removed and EtOAc was added and washed with water, brine and dried over sodium sulfate to obtain (R)-1-(6-fluoro-4-methoxy-3-(pyridin-3-yl)quinolin-2-yl)ethanamine as clear oil. To solution of (R)-1-(6-fluoro-4-methoxy-3-(pyridin-3-yl)quinolin-2-yl)ethanamine (13.9 mg, 0.047 mmol) in BuOH (1.000 mL) was added 4-amino-6-chloro-pyrimidine-5-carbonitrile (7.12 mg, 0.046 mmol) and DIEA (8.05 μL, 0.046 mmol). The resulting mixture was heated to 100° C. The solvent was removed and crude residue was subjected to preparatory. TLC using 3% MeOH (with 7N Ammonia)/DCM to obtain (R)-4-amino-6-(1-(6-fluoro-4-methoxy-3-(pyridin-3-yl)quinolin-2-yl)ethylamino)pyrimidine-5-carbonitrile as a light yellowish solid.

Example 51: 4-Amino-6-(((1R)-1-(6-fluoro-4-methoxy-3-(3-pyridinyl)-2-quinolinyl)ethyl)amino)-5-pyrimidinecarbonitrile

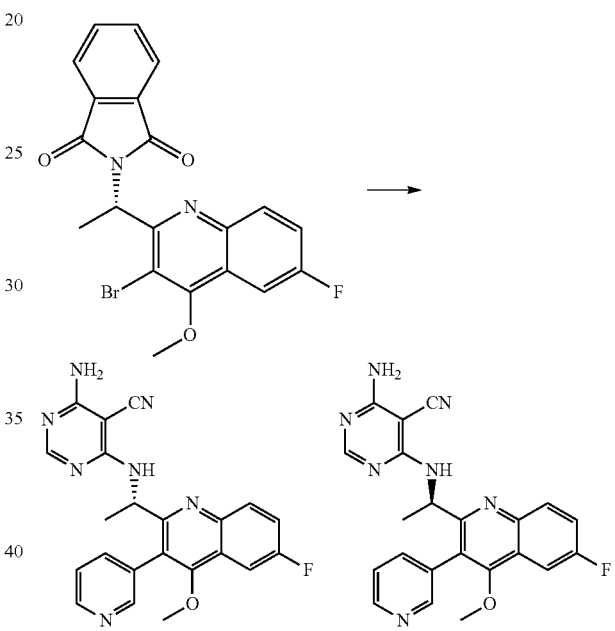

A solution of (S)-2-(1-(3-bromo-6-fluoro-4-methoxyquinolin-2-yl)ethyl)isoindoline-1,3-dione (100 mg, 0.233 mmol), pyridin-3-ylboronic acid (57.3 mg, 0.466 mmol) and potassium carbonate (97 mg, 0.699 mmol) in DME (2 mL) was purged with N$_2$ followed by the addition of Pd(PPh$_3$)$_4$ (26.9 mg, 0.023 mmol) and the resulting mixture was heated to 100° C. overnight. The solvent was removed and EtOAc was added and washed with water, brine and dried over sodium sulfate. The crude residue was subjected to combi-flash purification using 1:1 EtOAc/hexane to obtain (S)-2-(1-(6-fluoro-4-methoxy-3-(pyridin-3-yl)quinolin-2-yl)ethyl)isoindoline-1,3-dione as a clear oil. A solution of (S)-2-(1-(6-fluoro-4-methoxy-3-(pyridin-3-yl)quinolin-2-yl)ethyl)isoindoline-1,3-dione (23.7 mg, 0.055 mmol) and hydrazine (1.740 μL, 0.055 mmol) in EtOH (1 mL) was heated to 60° C. for 30 min. The solvent was removed and EtOAc was added and washed with water, brine and dried over sodium sulfate to obtain (S)-1-(6-fluoro-4-methoxy-3-(pyridin-3-yl)quinolin-2-yl)ethanamine. To a solution of (S)-1-(6-fluoro-4-methoxy-3-(pyridin-3-yl)quinolin-2-yl) ethanamine in BuOH (1.0 mL) was added 4-amino-6-chloropyrimidine-5-carbonitrile (8.57 mg, 0.055 mmol) and DIEA (9.68 μL, 0.055 mmol). The resulting mixture was heated to 100° C. for 1 h. The crude solution was allowed to cool to rt. and ppt was observed. The solid was filtered and the filtrate was concd and subjected to preparatory TLC purification. ¹H-NMR (400 Hz, CD₃OD) δ ppm 1.41 (5H, d, J=6.65 Hz) 3.66 (3H, s) 5.42 (1H, q, J=6.59 Hz) 7.66 (2H, m) 7.83 (1H, dd, J=9.39, 2.93 Hz) 7.96 (1H, s) 8.17 (2H, dd, J=9.19, 5.09 Hz) 8.69 (2H, dd, J=4.89, 1.57 Hz). Mass Spectrum (ESI) m/e=415 (M+1).

Example 52: 4-Amino-6-(((1S)-1-(6-fluoro-4-methoxy-3-(3-pyridinyl)-2-quinolinyl)ethyl)amino)-5-pyrimidinecarbonitrile ¹H-NMR (500 Hz, CD₃OD) δ ppm 1.41 (3H, d) 3.65 (3H, s) 5.41 (2H, m) 7.66 (2H, m) 7.83 (1H, dd, J=9.41, 2.32 Hz) 7.96 (1H, s) 8.17 (2H, dd, J=9.29, 5.14 Hz) 8.69 (2H, d, J=4.89 Hz). Mass Spectrum (ESI) m/e=415 (M+1).

Example 53: Methyl 2-(1-aminoethyl)-6-fluoro-3-phenylquinoline-4-carboxylate brine, dried over sodium sulfate. Removal of solvents followed with purification on column chromatography on silica gel (hexane/EtOAc, 1/9) gave methyl 2-ethyl-6-fluoro-3-phenylquinoline-4-carboxylate as an off-white solid. ¹H-NMR (400 Hz, CDCl₃) δ 8.14 (dd, J=8.0, 4.0 Hz, 1H), 7.40-7.54 (m, 5H), 7.26-7.35 (m, 2H), 3.62 (s, 3H), 2.85 (q, J=8.0 Hz, 2H), 1.23 (t, J=8.0 Hz, 3H). Mass Spectrum (ESI) m/e=310 (M+1). Methyl 2-ethyl-6-fluoro-3-phenylquinoline-4-carboxylate (1.00 g, 3.2 mmol) and 1,3-dibromo-5,5-dimethylhydantoin (647 mg, 0.7 eq) were suspended in carbon tetrachloride (30 mL) and treated with benzoyl peroxide (78 mg, 0.1 eq) and the mixture was heated at reflux for 3 h. The reaction mixture was cooled to rt and treated with satd aq. sodium bicarbonate solution (10 mL). The layers were separated and the aq. layer was extracted with DCM (3 mL×2). The combined organic layers were washed with brine (30 mL), dried over sodium sulfate, filtered, and concd under reduced pressure to give methyl 2-(1-bromoethyl)-6-fluoro-3-phenylquinoline-4-carboxylate as a yellow solid (crude, 1.4 g). To a solution of methyl

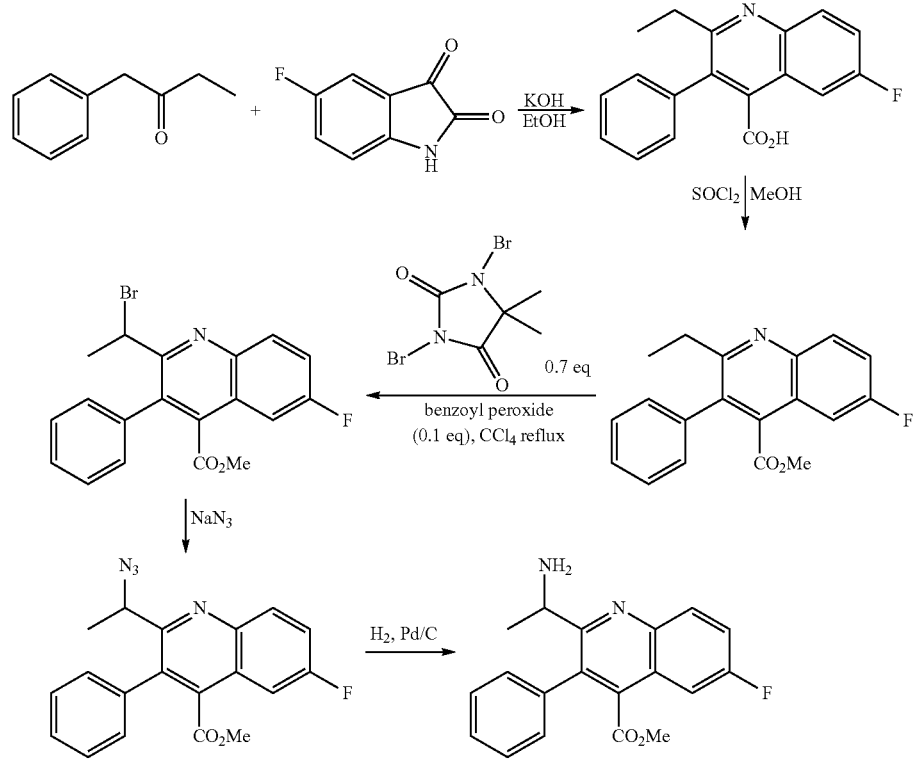

A mixture of 5-fluoroisatin (5.00 g, 30.3 mmol), 1-phenylbutan-2-one (4.94 g, 1.1 eq) and KOH (5.1 g, 3.0 eq) in EtOH (100 mL) was heated to reflux for 3 h. After cooling to rt, the reaction mixture was concd, diluted with water, extracted with ether twice and neutralized to pH 5. The resulted solid was filtered, washed with water and dried in the air to give a mixture of isomers. The solid was suspended in DCM (100 mL) and treated with SOCl₂ (18 g, 5.0 eq) at rt overnight. The solvent was removed and treated with MeOH (50 mL) at rt for 2 h. Removal of solvent followed with addition of satd sodium bicarbonate solution gave a brown oil. The reaction mixture was extracted with EtOAc (20 mL×2), the combined organics were washed with water, 2-(1-bromoethyl)-6-fluoro-3-phenylquinoline-4-carboxylate (1.17 g, 3.00 mmol) in DMF (6 mL) was added NaN₃ (0.293 g, 1.5 eq) at rt. After 2 h, LCMS showed completion. The reaction mixture was diluted with water and extracted with EtOAc (10 mL×2). The organic layers were combined, washed with water, brine, dried, concd to give methyl 2-(1-azidoethyl)-6-fluoro-3-phenylquinoline-4-carboxylate as a tan oil. Mass Spectrum (ESI) m/e=351 (M+1). A solution of methyl 2-(1-azidoethyl)-6-fluoro-3-phenylquinoline-4-carboxylate (1.25 g, 3.6 mmol) in MeOH (10 mL) was treated with 10% Pd—C (100 mg) under H₂ balloon overnight. The reaction mixture was filtered through a Celite™ pad and concd under reduced pressure to give methyl 2-(1-aminoethyl)-6-fluoro-3-phenylquinoline-4-carboxylate as a yellow oil. Mass Spectrum (ESI) m/e=325 (M+1).

Methyl 2-(1-(6-amino-5-cyanopyrimidin-4-ylamino)ethyl)-6-fluoro-3-phenylquinoline-4-carboxylate

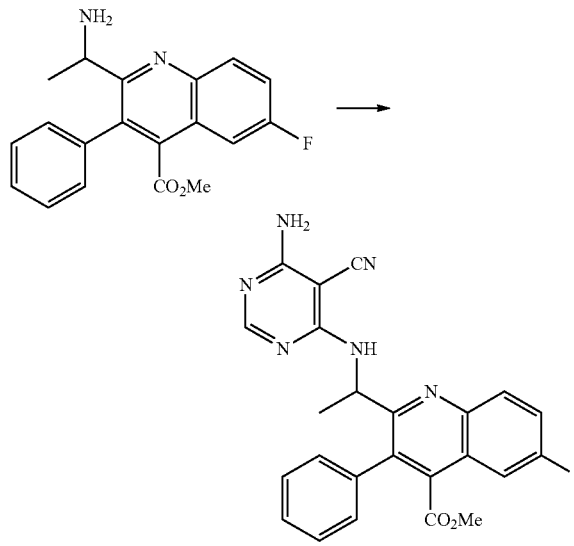

A mixture of methyl 2-(1-aminoethyl)-6-fluoro-3-phenylquinoline-4-carboxylate (200 mg, 0.62 mmol), 4-amino-6-chloropyrimidine-5-carbonitrile (95 mg, 1.0 eq) and Hunig's base (129 μL, 1.2 eq) in DMF (3 mL) was heated to 130° C. for 2 h. The reaction mixture was cooled to rt, diluted with water and extracted with EtOAc (20 mL×2). The organic layers were combined, washed with water, brine, dried, concd and purified by column chromatography on silica gel (DCM/MeOH/NH$_3$, 20/1/0.1) to give methyl 2-(1-(6-amino-5-cyanopyrimidin-4-ylamino)ethyl)-6-fluoro-3-phenylquinoline-4-carboxylate as a white solid. $^1$H-NMR (400 Hz, DMSO-d$^6$) δ 8.16 (dd, J=8.0, 4.0 Hz, 1H), 7.91 (s, 1H), 7.81 (td, J=8.0, 4.0 Hz, 1H), 7.59 (dd, J=8.0, 4.0 Hz, 1H), 7.45-7.52 (m, 5H), 7.35 (dd, J=8.0, 4.0 Hz, 1H), 7.25 (s, br, 2H), 5.30-5.40 (m, 1H), 3.59 (s, 3H), 1.30 (t, J=8.0 Hz, 3H). Mass Spectrum (ESI) m/e=443 (M+1).

Example 54: 2-(1-(6-Amino-5-cyanopyrimidin-4-ylamino)ethyl)-6-fluoro-3-phenylquinoline-4-carboxylic acid and 2-(1-(6-amino-5-carbamoylpyrimidin-4-ylamino)ethyl)-6-fluoro-3-phenylquinoline-4-carboxylic acid

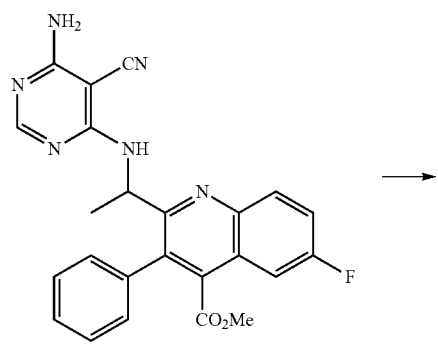

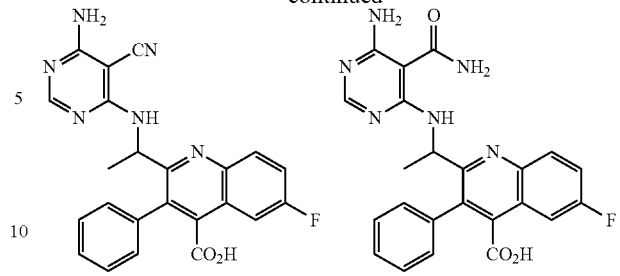

A suspension of methyl 2-(1-(6-amino-5-cyanopyrimidin-4-ylamino)ethyl)-6-fluoro-3-phenylquinoline-4-carboxylate (150 mg, 0.34 mmol) in a mixture of MeOH (3 mL), THF (3 mL) and 1 N LiOH (3 mL) was stirred at 60° C. for 3 h. Removal of the solvents followed with neutralizing the aq. residue gave a white solid, which was dissolved in DMF and purified by reverse HPLC (MeCN/H$_2$O/0.1% TFA, 10-50%) to give 2-(1-(6-amino-5-cyanopyrimidin-4-ylamino)ethyl)-6-fluoro-3-phenylquinoline-4-carboxylic acid as a white powder. $^1$H-NMR (400 Hz, DMSO-d$^6$) δ 8.16 (dd, J=8.0, 4.0 Hz, 1H), 7.97 (s, 1H), 7.81 (td, J=8.0, 4.0 Hz, 1H), 7.72 (dd, J=8.0, 4.0 Hz, 1H), 7.38-7.52 (m, 8H), 5.30-5.40 (m, 1H), 1.30 (t, J=8.0 Hz, 3H). Mass Spectrum (ESI) m/e=429 (M+1). 2-(1-(6-Amino-5-carbamoylpyrimidin-4-ylamino)ethyl)-6-fluoro-3-phenylquinoline-4-carboxylic acid as a white solid. $^1$H-NMR (400 Hz, DMSO-d$^6$) δ 9.0 (s, br, 1H), 8.16 (dd, J=8.0, 4.0 Hz, 1H), 8.08 (s, 1H), 7.80-7.85 (m, 2H), 7.40-7.53 (m, 5H), 7.30 (s, br, 1H), 5.30-5.40 (m, 1H), 1.27 (t, J=8.0 Hz, 3H). Mass Spectrum (ESI) m/e=447 (M+1).

Example 55: tert-Butyl 1-(6-fluoro-4-(hydroxymethyl)-3-phenylquinolin-2-yl)ethylcarbamate

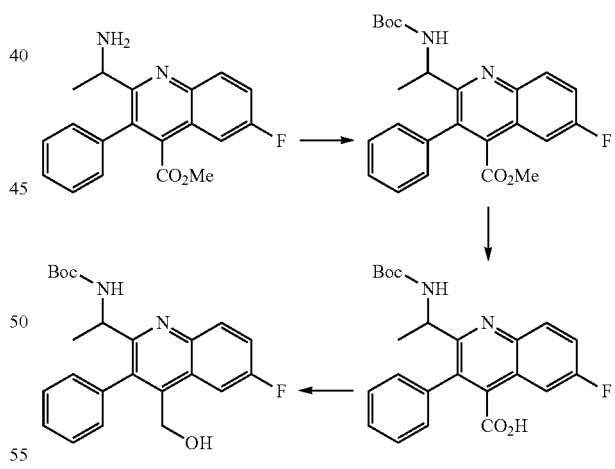

A mixture of methyl 2-(1-aminoethyl)-6-fluoro-3-phenylquinoline-4-carboxylate (1.3 g, 4.0 mmol) and Boc$_2$O (1.3 g, 1.5 eq) in THF (20 mL) was treated with Et$_3$N (0.84 mL, 1.5 eq). After refluxing for 2 h, the reaction mixture was concd and purified by silica gel column (EtOAc/hexane, 1/4) to give methyl 2-(1-(tert-butoxycarbonylamino)-ethyl)-6-fluoro-3-phenylquinoline-4-carboxylate as a white solid. A mixture of methyl 2-(1-(tert-butoxycarbonylamino)-ethyl)-6-fluoro-3-phenylquinoline-4-carboxylate (200 mg, 0.47 mmol) in THF (2 mL), MeOH (2 mL) and 1 N LiOH solution in water (3 mL) was heated to 60° C. for 4 h before removal of solvents. The residue was acidified to pH 4 with 3N HCl. The resulted solid was filtered, washed with water and dried in the air to give 2-(1-(tert-butoxycarbonylamino)ethyl)-6-fluoro-3-phenylquinoline-4-carboxylic acid as a white solid. Mass Spectrum (ESI) m/e=411 (M+1). 2-(1-(tert-Butoxy-carbonylamino)ethyl)-6-fluoro-3-phenylquinoline-4-carboxylic acid was suspended in THF (5 mL) at −10° C. and treated with $Et_3N$ (0.1 mL, 1.5 eq) followed with $ClCO_2Pr^i$ (1M in tol, 0.71 mL, 1.5 eq). The reaction mixture was stirred at this temperature for 1.5 h before addition of ice-water (2 mL) followed by $NaBH_4$ (10 eq, 178 mg). The reaction mixture was stirred overnight and partitioned between EtOAc (10 mL) and water (5 mL). The organic layer was separated, washed with water, brine, dried and concd. The residue was purified by column chromatography on silica gel (EtOAc/hexane, 1/1) to give tert-butyl 1-(6-fluoro-4-(hydroxymethyl)-3-phenylquinolin-2-yl)ethylcarbamate as a white solid. Mass Spectrum (ESI) m/e=397 (M+1).

4-Amino-6-(1-(6-fluoro-4-(hydroxymethyl)-3-phenylquinolin-2-yl)ethyl-amino)pyrimidine-5-carbonitrile

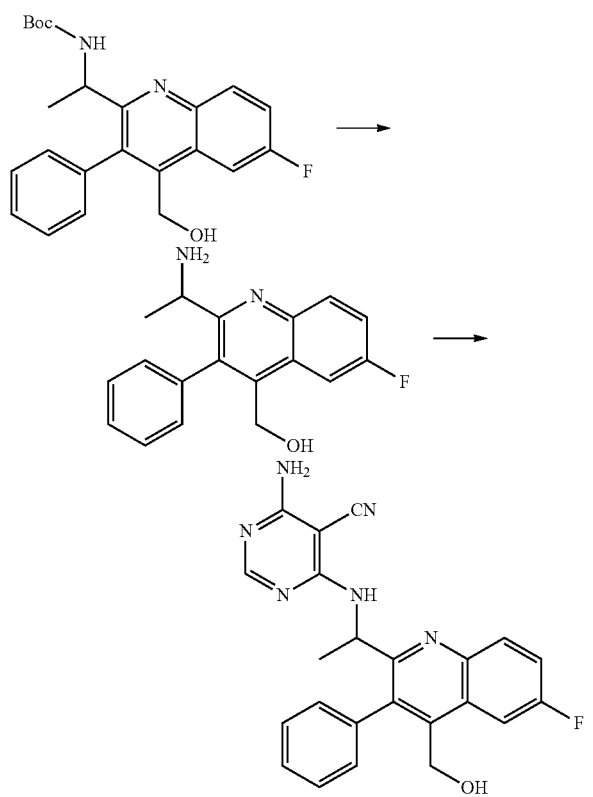

To a solution of tert-butyl 1-(6-fluoro-4-(hydroxymethyl)-3-phenylquinolin-2-yl)-ethylcarbamate (130 mg, 0.33 mmol) in DCM (2 mL) was added TFA (2 mL) at rt. The mixture was stirred at rt for 30 min before removal of solvents. The residue was treated with benzene and concd under reduced pressure and stored under high vacuum for 2 h to give (2-(1-aminoethyl)-6-fluoro-3-phenylquinolin-4-yl)methanol as TFA salt. A mixture of (2-(1-aminoethyl)-6-fluoro-3-phenylquinolin-4-yl)methanol TFA salt (0.33 mmol, crude), 4-amino-6-chloropyrimidine-5-carbonitrile (50.7 mg, 1.0 eq) and Hunig's base (229 µL, 4.0 eq) in n-BuOH (3 mL) was heated to 120° C. overnight. The mixture was cooled to rt and purified by reverse phase HPLC (MeCN/$H_2O$/0.1% TFA, 10-50%) to give 4-amino-6-(1-(6-fluoro-4-(hydroxymethyl)-3-phenylquinolin-2-yl)ethyl-amino)pyrimidine-5-carbonitrile TFA salt as a white powder. $^1$H-NMR (400 Hz, $CD_3OD$) δ 8.20 (dd, J=8.0, 4.0 Hz, 1H), 8.13 (s, 1H), 8.06 (dd, J=8.0, 4.0 Hz, 1H), 7.67 (td, J=8.0, 4.0 Hz, 1H), 7.52-7.60 (m, 3H), 7.44-7.46 (m, 2H), 5.49 (q, J=8.0 Hz, 1H), 4.75 (d, J=12 Hz, 1H), 4.70 (d, J=12 Hz, 1H), 1.43 (d, J=8.0 Hz, 3H). Mass Spectrum (ESI) m/e=415 (M+1).

Example 56: tert-Butyl 1-(6-fluoro-4-(methylsulfonylmethyl)-3-phenylquinolin-2-yl)-ethylcarbamate

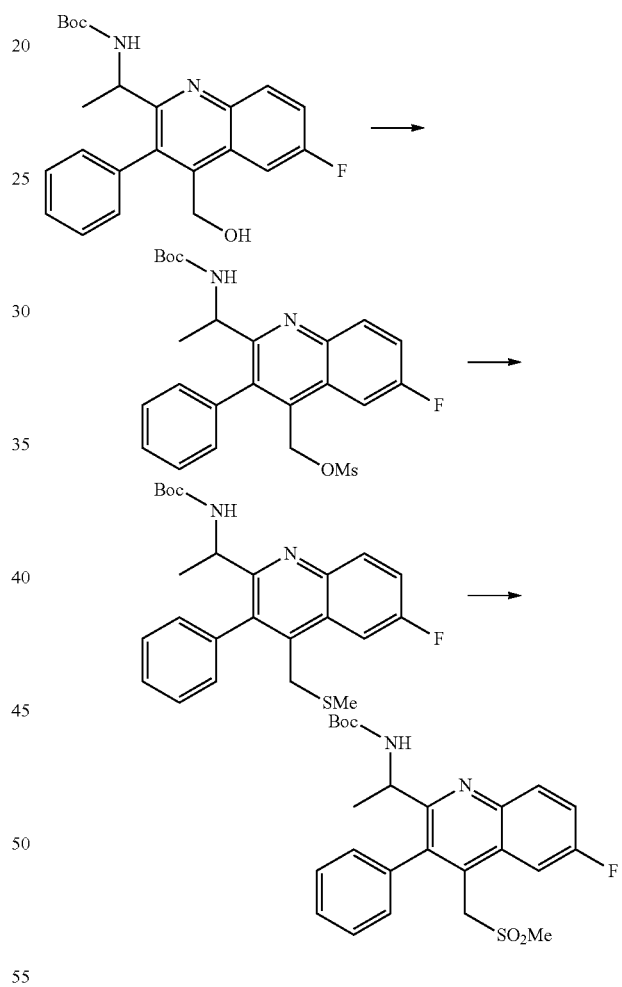

A solution of tert-butyl 1-(6-fluoro-4-(hydroxymethyl)-3-phenylquinolin-2-yl)-ethylcarbamate (220 mg, 0.56 mmol) in DCM (5 mL) at −10° C. was treated with $Et_3N$ (0.11 mL, 1.4 eq) followed with MsCl (0.053 mL, 1.2 eq). The reaction mixture was slowly warmed to rt. and washed with $NaHCO_3$, brine, dried and concd to give (2-(1-(tert-butoxycarbonylamino)ethyl)-6-fluoro-3-phenylquinolin-4-yl)methyl methane-sulfonate as a white solid. Mass Spectrum (ESI) m/e=475 (M+1). A solution of (2-(1-(tert-butoxycarbonylamino)ethyl)-6-fluoro-3-phenylquinolin-4-yl)methyl methanesulfonate (100 mg, 0.21 mmol) in DMF (2 mL) was treated with NaSMe (17.7 mg, 1.2 eq) at rt. After 2 h, the reaction mixture was partitioned between EtOAc (10 mL) and water (10 mL). The organic layer was separated, washed, dried and concd to give an oil which was purified by combiflash (EtOAc/hexane, 1/4) to give tert-butyl 1-(6-fluoro-4-(methylthiomethyl)-3-phenylquinolin-2-yl)ethyl-carbamate as a white solid. A solution of tert-butyl 1-(6-fluoro-4-(methylthiomethyl)-3-phenylquinolin-2-yl)ethyl-carbamate (64 mg, 0.15 mmol) in a mixture of acetone (4 mL), THF (2 mL) and water (2 mL) was treated with NMO (88 mg, 5.0 eq) followed with OsO4 (1 crop) at 0° C. The reaction mixture was then stirred at rt overnight and partitioned between NaHCO3 solution and EtOAc (10 mL). The organic layer was washed with NaS2O3, water, brine, dried and concd to give tert-butyl 1-(6-fluoro-4-(methylsulfonyl-methyl)-3-phenylquinolin-2-yl)ethylcarbamate as a white solid. Mass Spectrum (ESI) m/e=459 (M+1).

4-Amino-6-(1-(6-fluoro-4-(methylsulfonylmethyl)-3-phenylquinolin-2-yl)-ethylamino)pyrimidine-5-carbonitrile

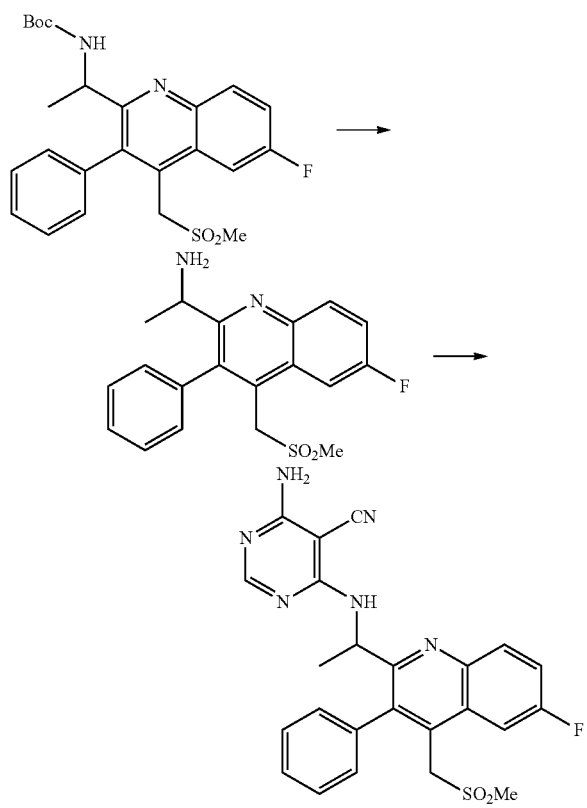

4-Amino-6-(1-(6-fluoro-4-(methylsulfonylmethyl)-3-phenylquinolin-2-yl)ethyl-amino)pyrimidine-5-carbonitrile was made in the similar manner as the preparation of 4-amino-6-(1-(6-fluoro-4-(hydroxymethyl)-3-phenylquino-lin-2-yl)-ethylamino)pyrimidine-5-carbonitrile. $^1$H-NMR (400 Hz, CD$_3$OD) δ 8.22 (dd, J=8.0, 4.0 Hz, 1H), 8.09 (s, 1H), 8.07 (dd, J=8.0, 4.0 Hz, 1H), 7.69 (td, J=8.0, 4.0 Hz, 1H), 7.52-7.60 (m, 3H), 7.44-7.46 (m, 2H), 5.43 (q, J=8.0 Hz, 1H), 4.87 (2H, overlapped with solvent peak), 2.90 (s, 3H), 1.45 (d, J=8.0 Hz, 3H). Mass Spectrum (ESI) m/e=477 (M+1).

Example 57: 2-Ethyl-6-fluoro-3-(pyridin-2-yl)qui-noline-4-carboxylic acid and 2-ethyl-6-fluoro-3-(pyridin-2-yl)quinoline-4-carboxamide

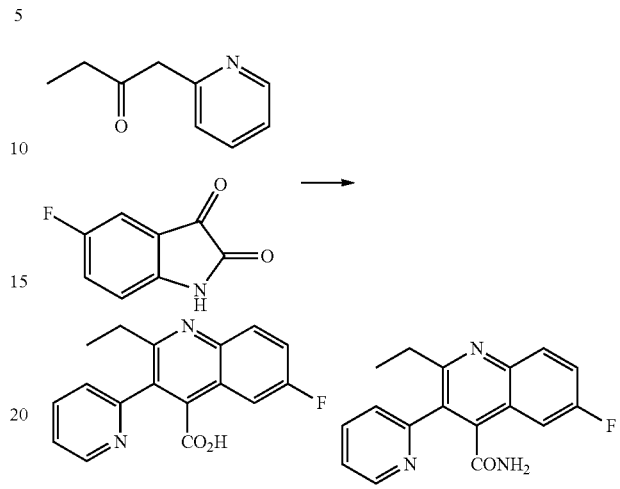

A mixture of the known 1-(pyridin-2-yl)butan-2-one (19.9 g, 80% purity), 5-fluoroisatin (22.0 g, 1.0 eq), KOH (22.3 g, 3.0 eq), EtOH (100 mL) and water (100 mL) was heated to 90° C. overnight. Solvents were concd to 100 mL and extracted with ether twice. The resulted solid was filtered, washed with water and dried in the air to provide 2-ethyl-6-fluoro-3-(pyridin-2-yl)quinoline-4-carboxamide (presumed to have formed via impurity). $^1$H-NMR (500 Hz, DMSO-d$^6$) δ 8.71 (dd, J=10.0, 5.0 Hz, 1H), 8.14 (dd, J=10.0, 5.0 Hz, 1H), 8.03 (s, 1H), 7.94 (td, J=10.0, 5.0 Hz, 1H), 7.72-7.76 (m, 2H), 7.56 (d, J=10.0 Hz, 1H), 7.51 (dd, J=10.0, 5.0 Hz, 1H), 7.46-7.48 (m, 1H), 2.47 (q, J=5.0 Hz, 2H), 1.12 (t, J=5.0 Hz, 3H). Mass Spectrum (ESI) m/e=296 (M+1). The filtrate was acidified with conc. HCl to pH 3-4. The resulted brown solid was filtered and dried in the air. The filtrate was concd again to give additional material. The filtrate was concd and freeze-dried and extracted with 20% MeOH in DCM (200 mL). Removal of solvents gave a red oily material used for the next step. $^1$H-NMR (500 Hz, DMSO-d$^6$) δ 8.72 (dd, J=10.0, 5.0 Hz, 1H), 8.18 (dd, J=10.0, 5.0 Hz, 1H), 7.96 (td, J=10.0, 5.0 Hz, 1H), 7.78 (td, J=10.0, 5.0 Hz, 1H), 7.56-7.60 (m, 2H), 2.47 (q, J=5.0 Hz, 2H), 1.12 (t, J=5.0 Hz, 3H). Mass Spectrum (ESI) m/e=297 (M+1).

Methyl 2-(1-(6-amino-5-cyanopyrimidin-4-ylamino) ethyl)-6-fluoro-3-(pyridin-2-yl)quinoline-4-carboxy-late

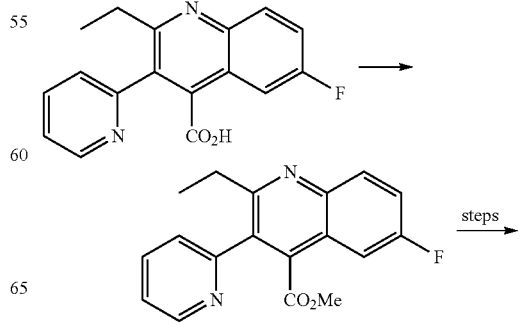

-continued

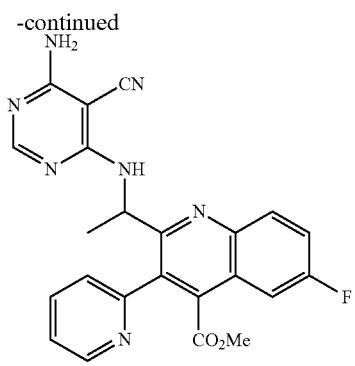

To a solution of 2-ethyl-6-fluoro-3-(pyridin-2-yl)quinoline-4-carboxylic acid (15 g, crude, 50.6 mmol) in 75 mL MeOH was added TMSCHN$_2$ (2M, 46.5 mL, 1.8 eq) at 0° C., the reaction mixture was stirred at rt for 2 h. Removal of solvents followed with column chromatography on silica gel (EtOAc/hexane, 2/3) gave methyl 2-ethyl-6-fluoro-3-(pyridin-2-yl)quinoline-4-carboxylate as a pink solid. $^1$H-NMR (400 Hz, CDCl$_3$) δ 8.78 (dd, J=8.0, 4.0 Hz, 1H), 8.16 (dd, J=8.0, 4.0 Hz, 1H), 7.85 (td, J=8.0, 4.0 Hz, 1H), 7.53-7.58 (m, 2H), 7.45 (dd, J=8.0, 4.0 Hz, 1H), 7.38 (dd, J=8.0, 4.0 Hz, 1H), 3.66 (s, 3H), 2.94 (q, J=8.0 Hz, 2H), 1.25 (t, J=8.0 Hz, 3H). Methyl 2-(1-(6-amino-5-cyanopyrimidin-4-ylamino)ethyl)-6-fluoro-3-(pyridin-2-yl)quinoline-4-carboxylate was synthesized starting from methyl 2-ethyl-6-fluoro-3-(pyridin-2-yl)quinoline-4-carboxylate in the similar manner as previously described for preparation of a corresponding phenyl analog methyl 2-(1-(6-amino-5-cyanopyrimidin-4-ylamino)ethyl)-6-fluoro-3-phenylquinoline-4-carboxylate. $^1$H-NMR (500 Hz, CD$_3$OD) δ 8.76 (d, J=5.0 Hz, 1H), 8.28 (dd, J=10.0, 5.0 Hz, 1H), 8.10 (s, 1H), 8.05 (td, J=10.0, 5.0 Hz, 1H), 7.76 (dd, J=10.0, 5.0 Hz, 1H), 7.69 (dd, J=10.0, 5.0 Hz, 1H), 7.57-7.60 (m, 1H), 5.65-5.75 (m, 1H), 3.68 (s, 3H), 1.48 (d, J=5.0 Hz, 3H). Mass Spectrum (ESI) m/e=444 (M+1).

Example 58: 2-Ethyl-6-fluoro-3-(pyridin-2-yl)quinoline-4-carbonitrile

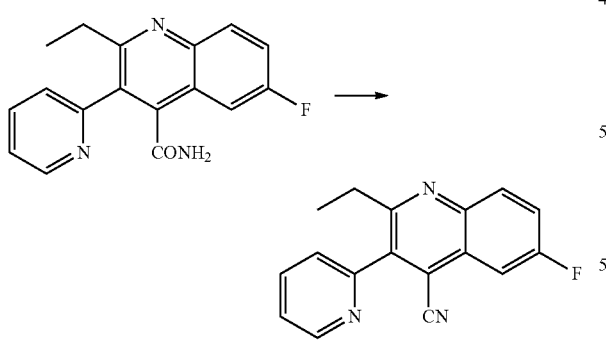

To a suspension of 2-ethyl-6-fluoro-3-(pyridin-2-yl)quinoline-4-carboxamide (200 mg, 0.68 mmol) in dioxane (3 mL) at 0° C. was added pyridine (2.1 eq, 0.115 mL) followed with trifluoroacetic anhydride (1.2 eq, 0.115 mL) dropwise, and the reaction mixture was warmed to rt. overnight. The resulted black reaction mixture was partitioned between DCM and a satd solution of NaHCO$_3$. The organic layer was separated, washed with brine, dried over sodium sulfate, concd and purified by column chromatography on silica gel (EtOAc/hexane, 2/3) to give a white solid. Mass Spectrum (ESI) m/e=278 (M+1).

2-(1-(6-Amino-5-cyanopyrimidin-4-ylamino)ethyl)-6-fluoro-3-(pyridin-2-yl)-quinoline-4-carbonitrile

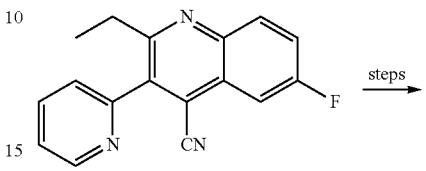

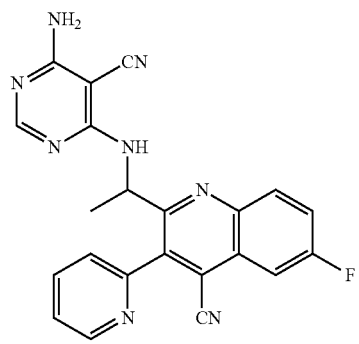

2-(1-(6-Amino-5-cyanopyrimidin-4-ylamino)ethyl)-6-fluoro-3-(pyridin-2-yl)-quinoline-4-carbonitrile was synthesized starting from 2-ethyl-6-fluoro-3-(pyridin-2-yl)quinoline-4-carbonitrile in a similar manner as previously described for preparation of methyl 2-(1-(6-amino-5-cyanopyrimidin-4-ylamino)ethyl)-6-fluoro-3-(pyridin-2-yl)quinoline-4-carboxylate. $^1$H-NMR (400 Hz, DMSO-d$^6$) δ 8.77 (d, J=4.0 Hz, 1H), 8.31 (dd, J=8.0, 4.0 Hz, 1H), 8.05 (td, J=8.0, 4.0 Hz, 1H), 7.98 (td, J=8.0, 4.0 Hz, 1H), 7.87 (s, 1H), 7.83-7.88 (m, 2H), 7.53-7.57 (m, 2H), 7.24 (s, br, 2H), 5.49-5.57 (m, 1H), 1.43 (d, J=4.0 Hz, 3H). Mass Spectrum (ESI) m/e=411 (M+1).

Example 59: 2-Ethyl-6-fluoro-3-(pyridin-2-yl)quinolin-4(1H)-one

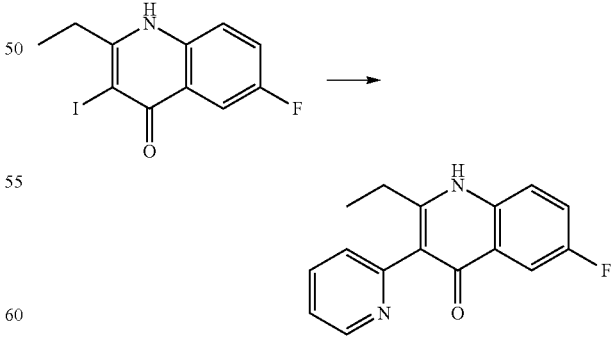

A mixture of 2-ethyl-6-fluoro-3-iodoquinolin-4(1H)-one (18.34 g, 57.8 mmol), 2-(tributylstannyl)pyridine (25.6 g, 1.2 eq), and tetrakis(triphenylphosphine)palladium(0) (3.34 g, 0.05 eq) in dioxane (600 mL) was purged with N$_2$ and heated to reflux overnight. After cooling to rt, removal of solvent followed with purification on column chromatography on silica gel (DCM/MeOH, 1/0 to 20/1 containing NH₃) gave 2-ethyl-6-fluoro-3-(pyridin-2-yl)quinolin-4(1H)-one as a white solid. Mass Spectrum (ESI) m/e=269 (M+1).

2-(1-(4-Chloro-6-fluoro-3-(pyridin-2-yl)quinolin-2-yl)ethyl)isoindoline-1,3-dione

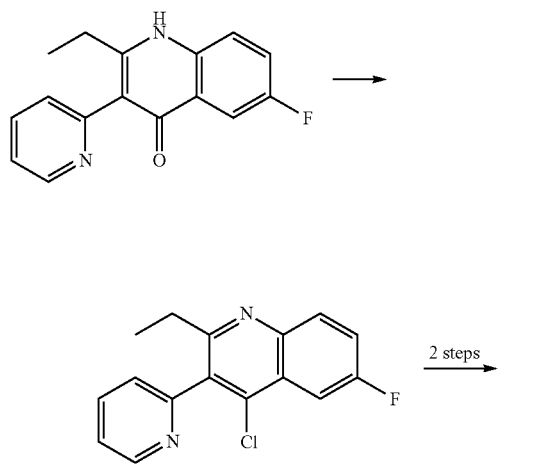

A suspension of 2-ethyl-6-fluoro-3-(pyridin-2-yl)quinolin-4(1H)-one (1000 mg, 3.7 mmol) in POCl₃ (5 mL) was heated to 100° C. for 2 h. After cooling to rt, the reaction mixture was poured into a mixture of ice and water and slowly warmed to rt. Solid NaHCO₃ was added until the solution reached pH 8. The resulted solid was extracted with EtOAc, washed with water, brine, dried, concd and purified by column chromatography on silica gel (EtOAc/hexane, 1/1) to give 4-chloro-2-ethyl-6-fluoro-3-(pyridin-2-yl)quinoline as a solid. 2-(1-(4-Chloro-6-fluoro-3-(pyridin-2-yl)quinolin-2-yl)ethyl)isoindoline-1,3-dione was obtained in the similar manner as described previously for the preparation of 2-(1-(3-(3,5-difluorophenyl)-6-fluoro-4-(methylthio)quinolin-2-yl)ethyl)isoindoline-1,3-dione. Mass Spectrum (ESI) m/e=432 (M+1).

tert-Butyl 1-(4-chloro-6-fluoro-3-(pyridin-2-yl)quinolin-2-yl)ethylcarbamate

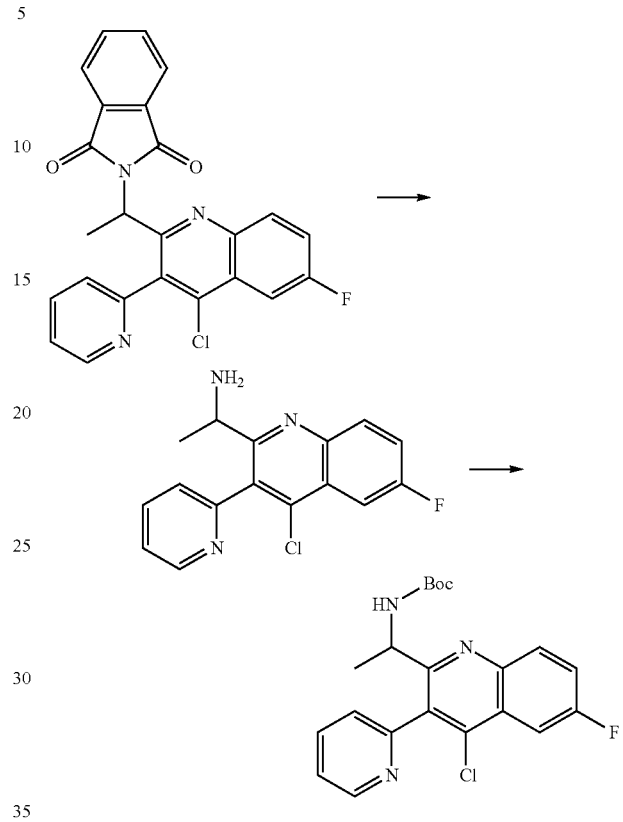

A suspension of 2-(1-(4-chloro-6-fluoro-3-(pyridin-2-yl)quinolin-2-yl)ethyl)isoindoline-1,3-dione (240 mg, 0.56 mmol) in EtOH (4 mL) was treated with hydrazine (0.4 mL) at 50° C. for 5 min. After cooling to rt, the reaction mixture was partitioned between water (5 mL) and EtOAc (10 mL). The organic layer was separated, washed with water, brine, dried and concd to give 1-(4-chloro-6-fluoro-3-(pyridin-2-yl)quinolin-2-yl)ethanamine as a white solid. This was dissolved in THF (5 mL) and treated with Et₃N (0.10 mL, 1.3 eq) followed by Boc₂O (146 mg, 1.2 eq). The solution was refluxed for 2 h. After cooling to rt, removal of solvents followed with column chromatography on silica gel (EtOAc/hexane, 1/1) gave tert-butyl 1-(4-chloro-6-fluoro-3-(pyridin-2-yl)quinolin-2-yl)ethylcarbamate as a white solid. Mass Spectrum (ESI) m/e=402 (M+1).

tert-Butyl 1-(4-(dimethylamino)-6-fluoro-3-(pyridin-2-yl)quinolin-2-yl)-ethylcarbamate

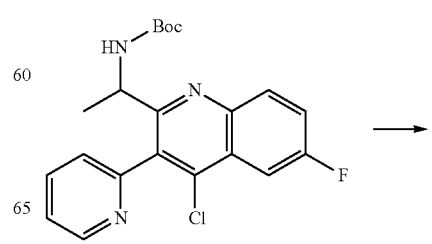

-continued

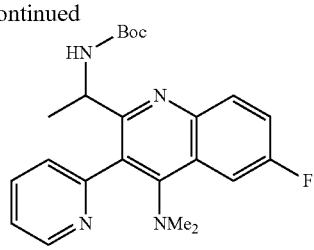

A suspension of tert-butyl 1-(4-chloro-6-fluoro-3-(pyridin-2-yl)quinolin-2-yl)-ethylcarbamate (57 mg, 0.14 mmol) in MeOH (1 mL) was treated with Me₂NH in THF (2.0 M, 2 mL) in a sealed tube at 80° C. for 5 hours and further at 50° C. overnight. Removal of the solvents gave tert-butyl 1-(4-(dimethylamino)-6-fluoro-3-(pyridin-2-yl)quinolin-2-yl)ethylcarbamate as a yellow film which was used directly for the next step. Mass Spectrum (ESI) m/e=411 (M+1).

4-Amino-6-(1-(4-(dimethylamino)-6-fluoro-3-(pyridin-2-yl)quinolin-2-yl)-ethylamino)pyrimidine-5-carbonitrile

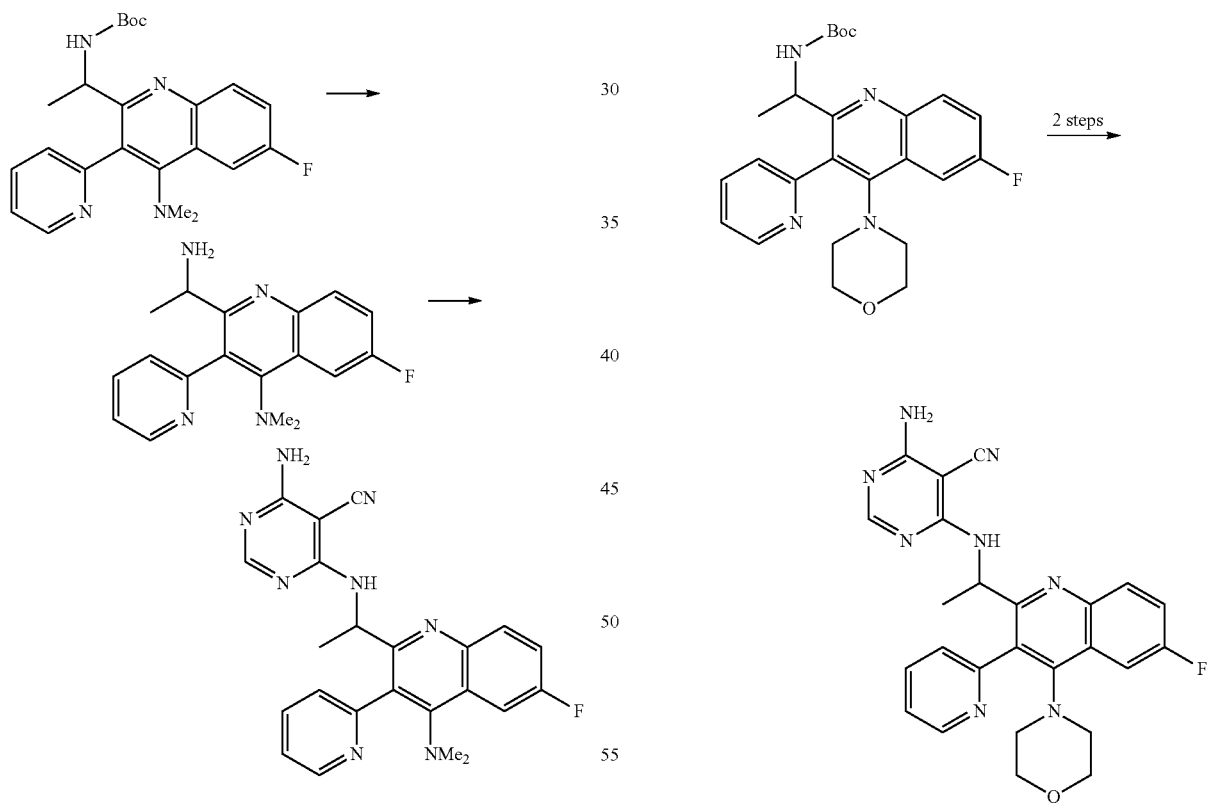

A solution of tert-butyl 1-(4-(dimethylamino)-6-fluoro-3-(pyridin-2-yl)quinolin-2-yl)ethylcarbamate (45 mg, 0.11 mmol) in DCM (2 mL) was treated with TFA (2 mL) at rt for 2 h. Solvents were removed under reduced pressure and the residue was stored under vacuum for 1 h to give 2-(1-aminoethyl)-6-fluoro-N,N-dimethyl-3-(pyridin-2-yl)quinolin-4-amine as TFA salt. This was treated with 4-amino-6-chloropyrimidine-5-carbonitrile (17 mg, 1.0 eq) and Hunig's base (0.038 mL, 2.0 eq) in n-BuOH (2 mL) at 120° C. overnight. After cooling to rt, the reaction mixture was diluted with 1 mL DMF and subjected to reverse phase HPLC (MeCN/water, 15-60%. 0.1% TFA) to give 4-amino-6-(1-(4-(dimethylamino)-6-fluoro-3-(pyridin-2-yl)quinolin-2-yl)ethylamino)pyrimidine-5-carbonitrile as a TFA salt. $^1$H-NMR (400 Hz, CD$_3$OD) δ 8.85 (d, J=8.0 Hz, 1H), 8.06-8.20 (m, 3H), 8.02 (s, 1H), 7.78-7.85 (m, 2H), 7.63-7.67 (m, 1H), 4.95-5.05 (m, 1H), 2.98 (s, 6H), 1.62 (d, J=8.0 Hz, 3H). Mass Spectrum (ESI) m/e=429 (M+1).

Example 60: 4-amino-6-(1-(6-fluoro-4-morpholino-3-(pyridin-2-yl)quinolin-2-yl)ethyl-amino)pyrimidine-5-carbonitrile

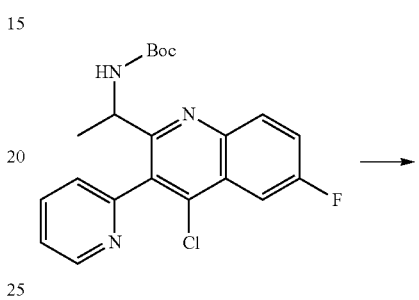

4-Amino-6-(1-(6-fluoro-4-morpholino-3-(pyridin-2-yl)quinolin-2-yl)ethylamino)-pyrimidine-5-carbonitrile was synthesized in a similar manner as the procedure for the preparation of 4-amino-6-(1-(4-(dimethylamino)-6-fluoro-3-(pyridin-2-yl)-quinolin-2-yl)ethylamino)pyrimidine-5-carbonitrile. $^1$H-NMR (400 Hz, CD$_3$OD) δ 8.88 (d, J=4.0 Hz, 1H), 7.67-8.24 (m, 7H), 5.30-5.40 (m, 1H), 4.95-5.05 (m, 1H), 3.70-3.72 (m, 4H), 2.92-3.20 (m, 4H), 1.56 (d, J=4.0 Hz, 3H). Mass Spectrum (ESI) m/e=471 (M+1).

Example 61: 4-Amino-6-(1-(6-fluoro-4-(3-hydroxyazetidin-1-yl)-3-(pyridin-2-yl)quinolin-2-yl)ethylamino)pyrimidine-5-carbonitrile

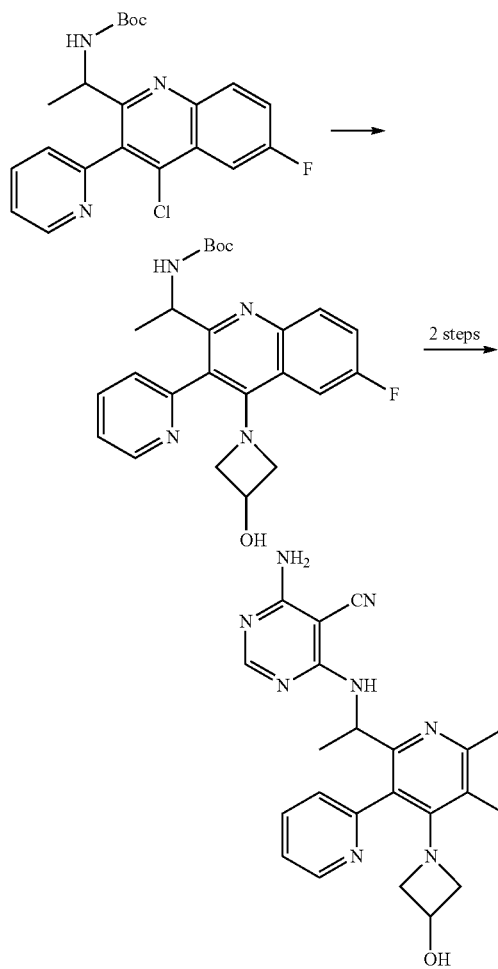

4-amino-6-(1-(6-fluoro-4-(3-hydroxyazetidin-1-yl)-3-(pyridin-2-yl)quinolin-2-yl)-ethylamino)pyrimidine-5-carbonitrile was synthesized in a similar manner as the procedure for preparation of 4-amino-6-(1-(4-(dimethylamino)-6-fluoro-3-(pyridin-2-yl)quinolin-2-yl)ethylamino) pyrimidine-5-carbonitrile. $^1$H-NMR (400 Hz, CD$_3$OD) δ 8.82 (d, J=4.0 Hz, 1H), 7.98-8.08 (m, 4H), 7.78-7.79 (m, 1H), 7.62-7.65 (m, 1H), 5.30-5.40 (m, 1H), 4.46-4.49 (m, 1H), 3.72-3.79 (m, 1H), 3.23-3.26 (m, 2H), 1.40 (d, J=4.0 Hz, 3H). Mass Spectrum (ESI) m/e=457 (M+1).

Example 62: (S)-2-(1-(6-Amino-5-cyanopyrimidin-4-ylamino)ethyl)-6-fluoro-N-methyl-3-phenylquinoline-4-carboxamide

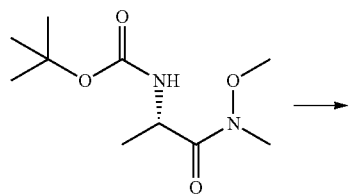

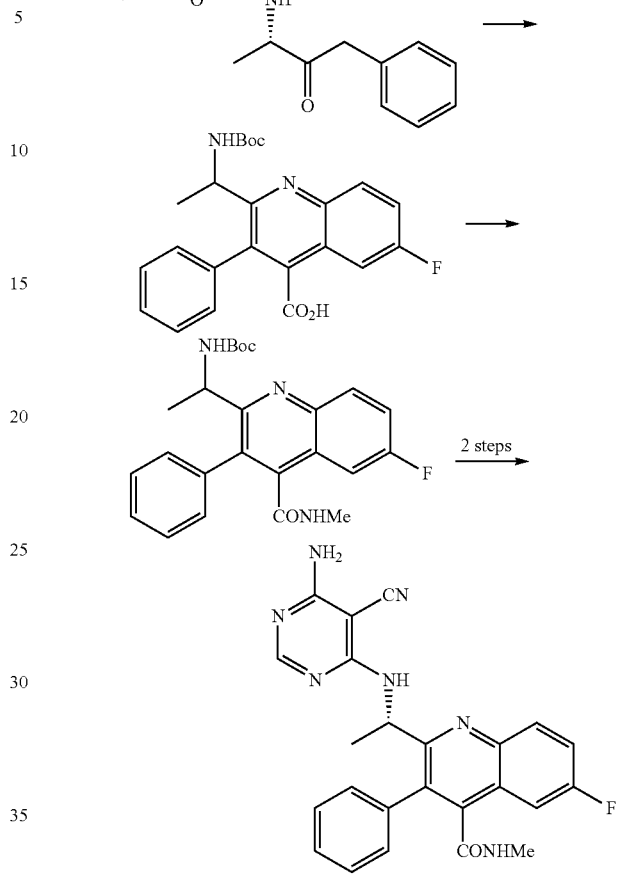

(S)-tert-butyl 1-(methoxy(methyl)amino)-1-oxopropan-2-ylcarbamate (1.16 g, 5 mmol) in THF (10 mL) was cooled to −15° C. and slowly charged with isopropylmagnesium chloride (2.0 M, 2.37 mL, 0.95 eq). After a clear solution was obtained, benzylmagnesium chloride (1.0M, 4.99 mL, 1.0 eq) was added dropwise with stirring at rt for 4 h. The reaction mixture was quenched with NH$_4$Cl solution and extracted with EtOAc (10 mL×2). The combined organic layers were washed with water, brine, dried over sodium sulfate, concd and purified by combiflash (EtOAc/hexane, up to 1/3) to give a colorless oil (S)-tert-butyl 3-oxo-4-phenylbutan-2-ylcarbamate. Mass Spectrum (ESI) m/e=264 (M+1). To a solution of (5)-tert-butyl 3-oxo-4-phenylbutan-2-ylcarbamate (24.6 g, 93 mmol) and 5-fluoroindoline-2,3-dione (15.41 g, 93 mmol) in EtOH (300 mL) was added KOH (15.71 g, 280 mmol). The resulting mixture was heated to 90° C. overnight, but racemization was observed via chiral HPLC with C10A30 min method. Water was added and EtOH was removed. The aq. layer was washed with Et$_2$O (2×), acidified with 1M HCl and the solid filtered. The aq. layer was extracted with EtOAc, washed with water, brine and dried over sodium sulfate. Both solids were combined to afford 2-(1-(tert-butoxycarbonylamino)ethyl)-6-fluoro-3-phenylquinoline-4-carboxylic acid. 5 g of 2-(1-(tert-butoxycarbonylamino)ethyl)-6-fluoro-3-phenylquinoline-4-carboxylic acid was purified by chiral HPLC (isopropanol/hexane gradient, AD column) to provide (S)-2-(1-(tert-butoxy-carbonylamino)ethyl)-6-fluoro-3-phenylquinoline-4-carboxylic acid. Mass Spectrum (ESI) m/e=411 (M+1). To a solution of 2-(1-(tert-butoxycarbonylamino)ethyl)-6-fluoro-3-phenylquinoline-4-carboxylic acid (4 g, 9.75 mmol) in DMF was added HATU (5.56 g, 14.62 mmol), DIEA (3.40 mL, 19.49 mmol) and methanamine (9.75 mL, 19.49 mmol). The resulting mixture was stirred at rt overnight. EtOAc was added. The organic layer was washed with water, brine and dried over sodium sulfate. The solution was filtered and concd in vacuo to give a yellow solid. The crude yellow solid was absorbed onto a plug of silica gel and purified by chromatography eluting with a gradient of 0% to 60% EtOAc in hexane, to provide tert-butyl 1-(6-fluoro-4-(methylcarbamoyl)-3-phenylquinolin-2-yl)ethylcarbamate as light-yellow solid. Mass Spectrum (ESI) m/e=424 (M+1). To tert-butyl 1-(6-fluoro-4-(methylcarbamoyl)-3-phenylquinolin-2-yl)ethylcarbamate (20.41 g, 48.2 mmol) was added 4N HCl/1,4-dioxane (20 mL, 80 mmol). The resulting mixture was stirred at rt for 1 h. Solvent was removed and the resulting 2-(1-aminoethyl)-6-fluoro-N-methyl-3-phenylquinoline-4-carboxamide was used without further purification. Mass Spectrum (ESI) m/e=324 (M+1). To a solution of 2-(1-aminoethyl)-6-fluoro-N-methyl-3-phenylquinoline-4-carboxamide in BuOH (100 mL) was added 4-amino-6-chloropyrimidine-5-carbonitrile (7.45 g, 48.2 mmol) and DIEA (25.2 mL, 145 mmol). The resulting mixture was heated to 100° C. for 3 h. The reaction was allowed to cool to rt and the ppt was filtered, washed with hexanes to afford 2-(1-(6-amino-5-cyanopyrimidin-4-ylamino)ethyl)-6-fluoro-N-methyl-3-phenylquinoline-4-carboxamide as an off white powder and purified on a chiral column (isopropanol/hexane gradient, AD column) to obtain (S)-2-(1-(6-amino-5-cyanopyrimidin-4-ylamino)ethyl)-6-fluoro-N-methyl-3-phenylquinoline-4-carboxamide.
$^1$H-NMR (400 Hz, CD$_3$OD) δ ppm 1.34 (d, 3H) 2.63 (s, 3H) 5.51 (q, J=6.52 Hz, 1H) 7.32-7.54 (m, 6H) 7.57-7.71 (m, 1H) 7.93 (s, 1H) 8.18 (dd, J=9.39, 5.28 Hz, 1H). Mass Spectrum (ESI) m/e=442 (M+1).

Example 63: 2-(1-(6-Amino-5-cyanopyrimidin-4-ylamino)ethyl)-N-(cyclopropylmethyl)-6-fluoro-3-phenylquinoline-4-carboxamide

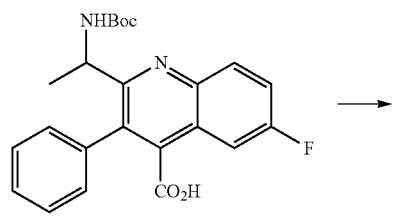

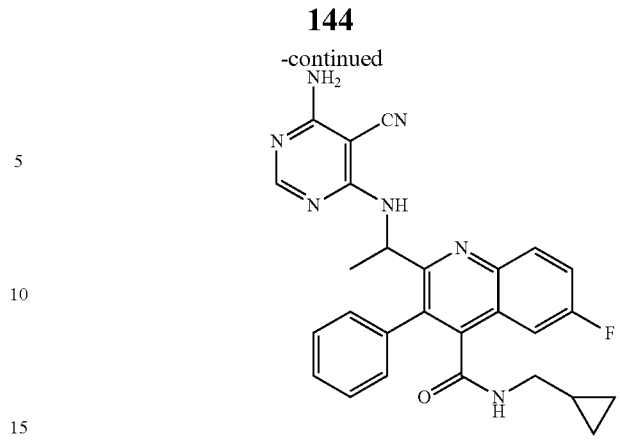

To a solution of 2-(1-(tert-butoxycarbonylamino)ethyl)-6-fluoro-3-phenylquinoline-4-carboxylic acid in DMF (1 mL) was added cyclopropylmethylamine (34.7 mg, 0.487 mmol), DIEA (0.085 mL, 0.487 mmol) and HATU (139 mg, 0.366 mmol). The resulting mixture was stirred at rt overnight. EtOAc was added and the mixture washed with water, brine and dried over sodium sulfate. The solvent was removed in vacuo. The crude residue was subjected to combi-flash purification using 0-100% EtOAc/hexanes to obtain tert-butyl 1-(4-(cyclo-propylmethylcarbamoyl)-6-fluoro-3-phenylquinolin-2-yl)ethylcarbamate. Mass Spectrum (ESI) m/e=464 (M+1). To a solution of tert-butyl 1-(4-(cyclopropyl-methylcarbamoyl)-6-fluoro-3-phenylquinolin-2-yl)ethylcarbamate (98.4 mg, 0.212 mmol) in DCM (1 mL) was added TFA (1 mL, 13.0 mmol) and the resulting mixture was stirred at rt for 1 h. The solvent was removed and the crude 2-(1-aminoethyl)-N-(cyclopropylmethyl)-6-fluoro-3-phenylquinoline-4-carboxamide was used without further purification. Mass Spectrum (ESI) m/e=364 (M+1). To a solution of 2-(1-aminoethyl)-N-(cyclopropylmethyl)-6-fluoro-3-phenylquinoline-4-carboxamide in BuOH (1 mL) was added 4-amino-6-chloropyrimidine-5-carbonitrile (37.7 mg, 0.244 mmol) and DIEA (0.085 mL, 0.487 mmol) the resulting mixture was stirred at 100° C. for 1 h. The crude reaction mixture was purified using preparatory HPLC to obtain 2-(1-(6-amino-5-cyanopyrimidin-4-ylamino)ethyl)-N-(cyclopropylmethyl)-6-fluoro-3-phenylquinoline-4-carboxamide. $^1$H-NMR (400 Hz, CD$_3$OD) δ ppm 0.05 (d, 2H) 0.37 (dd, J=8.51, 1.47 Hz, 2H) 0.58-0.74 (m, 1H) 1.45 (d, J=6.85 Hz, 3H) 2.96-3.10 (m, 2H) 5.61 (q, J=6.39 Hz, 1H) 7.42-7.59 (m, 6H) 7.63-7.78 (m, 1H) 8.10 (s, 1H) 8.22 (dd, J=9.19, 5.28 Hz, 1H) 8.57-8.73 (m, 1H). Mass Spectrum (ESI) m/e=482 (M+1).

Example 64: 2-(1-(6-Amino-5-cyanopyrimidin-4-ylamino)ethyl)-6-fluoro-N-isopropyl-3-phenylquinoline-4-carboxamide

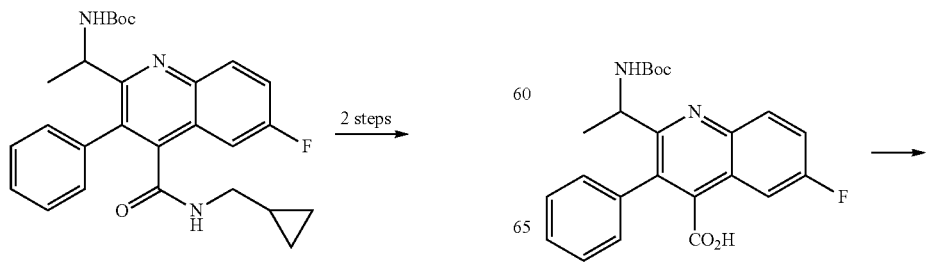

-continued

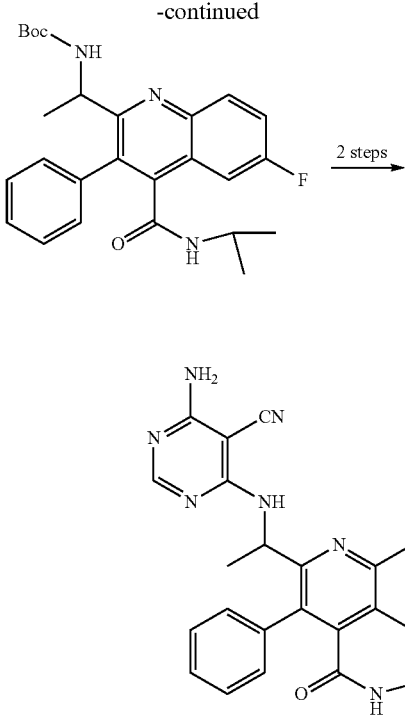

Example 65: (S)-2-(1-(6-Amino-5-cyanopyrimidin-4-ylamino)ethyl)-N-ethyl-6-fluoro-3-phenylquinoline-4-carboxamide

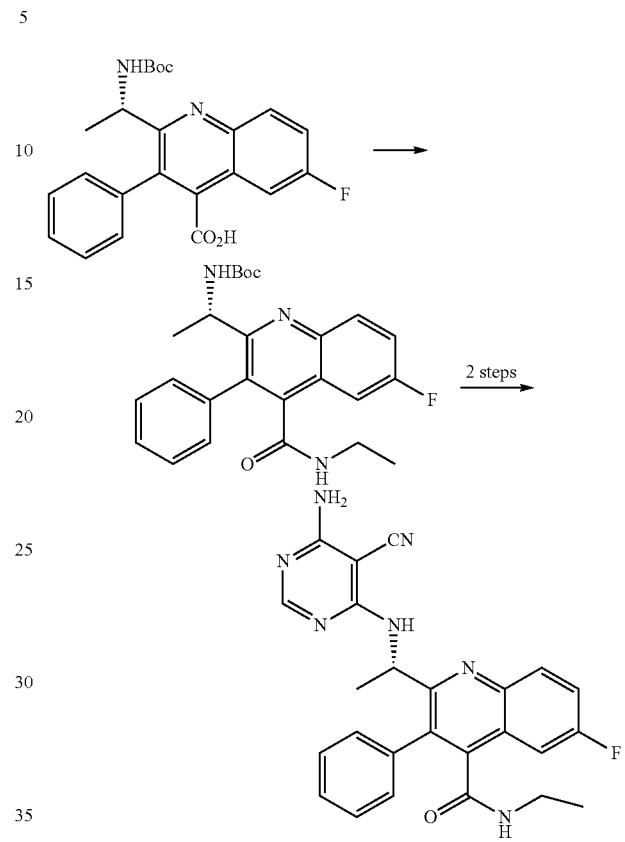

To a solution of 2-(1-(tert-butoxycarbonylamino)ethyl)-6-fluoro-3-phenylquinoline-4-carboxylic acid in DMF (1 mL) was added isopropylamine (28.8 mg, 0.487 mmol) DIEA (0.085 mL, 0.487 mmol) and HATU (139 mg, 0.336 mmol). The resulting mixture was stirred at rt overnight. EtOAc was added to the mixture washed with water, brine and dried over sodium sulfate. The solvent was removed in vacuo. The crude residue was subjected to combiflash purification using 0-100% EtOAc/Hexanes to obtain tert-butyl 1-(6-fluoro-4-(isopropylcarbamoyl)-3-phenylquinolin-2-yl)ethylcarbamate. Mass Spectrum (ESI) m/e=452 (M+1). To a pure of tert-butyl 1-(6-fluoro-4-(isopropylcarbamoyl)-3-phenylquinolin-2-yl)ethylcarbamate (95 mg, 0.210 mmol) was added 4N HCl/1,4-dioxane (0.5 mL, 2.000 mmol) and the resulting mixture was stirred at rt for 1 h. The solvent was removed in vacuo and the crude 2-(1-aminoethyl)-6-fluoro-N-isopropyl-3-phenylquinoline-4-carboxamide used without further purification. Mass Spectrum (ESI) m/e=352 (M+1). To a solution of 2-(1-aminoethyl)-6-fluoro-N-isopropyl-3-phenylquinoline-4-carboxamide in BuOH (1 mL) was added 4-amino-6-chloropyrimidine-5-carbonitrile (37.7 mg, 0.244 mmol) and DIEA (0.085 mL, 0.487 mmol) and the resulting mixture was stirred at 100° C. overnight. Upon cooling, a solid precipitated and was filtered. The filtrate was removed and purified via preparatory TLC using 5% MeOH/DCM to obtain 2-(1-(6-amino-5-cyanopyrimidin-4-ylamino)ethyl)-6-fluoro-N-isopropyl-3-phenylquinoline-4-carboxamide as white solid. $^1$H-NMR (400 Hz, CD$_3$OD) δ ppm 0.80 (br. s., 3H) 0.95 (d, J=6.65 Hz, 3H) 1.34 (d, J=6.65 Hz, 3H) 3.93 (quin, J=6.55 Hz, 1H) 5.52 (q, J=6.52 Hz, 1H) 7.34-7.58 (m, 6H) 7.58-7.73 (m, 1H) 7.93 (s, 1H) 8.10-8.24 (m, 1H). Mass Spectrum (ESI) m/e=470 (M+1).

To a solution of (S)-2-(1-(tert-butoxycarbonylamino)ethyl)-6-fluoro-3-phenylquinoline-4-carboxylic acid (125 mg, 0.305 mmol) in DMF (1 mL) was added ethylamine (0.304 mL, 0.609 mmol), DIEA (0.106 mL, 0.609 mmol) and HATU (174 mg, 0.457 mmol). The resulting mixture was stirred at rt for 2 h. The solvent was removed in vacuo and diluted with EtOAc. The organic layer was washed with water, brine and dried over sodium sulfate. The solvent was removed, and the crude residue was purified via combiflash using 30% EtOAc/hexane to obtain (S)-tert-butyl 1-(4-(ethylcarbamoyl)-6-fluoro-3-phenylquinolin-2-yl)ethylcarbamate. Mass Spectrum (ESI) m/e=438 (M+1). To a pure residue of (S)-tert-butyl 1-(4-(ethylcarbamoyl)-6-fluoro-3-phenylquinolin-2-yl)ethylcarbamate (120 mg, 0.274 mmol) was added 4N HCl/1,4-dioxane (1 mL, 0.274 mmol). The resulting mixture was stirred at rt for 1 h. The solvent was removed in vacuo and the crude (S)-2-(1-aminoethyl)-N-ethyl-6-fluoro-3-phenylquinoline-4-carboxamide used without further purification. Mass Spectrum (ESI) m/e=338 (M+1). To a solution of (S)-2-(1-aminoethyl)-N-ethyl-6-fluoro-3-phenylquinoline-4-carboxamide in DMF (1 mL) was added 4-amino-6-chloropyrimidine-5-carbonitrile (106 mg, 0.686 mmol) and DIEA (106 mg, 0.823 mmol). The resulting mixture was heated to 95° C. overnight. The solvent was removed and crude residue was subjected to preparatory TLC purification using 5% MeOH/DCM to obtain (S)-2-(1-(6-amino-5-cyanopyrimidin-4-ylamino)ethyl)-N-ethyl-6-fluoro-3-phenylquinoline-4-carboxamide as white solid. $^1$H-NMR (400 Hz, CD$_3$OD) δ ppm 0.78 (2H, t), 1.36 (3H, d, J=6.65 Hz), 3.16 (2H, m), 5.53 (1H, q, J=6.65

Hz), 7.45 (5H, m), 7.64 (1H, td, J=8.80, 2.93 Hz), 7.95 (1H, s), 8.18 (1H, dd, J=9.39, 5.28 Hz), 8.46 (1H, t, J=6.16 Hz). Mass Spectrum (ESI) m/e=456 (M+1).

Alternate general procedure F for the preparation of 2-(1-(6-amino-5-cyanopyrimidin-4-ylamino)ethyl)-6-fluoro-3-phenylquinoline-4-carboxamides

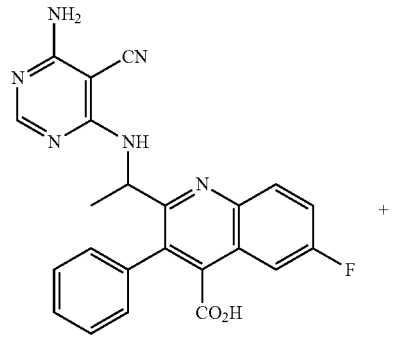

+

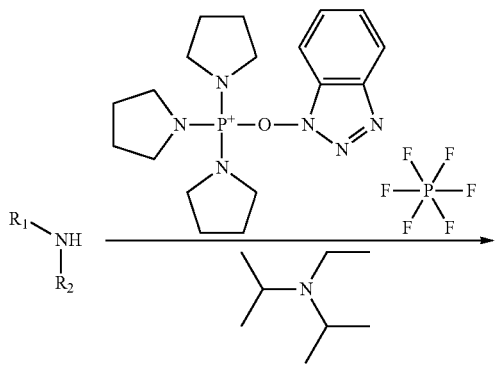

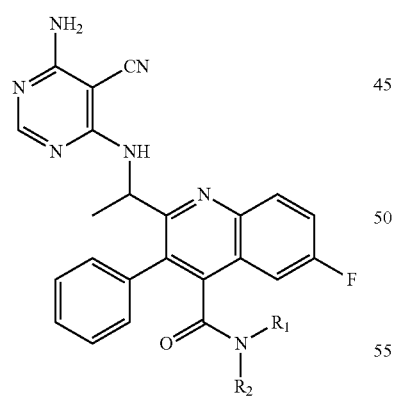

To a solution of 2-(1-(6-amino-5-cyanopyrimidin-4-ylamino)ethyl)-6-fluoro-3-phenylquinoline-4-carboxylic acid (0.16 mmol) in DMF (1 mL) was added amine (1.5 eq), DIEA (1.1 eq) and PyBop (2.2 eq) and the resulting mixture was stirred at rt for 1 h. The crude mixture was subjected to HPLC purification or preparative TLC for purification.

The following compounds were synthesized according to general procedure F or the procedure exemplified by examples: 62, 63, 64 or 65.

Example 66: 2-(-1-((6-Amino-5-cyano-4-pyrimidinyl)amino)ethyl)-6-fluoro-N-methyl-3-phenyl-4-quinolinecarboxamide

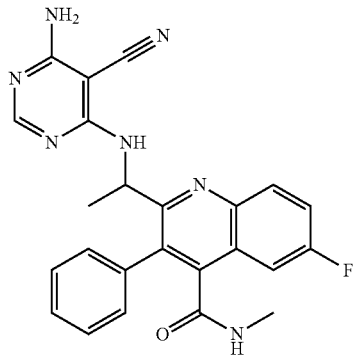 [SMILES: CNC(=O)c1c(-c2ccccc2)c(C(C)Nc2ncnc(N)c2C#N)nc2ccc(F)cc12]

$^1$H-NMR (400 Hz, CD$_3$OD) δ ppm 1.36 (d, 3H) 2.66 (s, 3H) 5.47-5.59 (m, 1H) 7.35-7.57 (m, 6H) 7.61-7.72 (m, 1H) 7.95 (s, 1H) 8.20 (dd, J=9.39, 5.28 Hz, 1H). Mass Spectrum (ESI) m/e=442 (M+1).

Example 67: 2-(1-(((6-Amino-5-cyano-4-pyrimidinyl)amino)ethyl)-6-fluoro-N,N-dimethyl-3-phenyl-4-quinolinecarboxamide

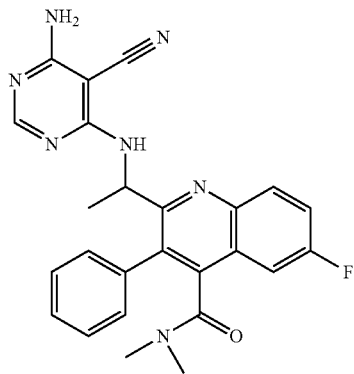 [SMILES: CC(Nc1ncnc(N)c1C#N)c1nc2ccc(F)cc2c(C(=O)N(C)C)c1-c1ccccc1]

$^1$H-NMR (400 Hz, CD$_3$OD) δ ppm 1.42 (3H, d) 2.67 (3H, s) 2.78 (3H, s) 5.35 (1H, q, J=6.78 Hz) 7.24 (1H, dd, J=9.19, 2.54 Hz) 7.35 (5H, m) 7.57 (1H, td, J=8.80, 2.54 Hz) 7.76 (1H, s) 8.12 (1H, dd, J=9.10, 5.38 Hz). Mass Spectrum (ESI) m/e=456 (M+1).

Example 68: 2-(1-(((6-Amino-5-cyano-4-pyrimidinyl)amino)ethyl)-6-fluoro-N,N-dimethyl-3-phenyl-4-quinolinecarboxamide

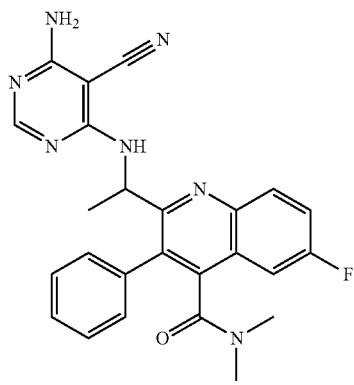 [SMILES: CC(Nc1ncnc(N)c1C#N)c1nc2ccc(F)cc2c(C(=O)N(C)C)c1-c1ccccc1]

¹H-NMR (400 Hz, CD₃OD) δ ppm 1.16 (3H, d) 2.50 (3H, s) 2.74 (3H, s) 5.51 (1H, q, J=6.65 Hz) 7.26 (1H, dd, J=9.29, 2.64 Hz) 7.34 (1H, m) 7.43 (3H, m) 7.50 (1H, m) 7.58 (1H, m) 7.88 (1H, s) 8.11 (1H, dd, J=9.39, 5.28 Hz). Mass Spectrum (ESI) m/e=456 (M+1).

Example 69: 2-((1S)-1-((6-Amino-5-cyano-4-pyrimidinyl)amino)ethyl)-6-fluoro-N,N-dimethyl-3-phenyl-4-quinolinecarboxamide

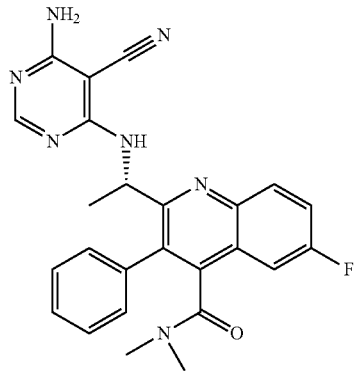 [SMILES: C[C@H](Nc1ncnc(N)c1C#N)c1nc2ccc(F)cc2c(C(=O)N(C)C)c1-c1ccccc1]

¹H-NMR (400 Hz, CD₃OD) δ ppm 1.29 (3H, d) 2.63 (3H, s) 2.86 (3H, s) 5.64 (1H, q, J=6.72 Hz) 7.38 (1H, dd, J=9.29, 2.64 Hz) 7.46 (1H, m) 7.55 (3H, m) 7.62 (1H, m) 7.70 (1H, m) 8.02 (1H, m) 8.24 (1H, dd, J=9.19, 5.28 Hz). Mass Spectrum (ESI) m/e=456 (M+1).

Example 70: 2-((1S)-1-((6-Amino-5-cyano-4-pyrimidinyl)amino)ethyl)-6-fluoro-N,N-dimethyl-3-phenyl-4-quinolinecarboxamide

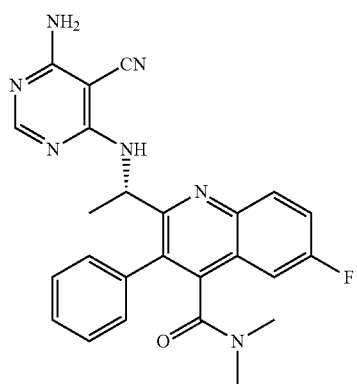 [SMILES: C[C@H](Nc1ncnc(N)c1C#N)c1nc2ccc(F)cc2c(C(=O)N(C)C)c1-c1ccccc1]

¹H-NMR (400 Hz, CD₃OD) δ ppm 1.50 (3H, d) 2.65 (3H, s) 2.78 (3H, s) 5.46 (1H, q, J=6.65 Hz) 7.26 (1H, dd, J=9.19, 2.74 Hz) 7.35 (5H, m) 7.58 (1H, td, J=8.80, 2.74 Hz) 7.91 (1H, s) 8.12 (1H, dd, J=9.29, 5.38 Hz). Mass Spectrum (ESI) m/e=456 (M+1).

Example 71: 4-Amino-6-((1-(6-fluoro-3-phenyl-4-(1-pyrrolidinylcarbonyl)-2-quinolinyl)-ethyl)amino)-5-pyrimidinecarbonitrile

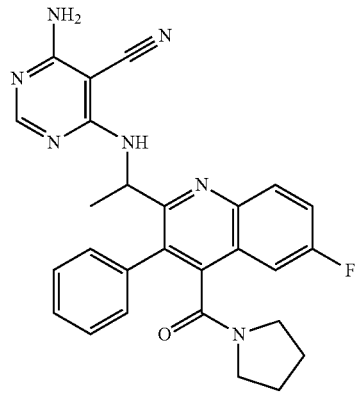 [SMILES: CC(Nc1ncnc(N)c1C#N)c1nc2ccc(F)cc2c(C(=O)N2CCCC2)c1-c1ccccc1]

¹H-NMR (400 Hz, CD₃OD) δ ppm 0.92 (4H, m) 1.26 (2H, m) 1.57 (3H, m) 1.69 (2H, m) 3.02 (1H, m) 3.58 (1H, d) 5.49 (1H, q, J=6.72 Hz) 5.69 (1H, q, J=6.72 Hz) 7.46 (9H, m) 7.67 (2H, m) 7.87 (1H, m) 8.03 (1H, s) 8.23 (1H, dd, J=9.19, 5.28 Hz). Mass Spectrum (ESI) m/e=482 (M+1).

Example 72: 4-Amino-6-((-1-(6-fluoro-3-phenyl-4-(1-piperazinylcarbonyl)-2-quinolinyl)-ethyl)amino)-5-pyrimidinecarbonitrile

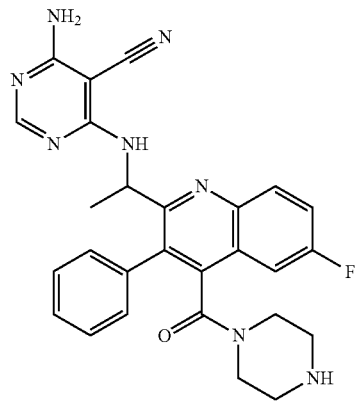 [SMILES: CC(Nc1ncnc(N)c1C#N)c1nc2ccc(F)cc2c(C(=O)N2CCNCC2)c1-c1ccccc1]

¹H-NMR (400 Hz, CD₃OD) δ ppm 1.28 (3H, d) 2.50 (1H, s) 2.71 (1H, d, J=16.24 Hz) 2.94 (1H, d, J=7.04 Hz) 3.15 (1H, m) 3.68 (1H, d, J=7.24 Hz) 3.85 (1H, s) 5.79 (1H, d, J=6.65 Hz) 7.51 (2H, m) 7.61 (3H, m) 7.71 (2H, m) 8.15 (1H, s) 8.26 (1H, dd, J=9.19, 5.28 Hz). Mass Spectrum (ESI) m/e=497 (M+1).

Example 73: 4-Amino-6-(((1S)-1-(6-fluoro-3-phenyl-4-(1-piperazinylcarbonyl)-2-quinolinyl)ethyl)amino)-5-pyrimidinecarbonitrile

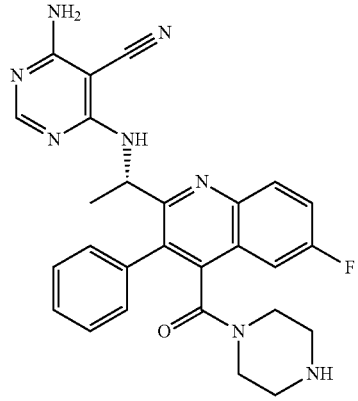 [SMILES: C[C@H](Nc1ncnc(N)c1C#N)c1nc2ccc(F)cc2c(C(=O)N2CCNCC2)c1-c1ccccc1]

$^1$H-NMR (400 Hz, CD$_3$OD) δ ppm 1.30 (3H, d) 2.52 (1H, m) 2.72 (1H, m) 2.97 (1H, m) 3.17 (1H, m) 3.28 (1H, m) 3.71 (1H, m) 3.89 (1H, ddd, J=14.48, 7.53, 3.42 Hz) 5.82 (1H, q, J=6.85 Hz) 7.52 (3H, m) 7.62 (2H, m) 7.71 (2H, m) 8.26 (2H, m). Mass Spectrum (ESI) m/e=497 (M+1).

Example 74: 4-Amino-6-((1-(6-fluoro-4-((4-methyl-1-piperazinyl)carbonyl)-3-phenyl-2-quinolinyl)ethyl)amino)-5-pyrimidinecarbonitrile

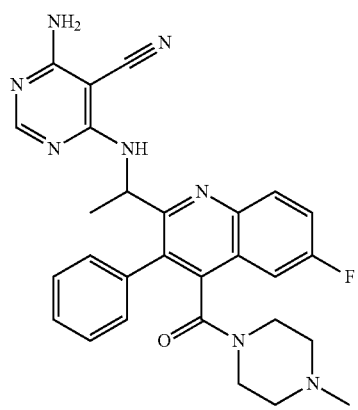 [SMILES: CC(Nc1ncnc(N)c1C#N)c1nc2ccc(F)cc2c(C(=O)N2CCN(C)CC2)c1-c1ccccc1]

$^1$H-NMR (400 Hz, CD$_3$OD) δ ppm 1.27 (3H, d, J=6.7 Hz) 2.76-2.90 (4H, m) 4.87-4.92 (4H, m) 5.71-5.81 (1H, m) 7.51 (2H, d, J=9.2 Hz) 7.60 (2H, br. s) 7.65-7.76 (3H, m) 8.13 (1H, s) 8.25 (1H, dd, J=9.3, 5.4 Hz). Mass Spectrum (ESI) m/e=511 (M+1).

Example 75: 4-Amino-6-((1-(6-fluoro-4-(4-morpholinylcarbonyl)-3-phenyl-2-quinolinyl)-ethyl)amino)-5-pyrimidinecarbonitrile

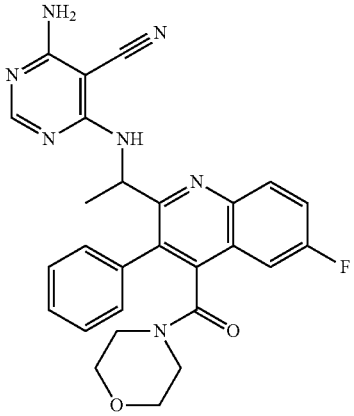 [SMILES: CC(Nc1ncnc(N)c1C#N)c1nc2ccc(F)cc2c(C(=O)N2CCOCC2)c1-c1ccccc1]

$^1$H-NMR (400 Hz, CD$_3$OD) δ ppm 1.66 (4H, d) 3.03-3.29 (4H, m) 3.42-3.54 (2H, m) 3.58-3.75 (2H, m) 5.54 (1H, q, J=6.52 Hz) 7.41 (1H, dd, J=9.10, 2.64 Hz) 7.44-7.62 (4H, m) 7.68 (1H, ddd, J=9.29, 8.31, 2.74 Hz) 7.81 (1H, s) 7.97 (1H, s) 8.23 (1H, dd, J=9.19, 5.28 Hz). Mass Spectrum (ESI) m/e=498 (M+1).

Example 76: 4-Amino-6-((-1-(6-fluoro-4-(4-morpholinylcarbonyl)-3-phenyl-2-quinolinyl)-ethyl)amino)-5-pyrimidinecarbonitrile

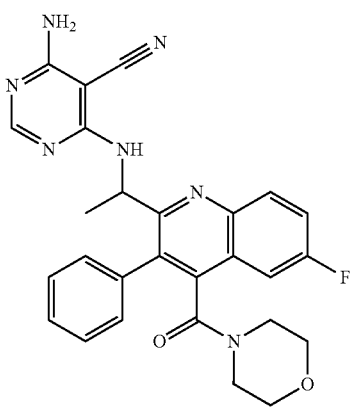 [SMILES: CC(Nc1ncnc(N)c1C#N)c1nc2ccc(F)cc2c(C(=O)N2CCOCC2)c1-c1ccccc1]

$^1$H-NMR (400 Hz, CD$_3$OD) δ ppm 1.28 (2H, d) 2.92 (1H, d, J=5.67 Hz) 2.95-3.11 (2H, m) 3.14-3.27 (1H, m) 3.35-3.42 (1H, m) 3.46-3.56 (1H, m) 3.56-3.76 (2H, m) 5.76 (1H, q, J=6.78 Hz) 7.42 (1H, dd, J=9.19, 2.74 Hz) 7.50-7.64 (4H, m) 7.68 (1H, ddd, J=9.19, 8.22, 2.74 Hz) 7.78 (1H, s) 8.14 (1H, s) 8.23 (1H, dd, J=9.19, 5.28 Hz). Mass Spectrum (ESI) m/e=409 (M+1). Mass Spectrum (ESI) m/e=498 (M+1).

Example 77: 4-Amino-6-((1-(6-fluoro-4-(((3R)-3-hydroxy-1-pyrrolidinyl)carbonyl)-3-phenyl-2-quinolinyl)ethyl)amino)-5-pyrimidinecarbonitrile

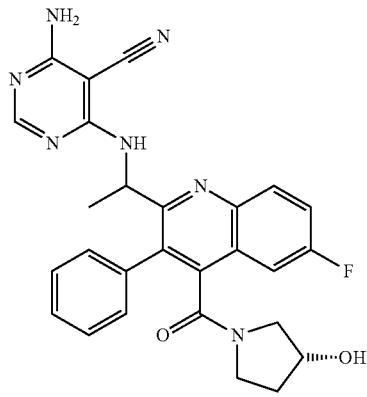

$^1$H-NMR (400 Hz, CD$_3$OD) δ ppm 1.54 (d, J=6.65 Hz, 3H) 2.84-2.97 (m, 1H) 2.98-3.16 (m, 1H) 3.16-3.28 (m, 3H) 3.59-3.82 (m, 1H) 5.51-5.64 (m, 1H) 7.33-7.51 (m, 4H) 7.64-7.78 (m, 2H) 8.00-8.05 (m, 1H) 8.08 (s, 1H) 8.24 (ddd, J=9.10, 5.48, 3.23 Hz, 1H). Mass Spectrum (ESI) m/e=498 (M+1).

Example 78: 4-Amino-6-((-1-(6-fluoro-4-(((3S)-3-hydroxy-1-pyrrolidinyl)carbonyl)-3-phenyl-2-quinolinyl)ethyl)amino)-5-pyrimidinecarbonitrile

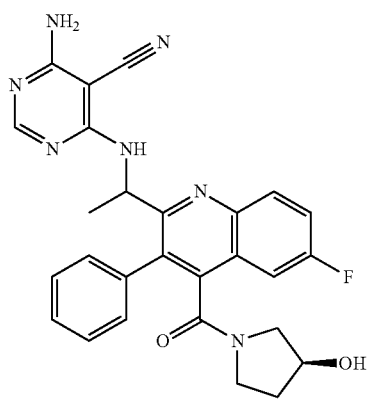 [SMILES: CC(Nc1ncnc(N)c1C#N)c1nc2ccc(F)cc2c(C(=O)N2CC[C@H](O)C2)c1-c1ccccc1]

$^1$H-NMR (400 Hz, CD$_3$OD) δ ppm 1.27 (d, 2H) 1.65 (d, J=6.65 Hz, 3H) 2.96-3.13 (m, 1H) 3.13-3.32 (m, 2H) 3.43-3.56 (m, 1H) 3.56-3.77 (m, 1H) 5.48-5.60 (m, OH) 5.76 (q, J=6.85 Hz, 0H) 7.38-7.62 (m, 4H) 7.62-7.72 (m, J=9.19, 8.27, 2.91, 2.91 Hz, 1H) 7.77 (s, 1H) 7.96 (s, 1H) 8.14 (s, 1H) 8.19-8.29 (m, 1H). Mass Spectrum (ESI) m/e=498 (M+1).

Example 79: 4-Amino-6-((1-(6-fluoro-4-(((3S)-3-hydroxy-1-pyrrolidinyl)carbonyl)-3-phenyl-2-quinolinyl)ethyl)amino)-5-pyrimidinecarbonitrile (rotomer of Example 77)

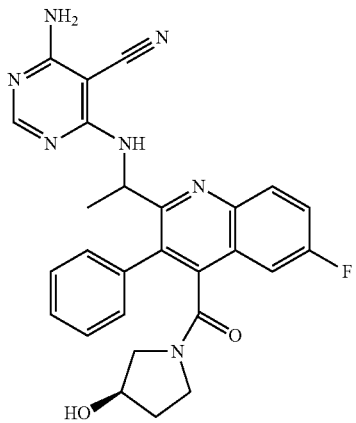 [SMILES: CC(Nc1ncnc(N)c1C#N)c1nc2ccc(F)cc2c(C(=O)N2CC[C@@H](O)C2)c1-c1ccccc1]

$^1$H-NMR (400 Hz, CD$_3$OD) δ ppm 1.30 (d, 3H) 2.88-3.13 (m, 2H) 3.21 (td, J=7.48, 3.62 Hz, 1H) 3.52 (d, J=5.87 Hz, 1H) 3.58-3.73 (m, 2H) 5.77 (q, J=6.78 Hz, 1H) 7.44 (dd, J=9.19, 2.54 Hz, 1H) 7.49-7.65 (m, 5H) 7.70 (td, J=8.71, 2.74 Hz, 1H) 8.19 (s, 1H) 8.24 (dd, J=9.29, 5.18 Hz, 1H). Mass Spectrum (ESI) m/e=498 (M+1).

Example 80: 4-Amino-6-((1-(4-((1,1-dioxido-4-thiomorpholinyl)carbonyl)-6-fluoro-3-phenyl-2-quinolinyl)ethyl)amino)-5-pyrimidinecarbonitrile

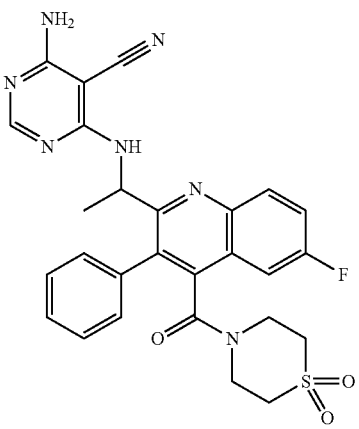 [SMILES: CC(Nc1ncnc(N)c1C#N)c1nc2ccc(F)cc2c(C(=O)N2CCS(=O)(=O)CC2)c1-c1ccccc1]

$^1$H-NMR (400 Hz, CD$_3$OD) δ ppm 1.39 (3H, d, J=6.65 Hz) 1.66 (0H, d, J=7.24 Hz) 1.87 (1H, m) 2.00 (4H, m) 3.17 (1H, m) 3.50 (1H, m) 4.91 (1H, m) 7.39 (1H, s) 7.51 (1H, dd, J=7.24, 1.17 Hz) 7.64 (1H, d, J=7.63 Hz) 7.75 (1H, m) 7.84 (1H, s) 7.91 (1H, s) 8.00 (1H, d, J=8.41 Hz) 8.24 (1H, s) 8.32 (1H, m). Mass Spectrum (ESI) m/e=546 (M+1).

Example 81: 4-Amino-6-(((1S)-1-(4-((1,1-dioxido-4-thiomorpholinyl)carbonyl)-6-fluoro-3-phenyl-2-quinolinyl)ethyl)amino)-5-pyrimidinecarbonitrile

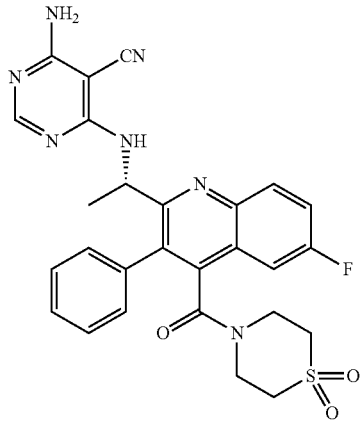 [SMILES: C[C@H](Nc1ncnc(N)c1C#N)c1nc2ccc(F)cc2c(C(=O)N2CCS(=O)(=O)CC2)c1-c1ccccc1]

$^1$H-NMR (400 MHz, DMSO-d$_6$) δ ppm 1.32 (3H, d, J=6.65 Hz) 2.34 (1H, t, J=1.86 Hz) 2.68 (1H, d, J=1.76 Hz) 3.44 (1H, s) 3.61 (3H, s) 5.39 (1H, t, J=6.85 Hz) 7.26 (1H, br. s.) 7.36 (1H, m) 7.49 (3H, m) 7.60 (1H, dd, J=9.59, 2.74 Hz) 7.82 (1H, m) 7.93 (1H, s) 8.18 (1H, dd, J=9.19, 5.48 Hz). Mass Spectrum (ESI) m/e=546 (M+1).

Example 82: 4-Amino-6-(((1S)-1-(4-((1,1-dioxido-4-thiomorpholinyl)carbonyl)-6-fluoro-3-phenyl-2-quinolinyl)ethyl)amino)-5-pyrimidinecarbonitrile (rotomer of Example 81)

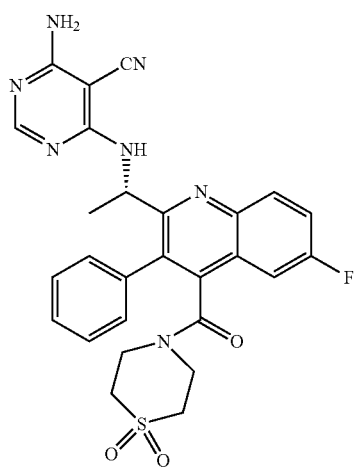 [SMILES: C[C@H](Nc1ncnc(N)c1C#N)c1nc2ccc(F)cc2c(C(=O)N2CCS(=O)(=O)CC2)c1-c1ccccc1]

$^1$H-NMR (400 Hz, CD$_3$OD) δ ppm 1.55 (3H, d, J=6.65 Hz) 3.38 (4H, m) 4.89 (4H, m) 5.70 (1H, q, J=6.65 Hz) 6.48 (1H, m) 7.52 (2H, m) 7.71 (7H, m) 7.84 (1H, ddd, J=9.29, 8.31, 2.74 Hz) 8.05 (1H, m) 8.12 (1H, s) 8.37 (1H, dd, J=9.39, 5.28 Hz). Mass Spectrum (ESI) m/e=546 (M+1).

Example 83: 4-Amino-6-((1-(6-fluoro-4-((3-hydroxy-1-azetidinyl)carbonyl)-3-phenyl-2-quinolinyl)ethyl)amino)-5-pyrimidinecarbonitrile

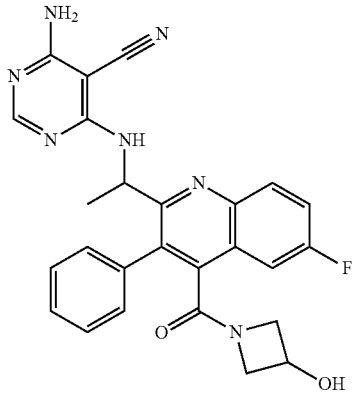 [SMILES: CC(Nc1ncnc(N)c1C#N)c1nc2ccc(F)cc2c(C(=O)N2CC(O)C2)c1-c1ccccc1]

$^1$H-NMR (400 Hz, CD$_3$OD) δ ppm 1.32 (3H, dd, J=6.65, 1.17 Hz) 1.63 (2H, m) 3.50 (2H, m) 3.92 (2H, m) 4.11 (1H, m) 4.39 (1H, m) 4.59 (1H, m) 5.61 (1H, dd, J=6.75, 3.03 Hz) 5.75 (1H, q, J=6.65 Hz) 7.54 (9H, m) 7.72 (2H, m) 8.05 (1H, d, J=4.89 Hz) 8.21 (1H, m) 8.25 (1H, m). Mass Spectrum (ESI) m/e=484 (M+1).

Example 84: 4-Amino-6-(((1S)-1-(6-fluoro-4-((3-hydroxy-1-azetidinyl)carbonyl)-3-phenyl-2-quinolinyl)ethyl)amino)-5-pyrimidinecarbonitrile

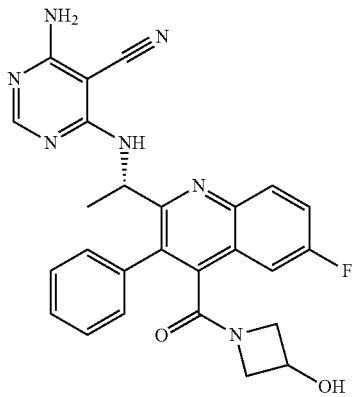 [SMILES: C[C@H](Nc1ncnc(N)c1C#N)c1nc2ccc(F)cc2c(C(=O)N2CC(O)C2)c1-c1ccccc1]

$^1$H-NMR (400 Hz, CD$_3$OD) δ ppm 1.26 (3H, d, J=6.65 Hz) 1.54 (2H, dd, J=7.63, 6.65 Hz) 3.52 (3H, m) 3.72 (1H, m) 3.91 (3H, m) 4.07 (0H, ddd, J=10.03, 6.70, 1.08 Hz) 4.19 (1H, m) 4.39 (1H, m) 4.57 (1H, m) 5.49 (1H, m) 5.67 (1H, qd, J=6.65, 2.54 Hz) 7.53 (11H, m) 7.69 (3H, m) 7.88 (1H, d, J=5.28 Hz) 8.02 (1H, d, J=1.37 Hz) 8.23 (2H, m). Mass Spectrum (ESI) m/e=484 (M+1).

Example 85: 4-Amino-6-((1-(6-fluoro-4-((3-methoxy-1-azetidinyl)carbonyl)-3-phenyl-2-quinolinyl)ethyl)amino)-5-pyrimidinecarbonitrile

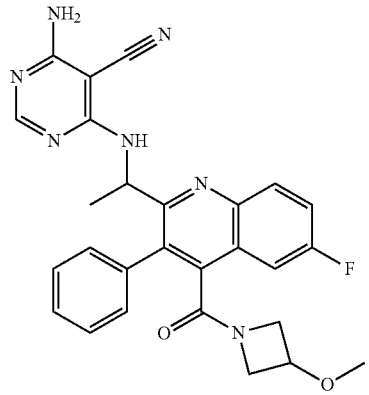 [SMILES: COC1CN(C(=O)c2c(-c3ccccc3)c(C(C)Nc3ncnc(N)c3C#N)nc3ccc(F)cc23)C1]

$^1$H-NMR (400 Hz, CD$_3$OD) δ ppm 1.32 (3H, d, J=6.65 Hz) 1.63 (3H, d, J=6.65 Hz) 3.15 (3H, s) 3.50 (1H, m) 3.87 (0H, m) 4.04 (0H, m) 4.35 (0H, m) 5.61 (0H, s) 5.75 (0H, s) 7.53 (5H, m) 7.74 (1H, m) 8.03 (1H, d, J=2.54 Hz) 8.18 (1H, d, J=1.37 Hz) 8.24 (1H, m). Mass Spectrum (ESI) m/e=498 (M+1).

Example 86: 2-(1-((6-Amino-5-cyano-4-pyrimidinyl)amino)ethyl)-6-fluoro-N-(2-(4-morpholinyl)ethyl)-3-phenyl-4-quinolinecarboxamide

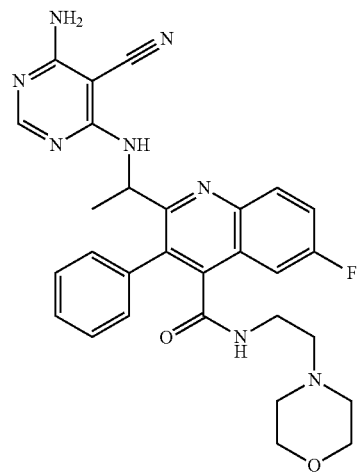 [SMILES: CC(Nc1ncnc(N)c1C#N)c1nc2ccc(F)cc2c(C(=O)NCCN2CCOCC2)c1-c1ccccc1]

$^1$H-NMR (400 Hz, CD$_3$OD) δ ppm 1.44 (3H, d, J=6.65 Hz) 2.80 (2H, td, J=6.85, 3.13 Hz) 3.38 (2H, m) 3.56 (2H, m) 4.83 (3H, m) 5.58 (1H, q, J=6.65 Hz) 7.48 (1H, m) 7.57 (5H, m) 7.71 (1H, td, J=8.80, 2.74 Hz) 8.05 (1H, s) 8.24 (1H, dd, J=9.29, 5.38 Hz). Mass Spectrum (ESI) m/e=541 (M+1).

Example 87A 2-(1-(6-Amino-5-cyanopyrimidin-4-ylamino)ethyl)-6-fluoro-N-methyl-3-(pyridin-2-yl)quinoline-4-carboxamide

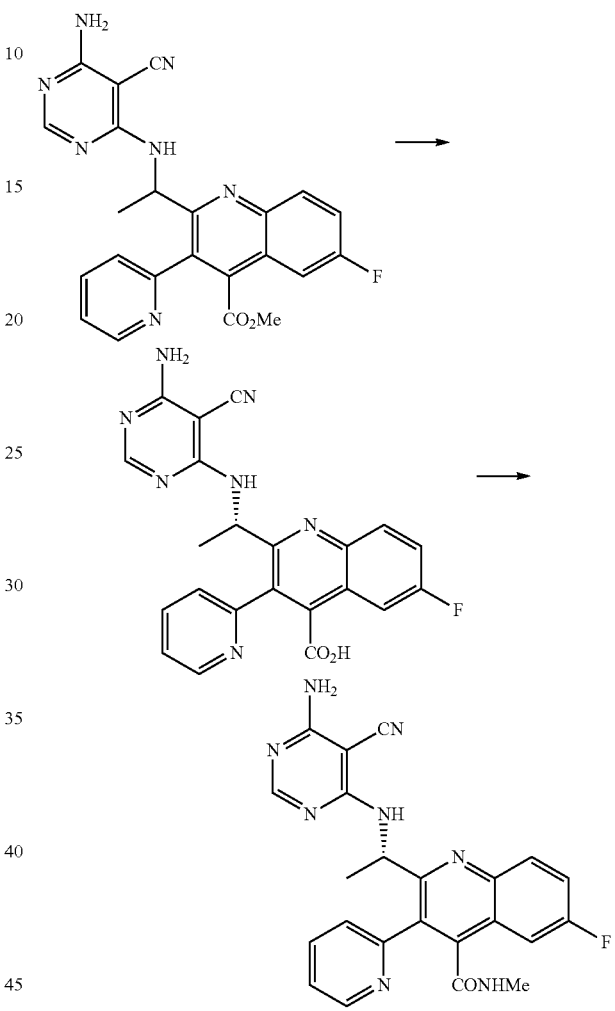

To a solution of methyl 2-(1-(6-amino-5-cyanopyrimidin-4-ylamino)ethyl)-6-fluoro-3-(pyridin-2-yl)quinoline-4-carboxylate (2 g, 4.51 mmol) in 20 mL pyridine was added LiI (1.81 g, 13.53 mmol). The resulting mixture was heated to 100° C. overnight. Solvent was removed and the crude residue was subject to combiflash using up to 20% MeOH/DCM to obtain 2-(1-(6-amino-5-cyanopyrimidin-4-ylamino)ethyl)-6-fluoro-3-(pyridin-2-yl)quinoline-4-carboxylic acid as a brown solid. The pure material was purified by chiral HPLC (Isopropanol/Hexane gradient, AD column) to obtain (S)-2-(1-(6-amino-5-cyanopyrimidin-4-ylamino)ethyl)-6-fluoro-3-(pyridin-2-yl)quinoline-4-carboxylic acid. Mass Spectrum (ESI) m/e=430 (M+1). To a solution of (S)-2-(1-(6-amino-5-cyanopyrimidin-4-ylamino)ethyl)-6-fluoro-3-(pyridin-2-yl)quinoline-4-carboxylic acid (100 mg, 0.233 mmol) was added methanamine (14.47 mg, 0.466 mmol), N-ethyl-N-isopropylpropan-2-amine (60.2 mg, 0.466 mmol) and PyBop (267 mg, 0.512 mmol). The resulting mixture was stirred at rt overnight. The solvent was removed and dissolved in EtOAc. It was washed with water, brine and dried over sodium sulfate. After removal of the organic phase in vacuo, the crude residue was subjected to HPLC purification and preparatory TLC purification using 2% MeOH/DCM with satd ammonia to afford (S)-2-(1-(6-amino-5-cyanopyrimidin-4-ylamino)ethyl)-6-fluoro-N-methyl-3-(pyridin-2-yl)quinoline-4-carboxamide. $^1$H-NMR (400 Hz, CD$_3$OD) δ ppm 1.43 (3H, d) 2.70 (3H, s) 5.60 (1H, q, J=6.65 Hz) 7.52 (2H, m) 7.64 (1H, dt, J=7.82, 1.17 Hz) 7.71 (1H, dd, J=2.84, 1.08 Hz) 7.96 (2H, m) 8.24 (1H, dd, J=9.29, 5.38 Hz) 8.73 (1H, m). Mass Spectrum (ESI) m/e=443 (M+1).

Example 87B (S)-2-(1-(6-Amino-5-cyanopyrimidin-4-ylamino) ethyl)-6-fluoro-N-methyl-3-(pyridin-2-yl)quinoline-4-carboxamide

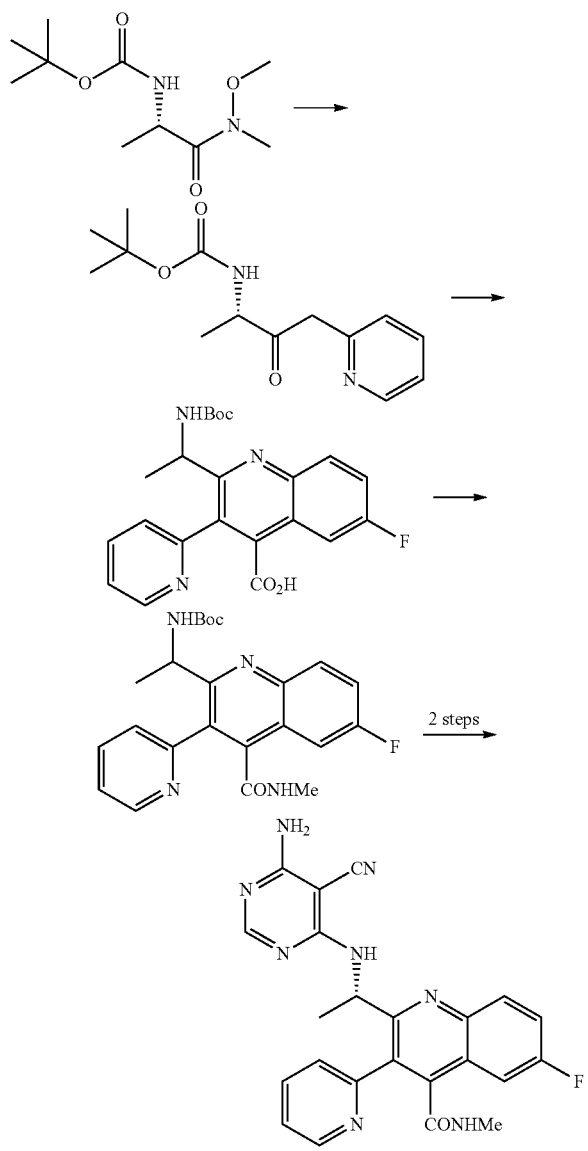

tert-Butyl 1-(methoxy(methyl)amino)-1-oxopropan-2-yl-carbamate (50.0 g, 215 mmol) in THF (450 mL) was cooled to −40° C. (dry ice/acetonitrile) and slowly charged with isopropylmagnesium chloride (2.0 M, 102.2 mL, 0.95 eq). After a clear solution was obtained (became clear at −20° C. and milky again at −40° C.), bromo(pyridin-2-ylmethyl) magnesium solution (see below for preparation) was added drop wise using cannula before warming to rt overnight. The reaction mixture was quenched with NH$_4$Cl solution and extracted with EtOAc (500 mL×2). The combined organic layers were washed with water, brine, dried over sodium sulfate, and concentrated under high vacuum to give (S)-tert-butyl 3-oxo-4-(pyridin-2-yl)butan-2-ylcarbamate as a tan oil. (Small scale reaction was purified by combiflash (EtOAc/hexane, up to 1/3) to give a red oil. Mass Spectrum (ESI) m/e=265 (M+1).

Bromo(pyridin-2-ylmethyl)magnesium

To a solution of picoline (31.9 mL, 1.5 eq) in THF (300 mL) was added MeLi (202 mL, 1.6 M, 1.5 eq) drop wise at −40° C. under nitrogen. The reaction mixture was allowed to warm to −20° C. and stirred for 10 min. and then cooled to −40° C. and magnesium bromide (59.4 g, 1.5 eq) was added in three portions. The reaction mixture was allowed to warm to rt, stirred for 30 min. to provide bromo(pyridin-2-ylmethyl)magnesium. KOH (25.05 g, 2.0 eq), 5-fluoroisatin (36.9 g, 1.0 eq) in EtOH (100 mL) and water (350 mL) were stirred at rt for 0.5 h before the addition of (S)-tert-butyl 3-oxo-4-phenylbutan-2-ylcarbamate (59.00 g, 223 mmol). The reaction mixture was heated to 85° C. overnight and cooled to rt. The reaction mixture was concd to remove EtOH and extracted with ether (100 mL×2). The filtrate was cooled at 0° C. and acidified with concd HCl. (50 mL). The dark homogenous solution became a light yellow suspension after adjusting to pH 4. The resulted yellow solid was filtered and dried in the air. A pale yellow solid was obtained. To the filtrate was added sodium sulfate (300 g), and the mixture was stirred at rt for 2 h followed by the addition of 20 mL conc. HCl. The mixture was stirred at rt for additional 2 h. The resulted solid was filtered, washed with cold water and dried in the air to give 2-(1-(tert-butoxycarbonyl-amino) ethyl)-6-fluoro-3-(pyridin-2-yl)quinoline-4-carboxylic acid as a pale yellow solid. Overall 2-(1-(tert-butoxycarbonylamino)ethyl)-6-fluoro-3-(pyridin-2-yl)quinoline-4-carboxylic acid was obtained as pale yellow solid. The racemic 2-(1-(tert-butoxycarbonylamino)ethyl)-6-fluoro-3-(pyridin-2-yl)quinoline-4-carboxylic acid was submitted for chiral HPLC separation to obtain (S)-2-(1-(tert-butoxycarbonylamino)ethyl)-6-fluoro-3-(pyridin-2-yl)quinoline-4-carboxylic acid. Mass Spectrum (ESI) m/e=412 (M+1). To a solution of 2-(1-(tert-butoxy-carbonylamino)ethyl)-6-fluoro-3-(pyridin-2-yl)quinoline-4-carboxylic acid (1.3 g, 3.16 mmol) in DMF (10 mL) was added methanamine (3.16 mL, 6.32 mmol), PyBOP (4.11 g, 7.90 mmol) and DIEA (1.21 mL, 6.95 mmol). The resulting mixture was stirred at rt overnight. The solvent was removed and diluted with EtOAc. The organic layer was washed with water (3×100 mL), brine and dried over sodium sulfate. The crude residue was subjected to combiflash purification using 20-70% EtOAc/hexane to afford tert-butyl 1-(6-fluoro-4-(methylcarbamoyl)-3-(pyridin-2-yl)quinolin-2-yl)ethylcarbamate as white foam. Mass Spectrum (ESI) m/e=425 (M+1). To a pure residue of tert-butyl 1-(6-fluoro-4-(methylcarbamoyl)-3-(pyridin-2-yl)quinolin-2-yl)ethylcarbamate (1 g, 2.36 mmol) was added 4N HCl/1,4-dioxane (8 mL, 32.0 mmol). The resulting mixture was stirred at rt for 30 min. The solvent was removed and crude 2-(1-aminoethyl)-6-fluoro-N-methyl-3-(pyridin-2-yl)quinoline-4-carboxamide was used without further purification. Mass Spectrum (ESI) m/e=325 (M+1). To a solution of 2-(1-aminoethyl)-6-fluoro-N-methyl-3-(pyridin-2-yl)quinoline-4-carboxamide in DMF (15 mL) was added 4-amino-6-chloropyrimidine-5-carbonitrile (0.364 g, 2.356 mmol) and DIEA (1.231 mL, 7.07 mmol). The resulting mixture was heated to 95° C. for 2 h. The solvent was partially removed. EtOAc was added and the mixture washed with water (3×100 mL), brine and dried over sodium sulfate. The solvent was removed in vacuo and purified by combiflash using 30% (10:1 MeOH/DCM)/DCM to afford 2-(1-(6-amino-5-cyanopyrimidin-4-ylamino)ethyl)-6-fluoro-N-methyl-3-(pyridin-2-yl)quinoline-4-carboxamide. After chiral HPLC separation (Isopropanol/Hexane gradient, AD column) (S)-2-(1-(6-amino-5-cyanopyrimidin-4-ylamino)ethyl)-6-fluoro-N-methyl-3-(pyridin-2-yl)quinoline-4-carboxamide was obtained.

Example 88: (S)-2-(1-(6-Amino-5-cyanopyrimidin-4-ylamino)ethyl)-N-ethyl-6-fluoro-3-(pyridin-2-yl)quinoline-4-carboximidamide

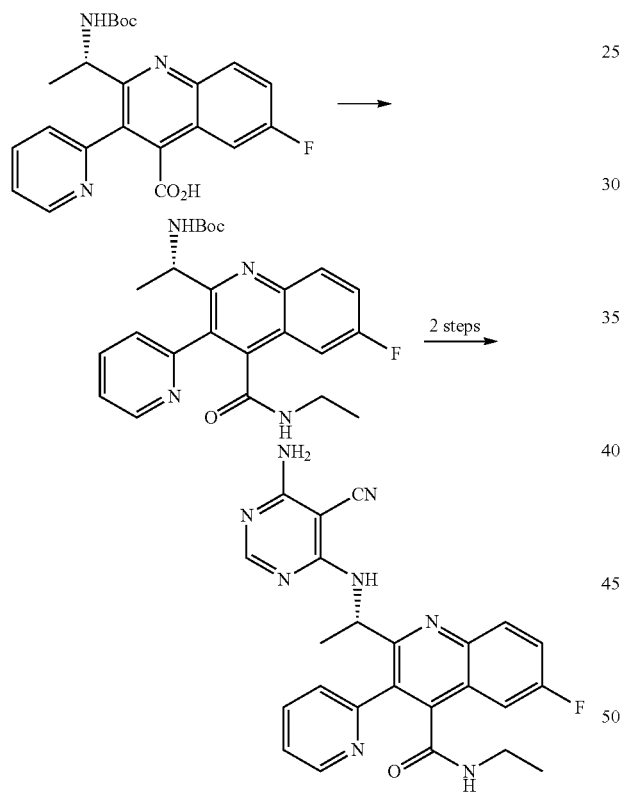

To a solution of (S)-2-(1-(tert-butoxycarbonylamino)ethyl)-6-fluoro-3-(pyridin-2-yl)quinoline-4-carboxylic acid (140 mg, 0.340 mmol) in DMF (1 mL) was added PyBOP (390 mg, 0.749 mmol), DIEA (0.119 mL, 0.681 mmol) and ethanamine (0.340 mL, 0.681 mmol). The resulting mixture was stirred at rt for 2 h. EtOAc was added. The organic solution was washed with water, brine and dried over sodium sulfate. The solvent was removed in vacuo. The crude residue was purified via combiflash using 50% EtOAc/hexane to obtain (S)-tert-butyl 1-(4-(ethylcarbamoyl)-6-fluoro-3-(pyridin-2-yl)quinolin-2-yl)ethylcarbamate as light yellow oil. Mass Spectrum (ESI) m/e=439 (M+1). To the light yellow oil (S)-tert-butyl 1-(4-(ethylcarbamoyl)-6-fluoro-3-(pyridin-2-yl)quinolin-2-yl)ethylcarbamate (125 mg, 0.285 mmol) was added 4N HCl/1,4-dioxane (1 mL, 32.9 mmol) and the resulting mixture stirred at rt for 1 h. Solvent was removed and (S)-2-(1-aminoethyl)-N-ethyl-6-fluoro-3-(pyridin-2-yl)quinoline-4-carboxamide was used without further purification. Mass Spectrum (ESI) m/e=339 (M+1). To a (S)-2-(1-aminoethyl)-N-ethyl-6-fluoro-3-(pyridin-2-yl)quinoline-4-carboxamide in DMF (1 mL) was added DIEA (0.199 mL, 1.140 mmol) and 4-amino-6-chloropyrimidine-5-carbonitrile (44.1 mg, 0.285 mmol). The resulting mixture was heated to 95° C. overnight. The solvent was removed in vacuo and the crude residue was purified via preparatory TLC using 5% MeOH/DCM to obtain (S)-2-(1-(6-amino-5-cyanopyrimidin-4-ylamino)ethyl)-N-ethyl-6-fluoro-3-(pyridin-2-yl)quinoline-4-carboxamide. ¹H-NMR (400 Hz, CD₃OD) δ ppm 0.87 (t, 3H) 1.43 (d, J=6.65 Hz, 3H) 3.16-3.27 (m, 2H) 5.59 (q, J=6.65 Hz, 1H) 7.48-7.59 (m, 2H) 7.63-7.77 (m, 2H) 7.92-8.03 (m, 2H) 8.23 (dd, J=9.29, 5.38 Hz, 1H) 8.74 (ddd, J=5.04, 1.81, 0.98 Hz, 1H). Mass Spectrum (ESI) m/e=457 (M+1).

Example 89: (S)-2-(1-(6-Amino-5-cyanopyrimidin-4-ylamino)ethyl)-6-fluoro-N-(2-hydroxyethyl)-3-(pyridin-2-yl)quinoline-4-carboxamide

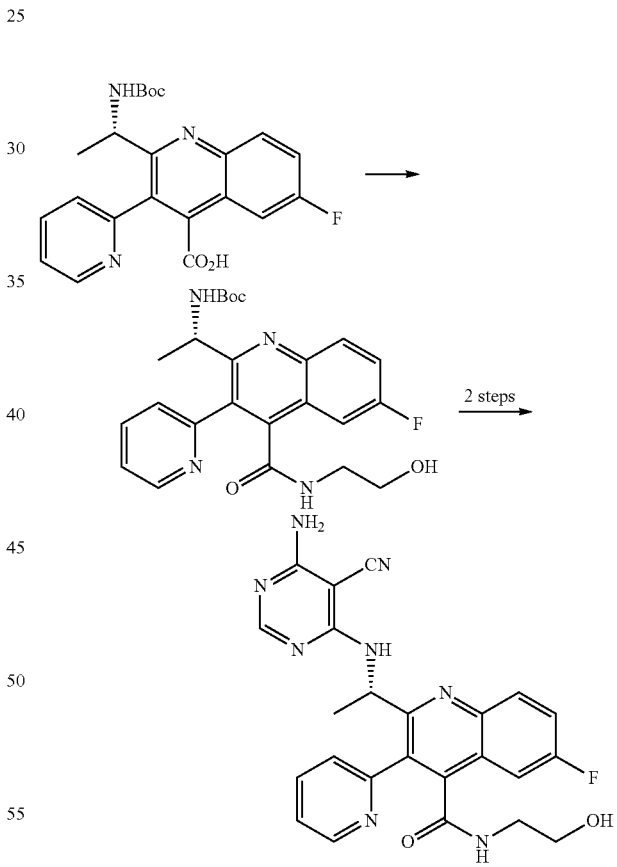

To a solution of (S)-2-(1-(tert-butoxycarbonylamino)ethyl)-6-fluoro-3-(pyridin-2-yl)quinoline-4-carboxylic acid (100 mg, 0.243 mmol) in DMF (1 mL) was added PyBOP (278 mg, 0.535 mmol), DIEA (0.127 mL, 0.729 mmol) and 2-aminoethanol (29.7 mg, 0.486 mmol). The resulting mixture was stirred at rt for 2 h. The solvent was removed and EtOAc was added. The organic solution was washed with water, brine and dried over sodium sulfate. Solvent was removed in vacuo and purified via combiflash using 5%

MeOH/DCM to obtain (5)-tert-butyl 1-(6-fluoro-4-(2-hydroxyethylcarbamoyl)-3-(pyridin-2-yl)quinolin-2-yl)ethylcarbamate as a dark yellow oil. Mass Spectrum (ESI) m/e=455 (M+1). To the dark yellow oil (5)-tert-butyl 1-(6-fluoro-4-(2-hydroxyethylcarbamoyl)-3-(pyridin-2-yl)quinolin-2-yl)ethylcarbamate (50 mg, 0.110 mmol) was added 4N HCl/1,4-dioxane (1 mL, 32.9 mmol). The resulting mixture was stirred at rt for 1 h. Solvent was removed and the crude (S)-2-(1-aminoethyl)-6-fluoro-N-(2-hydroxyethyl)-3-(pyridin-2-yl)quinoline-4-carboxamide was used without further purification. Mass Spectrum (ESI) m/e=355 (M+1). To a solution of the crude (S)-2-(1-aminoethyl)-6-fluoro-N-(2-hydroxyethyl)-3-(pyridin-2-yl)quinoline-4-carboxamide in DMF (1 mL) was added DIEA (0.058 mL, 0.330 mmol) and 4-amino-6-chloropyrimidine-5-carbonitrile (17.00 mg, 0.110 mmol). The resulting mixture was heated to 95° C. The solvent was removed and purified via preparatory TLC using 5% MeOH/DCM to obtain (S)-2-(1-(6-amino-5-cyanopyrimidin-4-ylamino)ethyl)-6-fluoro-N-(2-hydroxyethyl)-3-(pyridin-2-yl)quinoline-4-carboxamide. $^1$H-NMR (400 Hz, CD$_3$OD) δ ppm 1.37 (d, 3H) 3.20-3.26 (m, 2H) 3.32-3.37 (m, 2H) 5.52 (q, J=6.72 Hz, 1H) 7.46 (ddd, J=7.68, 4.94, 0.88 Hz, 1H) 7.54-7.69 (m, 3H) 7.82-7.97 (m, 2H) 8.18 (dd, J=9.19, 5.28 Hz, 1H) 8.67 (d, J=4.89 Hz, 1H). Mass Spectrum (ESI) m/e=472 (M+1).

Example 90: (S)-2-(1-(6-Amino-5-cyanopyrimidin-4-ylamino)ethyl)-N-cyclopropyl-6-fluoro-3-(pyridin-2-yl)quinoline-4-carboxamide

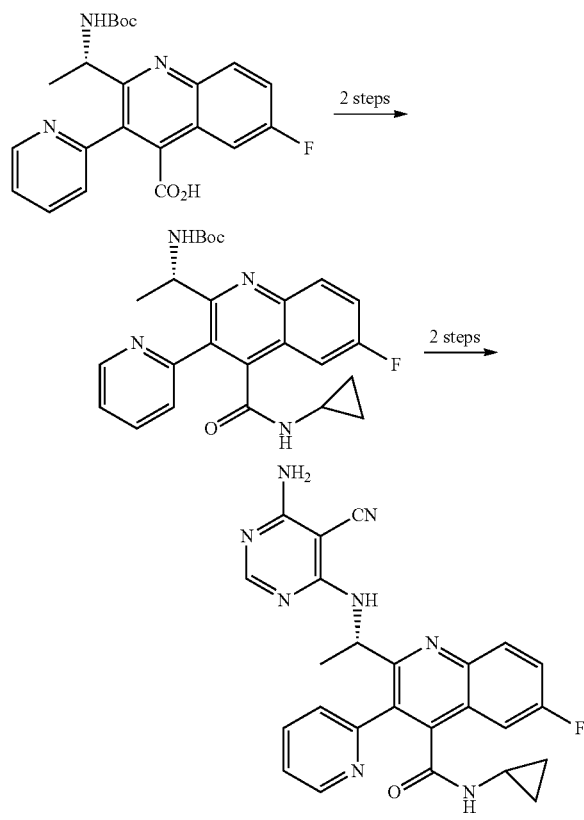

To a solution of (S)-2-(1-(tert-butoxycarbonylamino)ethyl)-6-fluoro-3-(pyridin-2-yl)quinoline-4-carboxylic acid (100 mg, 0.243 mmol) in DMF (1 mL) was added PyBOP (278 mg, 0.535 mmol), DIEA (0.085 mL, 0.486 mmol) and cyclopropanamine (0.034 mL, 0.486 mmol). The resulting mixture was stirred at rt for 2 h, followed by the addition of EtOAc. The organic solution was washed with water, brine and dried over sodium sulfate. The solvent was removed and the crude residue purified via combiflash using 50% EtOAc/Hexane to obtain a yellowish foam (5)-tert-butyl 1-(4-(cyclopropylcarbamoyl)-6-fluoro-3-(pyridin-2-yl)quinolin-2-yl)ethylcarbamate. Mass Spectrum (ESI) m/e=451 (M+1). To the yellow foam (5)-tert-butyl 1-(4-(cyclopropylcarbamoyl)-6-fluoro-3-(pyridin-2-yl)quinolin-2-yl)ethylcarbamate (85 mg, 0.189 mmol) was added 4N HCl/1,4-dioxane (1 mL, 32.9 mmol). The resulting mixture was stirred at rt for 1 h. The solvent was removed and the crude (S)-2-(1-aminoethyl)-N-cyclopropyl-6-fluoro-3-(pyridin-2-yl)quinoline-4-carboxamide was used without further purification. Mass Spectrum (ESI) m/e=351 (M+1). To a solution of (S)-2-(1-aminoethyl)-N-cyclopropyl-6-fluoro-3-(pyridin-2-yl)quinoline-4-carboxamide in DMF (1 mL) was added DIEA (0.099 mL, 0.566 mmol) and 4-amino-6-chloropyrimidine-5-carbonitrile (29.2 mg, 0.189 mmol). The resulting mixture was heated to 95° C. After the solvent was removed, the crude residue was purified using 5% MeOH/DCM with preparatory TLC to obtain (S)-2-(1-(6-amino-5-cyanopyrimidin-4-yl-amino)ethyl)-N-cyclopropyl-6-fluoro-3-(pyridin-2-yl)quinoline-4-carboxamide. $^1$H-NMR (400 Hz, CD$_3$OD) δ ppm 0.10 (br. s., 2H) 0.63 (dd, J=7.24, 1.37 Hz, 2H) 1.40 (d, J=6.65 Hz, 3H) 2.65 (dt, J=7.34, 3.57 Hz, 1H) 5.55 (q, J=6.52 Hz, 1H) 7.46-7.66 (m, 3H) 7.66-7.78 (m, 1H) 7.91 (s, 1H) 7.96 (td, J=7.73, 1.76 Hz, 1H) 8.21 (dd, J=9.29, 5.38 Hz, 1H) 8.71 (td, J=2.54, 0.98 Hz, 1H). Mass Spectrum (ESI) m/e=469 (M+1).

The following examples were synthesized by following procedures exemplified by examples 87A and/or 87B.

Example 91: 2-1-((6-Amino-5-cyano-4-pyrimidinyl)amino)ethyl)-6-fluoro-3-(2-pyridinyl)-4-quinolinecarboxylic acid

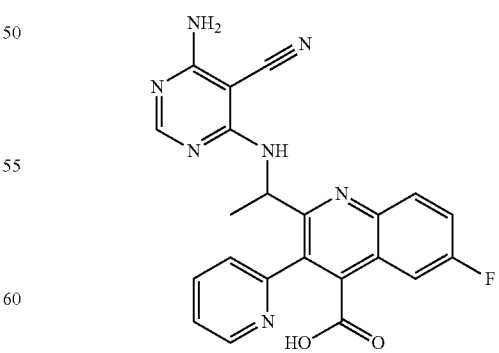

$^1$H-NMR (400 Hz, CD$_3$OD) δ ppm 1.49 (3H, d) 5.65 (1H, m) 7.62 (1H, ddd, J=7.78, 5.14, 0.98 Hz) 7.76 (3H, m) 8.10 (2H, m) 8.27 (1H, m) 8.77 (1H, d, J=5.09 Hz). Mass Spectrum (ESI) m/e=430 (M+1).

Example 92: 2-(-1-((6-Amino-5-cyano-4-pyrimidinyl)amino)ethyl)-6-fluoro-N-methyl-3-(2-pyridinyl)-4-quinolinecarboxamide

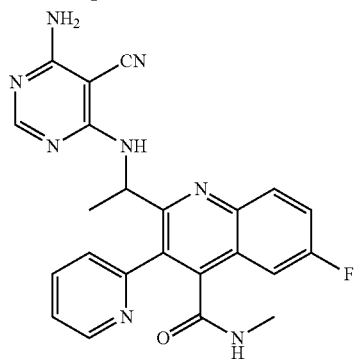

¹H-NMR (400 Hz, CD₃OD) δ ppm 1.43 (3H, d) 2.70 (3H, s) 5.60 (1H, q, J=6.65 Hz) 7.52 (2H, m) 7.64 (1H, d, J=7.83 Hz) 7.71 (1H, m) 7.97 (2H, m) 8.24 (1H, dd, J=9.29, 5.38 Hz) 8.73 (1H, m). Mass Spectrum (ESI) m/e=443 (M+1).

Example 93: 2-((1R)-1-((6-Amino-5-cyano-4-pyrimidinyl)amino)ethyl)-6-fluoro-N-methyl-3-(2-pyridinyl)-4-quinolinecarboxamide

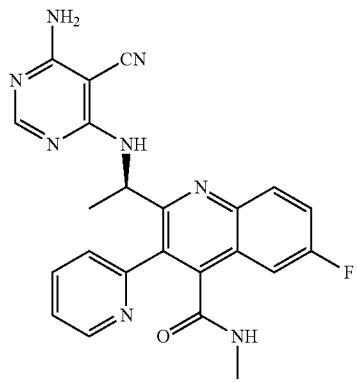 [SMILES: CNC(=O)c1c(-c2ccccn2)c([C@@H](C)Nc2ncnc(N)c2C#N)nc2ccc(F)cc12]

¹H-NMR (400 Hz, CD₃OD) δ ppm 1.43 (3H, d) 2.70 (3H, s) 5.60 (1H, q, J=6.65 Hz) 7.52 (2H, m) 7.65 (1H, m) 7.72 (1H, m) 7.98 (2H, m) 8.24 (1H, dd, J=9.39, 5.28 Hz) 8.74 (1H, ddd, J=4.89, 1.76, 0.98 Hz). Mass Spectrum (ESI) m/e=443 (M+1).

Example 94: 2-(1-((6-Amino-5-cyano-4-pyrimidinyl)amino)ethyl)-6-fluoro-N,N-dimethyl-3-(2-pyridinyl)-4-quinolinecarboxamide

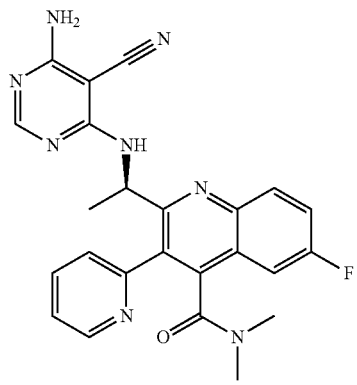 [SMILES: C[C@@H](Nc1ncnc(N)c1C#N)c1nc2ccc(F)cc2c(C(=O)N(C)C)c1-c1ccccn1]

¹H-NMR (400 Hz, CD₃OD) δ ppm 1.32 (3H, d) 1.57 (3H, d, J=6.60 Hz) 2.63 (3H, s) 2.73 (3H, s) 5.58 (1H, q, J=6.68 Hz) 5.72 (1H, q, J=6.60 Hz) 7.44 (3H, m) 7.56 (1H, dd, J=7.09, 5.14 Hz) 7.62 (2H, dd, J=14.06, 7.70 Hz) 7.73 (2H, m) 7.88 (1H, s) 7.93 (1H, td, J=7.83, 1.71 Hz) 8.01 (2H, m) 8.27 (2H, ddd, J=11.55, 9.23, 5.38 Hz) 8.71 (1H, d, J=4.89 Hz) 8.76 (1H, d, J=4.89 Hz). Mass Spectrum (ESI) m/e=457 (M+1).

Example 95: 4-Amino-6-((1-(6-fluoro-4-(1-piperazinylcarbonyl)-3-(2-pyridinyl)-2-quinolinyl)ethyl)amino)-5-pyrimidinecarbonitrile

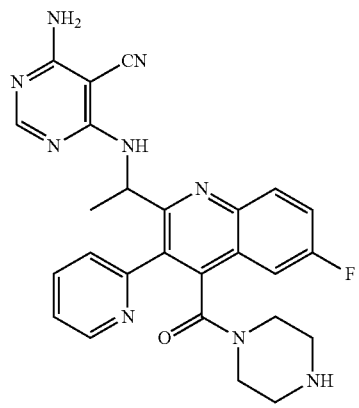 [SMILES: CC(Nc1ncnc(N)c1C#N)c1nc2ccc(F)cc2c(C(=O)N2CCNCC2)c1-c1ccccn1]

¹H-NMR (400 Hz, CD₃OD) δ ppm 5.33 (3H, d, J=6.65 Hz) 5.48 (3H, d, J=6.85 Hz) 6.76 (2H, m) 7.33 (4H, m) 7.77 (2H, m) 9.59 (1H, q, J=6.85 Hz) 9.74 (1H, q, J=6.78 Hz) 11.50 (2H, m) 11.70 (2H, m) 11.96 (2H, m) 12.24 (1H, ddd, J=12.67, 9.24, 5.28 Hz) 12.73 (1H, m). Mass Spectrum (ESI) m/e=498 (M+1).

Example 96: 4-Amino-6-(((1R)-1-(6-fluoro-4-((3-hydroxy-1-azetidinyl)carbonyl)-3-(2-pyridinyl)-2-quinolinyl)ethyl)amino)-5-pyrimidinecarbonitrile

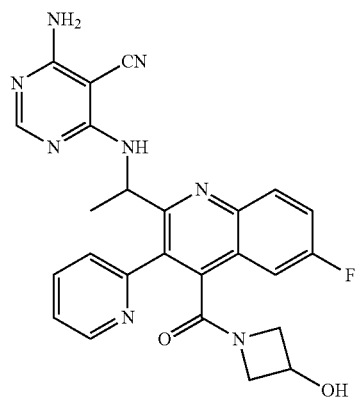 [SMILES: CC(Nc1ncnc(N)c1C#N)c1nc2ccc(F)cc2c(C(=O)N2CC(O)C2)c1-c1ccccn1]

¹H-NMR (400 MHz, DMSO-d₆) δ ppm 1.22 (3H, d, J=6.65 Hz) 1.27 (3H, d, J=6.65 Hz) 1.43 (1H, dd, J=12.13, 6.65 Hz) 3.66 (0H, s) 3.82 (1H, br. s.) 4.04 (1H, s) 4.10 (0H, d, J=5.28 Hz) 4.25 (0H, m) 4.43 (0H, br. s.) 5.50 (0H, d, J=5.67 Hz) 5.78 (0H, dd, J=6.55, 2.05 Hz) 7.44 (1H, d, J=5.09 Hz) 7.54 (3H, m) 7.88 (1H, m) 7.97 (1H, m) 8.18 (1H, m) 8.73 (1H, m). Mass Spectrum (ESI) m/e=485 (M+1).

Example 97: (S)-2-(1-(6-Amino-5-cyanopyrimidin-4-ylamino)ethyl)-N-methyl-3-phenylquinoline-4-carboxamide

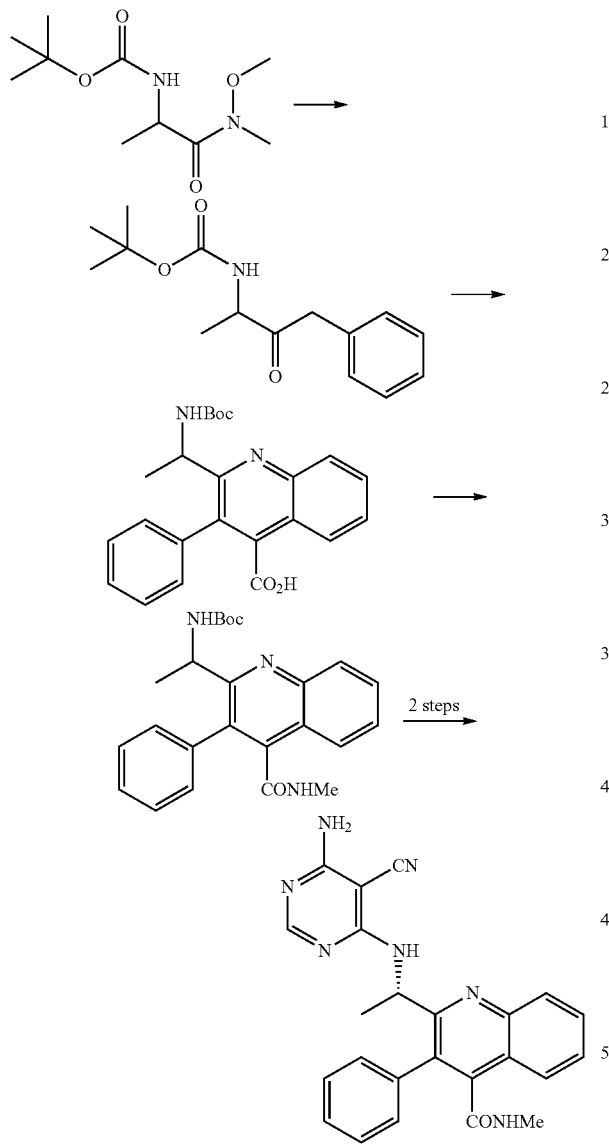

Tert-butyl 1-(methoxy(methyl)amino)-1-oxopropan-2-yl-carbamate (10.00 g, 43 mmol) in THF (80 mL) was cooled to −40° C. with MeCN and dry ice, and slowly charged with isopropylmagnesium chloride (2.0M, 20.45 mL, 0.95 eq). After addition of all reagents, a clear solution was obtained but quickly became milky. Benzylmagnesium chloride (2.0 M, 21.53 mL, 1.0 eq) was added dropwise with stirring at rt for 4 h. The reaction mixture was quenched with NH₄Cl solution and extracted with EtOAc (200 mL×2). The combined organic layers were washed with water, brine, dried over sodium sulfate, concd and purified by combiflash (EtOAc/hexane, up to 1/3) to give tert-butyl 3-oxo-4-(pyridin-2-yl)butan-2-ylcarbamate as a pale yellow oil, which became a white solid after drying under high vacuum. Mass Spectrum (ESI) m/e=264 (M+1). tert-Butyl 3-oxo-4-(pyridin-2-yl)butan-2-ylcarbamate (1.00 g, 3.8 mmol), KOH (0.426 g, 2.0 eq) and isatin (0.559 g, 1.0 eq) in EtOH (5 mL) and water (5 mL) were heated at 85° C. overnight. After cooling to rt, the reaction volume was reduced to 4 mL and extracted with ether twice. The filtrate was acidified with concd HCl to pH 3-4 until no solid was further formed. The solid was filtered, washed with water and dried in the air to give a yellow solid, 2-(1-(tert-butoxycarbonylamino)ethyl)-3-phenylquinoline-4-carboxylic acid. Mass Spectrum (ESI) m/e=393 (M+1). To a solution of 2-(1-(tert-butoxycarbonylamino)ethyl)-3-phenylquinoline-4-carboxylic acid (0.3 g, 0.76 mmol) in DMF (6 mL) was added PyBop (0.875 g, 1.68 mmol), DIEA (0.134 mL, 0.764 mmol) and methanamine (0.573 mL, 1.15 mmol, 2M). The resulting mixture was stirred at room temperature overnight. The solvent was removed in vacuo and replaced with EtOAc. The resulting solution was washed with water, brine and dried over sodium sulfate. The solvent was removed in vacuo and the crude residue subjected to combiflash purification to provide tert-butyl 1-(4-(methylcarbamoyl)-3-phenylquinolin-2-yl)ethylcarbamate as a white solid. Mass Spectrum (ESI) m/e=406 (M+1). To tert-butyl 1-(4-(methylcarbamoyl)-3-phenylquinolin-2-yl)ethylcarbamate (87 mg, 0.215 mmol) was added 4M HCl/1,4-dioxane (1 mL, 4 mmol) and the resulting solution was stirred at rt for 1 h. The solvent was removed and the crude 2-(1-aminoethyl)-N-methyl-3-phenylquinoline-4-carboxamide was used without further purification. Mass Spectrum (ESI) m/e=306 (M+1). To a solution of the crude 2-(1-amino-ethyl)-N-methyl-3-phenylquinoline-4-carboxamide in DMF (5 mL) was added 4-amino-6-chloropyrimidine-5-carbonitrile (33.2 mg, 0.215 mmol) and DIEA (0.112 mL, 0.644 mmol). The resulting mixture was stirred at 100° C. for 1 h. After the solvent was removed under reduced pressure, EtOAc was added and the organic layer was washed with water, brine and dried over sodium sulfate. The solvent was removed in vacuo and the crude residue was purified with chiral HPLC (Isopropanol/Hexane gradient, AD column) to provide (S)-2-(1-(6-amino-5-cyanopyrimidin-4-ylamino)ethyl)-N-methyl-3-phenylquinoline-4-carboxamide. ¹H-NMR (400 Hz, CD₃OD) δ ppm 1.37 (2H, d, J=6.60 Hz), 2.66 (1H, s), 5.52 (1H, m), 7.47 (5H, m), 7.68 (1H, m), 7.85 (2H, m), 7.97 (1H, m), 8.16 (1H, d, J=8.31 Hz) Mass Spectrum (ESI) m/e=424 (M+1).

Example 98: (S)-2-(1-(6-Amino-5-cyanopyrimidin-4-ylamino)ethyl)-8-fluoro-N-methyl-3-phenylquinoline-4-carboxamide

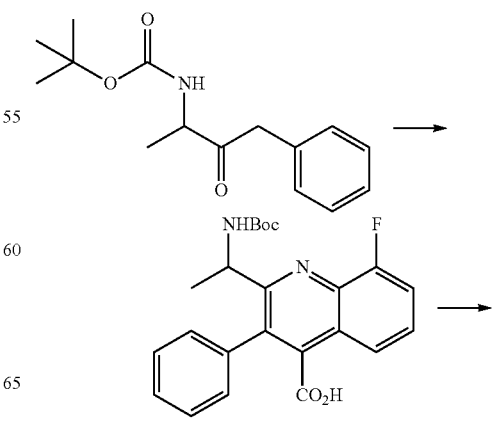

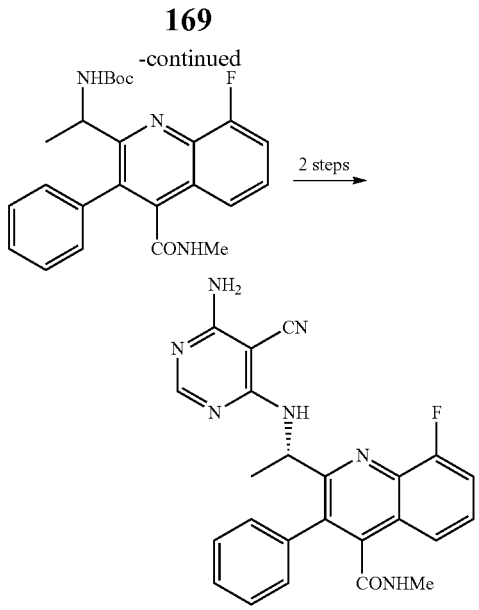

Tert-butyl 3-oxo-4-(pyridin-2-yl)butan-2-ylcarbamate was obtained for the route described above. A solution of Tert-butyl 3-oxo-4-(pyridin-2-yl)butan-2-ylcarbamate (1.00 g, 3.8 mmol), KOH (0.426 g, 2.0 eq) and 7-fluoroisatin (0.627 g, 1.0 eq) in EtOH (5 mL) and water (5 mL) were heated at 85° C. overnight. After cooling to rt, the reaction volume was reduced to 4 mL and extracted with Et$_2$O twice. The filtrate was acidified with concd HCl to pH 3-4 until no solid was further formed. The solid was filtered, washed with water and dried in the air to give a yellow solid 2-(1-(tert-butoxycarbonylamino)ethyl)-8-fluoro-3-phenylquinoline-4-carboxylic acid. Mass Spectrum (ESI) m/e=411 (M+1). To a solution of 2-(1-(tert-butoxy carbonylamino)ethyl)-8-fluoro-3-phenylquinoline-4-carboxylic acid (0.30 g, 0.73 mmol) in DMF (6 mL) was added PyBop (0.837 g, 1.61 mmol), DIEA (0.128 mL, 0.731 mmol) and methanamine (0.548 mL, 1.1 mmol, 2 M). The resulting mixture was stirred at room temperature overnight. The solvent was removed in vacuo and the crude residue was subjected to combiflash purification to provide tert-butyl 1-(8-fluoro-4-(methylcarbamoyl)-3-phenylquinolin-2-yl)ethylcarbamate as a white solid. Mass Spectrum (ESI) m/e=424 (M+1). To tert-butyl 1-(8-fluoro-4-(methylcarbamoyl)-3-phenylquinolin-2-yl)ethylcarbamate (280 mg, 0.661 mmol) was added 4M HCl/1,4-dioxane (1 mL, 4 mmol) and the resulting solution stirred at rt for 1 h. The solvent was removed and the crude 2-(1-aminoethyl)-8-fluoro-N-methyl-3-phenylquinoline-4-carboxamide was used without further purification. Mass Spectrum (ESI) m/e=324 (M+1). To a solution of 2-(1-aminoethyl)-8-fluoro-N-methyl-3-phenylquinoline-4-carboxamide in DMF (2 mL) was added 4-amino-6-chloropyrimidine-5-carbonitrile (102 mg, 0.661 mmol) and DIEA (0.346 mL, 1.984 mmol). The resulting mixture was stirred at 100° C. EtOAc was then added and the organic layer was washed with water, brine and dried over sodium sulfate. The solvent was removed in vacuo and the crude residue was purified by chiral HPLC (isopropanol/hexane gradient, AD column) to provide (S)-2-(1-(6-amino-5-cyanopyrimidin-4-ylamino)ethyl)-8-fluoro-N-methyl-3-phenylquinoline-4-carboxamide. $^1$H-NMR (500 Hz, CD$_3$OD) δ ppm 1.39 (3H, d, J=6.60 Hz), 2.65 (3H, s), 5.57 (1H, q, J=6.20 Hz), 7.43 (1H, m), 7.54 (5H, m), 7.65 (2H, m), 7.95 (1H, m). (ESI) m/e=442 (M+1).

Biological Assays
Recombinant Expression of PI3Ks

Full length p110 subunits of PI3k α, β and δ, N-terminally labeled with polyHis tag, were coexpressed with p85 with Baculo virus expression vectors in sf9 insect cells. P110/p85 heterodimers were purified by sequential Ni-NTA, Q-HP, Superdex-100 chromatography. Purified α, β and δ isozymes were stored at −20° C. in 20 mM Tris, pH 8, 0.2M NaCl, 50% glycerol, 5 mM DTT, 2 mM Na cholate. Truncated PI3Kγ, residues 114-1102, N-terminally labeled with poly-His tag, was expressed with Baculo virus in Hi5 insect cells. The γ isozyme was purified by sequential Ni-NTA, Superdex-200, Q-HP chromatography. The γ isozyme was stored frozen at −80° C. in NaH$_2$PO$_4$, pH 8, 0.2M NaCl, 1% ethylene glycol, 2 mM β-mercaptoethanol.

|  | Alpha | Beta | Delta | gamma |
| --- | --- | --- | --- | --- |
| 50 mM Tris | pH 8 | pH 7.5 | pH 7.5 | pH 8 |
| MgCl2 | 15 mM | 10 mM | 10 mM | 15 mM |
| Na cholate | 2 mM | 1 mM | 0.5 mM | 2 mM |
| DTT | 2 mM | 1 mM | 1 mM | 2 mM |
| ATP | 1 uM | 0.5 uM | 0.5 uM | 1 uM |
| PIP2 | none | 2.5 uM | 2.5 uM | none |
| time | 1 h | 2 h | 2 h | 1 h |
| [Enzyme] | 15 nM | 40 nM | 15 nM | 50 nM |

In Vitro PI3K Enzyme Assays

A PI3K Alphascreen® assay (PerkinElmer, Waltham, Mass.) was used to measure the activity of a panel of four phosphoinositide 3-kinases: PI3Kα, PI3Kβ, PI3Kγ, and PI3Kδ. Enzyme reaction buffer was prepared using sterile water (Baxter, Deerfield, Ill.) and 50 mM Tris HCl pH 7, 14 mM MgCl$_2$, 2 mM sodium cholate, and 100 mM NaCl. 2 mM DTT was added fresh the day of the experiment. The Alphascreen buffer was made using sterile water and 10 mM Tris HCl pH 7.5, 150 mM NaCl, 0.10% Tween 20, and 30 mM EDTA. 1 mM DTT was added fresh the day of the experiment. Compound source plates used for this assay were 384-well Greiner clear polypropylene plates containing test compounds at 5 mM and diluted 1:2 over 22 concentrations. Columns 23 and 24 contained only DMSO as these wells comprised the positive and negative controls, respectively. Source plates were replicated by transferring 0.5 uL per well into 384-well Optiplates (PerkinElmer, Waltham, Mass.).

Each PI3K isoform was diluted in enzyme reaction buffer to 2× working stocks. PI3Kα was diluted to 1.6 nM, PI3Kβ was diluted to 0.8 nM, PI3Kγ was diluted to 15 nM, and PI3Kδ was diluted to 1.6 nM. PI(4,5)P2 (Echelon Biosciences, Salt Lake City, Utah) was diluted to 10 μM and ATP was diluted to 20 μM. This 2× stock was used in the assays for PI3Kα and PI3Kβ. For assay of PI3Kγ and PI3Kδ, PI(4,5)P2 was diluted to 10 μM and ATP was diluted to 8 μM to prepare a similar 2× working stock. Alphascreen reaction solutions were made using beads from the anti-GST Alphascreen kit (PerkinElmer, Waltham, Mass.). Two 4× working stocks of the Alphascreen reagents were made in Alphascreen reaction buffer. In one stock, biotinylated-IP$_4$ (Echelon Biosciences, Salt Lake City, Utah) was diluted to 40 nM and streptavidin-donor beads were diluted to 80 μg/mL. In the second stock, PIP$_3$-binding protein (Echelon Biosciences, Salt Lake City, Utah) was diluted to 40 nM and anti-GST-acceptor beads were diluted to 80 μg/mL. As a negative control, a reference inhibitor at a concentration >>Ki (40 uM) was included in column 24 as a negative (100% inhibition) control.

Using a 384-well Multidrop (Titertek, Huntsville, Ala.), 10 μL/well of 2× enzyme stock was added to columns 1-24 of the assay plates for each isoform. 10 μL/well of the appropriate substrate 2× stock (containing 20 μM ATP for the PI3Kα and β assays and containing 8 μM ATP for the PI3Kγ and δ assays) was then added to Columns 1-24 of all plates. Plates were then incubated at room temperature for 20 minutes. In the dark, 10 μL/well of the donor bead solution was added to columns 1-24 of the plates to quench the enzyme reaction. The plates were incubated at room temperature for 30 minutes. Still in the dark, 10 μL/well of the acceptor bead solution was added to columns 1-24 of the plates. The plates were then incubated in the dark for 1.5 hours. The plates were read on an Envision multimode Plate Reader (PerkinElmer, Waltham, Mass.) using a 680 nm excitation filter and a 520-620 nm emission filter.

Alternative In Vitro Enzyme Assays.

Assays were performed in 25 μL with the above final concentrations of components in white polyproplyene plates (Costar 3355). Phosphatidyl inositol phosphoacceptor, PtdIns(4,5)P2 P4508, was from Echelon Biosciences. The ATPase activity of the alpha and gamma isozymes was not greatly stimulated by PtdIns(4,5)P2 under these conditions and was therefore omitted from the assay of these isozymes. Test compounds were dissolved in dimethyl sulfoxide and diluted with three-fold serial dilutions. The compound in DMSO (1 μL) was added per test well, and the inhibition relative to reactions containing no compound, with and without enzyme was determined. After assay incubation at rt, the reaction was stopped and residual ATP determined by addition of an equal volume of a commercial ATP bioluminescence kit (Perkin Elmer EasyLite) according to the manufacturer's instructions, and detected using a AnalystGT luminometer.

Human B Cells Proliferation Stimulate by Anti-IgM
Isolate Human B Cells:

Isolate PBMCs from Leukopac or from human fresh blood. Isolate human B cells by using Miltenyi protocol and B cell isolation kit II. -human B cells were Purified by using AutoMacs.column.

Activation of Human B Cells

Use 96 well Flat bottom plate, plate 50000/well purified B cells in B cell proliferation medium (DMEM+5% FCS, 10 mM Hepes, 50 μM 2-mercaptoethanol); 150 μL medium contain 250 ng/mL CD40L-LZ recombinant protein (Amgen) and 2 μg/mL anti-Human IgM antibody (Jackson ImmunoReseach Lab.#109-006-129), mixed with 50 μL B cell medium containing PI3K inhibitors and incubate 72 h at 37° C. incubator. After 72 h, pulse labeling B cells with 0.5-1 uCi/well $^3$H thymidine for overnight ~18 h, and harvest cell using TOM harvester.

Human B Cells Proliferation Stimulate by IL-4
Isolate Human B Cells:

Isolate human PBMCs from Leukopac or from human fresh blood. Isolate human B cells using Miltenyi protocol B cell isolation kit. Human B cells were Purified by AutoMacs.column.

Activation of Human B Cells

Use 96-well flat bottom plate, plate 50000/well purified B cells in B cell proliferation medium (DMEM+5% FCS, 50 μM 2-mercaptoethanol, 10 mM Hepes). The medium (150 μL) contain 250 ng/mL CD40 L-LZ recombinant protein (Amgen) and 10 ng/mL IL-4 (R&D system #204-IL-025), mixed with 50 150 μL B cell medium containing compounds and incubate 72 h at 37° C. incubator. After 72 h, pulse labeling B cells with 0.5-1 uCi/well 3H thymidine for overnight ~18 h, and harvest cell using TOM harvester.

Specific T Antigen (Tetanus Toxoid) Induced Human PBMC Proliferation Assays

Human PBMC are prepared from frozen stocks or they are purified from fresh human blood using a Ficoll gradient. Use 96 well round-bottom plate and plate 2×10$^5$ PBMC/well with culture medium (RPMI1640+10% FCS, 50 uM 2-Mercaptoethanol, 10 mM Hepes). For IC$_{50}$ determinations, PI3K inhibitors was tested from 10 μM to 0.001 μM, in half log increments and in triplicate. Tetanus toxoid, T cell specific antigen (University of Massachusetts Lab) was added at 1 μg/mL and incubated 6 days at 37° C. incubator. Supernatants are collected after 6 days for IL2 ELISA assay, then cells are pulsed with $^3$H-thymidine for ~18 h to measure proliferation.

GFP Assays for Detecting Inhibition of Class Ia and Class III PI3K

AKT1 (PKBa) is regulated by Class Ia PI3K activated by mitogenic factors (IGF-1, PDGF, insulin, thrombin, NGF, etc.). In response to mitogenic stimuli, AKT1 translocates from the cytosol to the plasma membrane Forkhead (FKHRL1) is a substrate for AKT1. It is cytoplasmic when phosphorylated by AKT (survival/growth). Inhibition of AKT (stasis/apoptosis)-forkhead translocation to the nucleus FYVE domains bind to PI(3)P. the majority is generated by constitutive action of PI3K Class III AKT Membrane Ruffling Assay (CHO-IR-AKT1-EGFP Cells/GE Healthcare)

Wash cells with assay buffer. Treat with compounds in assay buffer 1 h. Add 10 ng/mL insulin. Fix after 10 min at room temp and image Forkhead Translocation Assay (MDA MB468 Forkhead-DiversaGFP Cells)

Treat cells with compound in growth medium 1 h. Fix and image.

Class III PI(3)P Assay (U2OS EGFP-2XFYVE Cells/GE Healthcare)

Wash cells with assay buffer. Treat with compounds in assay buffer 1 h. Fix and image.

Control for all 3 Assays is 10 uM Wortmannin:
 AKT is cytoplasmic
 Forkhead is nuclear
 PI(3)P depleted from endosomes Biomarker Assay: B-Cell Receptor Stimulation of CD69 or B7.2 (CD86) Expression Heparinized human whole blood was stimulated with 10 μg/mL anti-IgD (Southern Biotech, #9030-01). 90 μL of the stimulated blood was then aliquoted per well of a 96-well plate and treated with 10 μL of various concentrations of blocking compound (from 10-0.0003 μM) diluted in IMDM+10% FBS (Gibco). Samples were incubated together for 4 h (for CD69 expression) to 6 h (for B7.2 expression) at 37° C. Treated blood (50 μL) was transferred to a 96-well, deep well plate (Nunc) for antibody staining with 10 μL each of CD45-PerCP (BD Biosciences, #347464), CD19-FITC (BD Biosciences, #340719), and CD69-PE (BD Biosciences, #341652). The second 50 μL of the treated blood was transferred to a second 96-well, deep well plate for antibody staining with 10 μL each of CD19-FITC (BD Biosciences, #340719) and CD86-PeCy5 (BD Biosciences, #555666). All stains were performed for 15-30 min in the dark at rt. The blood was then lysed and fixed using 450 μL of FACS lysing solution (BD Biosciences, #349202) for 15 min at rt. Samples were then washed 2× in PBS+2% FBS before FACS analysis. Samples were gated on either CD45/CD19 double positive cells for CD69 staining, or CD19 positive cells for CD86 staining.

Gamma Counterscreen: Stimulation of Human Monocytes for Phospho-AKT Expression

A human monocyte cell line, THP-1, was maintained in RPMI+10% FBS (Gibco). One day before stimulation, cells were counted using trypan blue exclusion on a hemocytometer and suspended at a concentration of $1\times10^6$ cells per mL of media. 100 μL of cells plus media ($1\times10^5$ cells) was then aliquoted per well of 4-96-well, deep well dishes (Nunc) to test eight different compounds. Cells were rested overnight before treatment with various concentrations (from 10-0.0003 μM) of blocking compound. The compound diluted in media (12 μL) was added to the cells for 10 min at 37° C. Human MCP-1 (12 μL, R&D Diagnostics, #279-MC) was diluted in media and added to each well at a final concentration of 50 ng/mL. Stimulation lasted for 2 min at rt. Pre-warmed FACS Phosflow Lyse/Fix buffer (1 mL of 37° C.) (BD Biosciences, #558049) was added to each well. Plates were then incubated at 37° C. for an additional 10-15 min. Plates were spun at 1500 rpm for 10 min, supernatant was aspirated off, and 1 mL of ice cold 90% MEOH was added to each well with vigorous shaking. Plates were then incubated either overnight at −70° C. or on ice for 30 min before antibody staining. Plates were spun and washed 2× in PBS+2% FBS (Gibco). Wash was aspirated and cells were suspended in remaining buffer. Rabbit pAKT (50 μL, Cell Signaling, #4058L) at 1:100, was added to each sample for 1 h at rt with shaking. Cells were washed and spun at 1500 rpm for 10 min. Supernatant was aspirated and cells were suspended in remaining buffer. Secondary antibody, goat anti-rabbit Alexa 647 (50 μL, Invitrogen, #A21245) at 1:500, was added for 30 min at rt with shaking. Cells were then washed 1× in buffer and suspended in 150 μL of buffer for FACS analysis. Cells need to be dispersed very well by pipetting before running on flow cytometer. Cells were run on an LSR II (Becton Dickinson) and gated on forward and side scatter to determine expression levels of pAKT in the monocyte population.

Gamma Counterscreen: Stimulation of Monocytes for Phospho-AKT Expression in Mouse Bone Marrow Mouse femurs were dissected from five female BALB/c mice (Charles River Labs.) and collected into RPMI+10% FBS media (Gibco). Mouse bone marrow was removed by cutting the ends of the femur and by flushing with 1 mL of media using a 25 gauge needle. Bone marrow was then dispersed in media using a 21 gauge needle. Media volume was increased to 20 mL and cells were counted using trypan blue exclusion on a hemocytometer. The cell suspension was then increased to $7.5\times10^6$ cells per 1 mL of media and 100 μL ($7.5\times10^5$ cells) was aliquoted per well into 4-96-well, deep well dishes (Nunc) to test eight different compounds. Cells were rested at 37° C. for 2 h before treatment with various concentrations (from 10-0.0003 μM) of blocking compound. Compound diluted in media (12 μL) was added to bone marrow cells for 10 min at 37° C. Mouse MCP-1 (12 μL, R&D Diagnostics, #479-JE) was diluted in media and added to each well at a final concentration of 50 ng/mL. Stimulation lasted for 2 min at rt. 1 mL of 37° C. pre-warmed FACS Phosflow Lyse/Fix buffer (BD Biosciences, #558049) was added to each well. Plates were then incubated at 37° C. for an additional 10-15 min. Plates were spun at 1500 rpm for 10 min. Supernatant was aspirated off and 1 mL of ice cold 90% MEOH was added to each well with vigorous shaking. Plates were then incubated either overnight at −70° C. or on ice for 30 min before antibody staining. Plates were spun and washed 2× in PBS+2% FBS (Gibco). Wash was aspirated and cells were suspended in remaining buffer. Fc block (2 μL, BD Pharmingen, #553140) was then added per well for 10 min at rt. After block, 50 μL of primary antibodies diluted in buffer; CD11b-Alexa488 (BD Biosciences, #557672) at 1:50, CD64-PE (BD Biosciences, #558455) at 1:50, and rabbit pAKT (Cell Signaling, #4058L) at 1:100, were added to each sample for 1 h at RT with shaking. Wash buffer was added to cells and spun at 1500 rpm for 10 min. Supernatant was aspirated and cells were suspended in remaining buffer. Secondary antibody; goat anti-rabbit Alexa 647 (50 μL, Invitrogen, #A21245) at 1:500, was added for 30 min at rt with shaking. Cells were then washed 1× in buffer and suspended in 100 μL of buffer for FACS analysis. Cells were run on an LSR II (Becton Dickinson) and gated on CD11b/CD64 double positive cells to determine expression levels of pAKT in the monocyte population.

pAKT In Vivo Assay

Vehicle and compounds are administered p.o. (0.2 mL) by gavage (Oral Gavage Needles Popper & Sons, New Hyde Park, N.Y.) to mice (Transgenic Line 3751, female, 10-12 wks Amgen Inc, Thousand Oaks, Calif.) 15 min prior to the injection i.v (0.2 mLs) of anti-IgM FITC (50 ug/mouse) (Jackson Immuno Research, West Grove, Pa.). After 45 min the mice are sacrificed within a $CO_2$ chamber. Blood is drawn via cardiac puncture (0.3 mL) (1 cc 25 g Syringes, Sherwood, St. Louis, Mo.) and transferred into a 15 mL conical vial (Nalge/Nunc International, Denmark). Blood is immediately fixed with 6.0 mL of BD Phosflow Lyse/Fix Buffer (BD Bioscience, San Jose, Calif.), inverted 3×'s and placed in 37° C. water bath. Half of the spleen is removed and transferred to an eppendorf tube containing 0.5 mL of PBS (Invitrogen Corp, Grand Island, N.Y.). The spleen is crushed using a tissue grinder (Pellet Pestle, Kimble/Kontes, Vineland, N.J.) and immediately fixed with 6.0 mL of BD Phosflow Lyse/Fix buffer, inverted 3×'s and placed in 37° C. water bath. Once tissues have been collected the mouse is cervically-dislocated and carcass to disposed. After 15 min, the 15 mL conical vials are removed from the 37° C. water bath and placed on ice until tissues are further processed. Crushed spleens are filtered through a 70 μm cell strainer (BD Bioscience, Bedford, Mass.) into another 15 mL conical vial and washed with 9 mL of PBS. Splenocytes and blood are spun @2,000 rpms for 10 min (cold) and buffer is aspirated. Cells are resuspended in 2.0 mL of cold (−20° C.) 90% methyl alcohol (Mallinckrodt Chemicals, Phillipsburg, N.J.). MeOH is slowly added while conical vial is rapidly vortexed. Tissues are then stored at −20° C. until cells can be stained for FACS analysis.

Multi-Dose TNP Immunization

Blood was collected by retro-orbital eye bleeds from 7-8 week old BALB/c female mice (Charles River Labs.) at day 0 before immunization. Blood was allowed to clot for 30 min and spun at 10,000 rpm in serum microtainer tubes (Becton Dickinson) for 10 min. Sera were collected, aliquoted in Matrix tubes (Matrix Tech. Corp.) and stored at −70° C. until ELISA was performed. Mice were given compound orally before immunization and at subsequent time periods based on the life of the molecule. Mice were then immunized with either 50 μg of TNP-LPS (Biosearch Tech., #T-5065), 50 μg of TNP-Ficoll (Biosearch Tech., #F-1300), or 100 μg of TNP-KLH (Biosearch Tech., #T-5060) plus 1% alum (Brenntag, #3501) in PBS. TNP-KLH plus alum solution was prepared by gently inverting the mixture 3-5 times every 10 min for 1 h before immunization. On day 5, post-last treatment, mice were $CO_2$ sacrificed and cardiac punctured. Blood was allowed to clot for 30 min and spun at 10,000 rpm in serum microtainer tubes for 10 min. Sera were collected, aliquoted in Matrix tubes, and stored at −70° C. until further analysis was performed. TNP-specific IgG1, IgG2a, IgG3 and IgM levels in the sera were then measured via ELISA. TNP-BSA (Biosearch Tech., #T-5050) was used to capture the TNP-specific antibodies. TNP-BSA (10 μg/mL) was used to coat 384-well ELISA plates (Corning Costar) overnight. Plates were then washed and blocked for 1 h using 10% BSA ELISA Block solution (KPL). After blocking, ELISA plates were washed and sera samples/standards were serially diluted and allowed to bind to the plates for 1 h. Plates were washed and Ig-HRP conjugated secondary antibodies (goat anti-mouse IgG1, Southern Biotech #1070-05, goat anti-mouse IgG2a, Southern Biotech #1080-05, goat anti-mouse IgM, Southern Biotech #1020-05, goat anti-mouse IgG3, Southern Biotech #1100-05) were diluted at 1:5000 and incubated on the plates for 1 h. TMB peroxidase solution (SureBlue Reserve TMB from KPL) was used to visualize the antibodies. Plates were washed and samples were allowed to develop in the TMB solution approximately 5-20 min depending on the Ig analyzed. The reaction was stopped with 2M sulfuric acid and plates were read at an OD of 450 nm.

The following compounds showed the associated data in the above PI3Kδ Alphascreen® assay:

| Compound | Ki (μM) |
|---|---|
| 4-amino-1-((1S)-1-(6-fluoro-3-(5-fluoro-3-pyridinyl)-2-quinolinyl)ethyl)-1H-pyrazolo[3,4-d]pyrimidine-3-carbonitrile | 0.024997 |
| 4-amino-1-((1R)-1-(6-fluoro-3-(5-fluoro-3-pyridinyl)-2-quinolinyl)ethyl)-1H-pyrazolo[3,4-d]pyrimidine-3-carbonitrile | 5.4689475 |
| 4-amino-6-(((1S)-1-(6-fluoro-3-(6-(methylsulfonyl)-2-pyridinyl)-2-quinolinyl)ethyl)amino)-5-pyrimidinecarbonitrile | 0.1297 |
| N-(1-(6-fluoro-3-(2-pyridinyl)-2-quinolinyl)ethyl)-9H-purin-6-amine | 0.0212875 |
| N-((1S)-1-(6-fluoro-3-(2-pyridinyl)-2-quinolinyl)ethyl)-9H-purin-6-amine | 0.004147 |
| N-((1R)-1-(6-fluoro-3-(2-pyridinyl)-2-quinolinyl)ethyl)-9H-purin-6-amine | 0.2168 |
| N-(1-(6-fluoro-3-(2-pyridinyl)-2-quinolinyl)ethyl)-4-pyrimidinamine | 11.632679 |
| N-(1-(6-fluoro-3-(2-pyridinyl)-2-quinolinyl)ethyl)-4,6-pyrimidinediamine | 3.7315 |
| N~4~-((1R)-1-(6-fluoro-3-(2-pyridinyl)-2-quinolinyl)ethyl)-2,4-pyrimidinediamine | 5.5205 |
| 4-amino-6-((1-(6-fluoro-3-(2-pyridinyl)-2-quinolinyl)ethyl)amino)-5-pyrimidinecarbonitrile | 0.004217 |
| 4-((1-(6-fluoro-3-(2-pyridinyl)-2-quinolinyl)ethyl)amino)-6-hydroxy-5-pyrimidinecarbonitrile | 0.0548 |
| 4-amino-1-((1S)-1-(6-fluoro-3-(2-pyridinyl)-2-quinolinyl)ethyl)-1H-pyrazolo[3,4-d]pyrimidine-3-carbonitrile | 0.0076745 |
| 4-amino-1-((1R)-1-(6-fluoro-3-(2-pyridinyl)-2-quinolinyl)ethyl)-1H-pyrazolo[3,4-d]pyrimidine-3-carbonitrile | 0.32 |
| 4-amino-6-((1-(5-chloro-3-(2-pyridinyl)-2-quinolinyl)ethyl)amino)-5-pyrimidinecarbonitrile | 0.0016 |
| 4-amino-6-(((1S)-1-(5-chloro-3-(2-pyridinyl)-2-quinolinyl)ethyl)amino)-5-pyrimidinecarbonitrile | 0.0004 |
| 4-amino-6-(((1R)-1-(5-chloro-3-(2-pyridinyl)-2-quinolinyl)ethyl)amino)-5-pyrimidinecarbonitrile | 0.0579 |
| 2-((1S)-1-((6-amino-5-cyano-4-pyrimidinyl)amino)ethyl)-3-(2-pyridinyl)-5-quinolinecarbonitrile | 0.0141 |
| 2-((1R)-1-((6-amino-5-cyano-4-pyrimidinyl)amino)ethyl)-3-(2-pyridinyl)-5-quinolinecarbonitrile | 2.64 |
| 4-amino-6-((1-(3-(2-pyridinyl)-1,8-naphthyridin-2-yl)ethyl)amino)-5-pyrimidinecarbonitrile | 0.225 |
| 4-amino-6-((1-(3-(2-pyridinyl)-1,6-naphthyridin-2-yl)ethyl)amino)-5-pyrimidinecarbonitrile | 0.47 |
| 4-amino-6-((1-(6-fluoro-4-(methylsulfonyl)-3-phenyl-2-quinolinyl)ethyl)amino)-5-pyrimidinecarbonitrile | 0.0013 |
| 4-amino-6-((1-(6-fluoro-4-(methylsulfanyl)-3-phenyl-2-quinolinyl)ethyl)amino)-5-pyrimidinecarbonitrile | 0.0024 |
| 4-amino-6-(((8-fluoro-3-(2-(methylsulfonyl)phenyl)-2-quinolinyl)methyl)amino)-5-pyrimidinecarbonitrile | 0.0307 |
| 4-amino-6-(((8-fluoro-3-(2-pyridinyl)-2-quinolinyl)methyl)amino)-5-pyrimidinecarbonitrile | 0.262 |
| 4-amino-6-(((8-fluoro-3-phenyl-2-quinolinyl)methyl)amino)-5-pyrimidinecarbonitrile | 0.0123 |
| 4-amino-6-(((5-fluoro-3-phenyl-2-quinolinyl)methyl)amino)-5-pyrimidinecarbonitrile | 0.107 |
| 4-amino-6-(((5-fluoro-3-(3-fluorophenyl)-2-quinolinyl)methyl)amino)-5-pyrimidinecarbonitrile | 0.102 |
| 4-amino-6-(((3-(3,5-difluorophenyl)-5-fluoro-2-quinolinyl)methyl)amino)-5-pyrimidinecarbonitrile | 0.246 |
| 4-amino-6-(((5-fluoro-3-(2-(methylsulfonyl)phenyl)-2-quinolinyl)methyl)amino)-5-pyrimidinecarbonitrile | 0.039 |
| 4-amino-6-(((5-fluoro-3-(2-pyridinyl)-2-quinolinyl)methyl)amino)-5-pyrimidinecarbonitrile | 0.137 |
| 4-amino-6-((-1-(4-(dimethylamino)-6-fluoro-3-(2-pyridinyl)-2-quinolinyl)ethyl)amino)-5-pyrimidinecarbonitrile | 0.0014 |

| Compound | Ki (μM) |
|---|---|
| 4-amino-6-((-1-(6-fluoro-4-(4-morpholinyl)-3-(2-pyridinyl)-2-quinolinyl)ethyl)amino)-5-pyrimidinecarbonitrile | 0.00119 |
| 4-amino-6-((-1-(6-fluoro-4-(3-hydroxy-1-azetidinyl)-3-(2-pyridinyl)-2-quinolinyl)ethyl)amino)-5-pyrimidinecarbonitrile | 0.00178 |
| 2-((1S)-1-((6-amino-5-cyano-4-pyrimidinyl)amino)ethyl)-6-fluoro-N,N-dimethyl-3-phenyl-4-quinolinecarboxamide | 0.0148 |
| 4-amino-6-(((1S)-1-(6-fluoro-4-(4-morpholinylcarbonyl)-3-phenyl-2-quinolinyl)ethyl)amino)-5-pyrimidinecarbonitrile | 0.000505 |
| 4-amino-6-(((1S)-1-(6-fluoro-4-(((3S)-3-hydroxy-1-pyrrolidinyl)carbonyl)-3-phenyl-2-quinolinyl)ethyl)amino)-5-pyrimidinecarbonitrile | 0.000657 |
| 4-amino-6-(((1S)-1-(4-((1,1-dioxido-4-thiomorpholinyl)carbonyl)-6-fluoro-3-phenyl-2-quinolinyl)ethyl)amino)-5-pyrimidinecarbonitrile | 0.00124 |
| 2-((1S)-1-((6-amino-5-cyano-4-pyrimidinyl)amino)ethyl)-6-fluoro-3-phenyl-4-quinolinecarbonitrile | 0.00276 |
| 2-((1S)-1-((6-amino-5-cyano-4-pyrimidinyl)amino)ethyl)-6-fluoro-3-phenyl-4-quinolinecarbonitrile | 0.00133 |
| 2-((1R)-1-((6-amino-5-cyano-4-pyrimidinyl)amino)ethyl)-6-fluoro-3-phenyl-4-quinolinecarbonitrile | 0.0591 |
| methyl 2-(-1-((6-amino-5-cyano-4-pyrimidinyl)amino)ethyl)-6-fluoro-3-phenyl-4-quinolinecarboxylate | 0.00156 |
| 2-((1S)-1-((6-amino-5-cyano-4-pyrimidinyl)amino)ethyl)-6-fluoro-3-phenyl-4-quinolinecarboxylic acid | 0.0742 |
| 2-((1S)-1-((6-amino-5-carbamoyl-4-pyrimidinyl)amino)ethyl)-6-fluoro-3-phenyl-4-quinolinecarboxylic acid | 0.00716 |
| 2-(-1-((6-amino-5-cyano-4-pyrimidinyl)amino)ethyl)-6-fluoro-N-methyl-3-phenyl-4-quinolinecarboxamide | 0.000796 |
| 4-amino-6-((-1-(6-fluoro-3-phenyl-4-(1-piperazinylcarbonyl)-2-quinolinyl)ethyl)amino)-5-pyrimidinecarbonitrile | 0.000542 |
| 4-amino-6-((-1-(6-fluoro-4-((4-methyl-1-piperazinyl)carbonyl)-3-phenyl-2-quinolinyl)ethyl)amino)-5-pyrimidinecarbonitrile | 0.00132 |
| 2-(-1-((6-amino-5-cyano-4-pyrimidinyl)amino)ethyl)-6-fluoro-N,N-dimethyl-3-phenyl-4-quinolinecarboxamide | 0.00101 |
| 4-amino-6-((-1-(6-fluoro-4-(((3R)-3-hydroxy-1-pyrrolidinyl)carbonyl)-3-phenyl-2-quinolinyl)ethyl)amino)-5-pyrimidinecarbonitrile | 0.0256 |
| 4-amino-6-(((1-(6-fluoro-3-phenyl-4-(1-pyrrolidinylcarbonyl)-2-quinolinyl)ethyl)amino)-5-pyrimidinecarbonitrile | 0.00706 |
| 4-amino-6-((-1-(6-fluoro-4-(4-morpholinylcarbonyl)-3-phenyl-2-quinolinyl)ethyl)amino)-5-pyrimidinecarbonitrile | 0.00288 |
| 4-amino-6-((-1-(6-fluoro-4-(((3S)-3-hydroxy-1-pyrrolidinyl)carbonyl)-3-phenyl-2-quinolinyl)ethyl)amino)-5-pyrimidinecarbonitrile | 0.00102 |
| 4-amino-6-((-1-(6-fluoro-4-(((3R)-3-hydroxy-1-pyrrolidinyl)-carbonyl)-3-phenyl-2-quinolinyl)ethyl)amino)-5-pyrimidine-carbonitrile | 0.00507 |
| 4-amino-6-(((1-(4-((1,1-dioxido-4-thiomorpholinyl)carbonyl)-6-fluoro-3-phenyl-2-quinolinyl)ethyl)amino)-5-pyrimidine-carbonitrile | 0.000556 |
| 4-amino-6-(((1-(6-fluoro-4-((3-hydroxy-1-azetidinyl)carbonyl)-3-phenyl-2-quinolinyl)ethyl)amino)-5-pyrimidinecarbonitrile | 0.000755 |
| 4-amino-6-(((1-(6-fluoro-4-((3-methoxy-1-azetidinyl)carbonyl)-3-phenyl-2-quinolinyl)ethyl)amino)-5-pyrimidinecarbonitrile | 0.00175 |
| 2-(1-((6-amino-5-cyano-4-pyrimidinyl)amino)ethyl)-6-fluoro-N-(2-(4-morpholinyl)ethyl)-3-phenyl-4-quinolinecarboxamide | 0.00102 |
| 4-amino-6-((-1-(6-fluoro-4-(hydroxymethyl)-3-phenyl-2-quinolinyl)ethyl)amino)-5-pyrimidinecarbonitrile | 0.00168 |
| 4-amino-6-(((1S)-1-(6-fluoro-3-phenyl-4-(1-piperazinylcarbonyl)-2-quinolinyl)ethyl)amino)-5-pyrimidinecarbonitrile | 0.000248 |
| 2-((1S)-1-((6-amino-5-cyano-4-pyrimidinyl)amino)ethyl)-6-fluoro-N-methyl-3-phenyl-4-quinolinecarboxamide | 0.00127 |
| 4-amino-6-((-1-(6-fluoro-4-((methylsulfonyl)methyl)-3-phenyl-2-quinolinyl)ethyl)amino)-5-pyrimidinecarbonitrile | 0.00138 |
| 4-amino-6-(((1S)-1-(6-fluoro-4-((3-hydroxy-1-azetidinyl)-carbonyl)-3-phenyl-2-quinolinyl)ethyl)amino)-5-pyrimidine-carbonitrile | 0.0013 |
| 4-amino-6-(((1S)-1-(4-((1,1-dioxido-4-thiomorpholinyl)carbonyl)-6-fluoro-3-phenyl-2-quinolinyl)ethyl)amino)-5-pyrimidinecarbonitrile | 0.00435 |
| 2-((1S)-1-((6-amino-5-cyano-4-pyrimidinyl)amino)ethyl)-6-fluoro-N,N-dimethyl-3-phenyl-4-quinolinecarboxamide | 0.00083 |
| 2-((1S)-1-((6-amino-5-cyano-4-pyrimidinyl)amino)ethyl)-6-fluoro-N,N-dimethyl-3-phenyl-4-quinolinecarboxamide | 0.0218 |
| 4-amino-6-((-1-(6-fluoro-4-(4-morpholinylmethyl)-3-phenyl-2-quinolinyl)ethyl)amino)-5-pyrimidinecarbonitrile | 0.00131 |
| 2-((1S)-1-((6-amino-5-cyano-4-pyrimidinyl)amino)ethyl)-N-ethyl-6-fluoro-3-phenyl-4-quinolinecarboxamide | 0.0673 |
| 2-(-1-((6-amino-5-cyano-4-pyrimidinyl)amino)ethyl)-6-fluoro-N-(1-methylethyl)-3-phenyl-4-quinolinecarboxamide | 0.00317 |
| 2-(-1-((6-amino-5-cyano-4-pyrimidinyl)amino)ethyl)-N-(cyclopropylmethyl)-6-fluoro-3-phenyl-4-quinolinecarboxamide | 0.00515 |

-continued

| Compound | Ki (µM) |
|---|---|
| 4-amino-6-(((1S)-1-(6-fluoro-4-methoxy-3-phenyl-2-quinolinyl)ethyl)amino)-5-pyrimidinecarbonitrile | 0.00118 |
| 4-amino-6-(((1R)-1-(6-fluoro-4-methoxy-3-phenyl-2-quinolinyl)ethyl)amino)-5-pyrimidinecarbonitrile | 0.271 |
| 4-amino-6-(((1S)-1-(3-(3,5-difluorophenyl)-6-fluoro-4-methoxy-2-quinolinyl)ethyl)amino)-5-pyrimidinecarbonitrile | 0.0684 |
| 4-amino-6-(-1-(6-fluoro-4-((2-methoxyethyl)amino)-3-phenyl-2-quinolinyl)ethyl)amino)-5-pyrimidinecarbonitrile | 0.00135 |
| 4-amino-6-(-1-(4-((2-(dimethylamino)ethyl)amino)-6-fluoro-3-phenyl-2-quinolinyl)ethyl)amino)-5-pyrimidinecarbonitrile | 0.00133 |
| 4-amino-6-(((1S)-1-(6-fluoro-4-((2-methoxyethyl)amino)-3-phenyl-2-quinolinyl)ethyl)amino)-5-pyrimidinecarbonitrile | 0.00061 |
| 4-amino-6-(((1R)-1-(6-fluoro-4-((2-methoxyethyl)amino)-3-phenyl-2-quinolinyl)ethyl)amino)-5-pyrimidinecarbonitrile | 0.0622 |
| 4-amino-6-(-1-(6-fluoro-4-((2-(methylsulfonyl)ethyl)amino)-3-phenyl-2-quinolinyl)ethyl)amino)-5-pyrimidinecarbonitrile | 0.000463 |
| 4-amino-6-(-1-(6-fluoro-4-((2-hydroxyethyl)amino)-3-phenyl-2-quinolinyl)ethyl)amino)-5-pyrimidinecarbonitrile | 0.000396 |
| 4-amino-6-(((1S)-1-(6-fluoro-4-((2-(methylsulfonyl)ethyl)amino)-3-phenyl-2-quinolinyl)ethyl)amino)-5-pyrimidinecarbonitrile | 0.000226 |
| 4-amino-6-(((1S)-1-(6-fluoro-4-(methylsulfonyl)-3-phenyl-2-quinolinyl)ethyl)amino)-5-pyrimidinecarbonitrile | 0.000741 |
| N-(1-(6-fluoro-4-(methylsulfonyl)-3-phenyl-2-quinolinyl)ethyl)-9H-purin-6-amine | 0.00234 |
| N-(-1-(5-fluoro-4-(methylsulfonyl)-3-phenyl-2-quinolinyl)ethyl)-9H-purin-6-amine | 0.00224 |
| 4-amino-6-((-1-(6-fluoro-4-((R)-(2-hydroxyethyl)sulfinyl)-3-phenyl-2-quinolinyl)ethyl)amino)-5-pyrimidinecarbonitrile | 0.00248 |
| 4-amino-6-(((1R)-1-(5-fluoro-4-(methylsulfonyl)-3-phenyl-2-quinolinyl)ethyl)amino)-5-pyrimidinecarbonitrile | 0.466 |
| 4-amino-6-(((1S)-1-(5-fluoro-4-(methylsulfonyl)-3-phenyl-2-quinolinyl)ethyl)amino)-5-pyrimidinecarbonitrile | 0.0013 |
| N-((1S)-1-(6-fluoro-4-(methylsulfonyl)-3-phenyl-2-quinolinyl)-ethyl)-9H-purin-6-amine | 0.00112 |
| N-((1R)-1-(6-fluoro-4-(methylsulfonyl)-3-phenyl-2-quinolinyl)-ethyl)-9H-purin-6-amine | 0.41 |
| 4-amino-6-((-1-(3-(3,5-difluorophenyl)-6-fluoro-4-(methylsulfonyl)-2-quinolinyl)ethyl)amino)-5-pyrimidinecarbonitrile | 0.00112 |
| 4-amino-6-((-1-(6-fluoro-4-((S)-(2-hydroxyethyl)sulfinyl)-3-phenyl-2-quinolinyl)amino)-5-pyrimidinecarbonitrile | 0.0018 |
| 2-(1-(6-Amino-5-cyanopyrimidin-4-ylamino)ethyl)-6-fluoro-N-methyl-3-(pyridin-2-yl)quinoline-4-carboxamide | 0.00239 |
| (S)-2-(1-(6-Amino-5-cyanopyrimidin-4-ylamino)ethyl)-N-ethyl-6-fluoro-3-(pyridin-2-yl)quinoline-4-carboximidamide | 0.0036 |
| (S)-2-(1-(6-Amino-5-cyanopyrimidin-4-ylamino)ethyl)-6-fluoro-N-(2-hydroxyethyl)-3-(pyridin-2-yl)quinoline-4-carboxamide | 0.00757 |
| (S)-2-(1-(6-Amino-5-cyanopyrimidin-4-ylamino)ethyl)-N-cyclopropyl-6-fluoro-3-(pyridin-2-yl)quinoline-4-carboxamide | 0.00164 |
| 2-1-(((6-Amino-5-cyano-4-pyrimidinyl)amino)ethyl)-6-fluoro-3-(2-pyridinyl)-4-quinolinecarboxylic acid | 0.119 |
| 2-(-1-((6-Amino-5-cyano-4-pyrimidinyl)amino)ethyl)-6-fluoro-N-methyl-3-(2-pyridinyl)-4-quinolinecarboxamide | 0.00176 |
| 2-((1R)-1-((6-Amino-5-cyano-4-pyrimidinyl)amino)ethyl)-6-fluoro-N-methyl-3-(2-pyridinyl)-4-quinolinecarboxamide | 0.123 |
| 2-(1-((6-Amino-5-cyano-4-pyrimidinyl)amino)ethyl)-6-fluoro-N,N-dimethyl-3-(2-pyridinyl)-4-quinolinecarboxamide | 0.00777 |
| 4-Amino-6-((1-(6-fluoro-4-(1-piperazinylcarbonyl)-3-(2-pyridinyl)-2-quinolinyl)ethyl)amino)-5-pyrimidinecarbonitrile | 0.00429 |
| 4-amino-6-(1-(6-fluoro-4-(3-hydroxyazetidine-1-carbonyl)-3-(pyridin-2-yl)quinolin-2-yl)ethylamino)pyrimidine-5-carbonitrile | 0.0119 |

For the treatment of PI3Kδ-mediated-diseases, such as rheumatoid arthritis, ankylosing spondylitis, osteoarthritis, psoriatic arthritis, psoriasis, inflammatory diseases, and autoimmune diseases, the compounds of the present invention may be administered orally, parentally, by inhalation spray, rectally, or topically in dosage unit formulations containing conventional pharmaceutically acceptable carriers, adjuvants, and vehicles. The term parenteral as used herein includes, subcutaneous, intravenous, intramuscular, intrasternal, infusion techniques or intraperitoneally.

Treatment of diseases and disorders herein is intended to also include the prophylactic administration of a compound of the invention, a pharmaceutical salt thereof, or a pharmaceutical composition of either to a subject (i.e., an animal, preferably a mammal, most preferably a human) believed to be in need of preventative treatment, such as, for example, rheumatoid arthritis, ankylosing spondylitis, osteoarthritis, psoriatic arthritis, psoriasis, inflammatory diseases, and autoimmune diseases and the like.

The dosage regimen for treating PI3Kδ-mediated diseases, cancer, and/or hyperglycemia with the compounds of this invention and/or compositions of this invention is based on a variety of factors, including the type of disease, the age, weight, sex, medical condition of the patient, the severity of the condition, the route of administration, and the particular compound employed. Thus, the dosage regimen may vary widely, but can be determined routinely using standard methods. Dosage levels of the order from about 0.01 mg to 30 mg per kilogram of body weight per day, preferably from about 0.1 mg to 10 mg/kg, more preferably from about 0.25 mg to 1 mg/kg are useful for all methods of use disclosed herein.

The pharmaceutically active compounds of this invention can be processed in accordance with conventional methods of pharmacy to produce medicinal agents for administration to patients, including humans and other mammals.

For oral administration, the pharmaceutical composition may be in the form of, for example, a capsule, a tablet, a suspension, or liquid. The pharmaceutical composition is preferably made in the form of a dosage unit containing a given amount of the active ingredient. For example, these may contain an amount of active ingredient from about 1 to 2000 mg, preferably from about 1 to 500 mg, more preferably from about 5 to 150 mg. A suitable daily dose for a human or other mammal may vary widely depending on the condition of the patient and other factors, but, once again, can be determined using routine methods.

The active ingredient may also be administered by injection as a composition with suitable carriers including saline, dextrose, or water. The daily parenteral dosage regimen will be from about 0.1 to about 30 mg/kg of total body weight, preferably from about 0.1 to about 10 mg/kg, and more preferably from about 0.25 mg to 1 mg/kg.

Injectable preparations, such as sterile injectable aq. or oleaginous suspensions, may be formulated according to the known are using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed, including synthetic mono- or diglycerides. In addition, fatty acids such as oleic acid find use in the preparation of injectables.

Suppositories for rectal administration of the drug can be prepared by mixing the drug with a suitable non-irritating excipient such as cocoa butter and polyethylene glycols that are solid at ordinary temperatures but liquid at the rectal temperature and will therefore melt in the rectum and release the drug.

A suitable topical dose of active ingredient of a compound of the invention is 0.1 mg to 150 mg administered one to four, preferably one or two times daily. For topical administration, the active ingredient may comprise from 0.001% to 10% w/w, e.g., from 1% to 2% by weight of the formulation, although it may comprise as much as 10% w/w, but preferably not more than 5% w/w, and more preferably from 0.1% to 1% of the formulation.

Formulations suitable for topical administration include liquid or semi-liquid preparations suitable for penetration through the skin (e.g., liniments, lotions, ointments, creams, or pastes) and drops suitable for administration to the eye, ear, or nose.

For administration, the compounds of this invention are ordinarily combined with one or more adjuvants appropriate for the indicated route of administration. The compounds may be admixed with lactose, sucrose, starch powder, cellulose esters of alkanoic acids, stearic acid, talc, magnesium stearate, magnesium oxide, sodium and calcium salts of phosphoric and sulfuric acids, acacia, gelatin, sodium alginate, polyvinyl-pyrrolidine, and/or polyvinyl alcohol, and tableted or encapsulated for conventional administration. Alternatively, the compounds of this invention may be dissolved in saline, water, polyethylene glycol, propylene glycol, ethanol, corn oil, peanut oil, cottonseed oil, sesame oil, tragacanth gum, and/or various buffers. Other adjuvants and modes of administration are well known in the pharmaceutical art. The carrier or diluent may include time delay material, such as glyceryl monostearate or glyceryl distearate alone or with a wax, or other materials well known in the art.

The pharmaceutical compositions may be made up in a solid form (including granules, powders or suppositories) or in a liquid form (e.g., solutions, suspensions, or emulsions). The pharmaceutical compositions may be subjected to conventional pharmaceutical operations such as sterilization and/or may contain conventional adjuvants, such as preservatives, stabilizers, wetting agents, emulsifiers, buffers etc.

Solid dosage forms for oral administration may include capsules, tablets, pills, powders, and granules. In such solid dosage forms, the active compound may be admixed with at least one inert diluent such as sucrose, lactose, or starch. Such dosage forms may also comprise, as in normal practice, additional substances other than inert diluents, e.g., lubricating agents such as magnesium stearate. In the case of capsules, tablets, and pills, the dosage forms may also comprise buffering agents. Tablets and pills can additionally be prepared with enteric coatings.

Liquid dosage forms for oral administration may include pharmaceutically acceptable emulsions, solutions, suspensions, syrups, and elixirs containing inert diluents commonly used in the art, such as water. Such compositions may also comprise adjuvants, such as wetting, sweetening, flavoring, and perfuming agents.

Compounds of the present invention can possess one or more asymmetric carbon atoms and are thus capable of existing in the form of optical isomers as well as in the form of racemic or non-racemic mixtures thereof. The optical isomers can be obtained by resolution of the racemic mixtures according to conventional processes, e.g., by formation of diastereoisomeric salts, by treatment with an optically active acid or base. Examples of appropriate acids are tartaric, diacetyltartaric, dibenzoyltartaric, ditoluoyltartaric, and camphorsulfonic acid and then separation of the mixture of diastereoisomers by crystallization followed by liberation of the optically active bases from these salts. A different process for separation of optical isomers involves the use of a chiral chromatography column optimally chosen to maximize the separation of the enantiomers. Still another available method involves synthesis of covalent diastereoisomeric molecules by reacting compounds of the invention with an optically pure acid in an activated form or an optically pure isocyanate. The synthesized diastereoisomers can be separated by conventional means such as chromatography, distillation, crystallization or sublimation, and then hydrolyzed to deliver the enantiomerically pure compound. The optically active compounds of the invention can likewise be obtained by using active starting materials. These isomers may be in the form of a free acid, a free base, an ester or a salt.

Likewise, the compounds of this invention may exist as isomers, that is compounds of the same molecular formula but in which the atoms, relative to one another, are arranged differently. In particular, the alkylene substituents of the compounds of this invention, are normally and preferably arranged and inserted into the molecules as indicated in the definitions for each of these groups, being read from left to right. However, in certain cases, one skilled in the art will appreciate that it is possible to prepare compounds of this invention in which these substituents are reversed in orientation relative to the other atoms in the molecule. That is, the substituent to be inserted may be the same as that noted above except that it is inserted into the molecule in the reverse orientation. One skilled in the art will appreciate that these isomeric forms of the compounds of this invention are to be construed as encompassed within the scope of the present invention.

The compounds of the present invention can be used in the form of salts derived from inorganic or organic acids. The salts include, but are not limited to, the following: acetate, adipate, alginate, citrate, aspartate, benzoate, benzenesulfonate, bisulfate, butyrate, camphorate, camphorsulfonate, digluconate, cyclopentanepropionate, dodecylsulfate, ethanesulfonate, glucoheptanoate, glycerophosphate, hemisulfate, heptanoate, hexanoate, fumarate, hydrochloride, hydrobromide, hydroiodide, 2-hydroxyethanesulfonate, lactate, maleate, methanesulfonate, nicotinate, 2-naphthalenesulfonate, oxalate, palmoate, pectinate, persulfate, 2-phenylpropionate, picrate, pivalate, propionate, succinate, tartrate, thiocyanate, tosylate, mesylate, and undecanoate. Also, the basic nitrogen-containing groups can be quaternized with such agents as lower alkyl halides, such as methyl, ethyl, propyl, and butyl chloride, bromides and iodides; dialkyl sulfates like dimethyl, diethyl, dibutyl, and diamyl sulfates, long chain halides such as decyl, lauryl, myristyl and stearyl chlorides, bromides and iodides, aralkyl halides like benzyl and phenethyl bromides, and others. Water or oil-soluble or dispersible products are thereby obtained.

Examples of acids that may be employed to from pharmaceutically acceptable acid addition salts include such inorganic acids as hydrochloric acid, sulfuric acid and phosphoric acid and such organic acids as oxalic acid, maleic acid, succinic acid and citric acid. Other examples include salts with alkali metals or alkaline earth metals, such as sodium, potassium, calcium or magnesium or with organic bases.

Also encompassed in the scope of the present invention are pharmaceutically acceptable esters of a carboxylic acid or hydroxyl containing group, including a metabolically labile ester or a prodrug form of a compound of this invention. A metabolically labile ester is one which may produce, for example, an increase in blood levels and prolong the efficacy of the corresponding non-esterified form of the compound. A prodrug form is one which is not in an active form of the molecule as administered but which becomes therapeutically active after some in vivo activity or biotransformation, such as metabolism, for example, enzymatic or hydrolytic cleavage. For a general discussion of prodrugs involving esters see Svensson and Tunek Drug Metabolism Reviews 165 (1988) and Bundgaard Design of Prodrugs, Elsevier (1985). Examples of a masked carboxylate anion include a variety of esters, such as alkyl (for example, methyl, ethyl), cycloalkyl (for example, cyclohexyl), aralkyl (for example, benzyl, p-methoxybenzyl), and alkylcarbonyloxyalkyl (for example, pivaloyloxymethyl). Amines have been masked as arylcarbonyloxymethyl substituted derivatives which are cleaved by esterases in vivo releasing the free drug and formaldehyde (Bungaard J. Med. Chem. 2503 (1989)). Also, drugs containing an acidic NH group, such as imidazole, imide, indole and the like, have been masked with N-acyloxymethyl groups (Bundgaard Design of Prodrugs, Elsevier (1985)). Hydroxy groups have been masked as esters and ethers. EP 039,051 (Sloan and Little, Apr. 11, 1981) discloses Mannich-base hydroxamic acid prodrugs, their preparation and use. Esters of a compound of this invention, may include, for example, the methyl, ethyl, propyl, and butyl esters, as well as other suitable esters formed between an acidic moiety and a hydroxyl containing moiety. Metabolically labile esters, may include, for example, methoxymethyl, ethoxymethyl, iso-propoxymethyl, α-methoxyethyl, groups such as α-(($C_1$-$C_4$)-alkyloxy)ethyl, for example, methoxyethyl, ethoxyethyl, propoxyethyl, iso-propoxyethyl, etc.; 2-oxo-1,3-dioxolen-4-ylmethyl groups, such as 5-methyl-2-oxo-1,3, dioxolen-4-ylmethyl, etc.; $C_1$-$C_3$ alkylthiomethyl groups, for example, methylthiomethyl, ethylthiomethyl, isopropylthiomethyl, etc.; acyloxymethyl groups, for example, pivaloyloxymethyl, α-acetoxymethyl, etc.; ethoxycarbonyl-1-methyl; or α-acyloxy-α-substituted methyl groups, for example α-acetoxyethyl.

Further, the compounds of the invention may exist as crystalline solids which can be crystallized from common solvents such as ethanol, N,N-dimethyl-formamide, water, or the like. Thus, crystalline forms of the compounds of the invention may exist as polymorphs, solvates and/or hydrates of the parent compounds or their pharmaceutically acceptable salts. All of such forms likewise are to be construed as falling within the scope of the invention.

While the compounds of the invention can be administered as the sole active pharmaceutical agent, they can also be used in combination with one or more compounds of the invention or other agents. When administered as a combination, the therapeutic agents can be formulated as separate compositions that are given at the same time or different times, or the therapeutic agents can be given as a single composition.

The foregoing is merely illustrative of the invention and is not intended to limit the invention to the disclosed compounds. Variations and changes which are obvious to one skilled in the art are intended to be within the scope and nature of the invention which are defined in the appended claims.

From the foregoing description, one skilled in the art can easily ascertain the essential characteristics of this invention, and without departing from the spirit and scope thereof, can make various changes and modifications of the invention to adapt it to various usages and conditions.

We claim:

1. A compound having the structure:

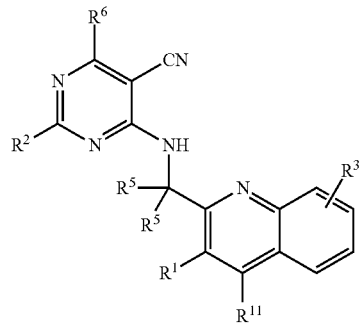

or any pharmaceutically-acceptable salt thereof, wherein:
$R^1$ is phenyl or pyridyl, both of which are substituted by 0, 1, 2 or 3 substituents independently selected from halo, $C_{1-6}$alk, $C_{1-4}$haloalk, cyano, nitro, —C(=O)$R^a$, —C(=O)O$R^a$, —C(=O)N$R^a R^a$, —C(=N$R^a$)N$R^a R^a$, —OR$^a$, —OC(=O)R$^a$, —OC(=O)NR$^a$R$^a$, —OC(=O)N(R$^a$)S(=O)$_2$R$^a$, —OC$_{2-6}$alkNR$^a$R$^a$, —OC$_{2-6}$alkOR$^a$, —SR$^a$, —S(=C)R$^a$, —S(=O)$_2$R$^a$ and —S(=O)$_2$NR$^a$R$^a$ R$^2$ is H;
R$^3$ is selected from H and halo;
R$^5$ is, independently, in each instance, H or C$_{1-6}$alk;
R$^6$ is NHR$^9$;
R$^9$ is H;
R$^{11}$ is selected from H, halo, C$_{1-6}$alk, C$_{1-4}$haloalk, cyano, nitro, —C(=O)R$^a$, —C(=O)OR$^a$, —C(=O)NR$^a$R$^a$, —C(=NR$^a$)NR$^a$R$^a$, —OR$^a$, —OC(=O)R$^a$, —OC(=O)NR$^a$R$^a$, —OC(=O)N(R$^a$)S(=O)$_2$R$^a$, —OC$_{2-6}$alkNR$^a$R$^a$, —OC$_{2-6}$alkOR$^a$, —SR$^a$, —S(=O)R$^a$, —S(=O)$_2$R$^b$, —S(=O)$_2$NR$^a$R$^a$, —S(=O)$_2$N(R$^a$)C(=O)R$^a$, —S(=O)$_2$N(R$^a$)C(=O)OR$^a$, —S(=O)$_2$N(R$^a$)C(=O)NR$^a$R$^a$, —NR$^a$R$^a$, —N(R$^a$)C(=O)R$^a$, —N(R$^a$)C(=O)OR$^a$, —N(R$^a$)C(=O)NR$^a$R$^a$, —N(R$^a$)C(=NR$^a$)NR$^a$R$^a$, —N(R$^a$)S(=O)$_2$R$^a$, —N(R$^a$)S(=O)$_2$NR$^a$R$^a$, —NR$^a$C$_{2-6}$alkNR$^a$R$^a$, —NR$^a$C$_{2-6}$alkOR$^a$, —NR$^a$C$_{2-6}$alkCO$_2$R$^a$, —NR$^a$C$_{2-6}$alkSO$_2$R$^b$, —CH$_2$C(=O)R$^a$, —CH$_2$C(=O)OR$^a$, —CH$_2$C(=O)NR$^a$R$^a$, —CH$_2$C(=NR$^a$)NR$^a$R$^a$, —CH$_2$OR$^a$, —CH$_2$OC(=O)R$^a$, —CH$_2$OC(=O)NR$^a$R$^a$, —CH$_2$OC(=O)N(R$^a$)S(=O)$_2$R$^a$, —CH$_2$OC$_{2-6}$alkNR$^a$R$^a$, —CH$_2$OC$_{2-6}$alkOR$^a$, —CH$_2$SR$^a$, —CH$_2$S(=O)R$^a$, —CH$_2$S(=O)$_2$R$^b$, —CH$_2$S(=O)$_2$NR$^a$R$^a$, —CH$_2$S(=O)$_2$N(R$^a$)C(=O)R$^a$, —CH$_2$S(=O)$_2$N(R$^a$)C(=O)OR$^a$, —CH$_2$S(=O)$_2$N(R$^a$)C(=O)NR$^a$R$^a$, —CH$_2$NR$^a$R$^a$, —CH$_2$N(R$^a$)C(=)R$^a$, —CH$_2$N(R$^a$)C(=O)OR$^a$, —CH$_2$N(R$^a$)C(=O)NR$^a$R$^a$, —CH$_2$N(R$^a$)C(=NR$^a$)NR$^a$R$^a$, —CH$_2$N(R$^a$)S(=O)$_2$R$^a$, —CH$_2$N(R$^a$)S(=O)$_2$NR$^a$R$^a$, —CH$_2$NR$^a$C$_{2-6}$alkNR$^a$R$^a$, —CH$_2$NR$^a$C$_{2-6}$alkOR$^a$, —CH$_2$NR$^a$C$_{2-6}$alkCO$_2$R$^a$, —CH$_2$NR$^a$C$_{2-6}$alkSO$_2$R$^b$, —CH$_2$R$^c$, —C(=O)R$^c$ and —C(=O)N(R$^a$)R$^c$;
R$^a$ is independently, at each instance, H or R$^b$;
R$^b$ is independently, at each instance, phenyl, benzyl or C$_{1-6}$alk, the phenyl, benzyl and C$_{1-6}$alk being substituted by 0, 1, 2 or 3 substituents selected from halo, C$_{1-4}$alk, C$_{1-3}$haloalk, —OH, —OC$_{1-4}$alk, —NH$_2$, —NHC$_{1-4}$alk and —N(C$_{1-4}$alk)C$_{1-4}$alk; and
R$^c$ is a saturated or partially-saturated 4-, 5- or 6-membered ring containing 1, 2 or 3 heteroatoms selected from N, O and S, the ring being substituted by 0, 1, 2 or 3 substituents selected from halo, C$_{1-4}$alk, C$_{1-3}$haloalk, —OC$_{1-4}$alk, —NH$_2$, —NHC$_{1-4}$alk and —N(C$_{1-4}$alk)C$_{1-4}$alk.

2. A compound selected:
4-amino-6-(((1S)-1-(6-fluoro-3-(6-(methylsulfonyl)-2-pyridinyl)-2-quinolinyl)ethyl)amino)-5-pyrimidinecarbonitrile;
4-amino-6-((1-(6-fluoro-3-(2-pyridinyl)-2-quinolinyl)ethyl)amino)-5-pyrimidinecarbonitrile;
4-((1-(6-fluoro-3-(2-pyridinyl)-2-quinolinyl)ethyl)amino)-6-hydroxy-5-pyrimidinecarbonitrile;
4-amino-6-((1-(5-chloro-3-(2-pyridinyl)-2-quinolinyl)ethyl)amino)-5-pyrimidinecarbonitrile;
4-amino-6-(((1S)-1-(5-chloro-3-(2-pyridinyl)-2-quinolinyl)ethyl)amino)-5-pyrimidinecarbonitrile;
4-amino-6-(((1R)-1-(5-chloro-3-(2-pyridinyl)-2-quinolinyl)ethyl)amino)-5-pyrimidinecarbonitrile;
2-((1S)-1-((6-amino-5-cyano-4-pyrimidinyl)amino)ethyl)-3-(2-pyridinyl)-5-quinolinecarbonitrile;
2-((1R)1-((6-amino-5-cyano-4-pyrimidinyl)amino)ethyl)-3-(2-pyridinyl)-5-quinolinecarbonitrile;
4-amino-6-((1-(3-(2-pyridinyl)-1,8-naphthyridin-2-yl)ethyl)amino)-5-pyrimidinecarbonitrile;
4-amino-6-((1-(3-(2-pyridinyl)-1,6-naphthyridin-2-yl)ethyl)amino)-5-pyrimidinecarbonitrile;
4-amino-6-((1-(6-fluoro-4-(methylsulfonyl)-3-phenyl-2-quinolinyl)ethyl)amino)-5-pyrimidinecarbonitrile;
4-amino-6-((1-(6-fluoro-4-(methylsulfanyl)-3-phenyl-2-quinolinyl)ethyl)amino)-5-pyrimidinecarbonitrile;
4-amino-6-(((8-fluoro-3-(2-(methylsulfonyl)phenyl)-2-quinolinyl)methyl)amino)-5-pyrimidinecarbonitrile;
4-amino-6-(((8-fluoro-3-(2-pyridinyl)-2-quinolinyl)methyl)amino)-5-pyrimidinecarbonitrile;
4-amino-6-((((8-fluoro-3-phenyl-2-quinolinyl)methyl)amino)-5-pyrimidinecarbonitrile;
4-amino-6-(((5-fluoro-3-phenyl-2-quinolinyl)methyl)amino)-5-pyrimidinecarbonitrile;
4-amino-6-(((5-fluoro-3-(3-fluorophenyl)-2-quinolinyl)methyl)amino)-5-pyrimidinecarbonitrile;
4-amino-6-(((3-(3,5-difluorophenyl)-5-fluoro-2-quinolinyl)methyl)amino)-5-pyrimidinecarbonitrile;
4-amino-6-(((5-fluoro-3-(2-(methylsulfonyl)phenyl)-2-quinolinyl)methyl)amino)-5-pyrimidinecarbonitrile;
4-amino-6-((5-fluoro-3-(2-pyridinyl)-2-quinolinyl)methyl)amino)-5-pyrimidinecarbonitrile;
4-amino-6-((-1-(4-(dimethylamino)-6-fluoro-3-(2-pyridinyl)-2-quinolinyl)ethyl)amino)-5-pyrimidinecarbonitrile;
4-amino-6-((-1-(6-fluoro-4-(4-morpholinyl)-3-(2-pyridinyl)-2-quinolinyl)ethyl)amino)-5-pyrimidinecarbonitrile;
4-amino-6-((-1-(6-fluoro-4-(3-hydroxy-1-azetidinyl)-3-(2-pyridinyl)-2-quinolinyl)ethyl)amino)-5-pyrimidinecarbonitrile;
2-((1S)-1-((6-amino-5-cyano-4-pyrimidinyl)amino)ethyl)-6-fluoro-N,N-dimethyl-3-phenyl-4-quinolinecarboxamide;
4-amino-6-(((1S)-1-(6-fluoro-4-(4-morpholinylcarbonyl)-3-phenyl-2-quinolinyl)ethyl)amino)-5-pyrimidinecarbonitrile;
4-amino-6-(((1S)-1-(6-fluoro-4-(((3S)-3-hydroxy-1-pyrrolidinyl)carbonyl)-3-phenyl-2-quinolinyl)ethyl)amino)-5-pyrimidinecarbonitrile;
4-amino-6-(((1S)-1-(4-((1,1-dioxido-4-thiomorpholinyl)carbonyl)-6-fluoro-3-phenyl-2-quinolinyl)ethyl)amino)-5-pyrimidinecarbonitrile;
2-((1S)-1-((6-amino-5-cyano-4-pyrimidinyl)amino)ethyl)-6-fluoro-3-phenyl-4-quinolinecarbonitrile;
2-((1S)-1-((6-amino-5-cyano-4-pyrimidinyl)amino)ethyl)-6-fluoro-3-phenyl-4-quinolinecarbonitrile;
2-((1R)1-((6-amino-5-cyano-4-pyrimidinyl)amino)ethyl)-6-fluoro-3-phenyl-4-quinolinecarbonitrile;
methyl 2-(-1-((6-amino-5-cyano-4-pyrimidinyl)amino)ethyl)-6-fluoro-3-phenyl-4-quinolinecarboxylate;
2-((1S)-1-((6-amino-5-cyano-4-pyrimidinyl)amino)ethyl)-6-fluoro-3-phenyl-4-quinolinecarboxylic acid;
2-(-1-((6-amino-5-cyano-4-pyrimidinyl)amino)ethyl)-6-fluoro-N-methyl-3-phenyl-4-quinolinecarboxamide;
4-amino-6-((-1-(6-fluoro-3-phenyl-4-(1-piperazinylcarbonyl)-2-quinolinyl)eethyl)amino)-5-pyrimidinecarbonitrile;
4-amino-6-((-1-(6-fluoro-4-((4-methyl-1-piperazinyl)carbonyl)-3-phenyl-2-quinolinyl)ethyl)amino)-5-pyrimidinecarbonitrile;
2-(-1-((6-amino-5-cyano-4-pyrimidinyl)amino)ethyl)-6-fluoro-N,N-dimethyl-3-phenyl-4-quinolinecarboxamide;

4-amino-6-((-1-(6-fluoro-4-(((3R)-3-hydroxy-1-pyrrolidinyl)carbonyl)-3-phenyl-2-quinolinyl)ethyl)amino)-5-pyrimidinecarbonitrile;
4-amino-6-((1-(6-fluoro-3-phenyl-4-(1-pyrrolidinylcarbonyl)-2-quinolinyl)ethyl)amino)-5-pyrimidinecarbonitrile;
4-amino-6-((-1-(6-fluoro-4-(4-morpholinylcarbonyl)-3-phenyl-2-quinolinyl)ethyl)amino)-5-pyrimidinecarbonitrile;
4-amino-6-((-1-(6-fluoro-4-(((3S)-3-hydroxy-1-pyrrolidinyl)carbonyl)-3-phenyl-2-quinolinyl)ethyl)amino)-5-pyrimidinecarbonitrile;
4-amino-6-((-1-(6-fluoro-4-(((3R)-3-hydroxy-1-pyrrolidinyl)-carbonyl)-3-phenyl-2-quinolinyl)ethyl)amino)-5-pyrimidine-carbonitrile;
4-amino-6-((1-(4-((1,1-dioxido-4-thiomorpholinyl)carbonyl)-6-fluoro-3-phenyl-2-quinolinyl)ethyl)amino)-5-pyrimidine-carbonitrile;
4-amino-6-((1-(6-fluoro-4-((3-hydroxy-1-azetidinyl)carbonyl)-3-phenyl-2-quinolinyl)ethyl)amino)-5-pyrimidinecarbonitrile;
4-amino-6-((1-(6-fluoro-4-((3-methoxy-1-azetidinyl)carbonyl)-3-phenyl-2-quinolinyl)ethyl)amino)-5-pyrimidinecarbonitrile;
2-(1-((6-amino-5-cyano-4-pyrimidinyl)amino)ethyl)-6-fluoro-N-(2-(4-morpholinyl)ethyl)-3-phenyl-4-quinolinecarboxamide;
4-amino-6-(-1-(6-fluoro-4-(hydroxymethyl)-3-phenyl-2-quinolinyl)ethyl)amino)-5-pyrimidinecarbonitrile;
4-amino-6-(((1S)-1-(6-fluoro-3-phenyl-4-(1-piperazinylcarbon-yl)-2-quinolinyl)ethyl)amino)-5-pyrimidinecarbonitrile;
2-((1S)-1-((6-amino-5-cyano-4-pyrimidinyl)amino)ethyl)-6-fluoro-N-methyl-3-phenyl-4-quinolinecarboxamide;
4-amino-6-((-1-(6-fluoro-4-((methylsulfonyl)methyl)-3-phenyl-2-quinolinyl)ethyl)amino)-5-pyrimidinecarbonitrile;
4-amino-6-(((1S)-1-(6-fluoro-4-((3-hydroxy-1-azetidinyl)-carbonyl)-3-phenyl-2-quinolinyl)ethyl)amino)-5-pyrimidine-carbonitrile;
4-amino-6-(((1S)-1-(4-((1,1-dioxido-4-thiomorpholinyl)carbonyl)-6-fluoro-3-phenyl-2-quinolinyl)ethyl)amino)-5-pyrimidinecarbonitrile;
2-((1S)-1-((6-amino-5-cyano-4-pyrimidinyl)amino)ethyl)-6-fluoro-N,N-dimethyl-3-phenyl-4-quinolinecarboxamide;
2-((1 S)-1-((6-amino-5-cyano-4-pyrimidinyl)amino)ethyl)-6-fluoro-N,N-dimethyl-3-phenyl-4-quinolinecarboxamide;
4-amino-6-((-1-(6-fluoro-4-(4-morpholinylmethyl)-3-phenyl-2-quinolinyl)ethyl)amino)-5-pyrimidinecarbonitrile;
2-((1S)-1-((6-amino-5-cyano-4-pyrimidinyl)amino)ethyl)-N-ethyl-6-fluoro-3-phenyl-4-quinolinecarboxamide;
2-(-1-((6-amino-5-cyano-4-pyrimidinylamino)ethyl)-6-fluoro-N-(1-methylethyl)-3-phenyl-4-quinolinecarboxamide;
2-(-1-((6-amino-5-cyano-4-pyrimidinyl)amino)ethyl)-N-(cyclopropylmethyl)-6-fluoro-3-phenyl-4-quinolinecarboxamide;
4-amino-6-(((1S)-1-(6-fluoro-4-methoxy-3-phenyl-2-quinolinyl)ethyl)amino)-5-pyrimidinecarbonitrile;
4-amino-6-(((1R)-1-(6-fluoro-4-methoxy-3-phenyl-2-quinolinyl)ethyl)amino)-5-pyrimidinecarbonitrile;
4-amino-6-(((1S)-1-(3-(3,5-difluorophenyl)-6-fluoro-4-methoxy-2-quinolinyl)ethyl)amino)-5-pyrimidinecarbonitrile;
4-amino-6-(-1-(6-fluoro-4-((2-methoxyethyl)amino)-3-phenyl-2-quinolinyl)ethyl)amino)-5-pyrimidinecarbonitrile;
4-amino-6-(-1-(4-((2-(dimethylamino)ethyl)amino)-6-fluoro-3-phenyl-2-quinolinyl)ethyl)amino)-5-pyrimidinecarbonitrile;
4-amino-6-(((1S)-1-(6-fluoro-4-((2-methoxyethyl)amino)-3-phenyl-2-quinolinyl)ethyl)amino)-5-pyrimidinecarbonitrile;
4-amino-6-(((1R)-1-(6-fluoro-4-((2-methoxyethyl)amino)-3-phenyl-2-quinolinyl)ethyl)amino)-5-pyrimidinecarbonitrile;
4-amino-6-(-1-(6-fluoro-4-((2-(methylsulfonyl)ethyl)amino)-3-phenyl-2-quinolinyl)ethyl)amino)-5-pyrimidinecarbonitrile;
4-amino-6-(-1-(6-fluoro-4-((2-hydroxyethyl)amino)-3-phenyl-2-quinolinyl)ethyl)amino)-5-pyrimidinecarbonitrile;
4-amino-6-(((1S)-1-(6-fluoro-4-((2-(methylsulfonyl)ethyl)amino)-3-phenyl-2-quinolinyl)ethyl)amino)-5-pyrimidinecarbonitrile;
4-amino-6-(((1S)-1-(6-fluoro-4-(methylsulfonyl)-3-phenyl-2-quinolinyl)ethyl)amino)-5-pyrimidinecarbonitrile;
4-amino-6-((-1-(6-fluoro-4-((R)-(2-hydroxyethyl)sulfinyl)-3-phenyl-2-quinolinyl)ethyl)amino)-5-pyrimidinecarbonitrile;
4-amino-6-(((1R)-1-(5-fluoro-4-(methylsulfonyl)-3-phenyl-2-quinolinyl)ethyl)amino)-5-pyrimidinecarbonitrile;
4-amino-6-(((1S)-1-(5-fluoro-4-(methylsulfonyl)-3-phenyl-2-quinolinyl)ethyl)amino)-5-pyrimidinecarbonitrile;
4-amino-6-((-1-(3-(3,5-difluorophenyl)-6-fluoro-4-(methyl-sulfonyl)-2-quinolinyl)ethyl)amino)-5-pyrimidinecarbonitrile;
4-amino-6-((-1-(6-fluoro-4-((S)-(2-hydroxyethyl)sulfinyl)-3-phenyl-2-quinolinyl)ethyl)amino)-5-pyrimidinecarbonitrile;
2-(1-(6-Amino-5-cyanopyrimidin-4-ylamino)ethyl)-6-fluoro-N-methy-3-(pyridin-2-yl)quinoline-4-carboxamide;
(S)-2-(1-(6-Amino-5-cyanopyrimidin-4-ylamino)ethyl)-N-ethyl-6-fluoro-3-(pyridin-2-yl)quinoline-4-carboximidamide;
(S)-2-(1-(6-Amino-5-cyanopyrimidin-4-ylamino)ethyl)-6-fluoro-N-(2-hydroxyethyl)-3-(pyridin-2-yl)quinoline-4-carboxamide;
(S)-2-(1-(6-Amino-5-cyanopyrimidin-4-ylamino)ethyl)-N-cyclopropyl-6-fluoro-3-(pyridin-2-yl)quinoline-4-carboxamide;
2-1-(((6-Amino-5-cyano-4-pyrimidinyl)amino)ethyl)-6-fluoro-3-(2-pyridinyl)-4-quinolinecarboxylic acid;
2-(-1-((6-Amino-5-cyano-4-pyrimidinyl)amino)ethyl)-6-fluoro-N-methyl-32-pyridinyl)-4-quinolinecarboxamide;
2-((1R)-1-((6-Amino-5-cyano-4-pyrimidinyl)amino)ethyl)-6-fluoro-N-methyl-3-(2-pyridinyl)-4-quinolinecarboxamide;
2-(1-((6-Amino-5-cyano-4-pyrimidinyl)amino)ethyl)-6-fluoro-N,N-dimethyl-3-(2-pyridinyl)-4-quinolinecarboxamide;

4-Amino-6-((1-(6-fluoro-4-(1-piperazinylcarbonyl)-3-(2-pyridinyl)-2-quinolinyl)ethyl)amino)-5-pyrimidinecarbonitrile; and 4-amino-6-(1-(6-fluoro-4-(3-hydroxyazetidine-1-carbonyl)-3-(pyridin-2-yl)quinolin-2-yl)ethylamino)pyrimidine-5-carbonitrile; or any pharmaceutically-acceptable salt thereof.

3. A pharmaceutical composition comprising a compound according to claim 1 and a pharmaceutically-acceptable diluent or carrier.

* * * * *